(12) United States Patent
Hilden et al.

(10) Patent No.: US 10,106,606 B2
(45) Date of Patent: Oct. 23, 2018

(54) TARGETING TISSUE FACTOR TO ACTIVATED PLATELETS

(71) Applicant: Novo Nordisk A/S, Bagsvaerd (DK)

(72) Inventors: Ida Hilden, Vanloese (DK); Lars Christian Petersen, Hoersholm (DK); Jens Breinholt, Dyssegaard (DK); Mette Dahl Andersen, Vaerloese (DK); Jais Rose Bjelke, Smoerum (DK); Thomas Egebjerg, Ganloese (DK); Jes Thorn Clausen, Hoeng (DK); Susanne Nedergaard Grell, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/090,002

(22) Filed: Apr. 4, 2016

(65) Prior Publication Data

US 2016/0272710 A1 Sep. 22, 2016

Related U.S. Application Data

(63) Continuation of application No. 13/391,755, filed as application No. PCT/EP2010/062519 on Aug. 26, 2010, now abandoned.

(60) Provisional application No. 61/239,142, filed on Sep. 2, 2009, provisional application No. 61/288,944, filed on Dec. 22, 2009.

(30) Foreign Application Priority Data

Aug. 27, 2009 (EP) .................................. 09168833

(51) Int. Cl.
| | | |
|---|---|---|
| *C07K 16/28* | (2006.01) | |
| *C07K 14/745* | (2006.01) | |
| *A61K 38/00* | (2006.01) | |

(52) U.S. Cl.
CPC ........ *C07K 16/2803* (2013.01); *C07K 14/745* (2013.01); *A61K 38/00* (2013.01); *C07K 2317/21* (2013.01); *C07K 2317/24* (2013.01); *C07K 2317/31* (2013.01); *C07K 2317/34* (2013.01); *C07K 2317/51* (2013.01); *C07K 2317/515* (2013.01); *C07K 2317/524* (2013.01); *C07K 2317/526* (2013.01); *C07K 2317/53* (2013.01); *C07K 2317/55* (2013.01); *C07K 2317/56* (2013.01); *C07K 2317/64* (2013.01); *C07K 2317/92* (2013.01); *C07K 2319/33* (2013.01)

(58) Field of Classification Search
None
See application file for complete search history.

(56) References Cited

U.S. PATENT DOCUMENTS

| | | |
|---|---|---|
| 7,553,936 B2 | 6/2009 | Mori et al. |
| 2004/0180409 A1 | 9/2004 | McVicar et al. |
| 2005/0059113 A1 | 3/2005 | Bedian et al. |
| 2008/0131423 A1 | 6/2008 | Mori et al. |
| 2009/0013114 A1 | 1/2009 | Sanders |

FOREIGN PATENT DOCUMENTS

| | | |
|---|---|---|
| WO | 2003/035688 A2 | 5/2003 |
| WO | 2006/096828 A2 | 9/2006 |

OTHER PUBLICATIONS

Kringelum et al (Molecular Immunology 53 (2013) 24-34).*
Nurden, A.T. et al., Platelets and Blood Cells, 2008, vol. 100, pp. 45-51.
Washington, A.V. et al., Journal of Clinical Investigation, 2009, vol. 119, No. 6, pp. 1489-1501.
Washington, A.V. et al., Blood, 2002, vol. 100, No. 10, pp. 3822-3824.
Barrow, A.D., Journal of Immunology, 2004, vol. 172, No. 10, pp. 5838-5842.
Gattis, J. L. et al., Jouornal of Biological Chemistry, 2006, vol. 281, No. 19, PAGS 13396-13403.
Washington, A.V., Blood, 2004, vol. 104, No. 4, pp. 1042-1047.
Giomarelli, B. et al., Thrombosis and Haemostasis, 2007, vol. 97, No. 6, pp. 955-963.
Marquez, J. A. et al., Journal of Molecular Biology, 2007, vol. 367, pp. 310-318.
Lu, Yen-Ta et al., Hybridoma, 2006, vol. 25, No. 1, pp. 20-26.
Morales, J. et al., Abstract No. pp. 23-065, Journal of Thrombosis and Haemostasis 2009, vol. 7, Supplement 2.
Hoyt, D. B., Seminars in Hematology, 2004, vol. 41, No. 1, pp. 40-43.
Gershoni, J. M. et al., Biodrugs, 2007, vol. 21, No. 3, PAGS 145-156.
Bowie et al,Deciphering the message in Protein Sequences:Tolerance to Amino Acid Substitution, Science, Year 1990, vol. 247, No. 4948, pp. 1306-1310.
Burgess W.H et al.,Poissible Dissociation of the Heparin-binding and Mitogenic Activities of Heparin-binding (Acidic Fibroblast) Growth Factor-I from Its Receptor binding Activities by Site-directed Mutagenesis of a Single Lysine Residue ,The Journal of Cell Biology, Year 1990, vol. 111, pp. 2129-2138.

(Continued)

*Primary Examiner* — Brian Gangle
*Assistant Examiner* — Andrea K McCollum
(74) *Attorney, Agent, or Firm* — Leon Y. Lum

(57) ABSTRACT

The current invention relates to procoagulant fusion proteins, polynucleotides that encode said fusion proteins and cells that expresses said fusion proteins. Furthermore, the current invention relates to fusion proteins for use as a medicament. Individuals that have a coagulopathy, such as haemophilia A and B with or without inhibitors, may be treated with fusions proteins of the current invention.

12 Claims, 31 Drawing Sheets

Specification includes a Sequence Listing.

(56) References Cited

OTHER PUBLICATIONS

Lazar E et al.Transforming growth Factor a mutation of Aspartic Acid 47 and Leucine 48 Results in Different Biological activities,Molecular and cellular Biology, Year 1988, vol. 8 pp. 1247-1252.
Bork P,Powers and Pitfalls in Sequence Analysis, The 70 percent hurdle, Genome Research, Year 2000, vol. 10 pp. 398-400.
Vajdos F.F. et al.Comprehensive Functional Maps of the Antigenbinding Site of an Anti-ErbB2 Antibody Obtained with Shotgun Scanning Mutagenesis, Journal of molecular biology, Year 2002. vol. 320, No. 2 pp. 415-428.
Brown M et al . Tolerance to Single, but Not Multiple, Amino Acid Replacements in Antibody V H CDR2, Journal of Immunology, Year 1996, vol. 156, No. 9, pp. 3285-3291.
Radaev et al., "Crystal Structure of the Human Myeloid Cell Activating Receptor TREM-1," Structure, 2003, vol. 11, No. 12, pp. 1527-1535.

\* cited by examiner

Fig. 1

```
      M   G   L   T   L   L   L   L   L   L   L   G   L   E   G   Q   G   I
  1 ATGGGCCTC ACCCTGCTC TTGCTGCTG CTCCTGGGA CTAGAAGGT CAGGGCATA

V   G   S   L   P   E   V   L   Q   A   P   V   G   S   S   I   L   V
 55 GTTGGCAGC CTCCCTGAG GTGCTGCAG GCACCCGTG GGAAGCTCC ATTCTGGTG

Q   C   H   Y   R   L   Q   D   V   K   A   Q   K   V   W   C   R   F
109 CAGTGCCAC TACAGGCTC CAGGATGTC AAAGCTCAG AAGGTGTGG TGCCGGTTC

L   P   E   G   C   Q   P   L   V   S   S   A   V   D   R   A   P
163 TTGCCGGAG GGGTGCCAG CCCCTGGTG TCCTCAGCT GTGGATCGC AGAGCTCCG

A   G   R   R   T   F   L   T   D   L   G   G   G   L   L   Q   V   E
217 GCGGGCAGG CGTACGTTT CTCACAGAC CTGGGTGGG GGCCTGCTG CAGGTGGAA

M   V   T   L   Q   E   E   D   A   G   E   Y   G   C   M   V   D   G
271 ATGGTTACC CTGCAGGAA GAGGATGCT GGCGAGTAT GGCTGCATG GTGGATGGG

A   R   G   P   Q   I   L   H   R   V   S   L   N   I   L   P   P   E
325 GCCAGGGGG CCCCAGATT TTGCACAGA GTCTCTCTG AACATACTG CCCCCAGAG

E   E   E   T   H   K   I   G   S   L   A   E   N   A   F   S   D
379 GAAGAAGAA GAGACCCAT AAGATTGGC AGTCTGGCT GAGAACGCA TTCTCAGAC

P   A   G   S   A   N   P   L   E   P   S   Q   D   E   K   S   I   P
433 CCTGCAGGC AGTGCCAAC CCTTTGGAA CCCAGCCAG GATGAGAAG AGCATCCCC

L   I   W   G   A   V   L   L   V   G   L   L   V   A   A   V   V   L
487 TTGATCTGG GGTGCTGTG CTCCTGGTA GGTCTGCTG GTGGCAGCG GTGGTGCTG

F   A   V   M   A   K   R   K   Q   G   N   R   L   G   V   C   G   R
541 TTTGCTGTG ATGGCCAAG AGGAAACAA GGGAACAGG CTTGGTGTC TGTGGCCGA

F   L   S   S   R   V   S   G   M   N   P   S   S   V   V   H   H   V
595 TTCCTGAGC AGCAGAGTT TCAGGCATG AATCCCTCC TCAGTGGTC CACCACGTC

S   D   S   G   P   A   E   L   P   L   D   V   P   H   I   R   L
649 AGTGACTCT GGACCGGCT GCTGAATTG CCTTTGGAT GTACCACAC ATTAGGCTT

D   S   P   P   S   F   D   N   T   T   Y   T   S   L   P   L   D   S
703 GACTCACCA CCTTCATTT GACAATACC ACCTACACC AGCCTACCT CTTGATTCC

P   S   G   K   P   S   L   P   A   P   S   S   L   P   P   L   P   P
757 CCATCAGGA AAACCTTCA CTCCCAGCT CCATCCTCA TTGCCCCCT CTACCTCCT

K   V   L   V   C   S   K   P   V   T   Y   A   T   V   I   F   P   G
811 AAGGTCCTG GTCTGCTCC AAGCCTGTG ACATATGCC ACAGTAATC TTCCCGGGA

G   N   K   G   G   T   S   C   G   P   A   Q   N   P   P   N   N
865 GGGAACAAG GGTGGAGGG ACCTCGTGT GGGCCAGCC CAGAATCCA CCTAACAAT

Q   T   P   S   S
919 CAGACTCCA TCCAGC
```

Fig. 2

```
    HindIII              M    G    L    T    L   L    L   L    L    L    G    L
  1 AAGCTTGCC GCCACCATG GGCCTCACC CTGCTCTTG CTGCTGCTC CTGGGACTA
    E    G    Q    G    I    V    G    S    L    P    E    V    L    Q    A    P    V    G
 55 GAAGGTCAG GGCATAGTT GGCAGCCTC CCTGAGGTG CTGCAGGCA CCCGTGGGA
    S    S    I    L    V    Q    C    H    Y    R    L    Q    D    V    K    A    Q    K
109 AGCTCCATT CTGGTGCAG TGCCACTAC AGGCTCCAG GATGTCAAA GCTCAGAAG
    V    W    C    R    F    L    P    E    G    C    Q    P    L    V    S    S    A    V
163 GTGTGGTGC CGGTTCTTG CCGGAGGGG TGCCAGCCC CTGGTGTCC TCAGCTGTG
    D    R    R    A    P    A    G    R    R    T    F    L    T    D    L    G    G    G
217 GATCGCAGA GCTCCGGCG GGCAGGCGT ACGTTCTC ACAGACCTG GGTGGGGGC
    L    L    Q    V    E    M    V    T    L    Q    E    E    D    A    G    E    Y    G
271 CTGCTGCAG GTGGAAATG GTTACCCTG CAGGAAGAG GATGCTGGC GAGTATGGC
    C    M    V    D    G    A    R    G    P    Q    I    L    H    R    V    S    L    N
325 TGCATGGTG GATGGGGCC AGGGGGCCC CAGATTTTG CACAGAGTC TCTCTGAAC
    I    L    P    P    E    E    E    E    T    H    K    I    G    S    L    A    E
379 ATACTGCCC CCAGAGGAA GAAGAAGAG ACCCATAAG ATTGGCAGT CTGGCTGAG
    N    A    F    S    D    P    A    G    S    A    N    P    L    E    P    S    Q    D
433 AACGCATTC TCAGACCCT GCAGGCAGT GCCAACCCT TTGGAACCC AGCCAGGAT E    K    S    I    P    H    H    H    H    H    H    *    EcoRI
487 GAGAAGAGC ATCCCCCAC CATCACCAT CACCATTAA GAATTC
```

```
        M   K   L      P   V   G      L   L   V      L   M   F      W   I   P      A   S   S
  1   ATGAAGTTG  CCTGTTGGG  CTGTTGGTG  CTGATGTTC  TGGATTCCA  GCTTCCAGC

S   D   V      V   M   T      Q   T   P      L   S   L      P   V   S      L   G   D
 55   AGTGATGTT  GTGATGACC  CAAACTCCA  CTCTCCCTG  CCTGTCAGT  CTTGGAGAT

Q   A   S      I   S   C      R   S   S      Q   S   L      V   H   R      N   G   N
109   CAAGCCTCC  ATCTCTTGC  AGATCTAGT  CAGAGCCTT  GTACACAGA  ATGGAAAC

T   Y   F      H   W   C      L   Q   K      P   G   Q      S   P   K      L   L   I
163   ACCTATTTT  CATTGGTGC  CTGCAGAAA  CCAGGCCAG  TCTCCAAAG  CTCCTGATC

Y   K   V      S   N   R      F   S   G      V   P   D      R   F   S      G   S   G
217   TACAAAGTT  TCCAACCGA  TTTTCTGGG  GTCCCAGAC  AGGTTCAGT  GGCAGTGGA

S   G   T      D   F   T      L   K   I      S   R   V      E   A   E      D   L   G
271   TCAGGGACA  GATTTCACA  CTCAAGATC  AGCAGAGTG  GAGGCTGAG  GATCTGGGA

V   Y   F      C   S   Q      S   T   H      V   P   Y      T   F   G      G   G   T
325   GTTTATTTC  TGCTCTCAA  AGTACACAT  GTTCCGTAC  ACGTTCGGA  GGGGGGACC

K   L   E      I   K   R
379   AAGCTGGAA  ATAAAACGT
```

B

```
              1           2           3           4           5           6
    1234567890123456789012345678ABCDEF890123456789012345678901234567890   Kabat
    DVVMTQTPLSLPVSLGDQASISCRSSQSLVHR-NGNTYFHWCLQKPGQSPKLLIYKVSNRFSGVPD    0012LC-V 7           8           9          10
    12345678901234567890123456789012345AB6789012345678                   Kabat
    RFSGSGSGTDFTLKISRVEAEDLGVYFCSQSTHVP--YTFGGGTKLEIKR                    0012LC-V
```

C

```
        M   D   F      G   L   I      F   F   I      V   A   L      L   K   G      V   Q   C
  1   ATGGATTTT  GGGCTGATT  TTTTTTATT  GTTGCTCTT  TTAAAAGGG  GTCCAGTGT

E   V   K      L   L   E      S   G   G      G   L   V      Q   P   G      G   S   L
 55   GAGGTGAAA  CTTCTCGAG  TCTGGAGGT  GGCCTGGTG  CAGCCTGGA  GGATCCCTG

K   L   S      C   A   A      S   G   F      D   F   S      R   Y   W      M   T   W
109   AAACTCTCC  TGTGCAGCC  TCAGGATTC  GATTTTAGT  AGATACTGG  ATGACTTGG

V   R   Q      A   P   G      K   G   L      E   W   I      G   E   I      N   P   D
163   GTCCGGCAG  GCTCCAGGG  AAAGGGCTA  GAATGGATT  GGAGAAATT  AATCCAGAT

S   S   T      I   N   Y      T   P   S      L   K   D      K   F   I      I   S   R
217   AGCAGTACG  ATAAACTAT  ACGCCATCT  CTAAAGGAT  AAATTCATC  ATCTCCAGA

D   N   A      K   N   T      L   Y   L      Q   M   S      E   V   R      S   E   D
271   GACAACGCC  AAGAATACG  CTGTACCTG  CAAATGAGC  GAAGTGAGA  TCTGAGGAC

T   A   L      Y   Y   C      A   S   G      V   F   T      S   W   G      Q   G   T
325   ACAGCCCTT  TATTACTGT  GCAAGCGGG  GTGTTTACT  TCCTGGGGC  CAAGGGACT

L   V   T      V   S   A
379   CTGGTCACT  GTCTCTGCA
```

```
            1         2         3         4          5         6
   1234567890123456789012345678901234 5AB67890123456789 012ABC34567890     Kabat
   EVKLLESGGGLVQPGGSLKLSCAASGFDFSRYWMT---WVRQAPGKGLEWIGEIN--PDSSTINYT      0012HC-V 7         8         9         10         11
   12345 67890123456789012ABC345678901234 567890ABCDEFGHIJK1 234567890123  Kabat
   PSLKDKFIISRDNAKNTLYLQMSEVRSEDTALYYCASGVFTS--------------WGQGTLVTVSA    0012HC-V
```

Fig. 4

```
      M   K   L   P   V   G   L   L   V   L   M   F   W   I   P   A   S   S
  1 ATGAAGTTG CCTGTTGGG CTGTTGGTG CTGATGTTC TGGATTCCA GCTTCCAGC

S   D   V   V   M   T   Q   T   P   L   S   L   P   V   S   L   G   D
 55 AGTGATGTT GTGATGACC CAAACTCCA CTCTCCCTG CCTGTCAGT CTTGGAGAT

Q   A   S   I   S   C   R   S   S   Q   S   L   V   H   R   N   G   N
109 CAAGCCTCC ATCTCTTGC AGATCTAGT CAGAGCCTT GTACACAGA AATGGAAAC

T   Y   F   H   W   C   L   Q   K   P   G   Q   S   P   K   L   L   I
163 ACCTATTTT CATTGGTGC CTGCAGAAA CCAGGCCAG TCTCCAAAG CTCCTGATC

Y   K   V   S   N   R   F   S   G   V   P   D   R   F   S   G   S   G
217 TACAAAGTT TCCAACCGA TTTTCTGGG GTCCCAGAC AGGTTCAGT GGCAGTGGA

S   G   T   D   F   T   L   K   I   S   R   V   E   A   E   D   L   G
271 TCAGGGACA GATTTCACA CTCAAGATC AGCAGAGTG GAGGCTGAG GATCTGGGA

V   Y   F   C   S   Q   S   T   H   V   P   Y   T   F   G   G   G   T
325 GTTTATTTC TGCTCTCAA AGTACACAT GTTCCGTAC ACGTTCGGA GGGGGGACC

K   L   E   I   K   R   T   V   A   A   P   S   V   F   I   F   P   P
379 AAGCTGGAA ATAAAACGT ACGGTGGCT GCACCATCT GTCTTCATC TTCCCGCCA

S   D   E   Q   L   K   S   G   T   A   S   V   V   C   L   L   N   N
433 TCTGATGAG CAGTTGAAA TCTGGAACT GCCTCTGTT GTGTGCCTG CTGAATAAC

F   Y   P   R   E   A   K   V   Q   W   K   V   D   N   A   L   Q   S
487 TTCTATCCC AGAGAGGCC AAAGTACAG TGGAAGGTG GATAACGCC CTCCAATCG

G   N   S   Q   E   S   V   T   E   Q   D   S   K   D   S   T   Y   S
541 GGTAACTCC CAGGAGAGT GTCACAGAG CAGGACAGC AAGGACAGC ACCTACAGC

L   S   S   T   L   T   L   S   K   A   D   Y   E   K   H   K   V   Y
595 CTCAGCAGC ACCCTGACG CTGAGCAAA GCAGACTAC GAGAAACAC AAAGTCTAC

A   C   E   V   T   H   Q   G   L   S   S   P   V   T   K   S   F   N
649 GCCTGCGAA GTCACCCAT CAGGGCCTG AGCTCGCCC GTCACAAAG AGCTTCAAC

R   G   E   C   E   D   Q   V   D   P   R   L   I   D   G   K
703 AGGGGAGAG TGTGAGGAC CAGGTGGAC CCCAGACTG ATCGACGGC AAG
```

Fig. 5

```
        M   D   F   G   L   I   F   F   I   V   A   L   L   K   G   V   Q   C
   1  ATGGATTTT GGGCTGATT TTTTTTATT GTTGCTCTT TTAAAAGGG GTCCAGTGT

E   V   K   L   L   E   S   G   G   G   L   V   Q   P   G   G   S   L
  55  GAGGTGAAA CTTCTCGAG TCTGGAGGT GGCCTGGTG CAGCCTGGA GGATCCCTG

K   L   S   C   A   A   S   G   F   D   F   S   R   Y   W   M   T   W
 109  AAACTCTCC TGTGCAGCC TCAGGATTC GATTTTAGT AGATACTGG ATGACTTGG

V   R   Q   A   P   G   K   G   L   E   W   I   G   E   I   N   P   D
 163  GTCCGGCAG GCTCCAGGG AAAGGGCTA GAATGGATT GGAGAAATT AATCCAGAT

S   S   T   I   N   Y   T   P   S   L   K   D   K   F   I   I   S   R
 217  AGCAGTACG ATAAACTAT ACGCCATCT CTAAAGGAT AAATTCATC ATCTCCAGA

D   N   A   K   N   T   L   Y   L   Q   M   S   E   V   R   S   E   D
 271  GACAACGCC AAGAATACG CTGTACCTG CAAATGAGC GAAGTGAGA TCTGAGGAC

T   A   L   Y   Y   C   A   S   G   V   F   T   S   W   G   Q   G   T
 325  ACAGCCCTT TATTACTGT GCAAGCGGG GTGTTTACT TCCTGGGGC CAAGGGACT

L   V   T   V   S   A   A   S   T   K   G   P   S   V   F   P   L   A
 379  CTGGTCACT GTCTCTGCA GCTAGCACC AAGGGCCCA TCCGTCTTC CCCCTGGCG

P   C   S   R   S   T   S   E   S   T   A   A   L   G   C   L   V   K
 433  CCCTGCTCC AGGAGCACC TCCGAGAGC ACAGCCGCC CTGGGCTGC CTGGTCAAG

D   Y   F   P   E   P   V   T   V   S   W   N   S   G   A   L   T   S
 487  GACTACTTC CCCGAACCG GTGACGGTG TCGTGGAAC TCAGGCGCC CTGACCAGC

G   V   H   T   F   P   A   V   L   Q   S   S   G   L   Y   S   L   S
 541  GGCGTGCAC ACCTTCCCG GCTGTCCTA CAGTCCTCA GGACTCTAC TCCCTCAGC

S   V   V   T   V   P   S   S   S   L   G   T   K   T   Y   T   C   N
 595  AGCGTGGTG ACCGTGCCC TCCAGCAGC TTGGGCACG AAGACCTAC ACCTGCAAC

V   D   H   K   P   S   N   T   K   V   D   K   R   V   E   S   K   Y
 649  GTAGATCAC AAGCCCAGC AACACCAAG GTGGACAAG AGAGTTGAG TCCAAATAT

G   P   P   C   P   P   C   P   A   P   E   F   L   G   G   P   S   V
 703  GGTCCCCCA TGCCCACCA TGCCCAGCA CCTGAGTTC CTGGGGGGA CCATCAGTC

F   L   F   P   P   K   P   K   D   T   L   M   I   S   R   T   P   E
 757  TTCCTGTTC CCCCCAAAA CCCAAGGAC ACTCTCATG ATCTCCCGG ACCCCTGAG

V   T   C   V   V   V   D   V   S   Q   E   D   P   E   V   Q   F   N
 811  GTCACGTGC GTGGTGGTG GACGTGAGC CAGGAAGAC CCCGAGGTC CAGTTCAAC

W   Y   V   D   G   V   E   V   H   N   A   K   T   K   P   R   E   E
 865  TGGTACGTG GATGGCGTG GAGGTGCAT AATGCCAAG ACAAAGCCG CGGGAGGAG

Q   F   N   S   T   Y   R   V   V   S   V   L   T   V   L   H   Q   D
 919  CAGTTCAAC AGCACGTAC CGTGTGGTC AGCGTCCTC ACCGTCCTG CACCAGGAC

W   L   N   G   K   E   Y   K   C   K   V   S   N   K   G   L   P   S
 973  TGGCTGAAC GGCAAGGAG TACAAGTGC AAGGTCTCC AACAAAGGC CTCCCGTCC

S   I   E   K   T   I   S   K   A   K   G   Q   P   R   E   P   Q   V
1027  TCCATCGAG AAAACCATC TCCAAAGCC AAAGGGCAG CCCCGAGAG CCACAGGTG

Y   T   L   P   P   S   Q   E   E   M   T   K   N   Q   V   S   L   T
1081  TACACCCTG CCCCCATCC CAGGAGGAG ATGACCAAG AACCAGGTC AGCCTGACC
```

Fig. 5 (cont.)

```
         C   L   V   K   G   F   Y   P   S   D   I   A   V   E   W   E   S   N
1135  TGCCTGGTC AAAGGCTTC TACCCCAGC GACATCGCC GTGGAGTGG GAGAGCAAT

G   Q   P   E   N   N   Y   K   T   T   P   P   V   L   D   S   D   G
1189  GGGCAGCCG GAGAACAAC TACAAGACC ACGCCTCCC GTGCTGGAC TCCGACGGC

S   F   F   L   Y   S   R   L   T   V   D   K   S   R   W   Q   E   G
1243  TCCTTCTTC CTCTACAGC AGGCTAACC GTGGACAAG AGCAGGTGG CAGGAGGGG

N   V   F   S   C   S   V   M   H   E   A   L   H   N   H   Y   T   Q
1297  AATGTCTTC TCATGCTCC GTGATGCAT GAGGCTCTG CACAACCAC TACACACAG

K   S   L   S   L   S   L   G   K
1351  AAGAGCCTC TCCCTGTCT CTGGGTAAA
```

Fig. 6

```
        M   D   F    G   L   I    F   F   I    V   A   L    L   K   G    V   Q   C
   1  ATGGATTTT GGGCTGATT TTTTTTATT GTTGCTCTT TTAAAAGGG GTCCAGTGT

E   V   K    L   L   E    S   G   G    G   L   V    Q   P   G    G   S   L
  55  GAGGTGAAA CTTCTCGAG TCTGGAGGT GGCCTGGTG CAGCCTGGA GGATCCCTG

K   L   S    C   A   A    S   G   F    D   F   S    R   Y   W    M   T   W
 109  AAACTCTCC TGTGCAGCC TCAGGATTC GATTTTAGT AGATACTGG ATGACTTGG

V   R   Q    A   P   G    K   G   L    E   W   I    G   E   I    N   P   D
 163  GTCCGGCAG GCTCCAGGG AAAGGGCTA GAATGGATT GGAGAAATT AATCCAGAT

S   S   T    I   N   Y    T   P   S    L   K   D    K   F   I    I   S   R
 217  AGCAGTACG ATAAACTAT ACGCCATCT CTAAAGGAT AAATTCATC ATCTCCAGA

D   N   A    K   N   T    L   Y   L    Q   M   S    E   V   R    S   E   D
 271  GACAACGCC AAGAATACG CTGTACCTG CAAATGAGC GAAGTGAGA TCTGAGGAC

T   A   L    Y   Y   C    A   S   G    V   F   T    S   W   G    Q   G   T
 325  ACAGCCCTT TATTACTGT GCAAGCGGG GTGTTTACT TCCTGGGGC CAAGGGACT

L   V   T    V   S   A    A   S   T    K   G   P    S   V   F    P   L   A
 379  CTGGTCACT GTCTCTGCA GCTAGCACC AAGGGCCCA TCCGTCTTC CCCCTGGCG

P   C   S    R   S   T    S   E   S    T   A   A    L   G   C    L   V   K
 433  CCCTGCTCC AGGAGCACC TCCGAGAGC ACAGCCGCC CTGGGCTGC CTGGTCAAG

D   Y   F    P   E   P    V   T   V    S   W   N    S   G   A    L   T   S
 487  GACTACTTC CCCGAACCG GTGACGGTG TCGTGGAAC TCAGGCGCC CTGACCAGC

G   V   H    T   F   P    A   V   L    Q   S   S    G   L   Y    S   L   S
 541  GGCGTGCAC ACCTTCCCG GCTGTCCTA CAGTCCTCA GGACTCTAC TCCCTCAGC

S   V   V    T   V   P    S   S   S    L   G   T    K   T   Y    T   C   N
 595  AGCGTGGTG ACCGTGCCC TCCAGCAGC TTGGGCACG AAGACCTAC ACCTGCAAC

BamHI
        V   D   H    K   P   S    N   T   K    V   D   K    R   V   E    S   K   G
 649  GTAGATCAC AAGCCCAGC AACACCAAG GTGGACAAG AGAGTTGAG TCCAAAGGA

S   G   G    G   G   S    G   G   G    G   S   G    G   G   G    S   S   G
 703  TCCGGAGGT GGCGGGTCT GGTGGCGGG GGATCAGGC GGGGGAGGT TCCTCAGGC

T   T   N    T   V   A    A   Y   N    L   T   W    K   S   T    N   F   K
 757  ACTACAAAT ACTGTGGCA GCATATAAT TTAACTTGG AAATCAACT AATTTCAAG

T   I   L    E   W   E    P   K   P    V   N   Q    V   Y   T    V   Q   I
 811  ACAATTTTG GAGTGGGAA CCCAAACCC GTCAATCAA GTCTACACT GTTCAAATA

S   T   K    S   G   D    W   K   S    K   C   F    Y   T   T    D   T   E
 865  AGCACTAAG TCAGGAGAT TGGAAAAGC AAATGCTTT TACACAACA GACACAGAG

C   D   L    T   D   E    I   V   K    D   V   K    Q   T   Y    L   A   R
 919  TGTGACCTC ACCGACGAG ATTGTGAAG GATGTGAAG CAGACGTAC TTGGCACGG

V   F   S    Y   P   A    G   N   V    E   S   T    G   S   A    G   E   P
 973  GTCTTCTCC TACCCGGCA GGGAATGTG GAGAGCACC GGTTCTGCT GGGGAGCCT

L   Y   E    N   S   P    E   F   T    P   Y   L    E   T   N    L   G   Q
1027  CTGTATGAG AACTCCCCA GAGTTCACA CCTTACCTG GAGACAAAC CTCGGACAG

P   T   I    Q   S   F    E   Q   V    G   T   K    V   N   V    T   V   E
1081  CCAACAATT CAGAGTTTT GAACAGGTG GGAACAAAA GTGAATGTG ACCGTAGAA
```

Fig. 6 (cont.)

```
          D   E   R   T   L   V   R   R   N   N   T   F   L   S   L   R   D   V
1135  GATGAACGG ACTTTAGTC AGAAGGAAC AACACTTTC CTAAGCCTC CGGGATGTT

F   G   K   D   L   I   Y   T   L   Y   Y   W   K   S   S   S   S   G
1189  TTTGGCAAG GACTTAATT TATACACTT TATTATTGG AAATCTTCA AGTTCAGGA

K   K   T   A   K   T   N   T   N   E   F   L   I   D   V   D   K   G
1243  AAGAAAACA GCCAAAACA AACACTAAT GAGTTTTTG ATTGATGTG GATAAAGGA

E   N   Y   C   F   S   V   Q   A   V   I   P   S   R   T   V   N   R
1297  GAAAACTAC TGTTTCAGT GTTCAAGCA GTGATTCCC TCCCGAACA GTTAACCGG

K   S   T   D   S   P   V   E   C   M   G   Q   E   K   G   E   F   R
1351  AAGAGTACA GACAGCCCG GTAGAGTGT ATGGGCCAG GAGAAAGGG GAATTTAGA

E
1405  GAA
```

Fig. 8
8A
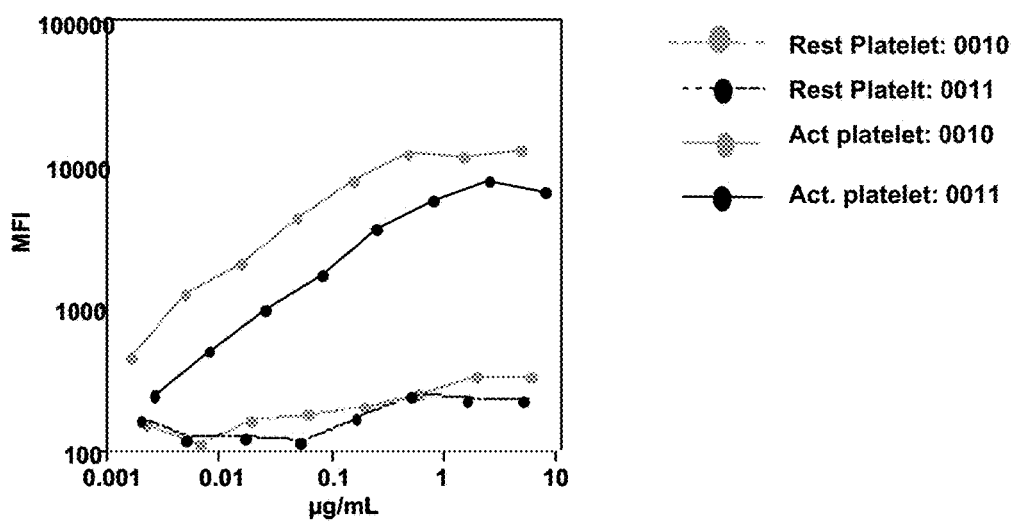
8B
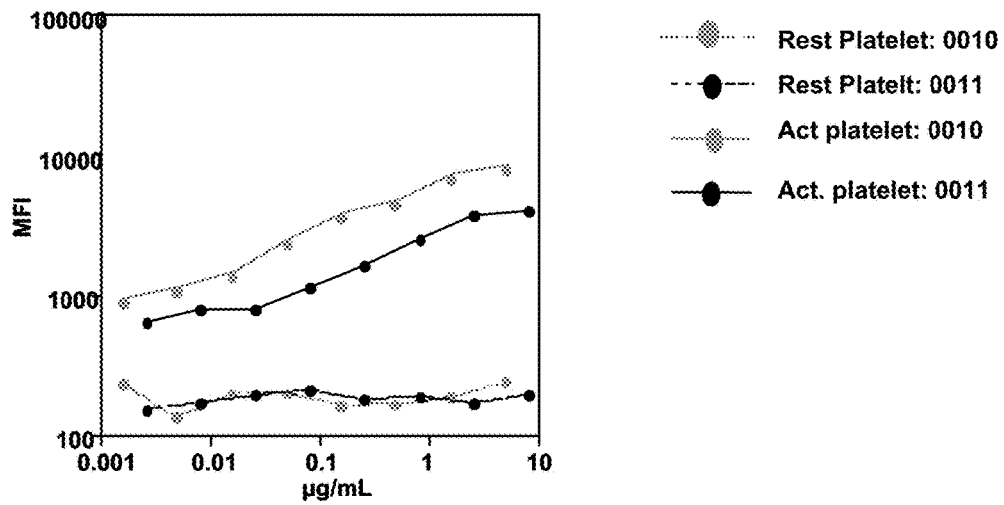

Fig. 10
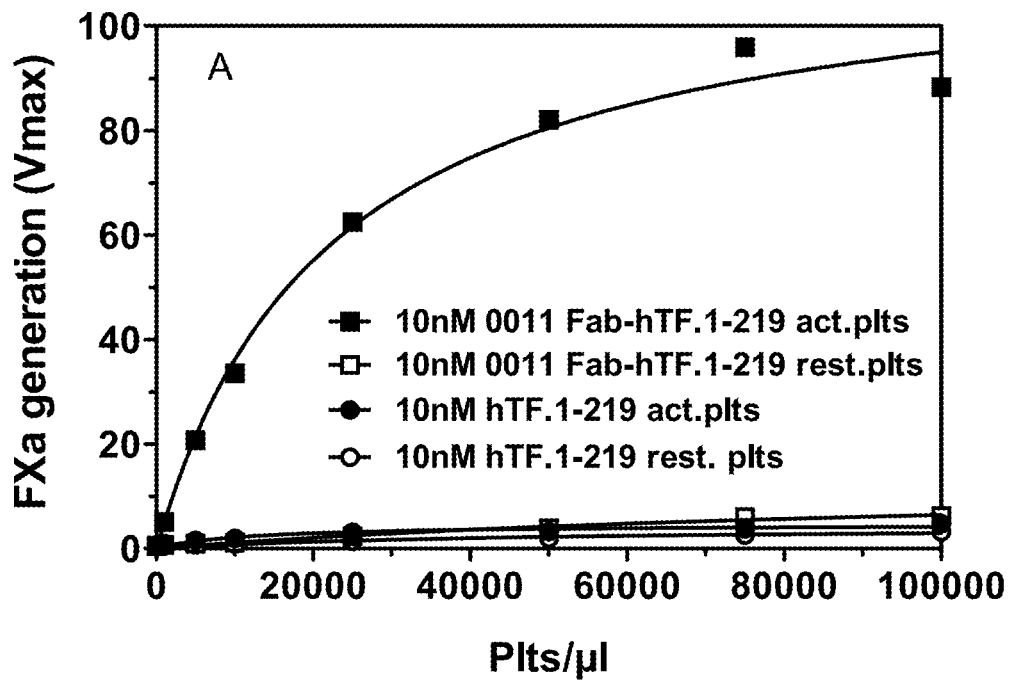
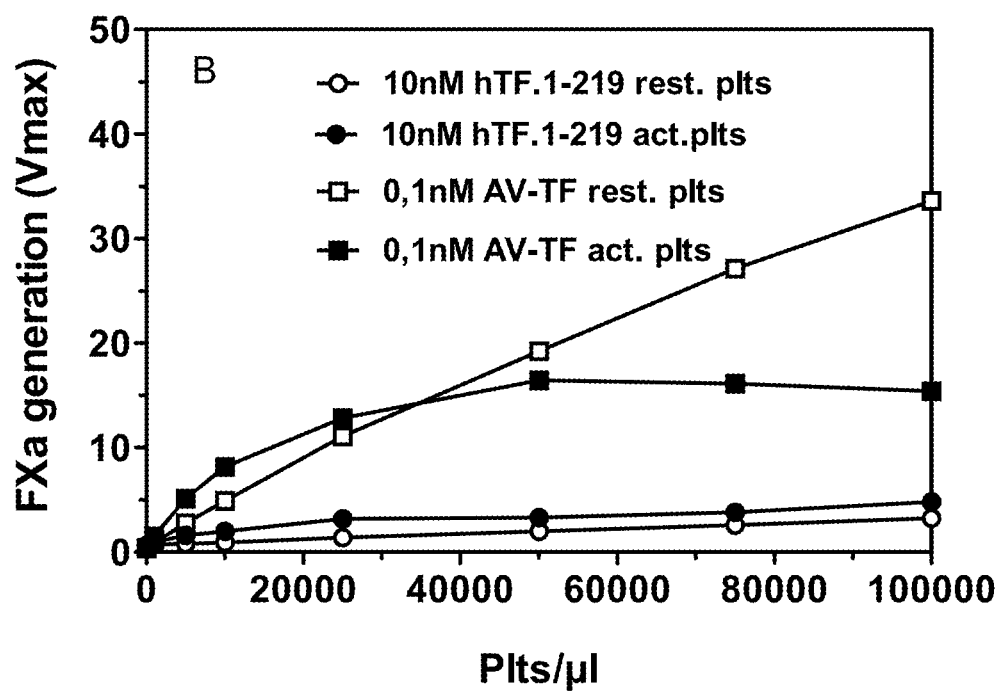

Fig. 11
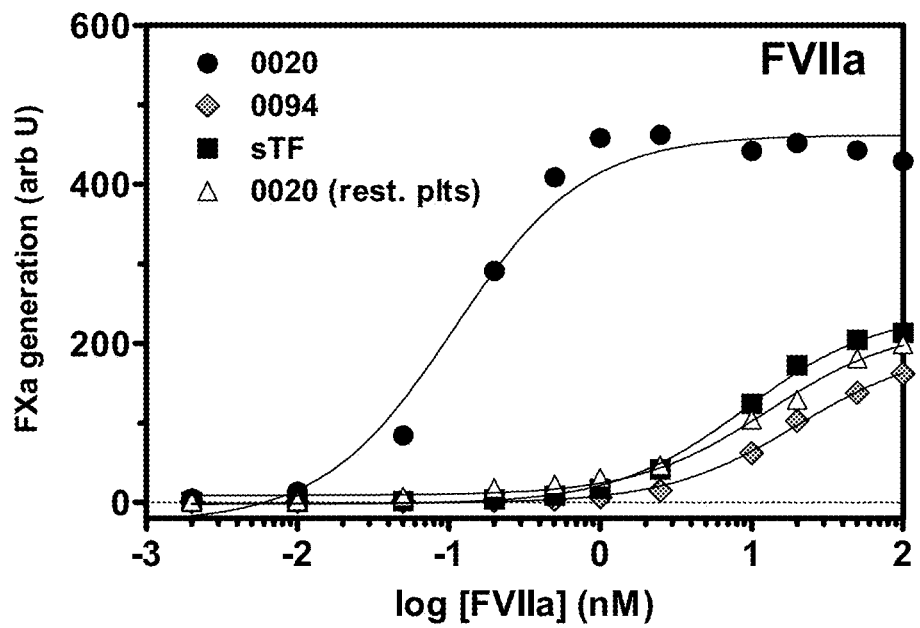
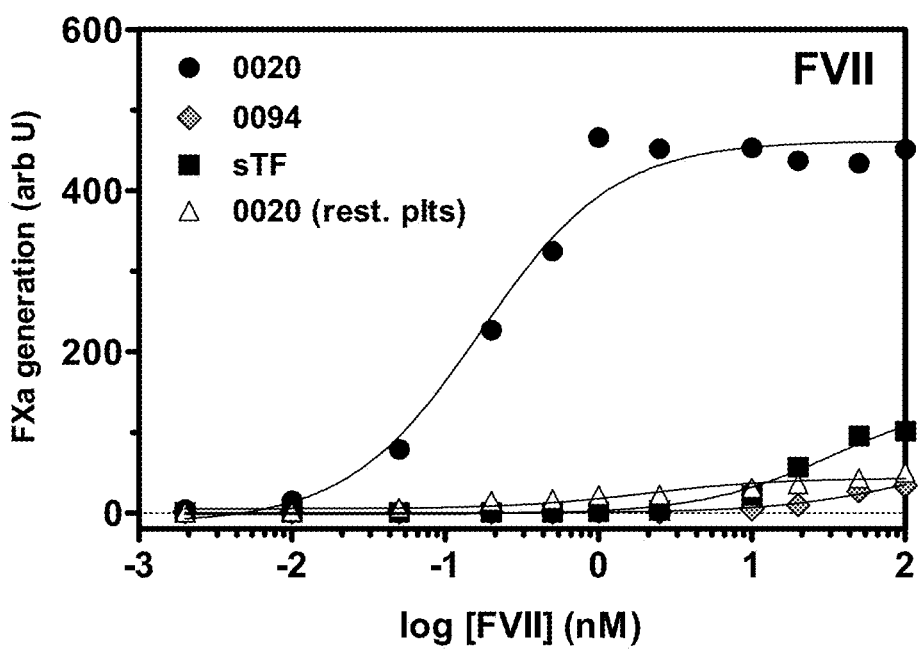

Fig. 12
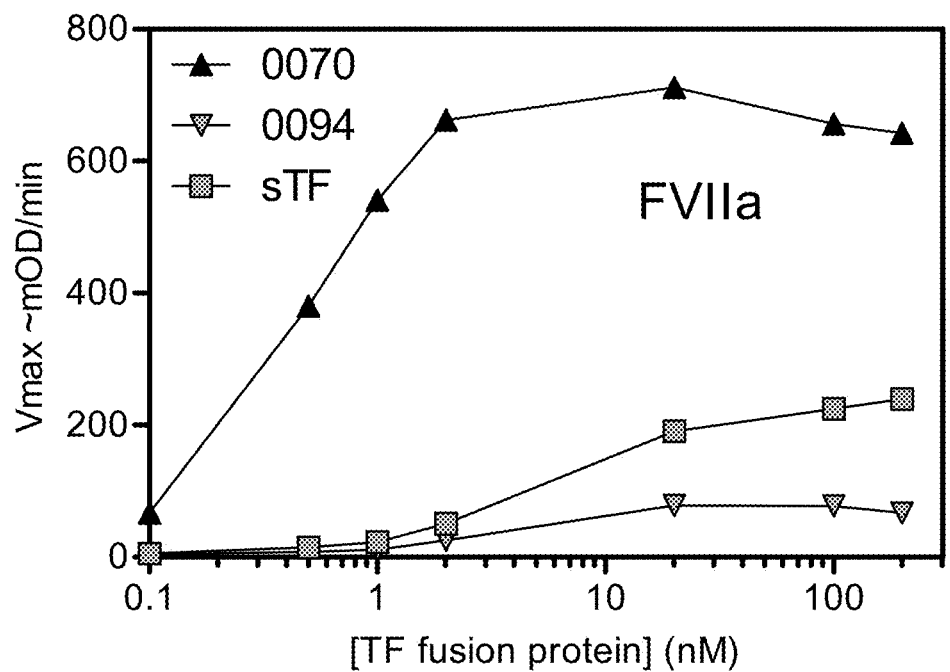
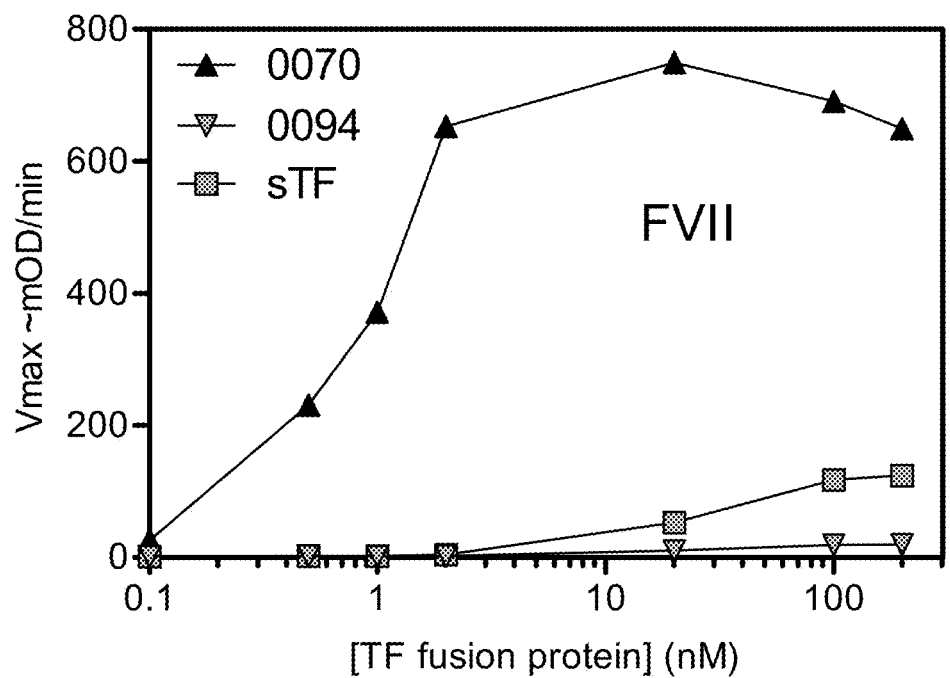

Fig. 13
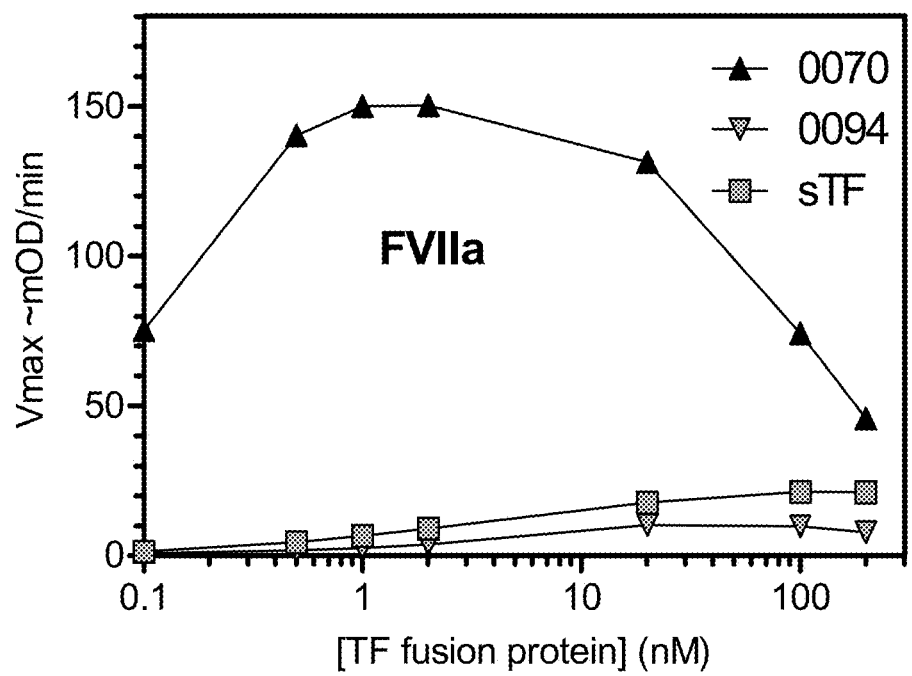
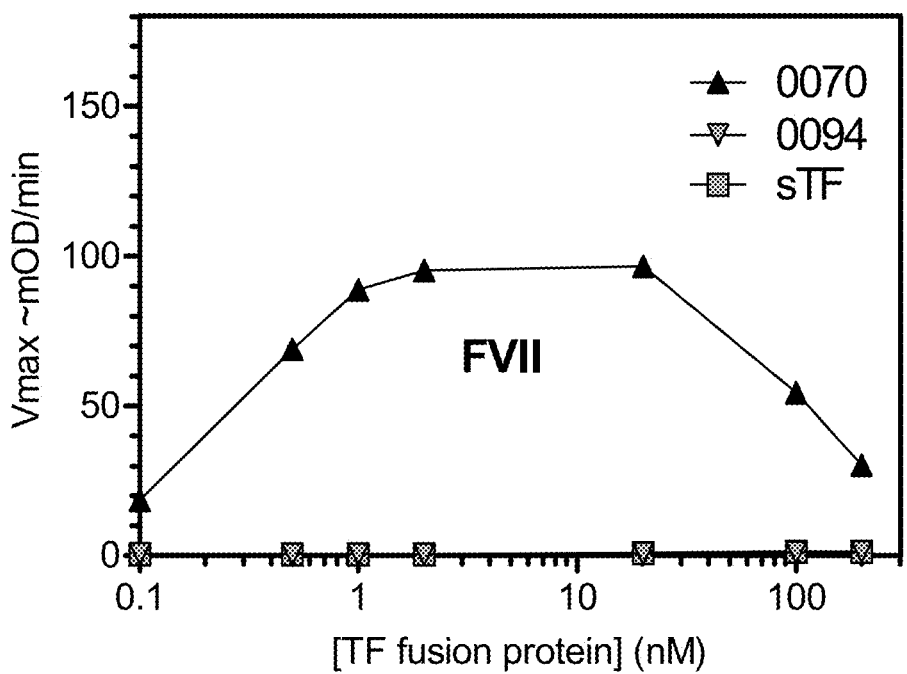

Fig.14
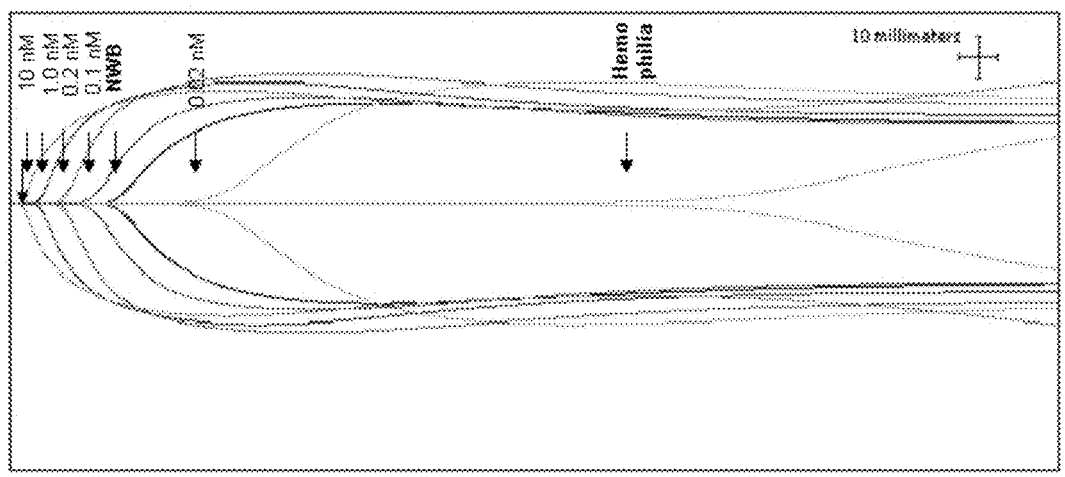
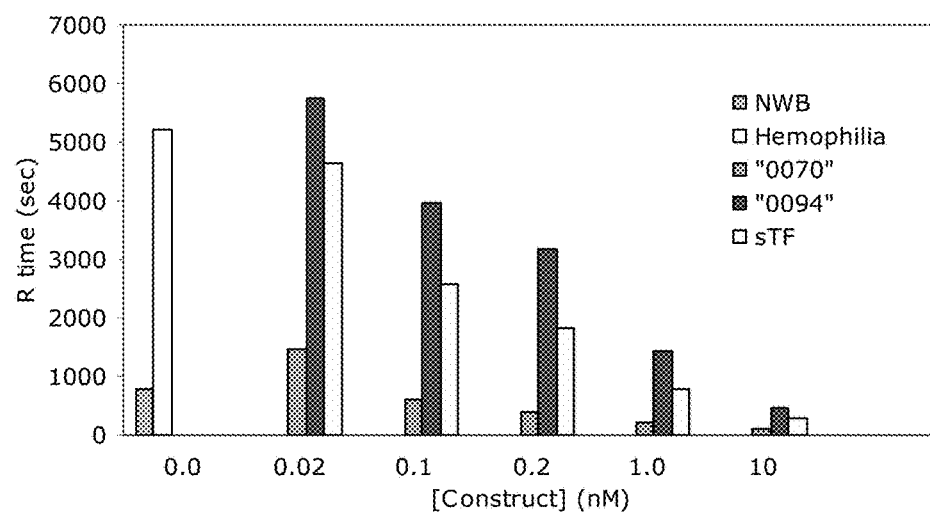

White: No difference
Black: 0023 Epitope

White: no difference
Black: 0051 epitope

White: no difference
Black: 0062 epitope

White: no difference
Black: 0061 epitope

White: no difference
Black: 0061 epitope

Fig. 27A

| mAb ID | mAb-TF fusion protein name | FVIIa-mediated FXa generation % Activity activated plts | n | FVII-mediated FXa generation % Activity activated plts | n | FVIIa-mediated FXa generation % Activity lipidated TLT-1 | FVII-mediated FXa generation % Activity lipidated TLT-1 |
|---|---|---|---|---|---|---|---|
| 0116 | mAb 0012-(HC-L0-TF)$_2$;LC$_2$ | | | | | | |
| 0086 | mAb 0012-(HC-L1-TF)$_2$;LC$_2$ | 19 | 1 | 23 | 1 | 91 | 62 |
| 0087 | mAb 0012-(HC-L2-TF)$_2$;LC$_2$ | 21 | 1 | 24 | 1 | 92 | 68 |
| 0088 | mAb 0012-(HC-L3-TF)$_2$;LC$_2$ | 23 | 1 | 23 | 1 | 100 | 70 |
| 0018 | mAb 0012-(HC-L4a-TF)$_2$;(LC-HPC4)$_2$ | | | | | 91 | 68 |
| 0013 | mAb 0012-(TF-L4b-HC)$_2$;LC$_2$ | 11 ± 6 | 2 | | | 42 | 20 |
| 0089 | mAb 0012-(HC-L5-TF)$_2$;LC$_2$ | 22 | 1 | 24 | 1 | 98 | 73 |
| 0090 | mAb 0012-(HC-L6-TF)$_2$;LC$_2$ | 22 | 1 | 29 | 1 | 99 | 72 |
| 0091 | mAb 0012-(HC-L7-TF)$_2$;LC$_2$ | 23 | 1 | 25 | 1 | 93 | 68 |
| 0093 | mAb 0012-(HC-L9-TF)$_2$;LC$_2$ | 23 | 1 | 23 | 1 | 88 | 64 |
| 0107 | mAb 0012-(LC-L0-TF)$_2$;HC$_2$ | 15 | 1 | 6 | 1 | 52 | 20 |
| 0108 | mAb 0012-(LC-L1-TF)$_2$;HC$_2$ | 18 | 1 | 13 | 1 | 66 | 32 |
| 0109 | mAb 0012-(LC-L2-TF)$_2$;HC$_2$ | 23 | 1 | 22 | 1 | 80 | 45 |
| 0045 | mAb 0012-(LC-L3-TF)$_2$;HC$_2$ | 23 ± 11 | 2 | 40 ± 1 | 2 | 86 | 59 |
| 0019 | mAb 0012-(LC-L4a-TF)$_2$;HC$_2$ | 18 ± 6 | 7 | 14 ± 9 | 4 | 85 | 59 |
| 0025 | mAb 0012-(TF-L4b-LC)$_2$;HC$_2$ | 6 ± 3 | 3 | 3 | 1 | | |
| 0046 | mAb 0012-(LC-L5-TF)$_2$;HC$_2$ | 24 ± 11 | 2 | 46 ± 4 | 2 | 87 | 68 |
| 0047 | mAb 0012-(LC-L6-TF)$_2$;HC$_2$ | 26 ± 8 | 2 | 47 ± 6 | 2 | 90 | 67 |
| 0048 | mAb 0012-(LC-L7-TF)$_2$;HC$_2$ | 24 ± 8 | 2 | 47 ± 5 | 2 | 86 | 68 |
| 0049 | mAb 0012-(LC-L8-TF)$_2$;HC$_2$ | 25 ± 9 | 2 | 45 ± 4 | 2 | 88 | 70 |
| 0050 | mAb 0012-(LC-L9-TF)$_2$;HC$_2$ | 24 ± 6 | 2 | 44 ± 3 | 2 | 84 | 64 |
| 0034 | mAb 0023-(HC-L4a-TF)$_2$;(LC-HPC4)$_2$ | 14 | 1 | 4 | 1 | | |
| 0035 | mAb 0023-(LC-L4a-TF)$_2$;HC$_2$ | 13 ± 3 | 3 | 5 | 1 | | |
| 0056 | mAb 0051-(HC-L4a-TF)$_2$;(LC-HPC4)$_2$ | 15 | 1 | 18 | 1 | | |
| 0055 | mAb 0051-(LC-L4a-TF)$_2$;HC$_2$ | 15 ± 1 | 2 | 12 ± 5 | 2 | | |
| 0060 | mAb 0052-(HC-L4a-TF)$_2$;(LC-HPC4)$_2$ | 10 | 1 | 7 | 1 | | |
| 0059 | mAb 0052-(LC-L4a-TF)$_2$;HC$_2$ | 7 | 1 | 2 ± 1 | 2 | | |
| 0096 | mAb isotype control-(HC-L4a-TF)$_2$;(LC-HPC4)$_2$ | | | | | | |
| 0110 | mAb isotype control-(LC-L4a-TF)$_2$;HC$_2$ | 3 | 1 | 2 | 1 | 27 | 11 |

Fig. 27B

| Fab ID | Fab-TF fusion protein name | FVIIa-mediated FXa generation % Activity activated plts | | FVII-mediated FXa generation % Activity activated plts | | FVIIa-mediated FXa generation % Activity lipidated TLT-1 | FVII-mediated FXa generation % Activity lipidated TLT-1 |
|---|---|---|---|---|---|---|---|
| 0073 | Fab 0012-$V_H$-CH1-L0-TF;LC-HPC4 | 80 ± 33 | 4 | 71 ± 44 | 4 | 106 | 98 |
| 0011 | Fab 0012-$V_H$-CH1-L4a-TF;LC-HPC4 | 84 ± 5 | 6 | 53 ± 18 | 7 | 72 | 60 |
| 0014 | Fab 0012-TF-L4b-$V_H$-CH1;LC-HPC4 | 5 ± 8 | 2 | 5 | 1 | 0 | 0 |
| 0057 | Fab 0012-$V_H$-CH1-L10-TF;LC-HPC4 | 81 ± 19 | 2 | 78 ± 21 | 2 | 93 | 87 |
| 0105 | Fab 0061-$V_H$-CH1-L10-TF;LC-HPC4 | 62 | 1 | 39 | 1 | 101 | 101 |
| 0106 | Fab 0082-$V_H$-CH1-L10-TF;LC-HPC4 | 57 | 1 | 40 | 1 | 103 | 103 |
| 0070 | Fab 0012-LC-L0-TF;$V_H$-CH1-HPC4 | 132 | 1 | 103 ± 21 | 4 | 98 | 90 |
| 0071 | Fab 0012-LC-L1-TF;$V_H$-CH1-HPC4 | 125 | 1 | 111 ± 21 | 4 | 101 | 97 |
| 0072 | Fab 0012-LC-L2-TF;$V_H$-CH1-HPC4 | 112 | 1 | 96 ± 21 | 4 | 106 | 96 |
| 0039 | Fab 0012-LC-L3-TF;$V_H$-CH1-HPC4 | 97 | 1 | 98 | 1 | 105 | 98 |
| 0030 | Fab 0012-LC-L4a-TF;$V_H$-CH1-HPC4 | 100 | 11 | 80 ± 35 | 11 | 100 | 97 |
| 0024 | Fab 0012-TF-L4b-LC;$V_H$-CH1-HPC4 | 9 ± 1 | 3 | 8 | 1 | 55 | 50 |
| 0041 | Fab 0012-LC-L6-TF;$V_H$-CH1-HPC4 | 91 | 1 | 95 | 1 | 101 | 94 |
| 0042 | Fab 0012-LC-L7-TF;$V_H$-CH1-HPC4 | 95 | 1 | 92 | 1 | 98 | 95 |
| 0043 | Fab 0012-LC-L8-TF;$V_H$-CH1-HPC4 | 81 | 1 | 86 | 1 | 98 | 94 |
| 0044 | Fab 0012-LC-L9-TF;$V_H$-CH1-HPC4 | 76 | 1 | 80 | 1 | 95 | 88 |
| 0063 | Fab 0023-LC-L3-TF;$V_H$-CH1-HPC4 | 43 | 1 | 20 | 1 | 42 | 26 |
| 0038 | Fab 0023-LC-L4a-TF;$V_H$-CH1-HPC4 | 21 | 1 | 21 | 1 | 40 | 24 |
| 0065 | Fab 0023-LC-L6-TF;$V_H$-CH1-HPC4 | 45 | 1 | 20 | 1 | 44 | 27 |
| 0066 | Fab 0023-LC-L7-TF;$V_H$-CH1-HPC4 | 35 | 1 | 17 | 1 | 40 | 25 |
| 0067 | Fab 0023-LC-L8-TF;$V_H$-CH1-HPC4 | 33 | 1 | 16 | 1 | 35 | 24 |
| 0068 | Fab 0023-LC-L9-TF;$V_H$-CH1-HPC4 | 32 | 1 | 14 | 1 | 38 | 24 |
| 0033 | Fab 0023-$V_H$-CH1-L4a-TF;LC-HPC4 | 45 | 1 | 14 | 1 | 53 | 26 |
| 0053 | Fab 0051-LC-L4a-TF;$V_H$-CH1-HPC4 | 69 ± 15 | 2 | 35 ± 17 | 2 | 43 | 22 |
| 0054 | Fab 0051-$V_H$-CH1-L4a-TF;LC-HPC4 | 72 | 1 | 43 | 1 | 48 | 22 |
| 0069 | Fab 0052-LC-L4a-TF;$V_H$-CH1-HPC4 | 20 | 1 | | | 29 | 9 |
| 0058 | Fab 0052-$V_H$-CH1-L4a-TF | 25 | 1 | 10 | 1 | 29 | 13 |
| 0120 | heterodimer#3 LC/HC-his/Fc-sTF | 28 | 1 | 38 | 1 | 54 | 36 |
| 0121 | heterodimer#5 LC-sTF/HC/Fc-his | 30 | 1 | 31 | 1 | 74 | 48 |
| 0094 | Fab isotype control-LC-L4a-TF;$V_H$-CH1-HPC4 | 3 | 1 | 2 | 1 | 7 | 0 |
| 0095 | Fab isotype control-$V_H$-CH1-L4a-TF;LC-HPC4 | 2 | 1 | 2 | 1 | 3 | 0 |
| 0128 | AP3Fab-LC-17GS-TF-HC-HPC4 | 164 | 1 | 218 | 1 | 69 | 43 |
| 0129 | AP3Fab-HC-17GS-TF-HC-HPC4 | 143 | 1 | 215 | 1 | 23 | 12 |
| 0030 (resting plts) | Fab 0012-LC-L4a-TF;$V_H$-CH1-HPC4 | 9 ± 8 | 12 | 7 ± 4 | 10 | | |
| sTF(1-219) | | 4 | 1 | 2 | 1 | 13 | 1 |
| Buffer | | 0 | 1 | 0 | 1 | 0 | 0 |

US 10,106,606 B2

SEQUENCE LISTING

<160> NUMBER OF SEQ ID NOS: 184

<210> SEQ ID NO 1
<211> LENGTH: 933
<212> TYPE: DNA
<213> ORGANISM: Homo sapiens

<400> SEQUENCE: 1

```
atgggcctca ccctgctctt gctgctgctc ctgggactag aaggtcaggg catagttggc      60
agcctccctg aggtgctgca ggcacccgtg ggaagctcca ttctggtgca gtgccactac     120
aggctccagg atgtcaaagc tcagaaggtg tggtgccggt tcttgccgga ggggtgccag     180
cccctggtgt cctcagctgt ggatcgcaga gctccagcgg gcaggcgtac gtttctcaca     240
gacctgggtg ggggcctgct gcaggtggaa atggttaccc tgcaggaaga ggatgctggc     300
gagtatggct gcatggtgga tgggccaggg ggccccaga ttttgcacag agtctctctg      360
aacatactgc ccccagagga agaagaagag acccataaga ttggcagtct ggctgagaac     420
gcattctcag accctgcagg cagtgccaac cctttggaac ccagccagga tgagaagagc     480
atcccttga tctggggtgc tgtgctcctg gtaggtctgc tggtggcagc ggtggtgctg      540
tttgctgtga tggccaagag gaaacaaggg aacaggcttg gtgtctgtgg ccgattcctg     600
agcagcagag tttcaggcat gaatccctcc tcagtggtcc accacgtcag tgactctgga     660
ccggctgctg aattgccttt ggatgtacca cacattaggc ttgactcacc accttcattt     720
gacaatacca cctacaccag cctacctctt gattccccat caggaaaacc ttcactccca     780
gctccatcct cattgccccc tctacctcct aaggtcctgg tctgctccaa gcctgtgaca     840
tatgccacag taatcttccc gggagggaac aagggtggag ggacctcgtg tgggccagcc     900
cagaatccac ctaacaatca gactccatcc agc                                  933
```

```
<210> SEQ ID NO 2
<211> LENGTH: 311
<212> TYPE: PRT
<213> ORGANISM: Homo sapiens

<400> SEQUENCE: 2

Met Gly Leu Thr Leu Leu Leu Leu Leu Gly Leu Glu Gly Gln
1               5                   10                  15

Gly Ile Val Gly Ser Leu Pro Glu Val Leu Gln Ala Pro Val Gly Ser
            20                  25                  30

Ser Ile Leu Val Gln Cys His Tyr Arg Leu Gln Asp Val Lys Ala Gln
        35                  40                  45

Lys Val Trp Cys Arg Phe Leu Pro Glu Gly Cys Gln Pro Leu Val Ser
50                  55                  60

Ser Ala Val Asp Arg Arg Ala Pro Ala Gly Arg Arg Thr Phe Leu Thr
65                  70                  75                  80

Asp Leu Gly Gly Gly Leu Leu Gln Val Glu Met Val Thr Leu Gln Glu
                    85                  90                  95

Glu Asp Ala Gly Glu Tyr Gly Cys Met Val Asp Gly Ala Arg Gly Pro
                100                 105                 110

Gln Ile Leu His Arg Val Ser Leu Asn Ile Leu Pro Pro Glu Glu Glu
            115                 120                 125

Glu Glu Thr His Lys Ile Gly Ser Leu Ala Glu Asn Ala Phe Ser Asp
130                 135                 140

Pro Ala Gly Ser Ala Asn Pro Leu Glu Pro Ser Gln Asp Glu Lys Ser
145                 150                 155                 160

Ile Pro Leu Ile Trp Gly Ala Val Leu Leu Val Gly Leu Leu Val Ala
                165                 170                 175

Ala Val Val Leu Phe Ala Val Met Ala Lys Arg Lys Gln Gly Asn Arg
                180                 185                 190

Leu Gly Val Cys Gly Arg Phe Leu Ser Ser Arg Val Ser Gly Met Asn
            195                 200                 205

Pro Ser Ser Val Val His His Val Ser Asp Ser Gly Pro Ala Ala Glu
210                 215                 220

Leu Pro Leu Asp Val Pro His Ile Arg Leu Asp Ser Pro Pro Ser Phe
225                 230                 235                 240

Asp Asn Thr Thr Tyr Thr Ser Leu Pro Leu Asp Ser Pro Ser Gly Lys
                245                 250                 255

Pro Ser Leu Pro Ala Pro Ser Ser Leu Pro Pro Leu Pro Pro Lys Val
            260                 265                 270

Leu Val Cys Ser Lys Pro Val Thr Tyr Ala Thr Val Ile Phe Pro Gly
        275                 280                 285

Gly Asn Lys Gly Gly Thr Ser Cys Gly Pro Ala Gln Asn Pro Pro
290                 295                 300

Asn Asn Gln Thr Pro Ser Ser
305                 310

<210> SEQ ID NO 3
<211> LENGTH: 528
<212> TYPE: DNA
<213> ORGANISM: Artificial sequence
<220> FEATURE:
<223> OTHER INFORMATION: /note = "extracellular domain of hTLT-1-His6"

<400> SEQUENCE: 3
aagcttgccg ccaccatggg cctcaccctg ctcttgctgc tgctcctggg actagaaggt    60
```

```
caggqcatag ttggcagcct ccctgaggtg ctgcaggcac ccgtgggaag ctccattctg      120
gtgcagtgcc actacaggct ccaggatgtc aaagctcaga aggtgtggtg ccggttcttg      180
ccggaggggt gccagcccct ggtgtcctca gctgtggatc gcagagctcc ggcgggcagg      240
cgtacgtttc tcacagacct gggtgggggc ctgctgcagg tggaaatggt taccctgcag      300
gaagaggatg ctggcgagta tggctgcatg gtggatgggg ccaggggggcc ccagattttg      360 cacagagtct ctctgaacat actgccccca gaggaagaag aagagaccca taagattggc      420
agtctggctg agaacgcatt ctcagaccct gcaggcagtg ccaacccttt ggaacccagc      480
caggatgaga agagcatccc ccaccatcac catcaccatt aagaattc                   528
```

<210> SEQ ID NO 4
<211> LENGTH: 168
<212> TYPE: PRT
<213> ORGANISM: Artificial sequence
<220> FEATURE:
<223> OTHER INFORMATION: /note = "extracellular domain of hTLT-1-His6"

<400> SEQUENCE: 4

```
Met Gly Leu Thr Leu Leu Leu Leu Leu Leu Gly Leu Glu Gly Gln
1               5                   10                  15

Gly Ile Val Gly Ser Leu Pro Glu Val Leu Gln Ala Pro Val Gly Ser
                20                  25                  30

Ser Ile Leu Val Gln Cys His Tyr Arg Leu Gln Asp Val Lys Ala Gln
            35                  40                  45

Lys Val Trp Cys Arg Phe Leu Pro Glu Gly Cys Gln Pro Leu Val Ser
        50                  55                  60

Ser Ala Val Asp Arg Arg Ala Pro Ala Gly Arg Arg Thr Phe Leu Thr
65                  70                  75                  80

Asp Leu Gly Gly Gly Leu Leu Gln Val Glu Met Val Thr Leu Gln Glu
                85                  90                  95

Glu Asp Ala Gly Glu Tyr Gly Cys Met Val Asp Gly Ala Arg Gly Pro
            100                 105                 110

Gln Ile Leu His Arg Val Ser Leu Asn Ile Leu Pro Pro Glu Glu Glu
        115                 120                 125

Glu Glu Thr His Lys Ile Gly Ser Leu Ala Glu Asn Ala Phe Ser Asp
    130                 135                 140

Pro Ala Gly Ser Ala Asn Pro Leu Glu Pro Ser Gln Asp Glu Lys Ser
145                 150                 155                 160

Ile Pro His His His His His His
                165
```

<210> SEQ ID NO 5
<211> LENGTH: 106
<212> TYPE: PRT
<213> ORGANISM: Artificial sequence
<220> FEATURE:
<223> OTHER INFORMATION: /note = "hTLT-1.20-125"

<400> SEQUENCE: 5

```
Gly Ser Leu Pro Glu Val Leu Gln Ala Pro Val Gly Ser Ser Ile Leu
1               5                   10                  15

Val Gln Cys His Tyr Arg Leu Gln Asp Val Lys Ala Gln Lys Val Trp
                20                  25                  30

Cys Arg Phe Leu Pro Glu Gly Cys Gln Pro Leu Val Ser Ser Ala Val
            35                  40                  45

Asp Arg Arg Ala Pro Ala Gly Arg Arg Thr Phe Leu Thr Asp Leu Gly
```

```
                       50                  55                  60
Gly Gly Leu Leu Gln Val Glu Met Val Thr Leu Gln Glu Glu Asp Ala
 65                  70                  75                  80

Gly Glu Tyr Gly Cys Met Val Asp Gly Ala Arg Gly Pro Gln Ile Leu
                 85                  90                  95

His Arg Val Ser Leu Asn Ile Leu Pro Pro
                100                 105

<210> SEQ ID NO 6
<211> LENGTH: 147
<212> TYPE: PRT
<213> ORGANISM: Artificial sequence
<220> FEATURE:
<223> OTHER INFORMATION: /note = "hTLT-1.16-162"

<400> SEQUENCE: 6

Gln Gly Ile Val Gly Ser Leu Pro Glu Val Leu Gln Ala Pro Val Gly
  1               5                  10                  15

Ser Ser Ile Leu Val Gln Cys His Tyr Arg Leu Gln Asp Val Lys Ala
                 20                  25                  30

Gln Lys Val Trp Cys Arg Phe Leu Pro Glu Gly Cys Gln Pro Leu Val
             35                  40                  45

Ser Ser Ala Val Asp Arg Arg Ala Pro Ala Gly Arg Arg Thr Phe Leu
 50                  55                  60

Thr Asp Leu Gly Gly Leu Leu Gln Val Glu Met Val Thr Leu Gln
 65                  70                  75                  80

Glu Glu Asp Ala Gly Glu Tyr Gly Cys Met Val Asp Gly Ala Arg Gly
                 85                  90                  95

Pro Gln Ile Leu His Arg Val Ser Leu Asn Ile Leu Pro Pro Glu Glu
                100                 105                 110

Glu Glu Glu Thr His Lys Ile Gly Ser Leu Ala Glu Asn Ala Phe Ser
             115                 120                 125

Asp Pro Ala Gly Ser Ala Asn Pro Leu Glu Pro Ser Gln Asp Glu Lys
        130                 135                 140

Ser Ile Pro
145

<210> SEQ ID NO 7
<211> LENGTH: 37
<212> TYPE: PRT
<213> ORGANISM: Artificial sequence
<220> FEATURE:
<223> OTHER INFORMATION: /note = "hTLT-1.126-162"

<400> SEQUENCE: 7

Glu Glu Glu Glu Glu Thr His Lys Ile Gly Ser Leu Ala Glu Asn Ala
  1               5                  10                  15

Phe Ser Asp Pro Ala Gly Ser Ala Asn Pro Leu Glu Pro Ser Gln Asp
                 20                  25                  30

Glu Lys Ser Ile Pro
             35

<210> SEQ ID NO 8
<211> LENGTH: 14
<212> TYPE: PRT
<213> ORGANISM: Artificial sequence
<220> FEATURE:
<223> OTHER INFORMATION: /note = "hTLT-1.129-142"

<400> SEQUENCE: 8
```

Glu Glu Thr His Lys Ile Gly Ser Leu Ala Glu Asn Ala Phe
1               5                   10

<210> SEQ ID NO 9
<211> LENGTH: 396
<212> TYPE: DNA
<213> ORGANISM: Homo sapiens

<400> SEQUENCE: 9
atgaagttgc ctgttgggct gttggtgctg atgttctgga ttccagcttc cagcagtgat      60
gttgtgatga cccaaactcc actctccctg cctgtcagtc ttggagatca agcctccatc     120
tcttgcagat ctagtcagag ccttgtacac agaaatggaa acacctattt tcattggtgc     180
ctgcagaaac caggccagtc tccaaagctc ctgatctaca agtttccaa ccgattttct      240 ggggtcccag acaggttcag tggcagtgga tcagggacag atttcacact caagatcagc     300
agagtggagg ctgaggatct ggagttttat ttctgctctc aaagtacaca tgttccgtac     360
acgttcggag gggggaccaa gctggaaata aaacgt                               396

<210> SEQ ID NO 10
<211> LENGTH: 132
<212> TYPE: PRT
<213> ORGANISM: Homo sapiens

<400> SEQUENCE: 10

Met Lys Leu Pro Val Gly Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
        35                  40                  45

Val His Arg Asn Gly Asn Thr Tyr Phe His Trp Cys Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg
    130

<210> SEQ ID NO 11
<211> LENGTH: 396
<212> TYPE: DNA
<213> ORGANISM: Homo sapiens

<400> SEQUENCE: 11
atggattttg gctgattttt ttttattgtt gctcttttaa aaggggtcca gtgtgaggtg      60
aaacttctcg agtctggagg tggcctggtg cagcctggag atccctgaa actctcctgt      120 gcagcctcag gattcgattt tagtagatac tggatgactt gggtccggca ggctccaggg     180
aaagggctag aatggattgg agaaattaat ccagatagca gtacgataaa ctatgccca     240 tctctaaagg ataaattcat catctcccaga gacaacgcca gaatacgct gtacctgcaa     300

```
atgagcgaag tgagatctga ggacacagcc ctttattact gtgcaagcgg ggtgtttact    360
tcctggggcc aagggactct ggtcactgtc tctgca                              396
```

<210> SEQ ID NO 12
<211> LENGTH: 132
<212> TYPE: PRT
<213> ORGANISM: Homo sapiens

<400> SEQUENCE: 12

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala
    130
```

<210> SEQ ID NO 13
<211> LENGTH: 657
<212> TYPE: DNA
<213> ORGANISM: Artificial sequence
<220> FEATURE:
<223> OTHER INFORMATION: /note = "TF (1-219)"

<400> SEQUENCE: 13

```
tcaggcacta caaatactgt ggcagcatat aatttaactt ggaaatcaac taatttcaag    60
acaattttgg agtgggaacc caaacccgtc aatcaagtct acactgttca ataagcact    120 aagtcaggag attggaaaag caatgctttt acacaacag acacagagtg tgacctcacc    180
gacgagattg tgaaggatgt gaagcagacg tacttggcac gggtcttctc ctacccggca    240
gggaatgtgg agagcaccgg ttctgctggg gagcctctgt atgagaactc cccagagttc    300
acaccttacc tggagacaaa cctcggacag ccaacaattc agagttttga acaggtggga    360
acaaaagtga atgtgaccgt agaagatgaa cggactttag tcagaaggaa caacactttc    420
ctaagcctcc gggatgtttt tggcaaggac ttaatttata cactttatta ttggaaatct    480
tcaagttcag gaagaaaac agccaaaaca aacactaatg agttttgat tgatgtggat    540 aaaggagaaa actactgttt cagtgttcaa gcagtgattc cctcccgaac agttaaccgg    600
aagagtacag acagcccggt agagtgtatg ggccaggaga aggggaatt tagagaa      657
```

<210> SEQ ID NO 14
<211> LENGTH: 219
<212> TYPE: PRT
<213> ORGANISM: Artificial sequence
<220> FEATURE:
<223> OTHER INFORMATION: /note = "TF (1-219)"

<400> SEQUENCE: 14

| Ser | Gly | Thr | Thr | Asn | Thr | Val | Ala | Ala | Tyr | Asn | Leu | Thr | Trp | Lys | Ser |
| 1 | | | | 5 | | | | | 10 | | | | | 15 | |

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
             35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
            210                 215

<210> SEQ ID NO 15
<211> LENGTH: 885
<212> TYPE: DNA
<213> ORGANISM: Artificial sequence
<220> FEATURE:
<223> OTHER INFORMATION: /note = "human tissue factor"

<400> SEQUENCE: 15

```
atggagaccc ctgcctggcc cgggtcccg cgccccgaga ccgccgtcgc tcggacgctc      60
ctgctcggct gggtcttcgc ccaggtggcc ggcgcttcag cactacaaa tactgtggca    120
gcatataatt taacttggaa atcaactaat ttcaagacaa ttttggagtg ggaacccaaa    180
cccgtcaatc aagtctacac tgttcaaata agcactaagt caggagattg gaaaagcaaa    240
tgcttttaca caacagacac agagtgtgac ctcaccgacg agattgtgaa ggatgtgaag    300
cagacgtact ggcacgggt cttctcctac ccggcaggga tgtggagag caccggttct     360
gctgggagc ctctgtatga aactccccca gagttcacac cttacctgga caaaacctc      420
ggacagccaa caattcagag ttttgaacag gtgggaacaa agtgaatgt gaccgtagaa      480
gatgaacgga ctttagtcag aaggaacaac actttcctaa gcctccggga tgttttggc      540
aaggacttaa tttatacact ttattattgg aaatcttcaa gttcaggaaa gaaaacagcc     600
aaaacaaaca ctaatgagtt tttgattgat gtggataaag gagaaaacta ctgtttcagt     660
gttcaagcag tgattcccta ccgaacagtt aaccggaaga gtacagacag cccggtagag     720
tgtatgggcc aggagaaagg gaattcagag gaaatattct acatcattgg agctgtggta     780
```
tttgtggtca tcatccttgt catcatcctg gctatatctc tacacaagtg tagaaaggca    840
ggagtggggc agagctggaa ggagaactcc ccactgaatg tttca    885

<210> SEQ ID NO 16
<211> LENGTH: 295
<212> TYPE: PRT
<213> ORGANISM: Artificial sequence
<220> FEATURE:
<223> OTHER INFORMATION: /note = "human tissue factor"

<400> SEQUENCE: 16

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270

Ser Leu His Lys Cys Arg Lys Ala Gly Val Gly Gln Ser Trp Lys Glu
        275                 280                 285

Asn Ser Pro Leu Asn Val Ser
    290                 295

<210> SEQ ID NO 17
<211> LENGTH: 1377
<212> TYPE: DNA
<213> ORGANISM: Artificial sequence
<220> FEATURE:
<223> OTHER INFORMATION: /note = "mAb 0012 HC"

<400> SEQUENCE: 17

```
atggattttg ggctgatttt ttttattgtt gctcttttaa aagggtcca gtgtgaggtg      60
aaacttctcg agtctggagg tggcctggtg cagcctggag atccctgaa actctcctgt     120
gcagcctcag gattcgattt tagtagatac tggatgactt gggtccggca ggctccaggg    180
aaagggctag aatggattgg agaaattaat ccagatagca gtacgataaa ctatacgcca    240
tctctaaagg ataaattcat catctccaga gacaacgcca gaatacgct gtacctgcaa     300
atgagcgaag tgagatctga ggacacagcc ctttattact gtgcaagcgg ggtgtttact    360
tcctggggcc aagggactct ggtcactgtc tctgcagcta gcaccaaggg cccatccgtc    420
ttccccctgg cgccctgctc caggagcacc tccgagagca gccgccct gggctgcctg     480
gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacg aagacctaca cctgcaacgt agatcacaag    660
cccagcaaca ccaaggtgga caagagagtt gagtccaaat atggtccccc atgcccacca    720
tgcccagcac ctgagttcct ggggggacca tcagtcttcc tgttcccccc aaaacccaag    780
gacactctca tgatctcccg gacccctgag gtcacgtgcg tggtggtgga cgtgagccag    840
gaagaccccg aggtccagtt caactggtac gtggatggcg tggaggtgca taatgccaag    900
acaaagccgc gggaggagca gttcaacagc acgtaccgtg tggtcagcgt cctcaccgtc    960
ctgcaccagg actggctgaa cggcaaggag tacaagtgca aggtctccaa caaaggcctc   1020
ccgtcctcca tcgagaaaac catctccaaa gccaaagggc agccccgaga gccacaggtg   1080
tacaccctgc cccatcccca ggaggagatg accaagaacc aggtcagcct gacctgcctg   1140
gtcaaaggct tctaccccag cgacatcgcc gtggagtggg agagcaatgg gcagccggag   1200
aacaactaca agaccacgcc tcccgtgctg gactccgacg gctccttctt cctctacagc   1260
aggctaaccg tggacaagag caggtggcag gaggggaatg tcttctcatg ctccgtgatg   1320
catgaggctc tgcacaacca ctacacacag aagagcctct ccctgtctct gggtaaa      1377
```

<210> SEQ ID NO 18
<211> LENGTH: 714
<212> TYPE: DNA
<213> ORGANISM: Artificial sequence
<220> FEATURE:
<223> OTHER INFORMATION: /note = "mAb 0012 LC, Fab 0012 LC"

<400> SEQUENCE: 18

```
atgaagttgc ctgttgggct gttggtgctg atgttctgga ttccagcttc cagcagtgat      60
gttgtgatga cccaaactcc actctccctg cctgtcagtc ttggagatca agcctccatc    120
tcttgcagat ctagtcagag ccttgtacac agaaatggaa acacctattt tcattggtgc    180
ctgcagaaac caggccagtc tccaaagctc ctgatctaca agtttccaa ccgatttttct    240
ggggtcccag acaggttcag tggcagtgga tcagggacag atttcacact caagatcagc    300
agagtggagg ctgaggatct gggagtttat ttctgctctc aaagtacaca tgttccgtac    360
acgttcggag gggggaccaa gctggaaata aaacgtacgg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
```
agcaccctga cgctgagcaa agcagactac gagaaacaca aagtctacgc ctgcgaagtc    660
acccatcagg gcctgagctc gcccgtcaca aagagcttca acaggggaga gtgt          714

<210> SEQ ID NO 19
<211> LENGTH: 1401
<212> TYPE: DNA
<213> ORGANISM: Artificial sequence
<220> FEATURE:
<223> OTHER INFORMATION: /note = "mAb 0023 HC"

<400> SEQUENCE: 19
atgaacttgg ggctcagctt gattttcctt gtccttgttt taaaaggtgt ccagtgtgaa    60
gtgaggctgg tggagtctgg gggaggctta gtgcagcctg agggtccct gaaactctcc     120 tgtgcaacct ctggattcac tttcagtgac tatttcatgt attggattcg ccagactcca    180
gagaagaggc tggagtgggt cgcatacatt agtaatggtg gtgatagcag ctcttatcca    240
gacactgtaa agggccgatt caccatctcc agagacaatg ccaagaacac cctgtacctg    300
caaatgagcc gtctgaagtc tgaggacaca gccatgtatt attgtgcaac aaataaaaac    360
tgggacgatt actatgatat ggactactgg ggtcaaggaa cctcagtcac cgtctcctca    420
gctagcacca agggcccatc cgtcttcccc ctggcgccct gctccaggag cacctccgag    480
agcacagccg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacgaagacc    660
tacacctgca acgtagatca caagcccagc aacaccaagg tggacaagag agttgagtcc    720
aaatatggtc ccccatgccc accatgccca gcacctgagt tcctgggggg accatcagtc    780
ttcctgttcc cccaaaacc caaggacact ctcatgatct cccggacccc tgaggtcacg    840
tgcgtggtgg tggacgtgag ccaggaagac cccgaggtcc agttcaactg gtacgtggat    900
ggcgtggagg tgcataatgc caagacaaag ccgcgggagg agcagttcaa cagcacgtac    960
cgtgtggtca gcgtcctcac cgtcctgcac caggactggc tgaacggcaa ggagtacaag    1020
tgcaaggtct ccaacaaagg cctcccgtcc tccatcgaga aaaccatctc caaagccaaa    1080
gggcagcccc gagagccaca ggtgtacacc ctgcccccat cccaggagga gatgaccaag    1140
aaccaggtca gcctgacctg cctggtcaaa ggcttctacc ccagcgacat cgccgtggag    1200
tgggagagca atgggcagcc ggagaacaac tacaagacca cgcctcccgt gctggactcc    1260
gacggctcct tcttcctcta cagcaggcta accgtggaca gagcaggtg gcaggagggg    1320 aatgtcttct catgctccgt gatgcatgag gctctgcaca accactacac acagaagagc    1380 ctctcccctgt ctctgggtaa a                                            1401

<210> SEQ ID NO 20
<211> LENGTH: 717
<212> TYPE: DNA
<213> ORGANISM: Artificial sequence
<220> FEATURE:
<223> OTHER INFORMATION: /note = "mAb 0023 LC"

<400> SEQUENCE: 20
atggattcac aggcccaggt tcttatattg ctgctgctat gggtatctgg ttcctgtggg    60
gacattgtgg tgtcacagtc tccatcctcc ctggctgtgt cagcaggaga gaaggtcact    120
atgagttgca atccagtcaa gagtctgctc aacagtagaa cccgaaagaa ctacttggct    180
tggtaccagc agaaaccagg gcagtctcct aaactgctga tctactgggc atccactagg    240

```
gaatctgggg tccctgatcg cttcacaggc agtggatctg ggacagattt cactctcacc    300
atcagcagtg tgcaggctga agacctggca gtttattact gcaagcaatc ttataatctg    360
ctcacgttcg gtgctgggac caagctggag ctgaaacgta cggtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgt      717
```

<210> SEQ ID NO 21
<211> LENGTH: 1401
<212> TYPE: DNA
<213> ORGANISM: Artificial sequence
<220> FEATURE:
<223> OTHER INFORMATION: /note = "mAb 0051 HC"

<400> SEQUENCE: 21

```
atgggttgga gctgtatcat cttctttctg gtagcaacag ctacaggtgt gcactcccag     60
gtccagctgg agcagtctgg ggctgagctg gtgaggcctg ggtctcagt gaagatttcc    120 tgcaagggtt ctggctacac attcactgat tattctatgc actgggtgaa gcagagtcat    180
gcaaagagtc tagagtggat tggagttatt agtacttact atggtgatgt taggtacaac    240
cagaagttca gggcaaggc cacaatgact gtagacaaat cctccagcac agcctatatg    300
gcacttgcca gactgacatc tgaggattct gccatctatt actgtgcaag agcccctatg    360
attacgacag gggcctggtt tgcttactgg ggccaaggga ctctggtcac tgtctctgca    420
gctagcacca agggcccatc cgtcttcccc ctggcgccct gctccaggag cacctccgag    480
agcacagccg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacgaagacc    660
tacacctgca acgtagatca caagcccagc aacaccaagg tggacaagag agttgagtcc    720
aaatatggtc ccccatgccc accatgccca gcacctgagt tcctgggggg accatcagtc    780
ttcctgttcc ccccaaaacc caaggacact ctcatgatct cccggacccc tgaggtcacg    840
tgcgtggtgg tggacgtgag ccaggaagac cccgaggtcc agttcaactg gtacgtggat    900
ggcgtggagg tgcataatgc caagacaaag ccgcgggagg agcagttcaa cagcacgtac    960
cgtgtggtca gcgtcctcac cgtcctgcac caggactggc tgaacggcaa ggagtacaag   1020
tgcaaggtct ccaacaaagg cctcccgtcc tccatcgaga aaaccatctc caaagccaaa   1080
gggcagcccc gagagccaca ggtgtacacc ctgcccccat cccaggagga tgaccaag    1140 aaccaggtca gcctgacctg cctggtcaaa ggcttctacc ccagcgacat cgccgtggag   1200
tgggagagca atgggcagcc ggagaacaac tacaagacca cgcctcccgt gctggactcc   1260
gacggctcct tcttcctcta cagcaggcta accgtggaca agagcaggtg gcaggagggg   1320
aatgtcttct catgctccgt gatgcatgag gctctgcaca accactacac acagaagagc   1380
ctctccctgt ctctgggtaa a                                              1401
```

<210> SEQ ID NO 22
<211> LENGTH: 702
<212> TYPE: DNA

<213> ORGANISM: Artificial sequence
<220> FEATURE:
<223> OTHER INFORMATION: /note = "mAb 0051 LC"

<400> SEQUENCE: 22

| | | | | | |
|---|---|---|---|---|---|
| atgaagtcac | agacccaggt | cttcgtattt | ctactgctct | gtgtgtctgg | tgctcatggg | 60 |
| agtattgtga | tgacccagac | tcccaaattc | ctgcttgtat | cagcaggaga | cagggttacc | 120 |
| ataacctgca | aggccagtca | gagtgtgagt | aatgatgtag | cttggtacca | acagaagcca | 180 |
| gggcagtctc | ctaaactgct | gataaactat | gcatccagtc | gctacactgg | aatccctgat | 240 |
| cgcttcactg | gcagtggata | tgggacggat | ttcactttca | ccatcagcac | tgtgcaggct | 300 |
| gaagacctgg | cagtttattt | ctgtcagcag | gattatagct | ctccgtacac | gttcggaggg | 360 |
| gggaccaagc | tggaaataga | acgtacggtg | gctgcaccat | ctgtcttcat | cttcccgcca | 420 |
| tctgatgagc | agttgaaatc | tggaactgcc | tctgttgtgt | gcctgctgaa | taacttctat | 480 |
| cccagagagg | ccaaagtaca | gtggaaggtg | gataacgccc | tccaatcggg | taactcccag | 540 |
| gagagtgtca | cagagcagga | cagcaaggac | agcacctaca | gcctcagcag | caccctgacg | 600 |
| ctgagcaaag | cagactacga | gaaacacaaa | gtctacgcct | gcgaagtcac | ccatcagggc | 660 |
| ctgagctcgc | ccgtcacaaa | gagcttcaac | aggggagagt | gt | | 702 |

<210> SEQ ID NO 23
<211> LENGTH: 1404
<212> TYPE: DNA
<213> ORGANISM: Artificial sequence
<220> FEATURE:
<223> OTHER INFORMATION: /note = "mAb 0052 HC"

<400> SEQUENCE: 23

| | | | | | |
|---|---|---|---|---|---|
| atgaatgga | cctgggtctt | tctcttcctc | ctgtcagtaa | ctgcaggtgt | ccattcccag | 60 |
| gtccagctgc | agcagtctgg | agctgagccg | atgaagcctg | gggcctcagt | gaagatatcc | 120 |
| tgcaaggcta | ctggctacac | atttagtagt | cactggatag | agtggataaa | acagaggcct | 180 |
| ggacatggcc | ttgagtggat | tggagagatt | ttacctggaa | gtggaaatac | taattacaat | 240 |
| gagaaattca | agggcaaggc | cacattcact | gcagatacat | cctccaacac | agcctacatg | 300 |
| caactcagca | gcctgacatc | tgaggactct | gccgtctatt | tctgtgcaag | agggtactac | 360 |
| ggtcttaact | acgactggta | tttcgatgtc | tggggcgcag | ggaccacggt | caccgtctcc | 420 |
| tcagctagca | ccaagggccc | atccgtcttc | cccctggcgc | cctgctccag | gagcacctcc | 480 |
| gagagcacag | ccgccctggg | ctgcctggtc | aaggactact | tccccgaacc | ggtgacggtg | 540 |
| tcgtggaact | caggcgccct | gaccagcggc | gtgcacacct | tcccggctgt | cctacagtcc | 600 |
| tcaggactct | actccctcag | cagcgtggtg | accgtgccct | ccagcagctt | gggcacgaag | 660 |
| acctacacct | gcaacgtaga | tcacaagccc | agcaacacca | aggtggacaa | gagagttgag | 720 |
| tccaaatatg | gtcccccatg | cccaccatgc | ccagcacctg | agttcctggg | gggaccatca | 780 |
| gtcttcctgt | tccccccaaa | acccaaggac | actctcatga | tctcccggac | ccctgaggtc | 840 |
| acgtgcgtgg | tggtggacgt | gagccaggaa | gaccccgagg | tccagttcaa | ctggtacgtg | 900 |
| gatggcgtgg | aggtgcataa | tgccaagaca | aagccgcggg | aggagcagtt | caacagcacg | 960 |
| taccgtgtgg | tcagcgtcct | caccgtcctg | caccaggact | ggctgaacgg | caaggagtac | 1020 |
| aagtgcaagg | tctccaacaa | aggcctcccg | tcctccatcg | agaaaaccat | ctccaaagcc | 1080 |
| aaagggcagc | cccgagagcc | acaggtgtac | accctgcccc | catcccagga | ggagatgacc | 1140 |
| aagaaccagg | tcagcctgac | ctgcctggtc | aaaggcttct | accccagcga | catcgccgtg | 1200 |

```
gagtgggaga gcaatgggca gccggagaac aactacaaga ccacgcctcc cgtgctggac    1260
tccgacggct ccttcttcct ctacagcagg ctaaccgtgg acaagagcag gtggcaggag    1320
gggaatgtct tctcatgctc cgtgatgcat gaggctctgc acaaccacta cacacagaag    1380
agcctctccc tgtctctggg taaa                                           1404
```

<210> SEQ ID NO 24
<211> LENGTH: 1404
<212> TYPE: DNA
<213> ORGANISM: Artificial sequence
<220> FEATURE:
<223> OTHER INFORMATION: /note = "mAb 0062 HC"

<400> SEQUENCE: 24

```
atggaatgga cctgggtctt tctcttcctc ctgtcagtaa ctgcaggtgt ccattcccag      60
gtccagctgc agcagtctgg agctgagccg atgaagcctg gggcctcagt gaagatatcc     120
tgcaaggcta ctggctacac atttagtagt cactggatag agtggataaa acagaggcct     180
ggacatggcc ttgagtggat tggagagatt ttacctggaa gtggaaatac taattacaat     240
gagaaattca gggcaaggc cacattcact gcagatacat cctccaacac agcctacatg     300
caactcagca gcctgacatc tgaggactct gccgtctatt actgtgcaag agggtactac     360
ggtcttaact acgactggta tttcgatgtc tggggcgcag ggaccacggt caccgtctcc     420
tcagctagca ccaagggccc atccgtcttc cccctggcgc cctgctccag gagcacctcc     480
gagagcacag ccgccctggg ctgcctggtc aaggactact cccccgaacc ggtgacggtg     540
tcgtggaact caggcgccct gaccagcggc gtgcacacct tcccggctgt cctacagtcc     600
tcaggactct actccctcag cagcgtggtg accgtgccct ccagcagctt gggcacgaag     660
acctacacct gcaacgtaga tcacaagccc agcaacacca aggtggacaa gagagttgag     720
tccaaatatg gtcccccatg cccaccatgc ccagcacctg agttcctggg gggaccatca     780
gtcttcctgt tccccccaaa acccaaggac actctcatga tctcccggac ccctgaggtc     840
acgtgcgtgg tggtggacgt gagccaggaa gaccccgagg tccagttcaa ctggtacgtg     900
gatggcgtgg aggtgcataa tgccaagaca aagccgcggg aggagcagtt caacagcacg     960
taccgtgtgg tcagcgtcct caccgtcctg caccaggact ggctgaacgg caaggagtac    1020
aagtgcaagg tctccaacaa aggcctcccg tcctccatcg agaaaaccat ctccaaagcc    1080
aaagggcagc cccgagagcc acaggtgtac accctgcccc catcccagga ggagatgacc    1140
aagaaccagg tcagcctgac ctgcctggtc aaaggcttct accccagcga catcgccgtg    1200
gagtgggaga gcaatgggca gccggagaac aactacaaga ccacgcctcc cgtgctggac    1260
tccgacggct ccttcttcct ctacagcagg ctaaccgtgg acaagagcag gtggcaggag    1320
gggaatgtct tctcatgctc cgtgatgcat gaggctctgc acaaccacta cacacagaag    1380
agcctctccc tgtctctggg taaa                                           1404
```

<210> SEQ ID NO 25
<211> LENGTH: 702
<212> TYPE: DNA
<213> ORGANISM: Artificial sequence
<220> FEATURE:
<223> OTHER INFORMATION: /note = "mAb 0052 LC, mAb 0062 LC"

<400> SEQUENCE: 25

```
atgatgtcct ctgctcagtt ccttggtctc ctgttgctct gttttcaagg taccagatgt      60
```

| | | |
|---|---|---|
| gatatccaga tgacacagac tacatcctcc ctgtctgcct ctctgggaga cagagtcacc | 120 | |
| attagttgca gggcaagtca ggacattagc aattatttaa actggtatca gcagaaacca | 180 | |
| gatggaactg ttaaactcct tatcttctac acatcaagat tacactcagg agtcccgtca | 240 | |
| aggttcagtg gcagtgggtc tgggacagat tattctctca ccattagcaa cctggaaccg | 300 | |
| gaagatattg ccacttacta ttgccaacag gatactaagc ttccgtacac gttcggaggg | 360 | |
| gggaccaaac tggagatgaa acgtacggtg gctgcaccat ctgtcttcat cttcccgcca | 420 | |
| tctgatgagc agttgaaatc tggaactgcc tctgttgtgt gcctgctgaa taacttctat | 480 | |
| cccagagagg ccaaagtaca gtggaaggtg gataacgccc tccaatcggg taactcccag | 540 | |
| gagagtgtca cagagcagga cagcaaggac agcacctaca gcctcagcag caccctgacg | 600 | |
| ctgagcaaag cagactacga aaacacaaa gtctacgcct gcgaagtcac ccatcagggc | 660 | |
| ctgagctcgc ccgtcacaaa gagcttcaac aggggagagt gt | 702 | |

<210> SEQ ID NO 26
<211> LENGTH: 1377
<212> TYPE: DNA
<213> ORGANISM: Artificial sequence
<220> FEATURE:
<223> OTHER INFORMATION: /note = "mAb 0061 HC"

<400> SEQUENCE: 26

| | | |
|---|---|---|
| atggattttg gctgattttt ttttattgtt gctcttttaa aaggggtcca gtgtgaggtg | 60 | |
| aaacttctcg agtctggagg tggcctggtg cagcctggag gatccctgaa actctcctgt | 120 | |
| gcagcctcag gattcgattt tagtagatac tggatgactt gggtccggca ggctccaggg | 180 | |
| aagggctag aatggattgg agaaattaat ccagatagca gtacgataaa ctataaccca | 240 | |
| tctctaaagg ataaattcat catctccaga gacaacgcca agaatacgct gtacctgcaa | 300 | |
| atgagcgaag tgagatctga ggacacagcc ctttattact gtgcaagcgg ggtgtttact | 360 | |
| tcctggggcc aagggactct ggtcactgtc tctgcagcta gcaccaaggg cccatccgtc | 420 | |
| ttccccctgg cgccctgctc caggagcacc tccgagagca gccgccct gggctgcctg | 480 | |
| gtcaaggact acttccccga accggtgacg gtgtcgtgga actcaggcgc cctgaccagc | 540 | |
| ggcgtgcaca ccttcccggc tgtcctacag tcctcaggac tctactccct cagcagcgtg | 600 | |
| gtgaccgtgc cctccagcag cttgggcacg aagacctaca cctgcaacgt agatcacaag | 660 | |
| cccagcaaca ccaaggtgga caagagagtt gagtccaaat atggtccccc atgcccacca | 720 | |
| tgcccagcac ctgagttcct ggggggacca tcagtcttcc tgttcccccc aaaacccaag | 780 | |
| gacactctca tgatctcccg gacccctgag gtcacgtgcg tggtggtgga cgtgagccag | 840 | |
| gaagaccccg aggtccagtt caactggtac gtggatggcg tggaggtgca taatgccaag | 900 | |
| acaaagccgc gggaggagca gttcaacagc acgtaccgtg tggtcagcgt cctcaccgtc | 960 | |
| ctgcaccagg actggctgaa cggcaaggag tacaagtgca aggtctccaa caaaggcctc | 1020 | |
| ccgtcctcca tcgagaaaac catctccaaa gccaaagggc agccccgaga gccacaggtg | 1080 | |
| tacaccctgc cccatcccca ggaggagatg accaagaacc aggtcagcct gacctgcctg | 1140 | |
| gtcaaaggct tctaccccag cgacatcgcc gtggagtggg agagcaatgg gcagccggag | 1200 | |
| aacaactaca agaccacgcc tcccgtgctg gactccgacg gctccttctt cctctacagc | 1260 | |
| aggctaaccg tggacaagag caggtggcag gaggggaatg tcttctcatg ctccgtgatg | 1320 | |
| catgaggctc tgcacaacca ctacacacag aagagcctct ccctgtctct gggtaaa | 1377 | |

```
<210> SEQ ID NO 27
<211> LENGTH: 1377
<212> TYPE: DNA
<213> ORGANISM: Artificial sequence
<220> FEATURE:
<223> OTHER INFORMATION: /note = "mAb 0082 HC"

<400> SEQUENCE: 27
atggattttg ggctgatttt ttttattgtt gctcttttaa aaggggtcca gtgtgaggtg      60
aaacttctcg agtctggagg tggcctggtg cagcctggag atccctgaa actctcctgt     120 gcagcctcag gattcgattt tagtagatac tggatgactt gggtccggca ggctccaggg    180
aaagggctag aatggattgg agaaattaat ccagatagca gtacgataaa ctatgcgcca    240
tctctaaagg ataaattcat catctccaga gacaacgcca gaatacgct gtacctgcaa    300 atgagcgaag tgagatctga ggacacagcc ctttattact gtgcaagcgg ggtgtttact    360
tcctggggcc aagggactct ggtcactgtc tctgcagcta gcaccaaggg cccatccgtc    420
ttccccctgg cgccctgctc caggagcacc tccgagagca gccgccct gggctgcctg     480 gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacg aagacctaca cctgcaacgt agatcacaag    660
cccagcaaca ccaaggtgga caagagagtt gagtccaaat atggtccccc atgcccacca    720
tgcccagcac ctgagttcct ggggggacca tcagtcttcc tgttcccccc aaaacccaag    780
gacactctca tgatctcccg gacccctgag gtcacgtgcg tggtggtgga cgtgagccag    840 gaagacccc aggtccagtt caactggtac gtggatggcg tggaggtgca taatgccaag    900
acaaagccgc gggaggagca gttcaacagc acgtaccgtg tggtcagcgt cctcaccgtc    960
ctgcaccagg actggctgaa cggcaaggag tacaagtgca aggtctccaa caaaggcctc   1020
ccgtcctcca tcgagaaaac catctcccaa agccaaagggc agccccgaga gccacaggtg   1080
tacaccctgc cccatccca ggaggagatg accaagaacc aggtcagcct gacctgcctg    1140
gtcaaaggct tctaccccag cgacatcgcc gtggagtggg agagcaatgg gcagccggag    1200
aacaactaca agaccacgcc tcccgtgctg gactccgacg gctccttctt cctctacagc    1260
aggctaaccg tggacaagag caggtggcag gaggggaatg tcttctcatg ctccgtgatg    1320
catgaggctc tgcacaacca ctacacacag aagagcctct ccctgtctct gggtaaa     1377

<210> SEQ ID NO 28
<211> LENGTH: 714
<212> TYPE: DNA
<213> ORGANISM: Artificial sequence
<220> FEATURE:
<223> OTHER INFORMATION: /note = "mAb 0061 LC, Fab 0061 LC, mAb 0082 LC,
      Fab 0082 LC"

<400> SEQUENCE: 28
atgaagttgc ctgttgggct gttggtgctg atgttctgga ttccagcttc agcagtgat      60 gttgtgatga cccaaactcc actctccctg cctgtcagtc ttggagatca agcctccatc    120
tcttgcagat ctagtcagag ccttgtacac agaaatggaa acacctattt tcattgggcc    180
ctgcagaaac caggccagtc tccaaagctc ctgatctaca agtttccaa ccgatttct     240 ggggtcccag acaggttcag tggcagtgga tcagggacag atttcacact caagatcagc    300
agagtggagg ctgaggatct gggagtttat ttctgctctc aaagtacaca tgttccgtac    360
acgttcggag gggggaccaa gctggaaata aaacgtacgg tggctgcacc atctgtcttc    420
```

```
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc     660 acccatcagg gcctgagctc gcccgtcaca aagagcttca caggggaga gtgt           714
```

<210> SEQ ID NO 29  
<211> LENGTH: 699  
<212> TYPE: DNA  
<213> ORGANISM: Artificial sequence  
<220> FEATURE:  
<223> OTHER INFORMATION: /note = "Fab 0012 VH-CH1"

<400> SEQUENCE: 29

```
atggattttg ggctgatttt ttttattgtt gctcttttaa aaggggtcca gtgtgaggtg    60
aaacttctcg agtctggagg tggcctggtg cagcctggag gatccctgaa actctcctgt   120
gcagcctcag gattcgattt tagtagatac tggatgactt gggtccggca ggctccaggg   180
aaagggctag aatggattgg agaaattaat ccagatagca gtacgataaa ctatacgcca   240
tctctaaagg ataaattcat catctccaga gacaacgcca gaatacgct gtacctgcaa    300 atgagcgaag tgagatctga ggacacagcc ctttattact gtgcaagcgg ggtgtttact   360
tcctggggcc aagggactct ggtcactgtc tctgcagcta gcaccaaggg cccatccgtc   420
ttccccctgg cgccctgctc caggagcacc tccgagagca gccgccct gggctgcctg    480 gtcaaggact acttccccga accggtgacg gtgtcgtgga actcaggcgc cctgaccagc   540
ggcgtgcaca ccttcccggc tgtcctacag tcctcaggac tctactccct cagcagcgtg   600
gtgaccgtgc cctccagcag cttgggcacg aagacctaca cctgcaacgt agatcacaag   660
cccagcaaca ccaaggtgga caagagagtt gagtccaaa                          699
```

<210> SEQ ID NO 30  
<211> LENGTH: 723  
<212> TYPE: DNA  
<213> ORGANISM: Artificial sequence  
<220> FEATURE:  
<223> OTHER INFORMATION: /note = "Fab 0023 VH-CH1"

<400> SEQUENCE: 30

```
atgaacttgg ggctcagctt gattttcctt gtccttgttt taaaaggtgt ccagtgtgaa    60
gtgaggctgt tggagtctgg gggaggctta gtgcagcctg agggtccct gaaactctcc    120 tgtgcaacct ctggattcac tttcagtgac tatttcatgt attggattcg ccagactcca   180
gagaagaggc tggagtgggt cgcatacatt agtaatggtg gtgatagcag ctcttatcca   240
gacactgtaa agggccgatt caccatctcc agagacaatg ccaagaacac cctgtacctg   300
caaatgagcc gtctgaagtc tgaggacaca gccatgtatt attgtgcaac aaataaaaac   360
tgggacgatt actatgatat ggactactgg ggtcaaggaa cctcagtcac cgtctcctca   420
gctagcacca agggcccatc cgtcttcccc ctggcgccct gctccaggag cacctccgag   480
agcacagccg cctgggctg cctggtcaag gactacttcc ccgaaccggt gacggtgtcg   540
tggaactcag gcgccctgac cagcggcgtg cacaccttcc cggctgtcct acagtcctca   600
ggactctact ccctcagcag cgtggtgacc gtgcctcca gcagcttggg cacgaagacc    660
tacacctgca acgtagatca caagcccagc aacaccaagg tggacaagag agttgagtcc   720
```

```
aaa                                                            723

<210> SEQ ID NO 31
<211> LENGTH: 723
<212> TYPE: DNA
<213> ORGANISM: Artificial sequence
<220> FEATURE:
<223> OTHER INFORMATION: /note = "Fab 0051 VH-CH1"

<400> SEQUENCE: 31
atgggttgga gctgtatcat cttctttctg gtagcaacag ctacaggtgt gcactcccag    60
gtccagctgg agcagtctgg ggctgagctg gtgaggcctg ggtctcagt gaagatttcc   120 tgcaagggtt ctggctacac attcactgat tattctatgc actgggtgaa gcagagtcat   180
gcaaagagtc tagagtggat tggagttatt agtacttact atggtgatgt taggtacaac   240
cagaagttca agggcaaggc cacaatgact gtagacaaat cctccagcac agcctatatg   300
gcacttgcca gactgacatc tgaggattct gccatctatt actgtgcaag agcccctatg   360
attacgacag gggcctggtt tgcttactgg ggccaaggga ctctggtcac tgtctctgca   420
gctagcacca agggcccatc cgtcttcccc ctggcgccct gctccaggag cacctccgag   480
agcacagccg ccctgggctg cctggtcaag gactacttcc ccgaaccggt gacggtgtcg   540
tggaactcag cgccctgac cagcggcgtg cacaccttcc cggctgtcct acagtcctca   600
ggactctact ccctcagcag cgtggtgacc gtgccctcca gcagcttggg cacgaagacc   660
tacacctgca acgtagatca caagcccagc aacaccaagg tggacaagag agttgagtcc   720
aaa                                                            723

<210> SEQ ID NO 32
<211> LENGTH: 726
<212> TYPE: DNA
<213> ORGANISM: Artificial sequence
<220> FEATURE:
<223> OTHER INFORMATION: /note = "Fab 0052 VH-CH1"

<400> SEQUENCE: 32
atggaatgga cctgggtctt tctcttcctc ctgtcagtaa ctgcaggtgt ccattcccag    60
gtccagctgc agcagtctgg agctgagccg atgaagcctg ggcctcagt gaagatatcc   120 tgcaaggcta ctggctacac atttagtagt cactggatag agtggataaa acagaggcct   180
ggacatggcc ttgagtggat tggagagatt ttacctggaa gtggaaatac taattacaat   240
gagaaattca gggcaaggc cacattcact gcagatacat cctccaacac agcctacatg   300
caactcagca gcctgacatc tgaggactct gccgtctatt gctgtgcaag agggtactac   360
ggtcttaact acgactggta tttcgatgtc tggggcgcag ggaccacggt caccgtctcc   420
tcagctagca ccaagggccc atccgtcttc cccctggcgc cctgctccag gagcacctcc   480
gagagcacag ccgccctggg ctgcctggtc aaggactact ccccgaacc ggtgacggtg   540 tcgtggaact caggcgccct gaccagcggc gtgcacacct tccggctgt cctacagtcc   600 tcaggactct actccctcag cagcgtggtg accgtgccct ccagcagctt gggcacgaag   660
acctacacct gcaacgtaga tcacaagccc agcaacacca aggtggacaa gagagttgag   720
tccaaa                                                         726

<210> SEQ ID NO 33
<211> LENGTH: 699
<212> TYPE: DNA
<213> ORGANISM: Artificial sequence
```

```
<220> FEATURE:
<223> OTHER INFORMATION: /note = "Fab 0061 VH-CH1"

<400> SEQUENCE: 33
atggattttg ggctgatttt ttttattgtt gctcttttaa aagggtgtcca gtgtgaggtg      60 aaacttctcg agtctggagg tggcctggtg cagcctggag gatccctgaa actctcctgt     120
gcagcctcag gattcgattt tagtagatac tggatgactt gggtccggca ggctccaggg     180
aaagggctag aatggattgg agaaattaat ccagatagca gtacgataaa ctataaccca     240
tctctaaagg ataaattcat catctccaga gacaacgcca gaatacgct gtacctgcaa      300 atgagcgaag tgagatctga ggacacagcc ctttattact gtgcaagcgg ggtgtttact     360
tcctggggcc aagggactct ggtcactgtc tctgcagcta gcaccaaggg cccatccgtc     420
ttccccctgg cgccctgctc caggagcacc tccgagagca cagccgccct gggctgcctg     480
gtcaaggact acttccccga accggtgacg gtgtcgtgga actcaggcgc cctgaccagc     540
ggcgtgcaca ccttccccgg ctgtcctaca gtcctcagga ctctactccct cagcagcgtg    600 gtgaccgtgc cctccagcag cttgggcacg aagacctaca cctgcaacgt agatcacaag     660
cccagcaaca ccaaggtgga caagagagtt gagtccaaa                            699

<210> SEQ ID NO 34
<211> LENGTH: 699
<212> TYPE: DNA
<213> ORGANISM: Artificial sequence
<220> FEATURE:
<223> OTHER INFORMATION: /note = "Fab 0082 VH-CH1"

<400> SEQUENCE: 34
atggattttg ggctgatttt ttttattgtt gctcttttaa aagggtgtcca gtgtgaggtg      60 aaacttctcg agtctggagg tggcctggtg cagcctggag gatccctgaa actctcctgt     120
gcagcctcag gattcgattt tagtagatac tggatgactt gggtccggca ggctccaggg     180
aaagggctag aatggattgg agaaattaat ccagatagca gtacgataaa ctatgcgcca     240
tctctaaagg ataaattcat catctccaga gacaacgcca gaatacgct gtacctgcaa      300 atgagcgaag tgagatctga ggacacagcc ctttattact gtgcaagcgg ggtgtttact     360
tcctggggcc aagggactct ggtcactgtc tctgcagcta gcaccaaggg cccatccgtc     420
ttccccctgg cgccctgctc caggagcacc tccgagagca cagccgccct gggctgcctg     480
gtcaaggact acttccccga accggtgacg gtgtcgtgga actcaggcgc cctgaccagc     540
ggcgtgcaca ccttccccgg ctgtcctaca gtcctcagga ctctactccct cagcagcgtg    600 gtgaccgtgc cctccagcag cttgggcacg aagacctaca cctgcaacgt agatcacaag     660
cccagcaaca ccaaggtgga caagagagtt gagtccaaa                            699

<210> SEQ ID NO 35
<211> LENGTH: 720
<212> TYPE: DNA
<213> ORGANISM: Artificial sequence
<220> FEATURE:
<223> OTHER INFORMATION: /note = "Fab AP-3 VH-VH1"

<400> SEQUENCE: 35
atggaatgga gcggggtctt tatctttctc ttgtcagtaa ctgcagatgt ccactcccag      60
gtccagttgc agcagtctgg agctgagctg gtaaggcctg ggacttcagt gaagatatcc     120
tgcaaggctt ctggctacac cttcactaac tactggctag gttgggtaaa gcagaggcct     180
```

```
ggacatggac ttgagtggat tggagatatt taccctggag gtggttataa taagtacaat    240
gagaatttca agggcaaggc cacactgact gcagacacat cctccagcac tgcctacatg    300
cagctcagta gcctgacatc tgaggactct gctgtctatt tctgtgcaag agagtatggt    360
aactacgact atgctatgga ctcctggggt caaggaacct cagtcaccgt ctcctcagct    420
agcaccaagg gcccatccgt cttccccctg gcgccctgct ccaggagcac ctccgagagc    480
acagccgccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac gaagacctac    660
acctgcaacg tagatcacaa gcccagcaac accaaggtgg acaagagagt tgagtccaaa    720
```

<210> SEQ ID NO 36  
<211> LENGTH: 717  
<212> TYPE: DNA  
<213> ORGANISM: Artificial sequence  
<220> FEATURE:  
<223> OTHER INFORMATION: /note = "Fab AP-3 LC"

<400> SEQUENCE: 36

```
atgaggtgcc tagctgagtt cctggggctg cttgtgctct ggatccctgg agccattggg     60
gatattgtga tgactcaggc tgcaccctct gtacctgtca ctcctggaga gtcagtatcc    120
atctcctgca ggtctagtag gagtctcctg catagtaatg caacactta cttgtgttgg    180 ttcctgcaga ggccaggcca gtctcctcag ctcctgatat atcggatgtc caaccttgcc    240
tcaggagtcc cagacaggtt cagtggcagt gggtcaggaa ctgctttcac actgagaatc    300
agtagagtgg aggctgagga tgtgggtgtt tattactgta tgcaacatct agaatatcca    360
ttcacgttcg gctcggggac aaagttggaa ataaaacgta cggtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgt     717
```

<210> SEQ ID NO 37  
<211> LENGTH: 717  
<212> TYPE: DNA  
<213> ORGANISM: Artificial sequence  
<220> FEATURE:  
<223> OTHER INFORMATION: /note = "Fab-AP-3 LC.C34S"

<400> SEQUENCE: 37

```
atgaggtgcc tagctgagtt cctggggctg cttgtgctct ggatccctgg agccattggg     60
gatattgtga tgactcaggc tgcaccctct gtacctgtca ctcctggaga gtcagtatcc    120
atctcctgca ggtctagtag gagtctcctg catagtaatg caacactta cttgtccttgg    180 ttcctgcaga ggccaggcca gtctcctcag ctcctgatat atcggatgtc caaccttgcc    240
tcaggagtcc cagacaggtt cagtggcagt gggtcaggaa ctgctttcac actgagaatc    300
agtagagtgg aggctgagga tgtgggtgtt tattactgta tgcaacatct agaatatcca    360
ttcacgttcg gctcggggac aaagttggaa ataaaacgta cggtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
```

```
tcgggtaact cccaggagag tgtcacagag caggacagca aggacagcac ctacagcctc      600
agcagcaccc tgacgctgag caaagcagac tacgagaaac acaaagtcta cgcctgcgaa      660
gtcacccatc agggcctgag ctcgcccgtc acaaagagct caacagggga gagtgt          717
```

<210> SEQ ID NO 38
<211> LENGTH: 741
<212> TYPE: DNA
<213> ORGANISM: Artificial sequence
<220> FEATURE:
<223> OTHER INFORMATION: /note = "hIgG4 hinge-CH2-CH3"

<400> SEQUENCE: 38

```
atggattttg ggctgatttt ttttattgtt gctcttttaa aaggggtcca gtgtgagtcc       60
aaatatggtc ccccatgccc accatgccca gcacctgagt tcctgggggg accatcagtc      120
ttcctgttcc ccccaaaacc caaggacact ctcatgatct cccggacccc tgaggtcacg      180
tgcgtggtgg tggacgtgag ccaggaagac cccgaggtcc agttcaactg gtacgtggat      240
ggcgtggagg tgcataatgc caagacaaag ccgcgggagg agcagttcaa cagcacgtac      300
cgtgtggtca gcgtcctcac cgtcctgcac caggactggc tgaacggcaa ggagtacaag      360
tgcaaggtct ccaacaaagg cctcccgtcc tccatcgaga aaaccatctc caaagccaaa      420
gggcagcccc gagagccaca ggtgtacacc ctgcccccat cccaggagga gatgaccaag      480
aaccaggtca gcctgacctg cctggtcaaa ggcttctacc ccagcgacat cgccgtggag      540
tgggagagca atgggcagcc ggagaacaac tacaagacca cgcctcccgt gctggactcc      600
gacggctcct tcttcctcta cagcaggcta accgtggaca agagcaggtg gcaggagggg      660
aatgtcttct catgctccgt gatgcatgag gctctgcaca accactacac acagaagagc      720
ctctccctgt ctctgggtaa a                                                741
```

<210> SEQ ID NO 39
<211> LENGTH: 459
<212> TYPE: PRT
<213> ORGANISM: Artificial sequence
<220> FEATURE:
<223> OTHER INFORMATION: /note = "mAb 0012, HC (mouse VH-human IgG4
    CH1-CH2-CH3)"

<400> SEQUENCE: 39

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
```

```
                130                 135                 140
Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
                195                 200                 205

Gly Thr Lys Thr Tyr Thr Cys Asn Val Asp His Lys Pro Ser Asn Thr
                210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser Gln Glu Asp Pro Glu Val Gln Phe Asn
                275                 280                 285

Trp Tyr Val Asp Gly Val Glu Val His Asn Ala Lys Thr Lys Pro Arg
                290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
                340                 345                 350

Gly Gln Pro Arg Glu Pro Gln Val Tyr Thr Leu Pro Pro Ser Gln Glu
                355                 360                 365

Glu Met Thr Lys Asn Gln Val Ser Leu Thr Cys Leu Val Lys Gly Phe
                370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
                420                 425                 430

Asn Val Phe Ser Cys Ser Val Met His Glu Ala Leu His Asn His Tyr
                435                 440                 445

Thr Gln Lys Ser Leu Ser Leu Gly Lys
450                 455

<210> SEQ ID NO 40
<211> LENGTH: 238
<212> TYPE: PRT
<213> ORGANISM: Artificial sequence
<220> FEATURE:
<223> OTHER INFORMATION: /note = "mAb 0012, LC (mouse VL - human Kappa
      CL); Fab 0012, LC (mouse VL - human Kappa CL)"

<400> SEQUENCE: 40

Met Lys Leu Pro Val Gly Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30
```

Ser Leu Gly Asp Gln Ala Ser Ile Ser Cys Arg Ser Ser Gln Ser Leu
            35                  40                  45

Val His Arg Asn Gly Asn Thr Tyr Phe His Trp Cys Leu Gln Lys Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                    85                  90                  95

Leu Lys Ile Ser Arg Val Glu Ala Glu Asp Leu Gly Val Tyr Phe Cys
                100                 105                 110

Ser Gln Ser Thr His Val Pro Tyr Thr Phe Gly Gly Gly Thr Lys Leu
                115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
                210                 215                 220

Leu Ser Ser Pro Val Thr Lys Ser Phe Asn Arg Gly Glu Cys
225                 230                 235

<210> SEQ ID NO 41
<211> LENGTH: 467
<212> TYPE: PRT
<213> ORGANISM: Artificial sequence
<220> FEATURE:
<223> OTHER INFORMATION: /note = "mAb 0023, HC (mouse VH-human IgG4
      CH1-CH2-CH3)"

<400> SEQUENCE: 41

Met Asn Leu Gly Leu Ser Leu Ile Phe Leu Val Leu Val Leu Lys Gly
 1               5                  10                  15

Val Gln Cys Glu Val Arg Leu Val Glu Ser Gly Gly Gly Leu Val Gln
                20                  25                  30

Pro Gly Gly Ser Leu Lys Leu Ser Cys Ala Thr Ser Gly Phe Thr Phe
                35                  40                  45

Ser Asp Tyr Phe Met Tyr Trp Ile Arg Gln Thr Pro Glu Lys Arg Leu
 50                  55                  60

Glu Trp Val Ala Tyr Ile Ser Asn Gly Gly Asp Ser Ser Tyr Pro
 65                  70                  75                  80

Asp Thr Val Lys Gly Arg Phe Thr Ile Ser Arg Asp Asn Ala Lys Asn
                    85                  90                  95

Thr Leu Tyr Leu Gln Met Ser Arg Leu Lys Ser Glu Asp Thr Ala Met
                100                 105                 110

Tyr Tyr Cys Ala Thr Asn Lys Asn Trp Asp Asp Tyr Tyr Asp Met Asp
                115                 120                 125

Tyr Trp Gly Gln Gly Thr Ser Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

-continued

```
Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465

<210> SEQ ID NO 42
<211> LENGTH: 239
<212> TYPE: PRT
<213> ORGANISM: Artificial sequence
<220> FEATURE:
<223> OTHER INFORMATION: /note = "mAb 0023, LC (mouse VL - human Kappa
      CL); Fab 0023, LC (mouse VL - human Kappa CL)"

<400> SEQUENCE: 42

Met Asp Ser Gln Ala Gln Val Leu Ile Leu Leu Leu Leu Trp Val Ser
1               5                   10                  15

Gly Ser Cys Gly Asp Ile Val Val Ser Gln Ser Pro Ser Ser Leu Ala
            20                  25                  30

Val Ser Ala Gly Glu Lys Val Thr Met Ser Cys Lys Ser Ser Gln Ser
```

35                  40                  45
Leu Leu Asn Ser Arg Thr Arg Lys Asn Tyr Leu Ala Trp Tyr Gln Gln
 50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Gln Ala Glu Asp Leu Ala Val Tyr
                100                 105                 110

Tyr Cys Lys Gln Ser Tyr Asn Leu Leu Thr Phe Gly Ala Gly Thr Lys
                115                 120                 125

Leu Glu Leu Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
                180                 185                 190

Ser Lys Asp Ser Thr Tyr Ser Leu Ser Ser Thr Leu Thr Leu Ser Lys
                195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 43
<211> LENGTH: 467
<212> TYPE: PRT
<213> ORGANISM: Artificial sequence
<220> FEATURE:
<223> OTHER INFORMATION: /note = "mAb 0051, HC (mouse VH-human IgG4 CH1-CH2-CH3)"

<400> SEQUENCE: 43

Met Gly Trp Ser Cys Ile Ile Phe Phe Leu Val Ala Thr Ala Thr Gly
 1               5                  10                  15

Val His Ser Gln Val Gln Leu Glu Gln Ser Gly Ala Glu Leu Val Arg
                20                  25                  30

Pro Gly Val Ser Val Lys Ile Ser Cys Lys Gly Ser Gly Tyr Thr Phe
                35                  40                  45

Thr Asp Tyr Ser Met His Trp Val Lys Gln Ser His Ala Lys Ser Leu
 50                  55                  60

Glu Trp Ile Gly Val Ile Ser Thr Tyr Tyr Gly Asp Val Arg Tyr Asn
 65                  70                  75                  80

Gln Lys Phe Lys Gly Lys Ala Thr Met Thr Val Asp Lys Ser Ser Ser
                 85                  90                  95

Thr Ala Tyr Met Ala Leu Ala Arg Leu Thr Ser Glu Asp Ser Ala Ile
                100                 105                 110

Tyr Tyr Cys Ala Arg Ala Pro Met Ile Thr Thr Gly Ala Trp Phe Ala
                115                 120                 125

Tyr Trp Gly Gln Gly Thr Leu Val Thr Val Ser Ala Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
    195                 200                 205

Val Thr Val Pro Ser Ser Leu Gly Thr Lys Thr Tyr Thr Cys Asn
210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465

<210> SEQ ID NO 44
<211> LENGTH: 234
<212> TYPE: PRT
<213> ORGANISM: Artificial sequence
<220> FEATURE:
<223> OTHER INFORMATION: /note = "mAb 0051, LC (mouse VL - human Kappa
      CL); Fab 0051, LC (mouse VL - human Kappa CL)"

<400> SEQUENCE: 44

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Ala Trp Tyr Gln Gln Lys Pro Gly Gln Ser Pro
 50                  55                  60

Lys Leu Leu Ile Asn Tyr Ala Ser Ser Arg Tyr Thr Gly Ile Pro Asp
 65                  70                  75                  80

Arg Phe Thr Gly Ser Gly Tyr Gly Thr Asp Phe Thr Phe Thr Ile Ser
                 85                  90                  95

Thr Val Gln Ala Glu Asp Leu Ala Val Tyr Phe Cys Gln Gln Asp Tyr
             100                 105                 110

Ser Ser Pro Tyr Thr Phe Gly Gly Gly Thr Lys Leu Glu Ile Glu Arg
         115                 120                 125

Thr Val Ala Ala Pro Ser Val Phe Ile Phe Pro Pro Ser Asp Glu Gln
 130                 135                 140

Leu Lys Ser Gly Thr Ala Ser Val Val Cys Leu Leu Asn Asn Phe Tyr
145                  150                 155                 160

Pro Arg Glu Ala Lys Val Gln Trp Lys Val Asp Asn Ala Leu Gln Ser
                 165                 170                 175

Gly Asn Ser Gln Glu Ser Val Thr Glu Gln Asp Ser Lys Asp Ser Thr
             180                 185                 190

Tyr Ser Leu Ser Ser Thr Leu Thr Leu Ser Lys Ala Asp Tyr Glu Lys
         195                 200                 205

His Lys Val Tyr Ala Cys Glu Val Thr His Gln Gly Leu Ser Ser Pro
 210                 215                 220

Val Thr Lys Ser Phe Asn Arg Gly Glu Cys
225                 230

<210> SEQ ID NO 45
<211> LENGTH: 468
<212> TYPE: PRT
<213> ORGANISM: Artificial sequence
<220> FEATURE:
<223> OTHER INFORMATION: /note = "mAb 0052, HC (mouse VH-human IgG4
      CH1-CH2-CH3)"

<400> SEQUENCE: 45

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Pro Met Lys
             20                  25                  30

Pro Gly Ala Ser Val Lys Ile Ser Cys Lys Ala Thr Gly Tyr Thr Phe
         35                  40                  45

Ser Ser His Trp Ile Glu Trp Ile Lys Gln Arg Pro Gly His Gly Leu
 50                  55                  60

Glu Trp Ile Gly Glu Ile Leu Pro Gly Ser Gly Asn Thr Asn Tyr Asn
65                  70                  75                  80

Glu Lys Phe Lys Gly Lys Ala Thr Phe Thr Ala Asp Thr Ser Ser Asn
                 85                  90                  95

Thr Ala Tyr Met Gln Leu Ser Ser Leu Thr Ser Glu Asp Ser Ala Val
             100                 105                 110

Tyr Cys Cys Ala Arg Gly Tyr Tyr Gly Leu Asn Tyr Asp Trp Tyr Phe
         115                 120                 125

Asp Val Trp Gly Ala Gly Thr Thr Val Thr Val Ser Ser Ala Ser Thr
 130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu

```
                165                 170                 175
Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys
465

<210> SEQ ID NO 46
<211> LENGTH: 234
<212> TYPE: PRT
<213> ORGANISM: Artificial sequence
<220> FEATURE:
<223> OTHER INFORMATION: /note = "mAb 0052, LC (mouse VL - human Kappa
      CL); mAb 0062, LC (mouse VL - human Kappa CL); Fab 0052, LC (mouse
      VL - human Kappa CL)"

<400> SEQUENCE: 46

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45
```

```
Ile Ser Asn Tyr Leu Asn Trp Tyr Gln Gln Lys Pro Asp Gly Thr Val
    50                  55                  60

Lys Leu Leu Ile Phe Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Glu Asp Ile Ala Thr Tyr Tyr Cys Gln Gln Asp Thr
            100                 105                 110

Lys Leu Pro Tyr Thr Phe Gly Gly Gly Thr Lys Leu Glu Met Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 47
<211> LENGTH: 459
<212> TYPE: PRT
<213> ORGANISM: Artificial sequence
<220> FEATURE:
<223> OTHER INFORMATION: /note = "mAb 0061, HC (mouse VH-human IgG4 CH1-
      CH2-CH3)"

<400> SEQUENCE: 47

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Asn Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
```

```
                    165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
            195                 200                 205

Gly Thr Lys Thr Tyr Thr Cys Asn Val Asp His Lys Pro Ser Asn Thr
        210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly Lys
    450                 455

<210> SEQ ID NO 48
<211> LENGTH: 238
<212> TYPE: PRT
<213> ORGANISM: Artificial sequence
<220> FEATURE:
<223> OTHER INFORMATION: /note = "mAb 0061, LC (mouse VL - human Kappa
      CL); Fab 0061, LC (mouse VL - human Kappa CL); mAb 0082, LC (mouse
      VL - human Kappa CL); Fab 0082, LC (mouse VL - human Kappa CL)"

<400> SEQUENCE: 48

Met Lys Leu Pro Val Gly Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Arg Asn Gly Asn Thr Tyr Phe His Trp Ala Leu Gln Lys Pro
        50                  55                  60
```

```
Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 49
<211> LENGTH: 468
<212> TYPE: PRT
<213> ORGANISM: Artificial sequence
<220> FEATURE:
<223> OTHER INFORMATION: /note = "mAb 0062, HC (mouse VH-human IgG4 CH1-
      CH2-CH3)"

<400> SEQUENCE: 49

Met Glu Trp Thr Trp Val Phe Leu Phe Leu Leu Ser Val Thr Ala Gly
 1               5                  10                  15

Val His Ser Gln Val Gln Leu Gln Gln Ser Gly Ala Glu Pro Met Lys
            20                  25                  30

Pro Gly Ala Ser Val Lys Ile Ser Cys Lys Ala Thr Gly Tyr Thr Phe
        35                  40                  45

Ser Ser His Trp Ile Glu Trp Ile Lys Gln Arg Pro Gly His Gly Leu
    50                  55                  60

Glu Trp Ile Gly Glu Ile Leu Pro Gly Ser Gly Asn Thr Asn Tyr Asn
 65                  70                  75                  80

Glu Lys Phe Lys Gly Lys Ala Thr Phe Thr Ala Asp Thr Ser Ser Asn
                 85                  90                  95

Thr Ala Tyr Met Gln Leu Ser Ser Leu Thr Ser Glu Asp Ser Ala Val
            100                 105                 110

Tyr Tyr Cys Ala Arg Gly Tyr Tyr Gly Leu Asn Tyr Asp Trp Tyr Phe
        115                 120                 125

Asp Val Trp Gly Ala Gly Thr Thr Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
```

```
              180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Lys Thr Tyr Thr Cys
        210                 215                 220
Asn Val Asp His Lys Pro Ser Asn Thr Lys Val Asp Lys Arg Val Glu
225                 230                 235                 240
Ser Lys Tyr Gly Pro Pro Cys Pro Pro Cys Pro Ala Pro Glu Phe Leu
                245                 250                 255
Gly Gly Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
Gln Glu Asp Pro Glu Val Gln Phe Asn Trp Tyr Val Asp Gly Val Glu
290                 295                 300
Val His Asn Ala Lys Thr Lys Pro Arg Glu Glu Gln Phe Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Gly Leu Pro Ser Ser
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Gln Glu Glu Met Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Arg Leu Thr
            420                 425                 430
Val Asp Lys Ser Arg Trp Gln Glu Gly Asn Val Phe Ser Cys Ser Val
        435                 440                 445
Met His Glu Ala Leu His Asn His Tyr Thr Gln Lys Ser Leu Ser Leu
    450                 455                 460
Ser Leu Gly Lys
465

<210> SEQ ID NO 50
<211> LENGTH: 459
<212> TYPE: PRT
<213> ORGANISM: Artificial sequence
<220> FEATURE:
<223> OTHER INFORMATION: /note = "mAb 0082, HC (mouse VH-human IgG4 CH1-
      CH2-CH3)"

<400> SEQUENCE: 50

Met Asp Phe Gly Leu Ile Phe Phe Ile Val Ala Leu Leu Lys Gly Val
1               5                   10                  15
Gln Cys Glu Val Lys Leu Leu Glu Ser Gly Gly Gly Leu Val Gln Pro
            20                  25                  30
Gly Gly Ser Leu Lys Leu Ser Cys Ala Ala Ser Gly Phe Asp Phe Ser
        35                  40                  45
Arg Tyr Trp Met Thr Trp Val Arg Gln Ala Pro Gly Lys Gly Leu Glu
    50                  55                  60
```

Trp Ile Gly Glu Ile Asn Pro Asp Ser Ser Thr Ile Asn Tyr Ala Pro
 65                  70                  75                  80

Ser Leu Lys Asp Lys Phe Ile Ile Ser Arg Asp Asn Ala Lys Asn Thr
                 85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly Lys
    450                 455

<210> SEQ ID NO 51
<211> LENGTH: 233
<212> TYPE: PRT

<213> ORGANISM: Artificial sequence
<220> FEATURE:
<223> OTHER INFORMATION: /note = "Fab 0012, mouse VH - human IgG4 CH1"

<400> SEQUENCE: 51

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
50                  55                  60

Trp Ile Gly Glu Ile Asn Pro Asp Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
210                 215                 220

Lys Val Asp Lys Arg Val Glu Ser Lys
225                 230
```

<210> SEQ ID NO 52
<211> LENGTH: 241
<212> TYPE: PRT
<213> ORGANISM: Artificial sequence
<220> FEATURE:
<223> OTHER INFORMATION: /note = "Fab 0023, mouse VH - human IgG4 CH1"

<400> SEQUENCE: 52

```
Met Asn Leu Gly Leu Ser Leu Ile Phe Leu Val Leu Val Leu Lys Gly
1               5                   10                  15

Val Gln Cys Glu Val Arg Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Phe Met Tyr Trp Ile Arg Gln Thr Pro Glu Lys Arg Leu
50                  55                  60

Glu Trp Val Ala Tyr Ile Ser Asn Gly Gly Asp Ser Ser Tyr Tyr Pro
65                  70                  75                  80

Asp Thr Val Lys Gly Arg Phe Thr Ile Ser Arg Asp Asn Ala Lys Asn
                85                  90                  95
```

```
Thr Leu Tyr Leu Gln Met Ser Arg Leu Lys Ser Glu Asp Thr Ala Met
            100                 105                 110
Tyr Tyr Cys Ala Thr Asn Lys Asn Trp Asp Asp Tyr Tyr Asp Met Asp
            115                 120                 125
Tyr Trp Gly Gln Gly Thr Ser Val Thr Val Ser Ser Ala Ser Thr Lys
130                 135                 140
Gly Pro Ser Val Phe Pro Leu Ala Pro Cys Ser Arg Ser Thr Ser Glu
145                 150                 155                 160
Ser Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
            195                 200                 205
Val Thr Val Pro Ser Ser Ser Leu Gly Thr Lys Thr Tyr Thr Cys Asn
            210                 215                 220
Val Asp His Lys Pro Ser Asn Thr Lys Val Asp Lys Arg Val Glu Ser
225                 230                 235                 240
Lys

<210> SEQ ID NO 53
<211> LENGTH: 241
<212> TYPE: PRT
<213> ORGANISM: Artificial sequence
<220> FEATURE:
<223> OTHER INFORMATION: /note = "Fab 0051, mouse VH - human IgG4 CH1"

<400> SEQUENCE: 53

Met Gly Trp Ser Cys Ile Ile Phe Phe Leu Val Ala Thr Ala Thr Gly
1               5                   10                  15
Val His Ser Gln Val Gln Leu Glu Gln Ser Gly Ala Glu Leu Val Arg
            20                  25                  30
Pro Gly Val Ser Val Lys Ile Ser Cys Lys Gly Ser Gly Tyr Thr Phe
            35                  40                  45
Thr Asp Tyr Ser Met His Trp Val Lys Gln Ser His Ala Lys Ser Leu
50                  55                  60
Glu Trp Ile Gly Val Ile Ser Thr Tyr Tyr Gly Asp Val Arg Tyr Asn
65                  70                  75                  80
Gln Lys Phe Lys Gly Lys Ala Thr Met Thr Val Asp Lys Ser Ser Ser
                85                  90                  95
Thr Ala Tyr Met Ala Leu Ala Arg Leu Thr Ser Glu Asp Ser Ala Ile
            100                 105                 110
Tyr Tyr Cys Ala Arg Ala Pro Met Ile Thr Thr Gly Ala Trp Phe Ala
            115                 120                 125
Tyr Trp Gly Gln Gly Thr Leu Val Thr Val Ser Ala Ala Ser Thr Lys
130                 135                 140
Gly Pro Ser Val Phe Pro Leu Ala Pro Cys Ser Arg Ser Thr Ser Glu
145                 150                 155                 160
Ser Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
            195                 200                 205
Val Thr Val Pro Ser Ser Ser Leu Gly Thr Lys Thr Tyr Thr Cys Asn
```

```
                 210                 215                 220

Val Asp His Lys Pro Ser Asn Thr Lys Val Asp Lys Arg Val Glu Ser
225                 230                 235                 240

Lys

<210> SEQ ID NO 54
<211> LENGTH: 242
<212> TYPE: PRT
<213> ORGANISM: Artificial sequence
<220> FEATURE:
<223> OTHER INFORMATION: /note = "Fab 0052, mouse VH - human IgG4 CH1"

<400> SEQUENCE: 54

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Pro Met Lys
                20                  25                  30

Pro Gly Ala Ser Val Lys Ile Ser Cys Lys Ala Thr Gly Tyr Thr Phe
            35                  40                  45

Ser Ser His Trp Ile Glu Trp Ile Lys Gln Arg Pro Gly His Gly Leu
        50                  55                  60

Glu Trp Ile Gly Glu Ile Leu Pro Gly Ser Gly Asn Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Cys Cys Ala Arg Gly Tyr Tyr Gly Leu Asn Tyr Asp Trp Tyr Phe
        115                 120                 125

Asp Val Trp Gly Ala Gly Thr Thr Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys

<210> SEQ ID NO 55
<211> LENGTH: 233
<212> TYPE: PRT
<213> ORGANISM: Artificial sequence
<220> FEATURE:
<223> OTHER INFORMATION: /note = "Fab 0082, mouse VH - human IgG4 CH1"

<400> SEQUENCE: 55

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
                20                  25                  30
```

Gly Gly Ser Leu Lys Leu Ser Cys Ala Ala Ser Gly Phe Asp Phe Ser
                35                  40                  45

Arg Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Ala Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
                100                 105                 110

Tyr Cys Ala Ser Gly Val Phe Thr Ser Trp Gly Gln Gly Thr Leu Val
                115                 120                 125

Thr Val Ser Ala Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
                195                 200                 205

Gly Thr Lys Thr Tyr Thr Cys Asn Val Asp His Lys Pro Ser Asn Thr
210                 215                 220

Lys Val Asp Lys Arg Val Glu Ser Lys
225                 230

<210> SEQ ID NO 56
<211> LENGTH: 240
<212> TYPE: PRT
<213> ORGANISM: Artificial sequence
<220> FEATURE:
<223> OTHER INFORMATION: /note = "Fab AP-3, mouse VH - human IgG4 CH1"

<400> SEQUENCE: 56

Met Glu Trp Ser Gly Val Phe Ile Phe Leu Leu Ser Val Thr Ala Asp
1               5                   10                  15

Val His Ser Gln Val Gln Leu Gln Gln Ser Gly Ala Glu Leu Val Arg
                20                  25                  30

Pro Gly Thr Ser Val Lys Ile Ser Cys Lys Ala Ser Gly Tyr Thr Phe
                35                  40                  45

Thr Asn Tyr Trp Leu Gly Trp Val Lys Gln Arg Pro Gly His Gly Leu
    50                  55                  60

Glu Trp Ile Gly Asp Ile Tyr Pro Gly Gly Gly Tyr Asn Lys Tyr Asn
65                  70                  75                  80

Glu Asn Phe Lys Gly Lys Ala Thr Leu Thr Ala Asp Thr Ser Ser Ser
                85                  90                  95

Thr Ala Tyr Met Gln Leu Ser Ser Leu Thr Ser Glu Asp Ser Ala Val
                100                 105                 110

Tyr Phe Cys Ala Arg Glu Tyr Gly Asn Tyr Asp Tyr Ala Met Asp Ser
                115                 120                 125

Trp Gly Gln Gly Thr Ser Val Thr Val Ser Ser Ala Ser Thr Lys Gly
                130                 135                 140

Pro Ser Val Phe Pro Leu Ala Pro Cys Ser Arg Ser Thr Ser Glu Ser
145                 150                 155                 160

```
Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Lys Thr Tyr Thr Cys Asn Val
        210                 215                 220

Asp His Lys Pro Ser Asn Thr Lys Val Asp Lys Arg Val Glu Ser Lys
225                 230                 235                 240

<210> SEQ ID NO 57
<211> LENGTH: 239
<212> TYPE: PRT
<213> ORGANISM: Artificial sequence
<220> FEATURE:
<223> OTHER INFORMATION: /note = "Fab AP-3, LC (mouse VL - human Kappa
      CL)"

<400> SEQUENCE: 57

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Ser Arg Ser
        35                  40                  45

Leu Leu His Ser Asn Gly Asn Thr Tyr Leu Cys Trp Phe Leu Gln Arg
50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Phe Thr Phe Gly Ser Gly Thr Lys
        115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235

<210> SEQ ID NO 58
<211> LENGTH: 239
<212> TYPE: PRT
<213> ORGANISM: Artificial sequence
<220> FEATURE:
<223> OTHER INFORMATION: /note = "Fab AP-3.LC.C34S, LC (mouse VL - human
```

Kappa CL)"

<400> SEQUENCE: 58

Met Arg Cys Leu Ala Glu Phe Leu Gly Leu Val Leu Trp Ile Pro
1               5                   10                  15

Gly Ala Ile Gly Asp Ile Val Met Thr Gln Ala Pro Ser Val Pro
            20                  25                  30

Val Thr Pro Gly Glu Ser Val Ser Ile Ser Cys Arg Ser Arg Ser
        35                  40                  45

Leu Leu His Ser Asn Gly Asn Thr Tyr Leu Ser Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Phe Thr Phe Gly Ser Gly Thr Lys
            115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 59
<211> LENGTH: 7
<212> TYPE: PRT
<213> ORGANISM: Artificial sequence
<220> FEATURE:
<223> OTHER INFORMATION: /note = "linker, L2"

<400> SEQUENCE: 59

Gly Ser Gly Gly Gly Gly Ser
1               5

<210> SEQ ID NO 60
<211> LENGTH: 12
<212> TYPE: PRT
<213> ORGANISM: Artificial sequence
<220> FEATURE:
<223> OTHER INFORMATION: /note = "linker, L3"

<400> SEQUENCE: 60

Gly Ser Gly Gly Gly Ser Gly Gly Gly Gly Ser
1               5                   10

<210> SEQ ID NO 61
<211> LENGTH: 17
<212> TYPE: PRT

<213> ORGANISM: Artificial sequence
<220> FEATURE:
<223> OTHER INFORMATION: /note = "linker, L4a"

<400> SEQUENCE: 61

Gly Ser Gly Gly Gly Gly Ser Gly Gly Gly Gly Ser Gly Gly Gly Gly
1               5                   10                  15
Ser

<210> SEQ ID NO 62
<211> LENGTH: 17
<212> TYPE: PRT
<213> ORGANISM: Artificial sequence
<220> FEATURE:
<223> OTHER INFORMATION: /note = "linker, L4b"

<400> SEQUENCE: 62

Gly Gly Gly Gly Ser Gly Gly Gly Gly Ser Gly Gly Gly Gly Ser Gly
1               5                   10                  15
Ser

<210> SEQ ID NO 63
<211> LENGTH: 22
<212> TYPE: PRT
<213> ORGANISM: Artificial sequence
<220> FEATURE:
<223> OTHER INFORMATION: /note = "linker, L5"

<400> SEQUENCE: 63

Gly Gly Gly Gly Ser Gly Ser Gly Gly Gly Gly Ser Gly Gly Gly Gly
1               5                   10                  15
Ser Gly Gly Gly Gly Ser
            20

<210> SEQ ID NO 64
<211> LENGTH: 27
<212> TYPE: PRT
<213> ORGANISM: Artificial sequence
<220> FEATURE:
<223> OTHER INFORMATION: /note = "linker, L6"

<400> SEQUENCE: 64

Gly Gly Gly Gly Ser Gly Gly Gly Gly Ser Gly Ser Gly Gly Gly Gly
1               5                   10                  15
Ser Gly Gly Gly Gly Ser Gly Gly Gly Gly Ser
            20                  25

<210> SEQ ID NO 65
<211> LENGTH: 32
<212> TYPE: PRT
<213> ORGANISM: Artificial sequence
<220> FEATURE:
<223> OTHER INFORMATION: /note = "linker, L7"

<400> SEQUENCE: 65

Gly Gly Gly Gly Ser Gly Gly Gly Gly Ser Gly Gly Gly Gly Ser Gly
1               5                   10                  15
Ser Gly Gly Gly Gly Ser Gly Gly Gly Gly Ser Gly Gly Gly Gly Ser
            20                  25                  30

<210> SEQ ID NO 66
<211> LENGTH: 37
<212> TYPE: PRT
<213> ORGANISM: Artificial sequence
<220> FEATURE:
<223> OTHER INFORMATION: /note = "linker, L8"

<400> SEQUENCE: 66

Gly Gly Gly Gly Ser Gly Gly Gly Ser Gly Gly Gly Gly Ser Gly
1               5                   10                  15

Gly Gly Gly Ser Gly Ser Gly Gly Gly Ser Gly Gly Gly Gly Ser
            20                  25                  30

Gly Gly Gly Gly Ser
        35

<210> SEQ ID NO 67
<211> LENGTH: 42
<212> TYPE: PRT
<213> ORGANISM: Artificial sequence
<220> FEATURE:
<223> OTHER INFORMATION: /note = "linker, L9"

<400> SEQUENCE: 67

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Ser Gly Gly Gly Gly Ser
            20                  25                  30

Gly Gly Gly Gly Ser Gly Gly Gly Gly Ser
        35                  40

<210> SEQ ID NO 68
<211> LENGTH: 16
<212> TYPE: PRT
<213> ORGANISM: Artificial sequence
<220> FEATURE:
<223> OTHER INFORMATION: /note = "linker, L10"

<400> SEQUENCE: 68

Tyr Gly Pro Pro Ser Pro Ser Ser Pro Ala Pro Glu Phe Leu Gly Gly
1               5                   10                  15

<210> SEQ ID NO 69
<211> LENGTH: 12
<212> TYPE: PRT
<213> ORGANISM: Artificial sequence
<220> FEATURE:
<223> OTHER INFORMATION: /note = "Purification tag, HPC4 tag"

<400> SEQUENCE: 69

Glu Asp Gln Val Asp Pro Arg Leu Ile Asp Gly Lys
1               5                   10

<210> SEQ ID NO 70
<211> LENGTH: 28
<212> TYPE: DNA
<213> ORGANISM: Artificial sequence
<220> FEATURE:
<223> OTHER INFORMATION: /note = "primer no. 50"

<400> SEQUENCE: 70
caacacttac ttgtcctggt tcctgcag                                    28

<210> SEQ ID NO 71
<211> LENGTH: 28
<212> TYPE: DNA
<213> ORGANISM: Artificial sequence
<220> FEATURE:
<223> OTHER INFORMATION: /note = "primer no. 51"

```
<400> SEQUENCE: 71
ctgcaggaac caggacaagt aagtgttg                                          28

<210> SEQ ID NO 72
<211> LENGTH: 36
<212> TYPE: DNA
<213> ORGANISM: Artificial sequence
<220> FEATURE:
<223> OTHER INFORMATION: /note = "primer no. 69"

<400> SEQUENCE: 72
gctctagact aacactcatt cctgttgaag ctcttg                                 36

<210> SEQ ID NO 73
<211> LENGTH: 39
<212> TYPE: DNA
<213> ORGANISM: Artificial sequence
<220> FEATURE:
<223> OTHER INFORMATION: /note = "primer no. 98"

<400> SEQUENCE: 73
tttaaagaat tcctaacact ctcccctgtt gaagctctt                              39

<210> SEQ ID NO 74
<211> LENGTH: 39
<212> TYPE: DNA
<213> ORGANISM: Artificial sequence
<220> FEATURE:
<223> OTHER INFORMATION: /note = "primer no. 100"

<400> SEQUENCE: 74
tttaaagaat tctcatttac ccagagacag ggagaggct                              39

<210> SEQ ID NO 75
<211> LENGTH: 21
<212> TYPE: DNA
<213> ORGANISM: Artificial sequence
<220> FEATURE:
<223> OTHER INFORMATION: /note = "primer no. 312"

<400> SEQUENCE: 75
gtctaccaca acacacgtga c                                                 21

<210> SEQ ID NO 76
<211> LENGTH: 27
<212> TYPE: DNA
<213> ORGANISM: Artificial sequence
<220> FEATURE:
<223> OTHER INFORMATION: /note = "primer no. 339"

<400> SEQUENCE: 76
actggatggt gggaagatgg atacagt                                           27

<210> SEQ ID NO 77
<211> LENGTH: 27
<212> TYPE: DNA
<213> ORGANISM: Artificial sequence
<220> FEATURE:
<223> OTHER INFORMATION: /note = "primer no. 341"

<400> SEQUENCE: 77
agatccaggg gctagcggat agacaga                                           27

<210> SEQ ID NO 78
<211> LENGTH: 30
```

```
<212> TYPE: DNA
<213> ORGANISM: Artificial sequence
<220> FEATURE:
<223> OTHER INFORMATION: /note = "primer no. 348"

<400> SEQUENCE: 78
ggagctggtg gtggcatctc aggacctttg                              30

<210> SEQ ID NO 79
<211> LENGTH: 30
<212> TYPE: DNA
<213> ORGANISM: Artificial sequence
<220> FEATURE:
<223> OTHER INFORMATION: /note = "primer no. 347"

<400> SEQUENCE: 79
cctgtaggac cagagggctc caaggacact                              30

<210> SEQ ID NO 80
<211> LENGTH: 48
<212> TYPE: DNA
<213> ORGANISM: Artificial sequence
<220> FEATURE:
<223> OTHER INFORMATION: /note = "primer no. 448"

<400> SEQUENCE: 80
tttaaaaagc ttgccgccac catggagacc cctgcctggc cccgggtc          48

<210> SEQ ID NO 81
<211> LENGTH: 48
<212> TYPE: DNA
<213> ORGANISM: Artificial sequence
<220> FEATURE:
<223> OTHER INFORMATION: /note = "primer no. 449"

<400> SEQUENCE: 81
tttaaagaat tcctattctc taaattcccc tttctcctgg cccataca          48

<210> SEQ ID NO 82
<211> LENGTH: 75
<212> TYPE: DNA
<213> ORGANISM: Artificial sequence
<220> FEATURE:
<223> OTHER INFORMATION: /note = "primer no. 466"

<400> SEQUENCE: 82
ggaggtggcg ggtctggtgg cgggggatca ggcgggggag gttcctcagg cactacaaat    60
actgtggcag catat                                                    75

<210> SEQ ID NO 83
<211> LENGTH: 75
<212> TYPE: DNA
<213> ORGANISM: Artificial sequence
<220> FEATURE:
<223> OTHER INFORMATION: /note = "primer no. 467"

<400> SEQUENCE: 83
ggaacctccc ccgcctgatc ccccgccacc agacccgcca cctccttctc taaattcccc    60
tttctcctgg cccat                                                    75

<210> SEQ ID NO 84
<211> LENGTH: 65
<212> TYPE: DNA
<213> ORGANISM: Artificial sequence
<220> FEATURE:
```

-continued

```
<223> OTHER INFORMATION: /note = "primer no. 483"

<400> SEQUENCE: 84
aaatttaagc ttactagtcc tgcaggttta acgaatttg gatccggagg tggcgggtct    60
ggtgg                                                              65

<210> SEQ ID NO 85
<211> LENGTH: 48
<212> TYPE: DNA
<213> ORGANISM: Artificial sequence
<220> FEATURE:
<223> OTHER INFORMATION: /note = "primer no. 484"

<400> SEQUENCE: 85
gaatttagcg gccgcgaatt cggatccgga acctcccccg cctgatcc               48

<210> SEQ ID NO 86
<211> LENGTH: 81
<212> TYPE: DNA
<213> ORGANISM: Artificial sequence
<220> FEATURE:
<223> OTHER INFORMATION: /note = "primer no. 485"

<400> SEQUENCE: 86
aaatttgaat tcttacttgc cgtcgatcag tctggggtcc acctggtcct cacactctcc    60
cctgttgaag ctctttgtga c                                            81

<210> SEQ ID NO 87
<211> LENGTH: 30
<212> TYPE: DNA
<213> ORGANISM: Artificial sequence
<220> FEATURE:
<223> OTHER INFORMATION: /note = "primer no. 486"

<400> SEQUENCE: 87
acggatctct agcaagcttc gtacggtggc                                   30

<210> SEQ ID NO 88
<211> LENGTH: 81
<212> TYPE: DNA
<213> ORGANISM: Artificial sequence
<220> FEATURE:
<223> OTHER INFORMATION: /note = "primer no. 487"

<400> SEQUENCE: 88
aaatttgaat tcttacttgc cgtcgatcag tctggggtcc acctggtcct ctttggactc    60
aactctcttg tccaccttgg t                                            81

<210> SEQ ID NO 89
<211> LENGTH: 45
<212> TYPE: DNA
<213> ORGANISM: Artificial sequence
<220> FEATURE:
<223> OTHER INFORMATION: /note = "primer no. 488"

<400> SEQUENCE: 89
aaatttgaat tcttatttgg actcaactct cttgtccacc ttggt                  45

<210> SEQ ID NO 90
<211> LENGTH: 30
<212> TYPE: DNA
<213> ORGANISM: Artificial sequence
<220> FEATURE:
<223> OTHER INFORMATION: /note = "primer no. 489"
```

```
<400> SEQUENCE: 90
acggatctct agcaagcttg ctagcaccaa                                    30

<210> SEQ ID NO 91
<211> LENGTH: 54
<212> TYPE: DNA
<213> ORGANISM: Artificial sequence
<220> FEATURE:
<223> OTHER INFORMATION: /note = "primer no. 490"

<400> SEQUENCE: 91
aaatttaagc ttgccgccac catggatttt gggctgattt ttttattgt tgct          54

<210> SEQ ID NO 92
<211> LENGTH: 45
<212> TYPE: DNA
<213> ORGANISM: Artificial sequence
<220> FEATURE:
<223> OTHER INFORMATION: /note = "primer no. 491"

<400> SEQUENCE: 92
aaatttgcta gctgcagaga cagtgaccag agtcccttgg cccca                   45

<210> SEQ ID NO 93
<211> LENGTH: 51
<212> TYPE: DNA
<213> ORGANISM: Artificial sequence
<220> FEATURE:
<223> OTHER INFORMATION: /note = "primer no. 492"

<400> SEQUENCE: 93
aaatttaagc ttgccgccac catgaagtca cagacccagg tcttcgtatt t            51

<210> SEQ ID NO 94
<211> LENGTH: 51
<212> TYPE: DNA
<213> ORGANISM: Artificial sequence
<220> FEATURE:
<223> OTHER INFORMATION: /note = "primer no. 493"

<400> SEQUENCE: 94
aaatttaagc ttgccgccac catgaagttg cctgttgggc tgttggtgct g            51

<210> SEQ ID NO 95
<211> LENGTH: 38
<212> TYPE: DNA
<213> ORGANISM: Artificial sequence
<220> FEATURE:
<223> OTHER INFORMATION: /note = "primer no. 494"

<400> SEQUENCE: 95
aaatttcgta cgttctattt ccagcttggt cccccctc                           38

<210> SEQ ID NO 96
<211> LENGTH: 42
<212> TYPE: DNA
<213> ORGANISM: Artificial sequence
<220> FEATURE:
<223> OTHER INFORMATION: /note = "primer no. 495"

<400> SEQUENCE: 96
aaatttcgta cgtttttattt ccagcttggt ccccccctccg aa                    42

<210> SEQ ID NO 97
```

```
<211> LENGTH: 69
<212> TYPE: DNA
<213> ORGANISM: Artificial sequence
<220> FEATURE:
<223> OTHER INFORMATION: /note = "primer no. 512"

<400> SEQUENCE: 97
aaatttggat ccgaggtgaa acttctcgag tctggaggtg gcctggtgca gcctggaggt      60
tccctgaaa                                                              69

<210> SEQ ID NO 98
<211> LENGTH: 36
<212> TYPE: DNA
<213> ORGANISM: Artificial sequence
<220> FEATURE:
<223> OTHER INFORMATION: /note = "primer no. 513"

<400> SEQUENCE: 98
tttaaaggat tctttaccca gagacaggga gaggct                                36

<210> SEQ ID NO 99
<211> LENGTH: 42
<212> TYPE: DNA
<213> ORGANISM: Artificial sequence
<220> FEATURE:
<223> OTHER INFORMATION: /note = "primer no. 514"

<400> SEQUENCE: 99
aaatttggat cctttggact caactctctt gtccaccttg gt                         42

<210> SEQ ID NO 100
<211> LENGTH: 54
<212> TYPE: DNA
<213> ORGANISM: Artificial sequence
<220> FEATURE:
<223> OTHER INFORMATION: /note = "primer no. 546"

<400> SEQUENCE: 100
aaatttaagc ttgccgccac catgaacttg gggctcagct tgattttcct tgtc            54

<210> SEQ ID NO 101
<211> LENGTH: 42
<212> TYPE: DNA
<213> ORGANISM: Artificial sequence
<220> FEATURE:
<223> OTHER INFORMATION: /note = "primer no. 547"

<400> SEQUENCE: 101
aaatttgcta gctgaggaga cggtgactga ggttccttga cc                         42

<210> SEQ ID NO 102
<211> LENGTH: 54
<212> TYPE: DNA
<213> ORGANISM: Artificial sequence
<220> FEATURE:
<223> OTHER INFORMATION: /note = "primer no. 548"

<400> SEQUENCE: 102
aaatttaagc ttgccgccac catggattca caggcccagg ttcttatatt gctg            54

<210> SEQ ID NO 103
<211> LENGTH: 42
<212> TYPE: DNA
<213> ORGANISM: Artificial sequence
<220> FEATURE:
<223> OTHER INFORMATION: /note = "primer no. 549"
```

```
<400> SEQUENCE: 103
aaatttcgta cgtttcagct ccagcttggt cccagcaccg aa                           42

<210> SEQ ID NO 104
<211> LENGTH: 48
<212> TYPE: DNA
<213> ORGANISM: Artificial sequence
<220> FEATURE:
<223> OTHER INFORMATION: /note = "primer no. 551"

<400> SEQUENCE: 104
aaatttaaat ttggatccga tgttgtgatg acccaaactc cactctcc                     48

<210> SEQ ID NO 105
<211> LENGTH: 42
<212> TYPE: DNA
<213> ORGANISM: Artificial sequence
<220> FEATURE:
<223> OTHER INFORMATION: /note = "primer no. 552"

<400> SEQUENCE: 105
aaatttaaat ttggatccac actctcccct gttgaagctc tt                           42

<210> SEQ ID NO 106
<211> LENGTH: 54
<212> TYPE: DNA
<213> ORGANISM: Artificial sequence
<220> FEATURE:
<223> OTHER INFORMATION: /note = "primer no. 572"

<400> SEQUENCE: 106
aaatttaagc ttgccgccac catggatttt gggctgattt ttttattgt tgct               54

<210> SEQ ID NO 107
<211> LENGTH: 49
<212> TYPE: DNA
<213> ORGANISM: Artificial sequence
<220> FEATURE:
<223> OTHER INFORMATION: /note = "primer no. 574"

<400> SEQUENCE: 107
aaatttaagc ttgccgccac catgaagttg cctgttgggc tgttggtgc                    49

<210> SEQ ID NO 108
<211> LENGTH: 84
<212> TYPE: DNA
<213> ORGANISM: Artificial sequence
<220> FEATURE:
<223> OTHER INFORMATION: /note = "primer no. 583"

<400> SEQUENCE: 108
aaatttggat ccggaacctc ccccgcctga tccccgcca ccagaccgc cacctccaca          60 ctctcccctg ttgaagctct ttgt                                               84

<210> SEQ ID NO 109
<211> LENGTH: 99
<212> TYPE: DNA
<213> ORGANISM: Artificial sequence
<220> FEATURE:
<223> OTHER INFORMATION: /note = "primer no. 584"

<400> SEQUENCE: 109
aaatttggat ccagacccgc cacctccgga acctcccccg cctgatcccc cgccaccaga        60
```

```
cccgccacct ccacactctc ccctgttgaa gctctttgt                              99
```

<210> SEQ ID NO 110
<211> LENGTH: 69
<212> TYPE: DNA
<213> ORGANISM: Artificial sequence
<220> FEATURE:
<223> OTHER INFORMATION: /note = "primer no. 585"

<400> SEQUENCE: 110

```
aaatttggat cctgatcccc cgccaccaga cccgccacct ccacactctc ccctgttgaa       60
gctctttgt                                                              69
```

<210> SEQ ID NO 111
<211> LENGTH: 69
<212> TYPE: DNA
<213> ORGANISM: Artificial sequence
<220> FEATURE:
<223> OTHER INFORMATION: /note = "primer no. 586"

<400> SEQUENCE: 111

```
aaatttggat ccggtggcgg gggatcaggc gggggaggtt cctcaggcac tacaaatact       60
gtggcagca                                                              69
```

<210> SEQ ID NO 112
<211> LENGTH: 87
<212> TYPE: DNA
<213> ORGANISM: Artificial sequence
<220> FEATURE:
<223> OTHER INFORMATION: /note = "primer no. 587"

<400> SEQUENCE: 112

```
aaatttggat ccggaacctc ccccgcctga tcccccgcca ccagacccgc cacctccttt       60
acccagagac agggagaggc tcttctg                                          87
```

<210> SEQ ID NO 113
<211> LENGTH: 102
<212> TYPE: DNA
<213> ORGANISM: Artificial sequence
<220> FEATURE:
<223> OTHER INFORMATION: /note = "primer no. 588"

<400> SEQUENCE: 113

```
aaatttggat ccagacccgc cacctccgga acctcccccg cctgatcccc cgccaccaga       60
cccgccacct cctttaccca gagacaggga gaggctcttc tg                        102
```

<210> SEQ ID NO 114
<211> LENGTH: 72
<212> TYPE: DNA
<213> ORGANISM: Artificial sequence
<220> FEATURE:
<223> OTHER INFORMATION: /note = "primer no. 589"

<400> SEQUENCE: 114

```
aaatttggat cctgatcccc cgccaccaga cccgccacct cctttaccca gagacaggga       60
gaggctcttc tg                                                          72
```

<210> SEQ ID NO 115
<211> LENGTH: 54
<212> TYPE: DNA
<213> ORGANISM: Artificial sequence
<220> FEATURE:
<223> OTHER INFORMATION: /note = "primer no. 590"

```
<400> SEQUENCE: 115
aaatttggat ccagacccgc cacctccaca ctctcccctg ttgaagctct ttgt         54

<210> SEQ ID NO 116
<211> LENGTH: 114
<212> TYPE: DNA
<213> ORGANISM: Artificial sequence
<220> FEATURE:
<223> OTHER INFORMATION: /note = "primer no. 591"

<400> SEQUENCE: 116
aaatttggat ccagacccgc cacctccaga cccgccacct ccggaacctc ccccgcctga   60
tcccccgcca ccagacccgc cacctccaca ctctcccctg ttgaagctct ttgt        114

<210> SEQ ID NO 117
<211> LENGTH: 57
<212> TYPE: DNA
<213> ORGANISM: Artificial sequence
<220> FEATURE:
<223> OTHER INFORMATION: /note = "primer no. 592"

<400> SEQUENCE: 117
aaatttggat cctgatcccc cgccaccttt acccagagac agggagaggc tcttctg      57

<210> SEQ ID NO 118
<211> LENGTH: 117
<212> TYPE: DNA
<213> ORGANISM: Artificial sequence
<220> FEATURE:
<223> OTHER INFORMATION: /note = "primer no. 593"

<400> SEQUENCE: 118
aaatttggat ccagacccgc cacctccaga cccgccacct ccggaacctc ccccgcctga   60
tcccccgcca ccagacccgc cacctccttt acccagagac agggagaggc tcttctg     117

<210> SEQ ID NO 119
<211> LENGTH: 45
<212> TYPE: DNA
<213> ORGANISM: Artificial sequence
<220> FEATURE:
<223> OTHER INFORMATION: /note = "primer no. 598"

<400> SEQUENCE: 119
ggaaacacct attttcattg ggccctgcag aaaccaggcc agtct                   45

<210> SEQ ID NO 120
<211> LENGTH: 45
<212> TYPE: DNA
<213> ORGANISM: Artificial sequence
<220> FEATURE:
<223> OTHER INFORMATION: /note = "primer no. 599"

<400> SEQUENCE: 120
agactggcct ggtttctgca gggcccaatg aaaataggtg tttcc                   45

<210> SEQ ID NO 121
<211> LENGTH: 36
<212> TYPE: DNA
<213> ORGANISM: Artificial sequence
<220> FEATURE:
<223> OTHER INFORMATION: /note = "primer no. 610"

<400> SEQUENCE: 121
```
gctctagact aacactcatt cctgttgaag ctcttg　　　　　　　　　　　　　　　36

<210> SEQ ID NO 122
<211> LENGTH: 38
<212> TYPE: DNA
<213> ORGANISM: Artificial sequence
<220> FEATURE:
<223> OTHER INFORMATION: /note = "primer no. 613"

<400> SEQUENCE: 122
aaaaatctag aatagacaga tgggggtgtc gttttggc　　　　　　　　　　　　　38

<210> SEQ ID NO 123
<211> LENGTH: 34
<212> TYPE: DNA
<213> ORGANISM: Artificial sequence
<220> FEATURE:
<223> OTHER INFORMATION: /note = "primer no. 614"

<400> SEQUENCE: 123
aaaaatctag acttgaccag gcatcctaga gtca　　　　　　　　　　　　　　　34

<210> SEQ ID NO 124
<211> LENGTH: 35
<212> TYPE: DNA
<213> ORGANISM: Artificial sequence
<220> FEATURE:
<223> OTHER INFORMATION: /note = "primer no. 615"

<400> SEQUENCE: 124
aaaaatctag aaggggccag tggatagact gatgg　　　　　　　　　　　　　　35

<210> SEQ ID NO 125
<211> LENGTH: 35
<212> TYPE: DNA
<213> ORGANISM: Artificial sequence
<220> FEATURE:
<223> OTHER INFORMATION: /note = "primer no. 616"

<400> SEQUENCE: 125
aaaaatctag aagggaccaa gggatagaca gatgg　　　　　　　　　　　　　　35

<210> SEQ ID NO 126
<211> LENGTH: 50
<212> TYPE: DNA
<213> ORGANISM: Artificial sequence
<220> FEATURE:
<223> OTHER INFORMATION: /note = "primer no. 617"

<400> SEQUENCE: 126
aaatttaagc ttgccgccac catggaatgg acctgggtct ttctcttcct　　　　　　50

<210> SEQ ID NO 127
<211> LENGTH: 39
<212> TYPE: DNA
<213> ORGANISM: Artificial sequence
<220> FEATURE:
<223> OTHER INFORMATION: /note = "primer no. 618"

<400> SEQUENCE: 127
aaatttgcta gctgaggaga cggtgaccgt ggtccctgc　　　　　　　　　　　　39

<210> SEQ ID NO 128
<211> LENGTH: 48
<212> TYPE: DNA
<213> ORGANISM: Artificial sequence

```
<220> FEATURE:
<223> OTHER INFORMATION: /note = "primer no. 619"

<400> SEQUENCE: 128
aaatttaagc ttgccgccac catgatgtcc tctgctcagt tccttggt         48

<210> SEQ ID NO 129
<211> LENGTH: 39
<212> TYPE: DNA
<213> ORGANISM: Artificial sequence
<220> FEATURE:
<223> OTHER INFORMATION: /note = "primer no. 620"

<400> SEQUENCE: 129
aaatttcgta cgtttcatct ccagtttggt ccccctcc                   39

<210> SEQ ID NO 130
<211> LENGTH: 50
<212> TYPE: DNA
<213> ORGANISM: Artificial sequence
<220> FEATURE:
<223> OTHER INFORMATION: /note = "primer no. 627"

<400> SEQUENCE: 130
aaatttaagc ttgccgccac catgggttgg agctgtatca tcttctttct       50

<210> SEQ ID NO 131
<211> LENGTH: 39
<212> TYPE: DNA
<213> ORGANISM: Artificial sequence
<220> FEATURE:
<223> OTHER INFORMATION: /note = "primer no. 628"

<400> SEQUENCE: 131
aaatttgcta gctgcagaga cagtgaccag agtcccttg                  39

<210> SEQ ID NO 132
<211> LENGTH: 45
<212> TYPE: DNA
<213> ORGANISM: Artificial sequence
<220> FEATURE:
<223> OTHER INFORMATION: /note = "primer no. 682"

<400> SEQUENCE: 132
gatagcagta cgataaacta tacccatct ctaaaggata aattc            45

<210> SEQ ID NO 133
<211> LENGTH: 45
<212> TYPE: DNA
<213> ORGANISM: Artificial sequence
<220> FEATURE:
<223> OTHER INFORMATION: /note = "primer no. 683"

<400> SEQUENCE: 133
gaatttatcc tttagagatg ggttatagtt tatcgtactg ctatc           45

<210> SEQ ID NO 134
<211> LENGTH: 45
<212> TYPE: DNA
<213> ORGANISM: Artificial sequence
<220> FEATURE:
<223> OTHER INFORMATION: /note = "primer no. 684"

<400> SEQUENCE: 134
tctgaggact ctgccgtcta ttactgtgca agagggtact acggt           45
```

<210> SEQ ID NO 135
<211> LENGTH: 45
<212> TYPE: DNA
<213> ORGANISM: Artificial sequence
<220> FEATURE:
<223> OTHER INFORMATION: /note = "primer no. 685"

<400> SEQUENCE: 135
accgtagtac cctcttgcac agtaatagac ggcagagtcc tcaga                45

<210> SEQ ID NO 136
<211> LENGTH: 81
<212> TYPE: DNA
<213> ORGANISM: Artificial sequence
<220> FEATURE:
<223> OTHER INFORMATION: /note = "primer no. 686"

<400> SEQUENCE: 136
tgctgccaca gtatttgtag tgcctgatcc ccccaggaac tcaggtgctg gggatgatgg    60
ggatggggga ccatatttgg a                                              81

<210> SEQ ID NO 137
<211> LENGTH: 51
<212> TYPE: DNA
<213> ORGANISM: Artificial sequence
<220> FEATURE:
<223> OTHER INFORMATION: /note = "primer no. 687"

<400> SEQUENCE: 137
ccagcacctg agttcctggg gggatcaggc actacaaata ctgtggcagc a             51

<210> SEQ ID NO 138
<211> LENGTH: 45
<212> TYPE: DNA
<213> ORGANISM: Artificial sequence
<220> FEATURE:
<223> OTHER INFORMATION: /note = "primer no. 688"

<400> SEQUENCE: 138
gatagcagta cgataaacta tgcgccatct ctaaaggata aattc                45

<210> SEQ ID NO 139
<211> LENGTH: 45
<212> TYPE: DNA
<213> ORGANISM: Artificial sequence
<220> FEATURE:
<223> OTHER INFORMATION: /note = "primer no. 689"

<400> SEQUENCE: 139
gaatttatcc tttagagatg gcgcatagtt tatcgtactg ctatc                45

<210> SEQ ID NO 140
<211> LENGTH: 54
<212> TYPE: DNA
<213> ORGANISM: Artificial sequence
<220> FEATURE:
<223> OTHER INFORMATION: /note = "primer no. 699"

<400> SEQUENCE: 140
aaatttggat ccggcggggg aggttcctca ggcactacaa atactgtggc agca         54

<210> SEQ ID NO 141
<211> LENGTH: 39
<212> TYPE: DNA
<213> ORGANISM: Artificial sequence
<220> FEATURE:
<223> OTHER INFORMATION: /note = "primer no. 700"

<400> SEQUENCE: 141
aaatttggat cctcaggcac tacaaatact gtggcagca                                    39

<210> SEQ ID NO 142
<211> LENGTH: 57
<212> TYPE: DNA
<213> ORGANISM: Artificial sequence
<220> FEATURE:
<223> OTHER INFORMATION: /note = "primer no. 701"

<400> SEQUENCE: 142
accaaggtgg acaagagagt tgagtccaaa tcaggcacta caaatactgt ggcagca               57

<210> SEQ ID NO 143
<211> LENGTH: 60
<212> TYPE: DNA
<213> ORGANISM: Artificial sequence
<220> FEATURE:
<223> OTHER INFORMATION: /note = "primer no. 702"

<400> SEQUENCE: 143
tgctgccaca gtatttgtag tgcctgattt ggactcaact ctcttgtcca ccttggtgtt            60

<210> SEQ ID NO 144
<211> LENGTH: 57
<212> TYPE: DNA
<213> ORGANISM: Artificial sequence
<220> FEATURE:
<223> OTHER INFORMATION: /note = "primer no. 703"

<400> SEQUENCE: 144
gtcacaaaga gcttcaacag gggagagtgt tcaggcacta caaatactgt ggcagca               57

<210> SEQ ID NO 145
<211> LENGTH: 57
<212> TYPE: DNA
<213> ORGANISM: Artificial sequence
<220> FEATURE:
<223> OTHER INFORMATION: /note = "primer no. 704"

<400> SEQUENCE: 145
tgctgccaca gtatttgtag tgcctgaaca ctctcccctg ttgaagctct tgtgac                57

<210> SEQ ID NO 146
<211> LENGTH: 60
<212> TYPE: DNA
<213> ORGANISM: Artificial sequence
<220> FEATURE:
<223> OTHER INFORMATION: /note = "primer no. 800"

<400> SEQUENCE: 146
cagaagagcc tctccctgtc tctgggtaaa tcaggcacta caaatactgt ggcagcatat            60

<210> SEQ ID NO 147
<211> LENGTH: 60
<212> TYPE: DNA
<213> ORGANISM: Artificial sequence
<220> FEATURE:
<223> OTHER INFORMATION: /note = "primer no. 801"

<400> SEQUENCE: 147
atatgctgcc acagtatttg tagtgcctga tttacccaga cagggagag gctcttctg              60

```
<210> SEQ ID NO 148
<211> LENGTH: 49
<212> TYPE: DNA
<213> ORGANISM: Artificial sequence
<220> FEATURE:
<223> OTHER INFORMATION: /note = "primer no. 842"

<400> SEQUENCE: 148
aaatttaagc ttgccgccac catgaggtgc ctagctgagt tcctggggc          49

<210> SEQ ID NO 149
<211> LENGTH: 45
<212> TYPE: DNA
<213> ORGANISM: Artificial sequence
<220> FEATURE:
<223> OTHER INFORMATION: /note = "primer no. 843"

<400> SEQUENCE: 149
aaatttcgta cgttttattt ccaactttgt ccccgagccg aacgt              45

<210> SEQ ID NO 150
<211> LENGTH: 49
<212> TYPE: DNA
<213> ORGANISM: Artificial sequence
<220> FEATURE:
<223> OTHER INFORMATION: /note = "primer no. 844"

<400> SEQUENCE: 150
aaatttaagc ttgccgccac catggaatgg agcggggtct ttatctttc          49

<210> SEQ ID NO 151
<211> LENGTH: 39
<212> TYPE: DNA
<213> ORGANISM: Artificial sequence
<220> FEATURE:
<223> OTHER INFORMATION: /note = "primer no. 845"

<400> SEQUENCE: 151
aaatttgcta gctgaggaga cggtgactga ggttccttg                     39

<210> SEQ ID NO 152
<211> LENGTH: 55
<212> TYPE: DNA
<213> ORGANISM: Artificial sequence
<220> FEATURE:
<223> OTHER INFORMATION: /note = "primer 1000"

<400> SEQUENCE: 152
ctgtctctgg gtaaacacca tcaccaccac cactgagaat tccccgacct cgacc   55

<210> SEQ ID NO 153
<211> LENGTH: 55
<212> TYPE: DNA
<213> ORGANISM: Artificial sequence
<220> FEATURE:
<223> OTHER INFORMATION: /note = "primer no. 1001"

<400> SEQUENCE: 153
gaggtcgggg aattctcagt ggtggtggtg atggtgttta cccagagaca gggag   55

<210> SEQ ID NO 154
<211> LENGTH: 48
<212> TYPE: DNA
<213> ORGANISM: Artificial sequence
<220> FEATURE:
<223> OTHER INFORMATION: /note = "primer no. 1002"
```

<400> SEQUENCE: 154
ctcttttaaa aggggtccag tgtgagtcca aatatggtcc cccatgcc    48

<210> SEQ ID NO 155
<211> LENGTH: 50
<212> TYPE: DNA
<213> ORGANISM: Artificial sequence
<220> FEATURE:
<223> OTHER INFORMATION: /note = "primer no. 1003"

<400> SEQUENCE: 155
catgggggac catatttgga ctcacactgg accccttta aaagagcaac    50

<210> SEQ ID NO 156
<211> LENGTH: 233
<212> TYPE: PRT
<213> ORGANISM: Artificial sequence
<220> FEATURE:
<223> OTHER INFORMATION: /note = "0061VH-CH1"

<400> SEQUENCE: 156

```
Met Asp Phe Gly Leu Ile Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
            35                  40                  45

Arg Tyr Trp Met Thr Trp Val Arg Gln Ala Pro Gly Lys Gly Leu Glu
50                  55                  60

Trp Ile Gly Glu Ile Asn Pro Asp Ser Ser Thr Ile Asn Tyr Asn Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
            115                 120                 125

Thr Val Ser Ala Ala Ser Thr Lys Gly Pro Ser Val Phe Pro Leu Ala
            130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Lys Thr Tyr Thr Cys Asn Val Asp His Lys Pro Ser Asn Thr
            210                 215                 220

Lys Val Asp Lys Arg Val Glu Ser Lys
225                 230
```

<210> SEQ ID NO 157
<211> LENGTH: 247
<212> TYPE: PRT
<213> ORGANISM: Artificial sequence
<220> FEATURE:
<223> OTHER INFORMATION: /note = "hIgG4-hinge-CH2-CH3"

<400> SEQUENCE: 157

Met Asp Phe Gly Leu Ile Phe Phe Ile Val Ala Leu Leu Lys Gly Val
1               5                   10                  15

Gln Cys Glu Ser Lys Tyr Gly Pro Pro Cys Pro Pro Cys Pro Ala Pro
            20                  25                  30

Glu Phe Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser Gln Glu Asp Pro Glu Val Gln Phe Asn Trp Tyr Val Asp
65                  70                  75                  80

Gly Val Glu Val His Asn Ala Lys Thr Lys Pro Arg Glu Glu Gln Phe
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Gly Leu
        115                 120                 125

Pro Ser Ser Ile Glu Lys Thr Ile Ser Lys Ala Lys Gly Gln Pro Arg
130                 135                 140

Glu Pro Gln Val Tyr Thr Leu Pro Pro Ser Gln Glu Glu Met Thr Lys
145                 150                 155                 160

Asn Gln Val Ser Leu Thr Cys Leu Val Lys Gly Phe Tyr Pro Ser Asp
            165                 170                 175

Ile Ala Val Glu Trp Glu Ser Asn Gly Gln Pro Glu Asn Asn Tyr Lys
        180                 185                 190

Thr Thr Pro Pro Val Leu Asp Ser Asp Gly Ser Phe Phe Leu Tyr Ser
    195                 200                 205

Arg Leu Thr Val Asp Lys Ser Arg Trp Gln Glu Gly Asn Val Phe Ser
210                 215                 220

Cys Ser Val Met His Glu Ala Leu His Asn His Tyr Thr Gln Lys Ser
225                 230                 235                 240

Leu Ser Leu Ser Leu Gly Lys
                245

<210> SEQ ID NO 158
<211> LENGTH: 6
<212> TYPE: PRT
<213> ORGANISM: Artificial sequence
<220> FEATURE:
<223> OTHER INFORMATION: /note = "His6 tag"

<400> SEQUENCE: 158

His His His His His His
1               5

<210> SEQ ID NO 159
<211> LENGTH: 172
<212> TYPE: PRT
<213> ORGANISM: Artificial sequence
<220> FEATURE:
<223> OTHER INFORMATION: /note = "hTLT-1.18-188"

<400> SEQUENCE: 159

Met Ile Val Gly Ser Leu Pro Glu Val Leu Gln Ala Pro Val Gly Ser
1               5                   10                  15

Ser Ile Leu Val Gln Cys His Tyr Arg Leu Gln Asp Val Lys Ala Gln
            20                  25                  30

```
Lys Val Trp Cys Arg Phe Leu Pro Glu Gly Cys Gln Pro Leu Val Ser
            35                  40                  45

Ser Ala Val Asp Arg Arg Ala Pro Ala Gly Arg Arg Thr Phe Leu Thr
 50                  55                  60

Asp Leu Gly Gly Gly Leu Leu Gln Val Glu Met Val Thr Leu Gln Glu
 65                  70                  75                  80

Glu Asp Ala Gly Glu Tyr Gly Cys Met Val Asp Gly Ala Arg Gly Pro
                 85                  90                  95

Gln Ile Leu His Arg Val Ser Leu Asn Ile Leu Pro Pro Glu Glu Glu
                100                 105                 110

Glu Glu Thr His Lys Ile Gly Ser Leu Ala Glu Asn Ala Phe Ser Asp
            115                 120                 125

Pro Ala Gly Ser Ala Asn Pro Leu Glu Pro Ser Gln Asp Glu Lys Ser
130                 135                 140

Ile Pro Leu Ile Trp Gly Ala Val Leu Leu Val Gly Leu Leu Val Ala
145                 150                 155                 160

Ala Val Val Leu Phe Ala Val Met Ala Lys Arg Lys
                165                 170

<210> SEQ ID NO 160
<211> LENGTH: 32
<212> TYPE: DNA
<213> ORGANISM: Artificial sequence
<220> FEATURE:
<223> OTHER INFORMATION: /note = "primer no. 1004"

<400> SEQUENCE: 160
ggaattccat atgatagttg gcagcctccc tg                              32

<210> SEQ ID NO 161
<211> LENGTH: 39
<212> TYPE: DNA
<213> ORGANISM: Artificial sequence
<220> FEATURE:
<223> OTHER INFORMATION: /note = "primer no. 1005"

<400> SEQUENCE: 161
ataagaatgc ggccgcctat ttcctcttgg ccatcacag                       39

<210> SEQ ID NO 162
<211> LENGTH: 215
<212> TYPE: PRT
<213> ORGANISM: Artificial sequence
<220> FEATURE:
<223> OTHER INFORMATION: /note = "Fab 0100 HC"

<400> SEQUENCE: 162

Glu Val Lys Leu Leu Glu Ser Gly Gly Gly Leu Val Gln Pro Gly Gly
 1               5                  10                  15

Ser Leu Lys Leu Ser Cys Ala Ala Ser Gly Phe Asp Phe Ser Arg Tyr
                 20                  25                  30

Trp Met Thr Trp Val Arg Gln Ala Pro Gly Lys Gly Leu Glu Trp Ile
            35                  40                  45

Gly Glu Ile Asn Pro Asp Ser Ser Thr Ile Asn Tyr Asn Pro Ser Leu
 50                  55                  60

Lys Asp Lys Phe Ile Ile Ser Arg Asp Asn Ala Lys Asn Thr Leu Tyr
 65                  70                  75                  80

Leu Gln Met Ser Glu Val Arg Ser Glu Asp Thr Ala Leu Tyr Tyr Cys
                 85                  90                  95
```

```
Ala Ser Gly Val Phe Thr Ser Trp Gly Gln Gly Thr Leu Val Thr Val
            100                 105                 110

Ser Ala Ala Ser Thr Lys Gly Pro Ser Val Phe Pro Leu Ala Pro Cys
            115                 120                 125

Ser Arg Ser Thr Ser Glu Ser Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
            195                 200                 205

Asp Lys Arg Val Glu Ser Lys
210                 215

<210> SEQ ID NO 163
<211> LENGTH: 219
<212> TYPE: PRT
<213> ORGANISM: Artificial sequence
<220> FEATURE:
<223> OTHER INFORMATION: /note = "Fab 0100 LC"

<400> SEQUENCE: 163

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Phe His Trp Ala Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
            85                  90                  95

Thr His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 164
```

<211> LENGTH: 113
<212> TYPE: PRT
<213> ORGANISM: Artificial Sequence
<220> FEATURE:
<223> OTHER INFORMATION: Synthetic

<400> SEQUENCE: 164

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Phe His Trp Cys Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Arg

<210> SEQ ID NO 165
<211> LENGTH: 114
<212> TYPE: PRT
<213> ORGANISM: Artificial Sequence
<220> FEATURE:
<223> OTHER INFORMATION: Synthetic

<400> SEQUENCE: 165

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Thr Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Glu Val Arg Ser Glu Asp Thr Ala Leu Tyr Tyr Cys
                85                  90                  95

Ala Ser Gly Val Phe Thr Ser Trp Gly Gln Gly Thr Leu Val Thr Val
            100                 105                 110

Ser Ala

<210> SEQ ID NO 166
<211> LENGTH: 250
<212> TYPE: PRT
<213> ORGANISM: Artificial Sequence
<220> FEATURE:
<223> OTHER INFORMATION: Synthetic

<400> SEQUENCE: 166

Met Lys Leu Pro Val Gly Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

```
Ser Leu Gly Asp Gln Ala Ser Ile Ser Cys Arg Ser Ser Gln Ser Leu
        35                  40                  45

Val His Arg Asn Gly Asn Thr Tyr Phe His Trp Cys Leu Gln Lys Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                    85                  90                  95

Leu Lys Ile Ser Arg Val Glu Ala Glu Asp Leu Gly Val Tyr Phe Cys
                100                 105                 110

Ser Gln Ser Thr His Val Pro Tyr Thr Phe Gly Gly Gly Thr Lys Leu
                115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                    165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys Glu Asp
225                 230                 235                 240

Gln Val Asp Pro Arg Leu Ile Asp Gly Lys
                    245                 250

<210> SEQ ID NO 167
<211> LENGTH: 750
<212> TYPE: DNA
<213> ORGANISM: Homo sapiens

<400> SEQUENCE: 167
atgaagttgc ctgttgggct gttggtgctg atgttctgga ttccagcttc cagcagtgat      60
gttgtgatga cccaaactcc actctccctg cctgtcagtc ttggagatca agcctccatc     120
tcttgcagat ctagtcagag ccttgtacac agaaatggaa acacctattt tcattggtgc     180
ctgcagaaac caggccagtc tccaaagctc ctgatctaca agtttccaa ccgatttttct     240 ggggtcccag acaggttcag tggcagtgga tcagggacag atttcacact caagatcagc     300
agagtggagg ctgaggatct gggagtttat ttctgctctc aaagtacaca tgttccgtac     360
acgttcggag gggggaccaa gctggaaata aaacgtacgg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660 acccatcagg gcctgagctc gcccgtcaca aagagcttca caggggaga gtgtgaggac     720 caggtggacc ccagactgat cgacggcaag                                      750

<210> SEQ ID NO 168
```

<211> LENGTH: 469
<212> TYPE: PRT
<213> ORGANISM: Artificial Sequence
<220> FEATURE:
<223> OTHER INFORMATION: Synthetic

<400> SEQUENCE: 168

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Thr Trp Val Arg Gln Ala Pro Gly Lys Gly Leu Glu
50                  55                  60

Trp Ile Gly Glu Ile Asn Pro Asp Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Glu Val Arg Ser Glu Asp Thr Ala Leu Tyr
            100                 105                 110

Tyr Cys Ala Ser Gly Val Phe Thr Ser Trp Gly Gln Gly Thr Leu Val
        115                 120                 125

Thr Val Ser Ala Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
210                 215                 220

Lys Val Asp Lys Arg Val Glu Ser Lys Gly Ser Gly Gly Gly Gly Ser
225                 230                 235                 240

Gly Gly Gly Gly Ser Gly Gly Gly Ser Ser Gly Thr Thr Asn Thr
                245                 250                 255

Val Ala Ala Tyr Asn Leu Thr Trp Lys Ser Thr Asn Phe Lys Thr Ile
            260                 265                 270

Leu Glu Trp Glu Pro Lys Pro Val Asn Gln Val Tyr Thr Val Gln Ile
        275                 280                 285

Ser Thr Lys Ser Gly Asp Trp Lys Ser Lys Cys Phe Tyr Thr Thr Asp
290                 295                 300

Thr Glu Cys Asp Leu Thr Asp Glu Ile Val Lys Asp Val Lys Gln Thr
305                 310                 315                 320

Tyr Leu Ala Arg Val Phe Ser Tyr Pro Ala Gly Asn Val Glu Ser Thr
                325                 330                 335

Gly Ser Ala Gly Glu Pro Leu Tyr Glu Asn Ser Pro Glu Phe Thr Pro
            340                 345                 350

Tyr Leu Glu Thr Asn Leu Gly Gln Pro Thr Ile Gln Ser Phe Glu Gln
        355                 360                 365

Val Gly Thr Lys Val Asn Val Thr Val Glu Asp Glu Arg Thr Leu Val
370                 375                 380
```

Arg Arg Asn Asn Thr Phe Leu Ser Leu Arg Asp Val Phe Gly Lys Asp
385                 390                 395                 400

Leu Ile Tyr Thr Leu Tyr Tyr Trp Lys Ser Ser Ser Gly Lys Lys
            405                 410                 415

Thr Ala Lys Thr Asn Thr Asn Glu Phe Leu Ile Asp Val Asp Lys Gly
            420                 425                 430

Glu Asn Tyr Cys Phe Ser Val Gln Ala Val Ile Pro Ser Arg Thr Val
            435                 440                 445

Asn Arg Lys Ser Thr Asp Ser Pro Val Glu Cys Met Gly Gln Glu Lys
    450                 455                 460

Gly Glu Phe Arg Glu
465

<210> SEQ ID NO 169
<211> LENGTH: 1407
<212> TYPE: DNA
<213> ORGANISM: Homo sapiens

<400> SEQUENCE: 169

| | | | | |
|---|---|---|---|---|
| atggattttg | ggctgatttt | ttttattgtt | gctcttttaa | aaggggtcca | gtgtgaggtg | 60 |
| aaacttctcg | agtctggagg | tggcctggtg | cagcctggag | gatccctgaa | actctcctgt | 120 |
| gcagcctcag | gattcgattt | tagtagatac | tggatgactt | gggtccggca | ggctccaggg | 180 |
| aagggctag | aatggattgg | agaaattaat | ccagatagca | gtacgataaa | ctatacgcca | 240 |
| tctctaaagg | ataaattcat | catctccaga | gacaacgcca | agaatacgct | gtacctgcaa | 300 |
| atgagcgaag | tgagatctga | ggacacagcc | ctttattact | gtgcaagcgg | ggtgtttact | 360 |
| tcctggggcc | aagggactct | ggtcactgtc | tctgcagcta | gcaccaaggg | cccatccgtc | 420 |
| ttccccctgg | cgccctgctc | caggagcacc | tccgagagca | cagccgccct | gggctgcctg | 480 |
| gtcaaggact | acttccccga | accggtgacg | gtgtcgtgga | actcaggcgc | cctgaccagc | 540 |
| ggcgtgcaca | ccttcccggc | tgtcctacag | tcctcaggac | tctactccct | cagcagcgtg | 600 |
| gtgaccgtgc | cctccagcag | cttgggcacg | aagacctaca | cctgcaacgt | agatcacaag | 660 |
| cccagcaaca | ccaaggtgga | caagagagtt | gagtccaaag | gatccggagg | tggcgggtct | 720 |
| ggtggcgggg | gatcaggcgg | gggaggttcc | tcaggcacta | caaatactgt | ggcagcatat | 780 |
| aatttaactt | ggaaatcaac | taatttcaag | acaattttgg | agtgggaacc | caaacccgtc | 840 |
| aatcaagtct | acactgttca | ataagcact | aagtcaggag | attggaaaag | caaatgcttt | 900 |
| tacacaacag | acacagagtg | tgacctcacc | gacgagattg | tgaaggatgt | gaagcagacg | 960 |
| tacttggcac | gggtcttctc | ctacccggca | gggaatgtgg | agagcaccgg | ttctgctggg | 1020 |
| gagcctctgt | atgagaactc | cccagagttc | acaccttacc | tggagacaaa | cctcggacag | 1080 |
| ccaacaattc | agagttttga | acaggtggga | acaaaagtga | atgtgaccgt | agaagatgaa | 1140 |
| cggactttag | tcagaaggaa | caacactttc | ctaagcctcc | gggatgtttt | tggcaaggac | 1200 |
| ttaatttata | cactttatta | ttggaaatct | tcaagttcag | gaagaaaac | agccaaaaca | 1260 |
| aacactaatg | agtttttgat | tgatgtggat | aaaggagaaa | actactgttt | cagtgttcaa | 1320 |
| gcagtgattc | cctcccgaac | agttaaccgg | aagagtacag | acagcccggt | agagtgtatg | 1380 |
| ggccaggaga | aaggggaatt | tagagaa | | | | 1407 |

<210> SEQ ID NO 170
<211> LENGTH: 106
<212> TYPE: PRT

```
<213> ORGANISM: Artificial Sequence
<220> FEATURE:
<223> OTHER INFORMATION: Synthetic

<400> SEQUENCE: 170

Gly Ser Leu Pro Glu Val Leu Gln Ala Pro Val Gly Ser Ser Ile Leu
1               5                   10                  15

Val Gln Cys His Tyr Arg Leu Gln Asp Val Lys Ala Gln Lys Val Trp
            20                  25                  30

Cys Arg Phe Leu Pro Glu Gly Cys Gln Pro Leu Val Ser Ala Val
        35                  40                  45

Asp Arg Arg Ala Pro Ala Gly Arg Arg Thr Phe Leu Thr Asp Leu Gly
    50                  55                  60

Gly Gly Leu Leu Gln Val Glu Met Val Thr Leu Gln Glu Glu Asp Ala
65                  70                  75                  80

Gly Glu Tyr Gly Cys Met Val Asp Gly Ala Arg Gly Pro Gln Ile Leu
                85                  90                  95

His Arg Val Ser Leu Asn Ile Leu Pro Pro
            100                 105

<210> SEQ ID NO 171
<211> LENGTH: 153
<212> TYPE: PRT
<213> ORGANISM: Artificial Sequence
<220> FEATURE:
<223> OTHER INFORMATION: Synthetic

<400> SEQUENCE: 171

Gln Gly Ile Val Gly Ser Leu Pro Glu Val Leu Gln Ala Pro Val Gly
1               5                   10                  15

Ser Ser Ile Leu Val Gln Cys His Tyr Arg Leu Gln Asp Val Lys Ala
            20                  25                  30

Gln Lys Val Trp Cys Arg Phe Leu Pro Glu Gly Cys Gln Pro Leu Val
        35                  40                  45

Ser Ala Val Asp Arg Arg Ala Pro Ala Gly Arg Arg Thr Phe Leu
    50                  55                  60

Thr Asp Leu Gly Gly Leu Leu Gln Val Glu Met Val Thr Leu Gln
65                  70                  75                  80

Glu Glu Asp Ala Gly Glu Thr Gly Cys Met Val Asp Gly Ala Arg Gly
                85                  90                  95

Pro Gln Ile Leu His Arg Val Ser Leu Asn Ile Leu Pro Pro Glu Glu
            100                 105                 110

Glu Glu Glu Thr His Lys Ile Gly Ser Leu Ala Glu Asn Ala Phe Ser
        115                 120                 125

Asp Pro Ala Gly Ser Ala Asn Pro Leu Glu Pro Ser Gln Asp Glu Lys
    130                 135                 140

Ser Ile Pro His His His His His His
145                 150

<210> SEQ ID NO 172
<211> LENGTH: 37
<212> TYPE: PRT
<213> ORGANISM: Artificial Sequence
<220> FEATURE:
<223> OTHER INFORMATION: Synthetic

<400> SEQUENCE: 172

Glu Glu Glu Glu Glu Thr His Lys Ile Gly Ser Leu Ala Glu Asn Ala
1               5                   10                  15
```

```
Phe Ser Asp Pro Ala Gly Ser Ala Asn Pro Leu Glu Pro Ser Gln Asp
            20                  25                  30

Glu Lys Ser Ile Pro
        35
```

<210> SEQ ID NO 173
<211> LENGTH: 44
<212> TYPE: PRT
<213> ORGANISM: Artificial Sequence
<220> FEATURE:
<223> OTHER INFORMATION: Synthetic

<400> SEQUENCE: 173

```
Leu Asn Ile Leu Pro Pro Glu Glu Glu Glu Thr His Lys Ile Gly
1               5                   10                  15

Ser Leu Ala Glu Asn Ala Phe Ser Asp Pro Ala Gly Ser Ala Asn Pro
            20                  25                  30

Leu Glu Pro Ser Gln Asp Glu Lys Ser Ile Pro Leu
        35                  40
```

<210> SEQ ID NO 174
<211> LENGTH: 12
<212> TYPE: PRT
<213> ORGANISM: Artificial Sequence
<220> FEATURE:
<223> OTHER INFORMATION: Synthetic

<400> SEQUENCE: 174

```
Val Gln Cys His Tyr Arg Leu Gln Asp Val Lys Ala
1               5                   10
```

<210> SEQ ID NO 175
<211> LENGTH: 6
<212> TYPE: PRT
<213> ORGANISM: Artificial Sequence
<220> FEATURE:
<223> OTHER INFORMATION: Synthetic

<400> SEQUENCE: 175

```
Leu Gly Gly Gly Leu Leu
1               5
```

<210> SEQ ID NO 176
<211> LENGTH: 8
<212> TYPE: PRT
<213> ORGANISM: Artificial Sequence
<220> FEATURE:
<223> OTHER INFORMATION: Synthetic

<400> SEQUENCE: 176

```
Gly Ala Arg Gly Pro Gln Ile Leu
1               5
```

<210> SEQ ID NO 177
<211> LENGTH: 12
<212> TYPE: PRT
<213> ORGANISM: Artificial Sequence
<220> FEATURE:
<223> OTHER INFORMATION: Synthetic

<400> SEQUENCE: 177

```
Leu Pro Glu Gly Cys Gln Pro Leu Val Ser Ser Ala
1               5                   10
```

```
<210> SEQ ID NO 178
<211> LENGTH: 11
<212> TYPE: PRT
<213> ORGANISM: Artificial Sequence
<220> FEATURE:
<223> OTHER INFORMATION: Synthetic

<400> SEQUENCE: 178

Arg Gly Pro Gln Ile Leu His Arg Val Ser Leu
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Synthetic

<400> SEQUENCE: 179

Val Gln Cys His Tyr Arg Leu Gln Asp Val Lys Ala
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Synthetic

<400> SEQUENCE: 180

Arg Gly Pro Gln Ile Leu His Arg Val Ser Leu
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Synthetic

<400> SEQUENCE: 181

Glu Thr His Lys Ile Gly Ser Leu Ala Glu Asn Ala
1               5                   10

<210> SEQ ID NO 182
<211> LENGTH: 9
<212> TYPE: PRT
<213> ORGANISM: Artificial Sequence
<220> FEATURE:
<223> OTHER INFORMATION: Synthetic

<400> SEQUENCE: 182

Ile Gly Ser Leu Ala Glu Asn Ala Phe
1               5

<210> SEQ ID NO 183
<211> LENGTH: 10
<212> TYPE: PRT
<213> ORGANISM: Artificial Sequence
<220> FEATURE:
<223> OTHER INFORMATION: Synthetic

<400> SEQUENCE: 183

Lys Ile Gly Ser Leu Ala Glu Asn Ala Phe
1               5                   10

<210> SEQ ID NO 184
```

```
<211> LENGTH: 16
<212> TYPE: PRT
<213> ORGANISM: Artificial Sequence
<220> FEATURE:
<223> OTHER INFORMATION: Synthetic

<400> SEQUENCE: 184

Glu Thr His Lys Ile Gly Ser Leu Ala Glu Asn Ala Phe Ser Asp Pro
1               5                   10                  15
```

TARGETING TISSUE FACTOR TO ACTIVATED PLATELETS

CROSS-REFERENCE TO RELATED APPLICATIONS

This application is a continuation of U.S. application Ser. No. 13/391,755 filed on Mar. 22, 2012 which is a 35 U.S.C. § 371 national stage application of International Patent Application PCT/EP2010/062519 (published as WO 2011/023785 A1), filed Aug. 26, 2010, which claimed priority of European Patent Application 09168833.3, filed Aug. 27, 2009; this application further claims priority under 35 U.S.C. § 119 of U.S. Provisional Application 61/239,142, filed Sep. 2, 2009 and U.S. Provisional Application 61/288,944, filed Dec. 22, 2009; the contents of which are incorporated herein by reference.

FIELD OF THE INVENTION

The current invention relates to procoagulant fusion proteins, a polynucleotides that encode said procoagulant fusion proteins, cells that expresses said procoagulant fusion protein and uses thereof.

INCORPORATION-BY-REFERENCE OF THE SEQUENCE LISTING

In accordance with 37 C.F.R. § 1.52(e)(5), Applicants enclose herewith the Sequence Listing for the above-captioned application entitled "8076US04_SeqList_ST25", created on Apr. 1, 2016. The Sequence Listing is made up of 156,612 bytes, and the information contained in the attached "8076US04_SeqList_ST25" is identical to the information in the specification as originally filed. No new matter is added.

BACKGROUND OF THE INVENTION

Tissue factor (TF), a transmembrane glycoprotein, is the primary cellular initiator of blood coagulation. It is predominantly expressed on the surface of sub-endothelial cells, such as smooth muscle cells and fibroblasts, and binds both zymogen coagulation Factor VII (FVII) and the activated form, Factor VIIa (FVIIa) when the integrity of the endothelium is interrupted, such as when blood vessels are severed. When TF binds FVII, it promotes FVII to FVIIa activation. TF also greatly enhances the proteolytic activity of Factor VIIa towards its physiologic substrates, Factors IX and X. FVIIa retains a zymogen-like state in solution, acting as a relatively poor enzyme. TF provides a scaffold for optimal macromolecular exosite interaction, induces conformational changes in the protease domain of FVIIa leading to maturation of its active site and orientates FVIIa on a cell surface for optimal substrate interaction. Together these effects results in an enhanced catalytic capability of FVIIa of several orders of magnitude. Hence, TF is a co-factor for FVIIa in the initiation complex of what is traditionally referred to as the extrinsic pathway of blood coagulation. Subsequent steps of the coagulation cascade finally result in the formation of a fibrin polymer which is bound by activated platelets and crosslinked with FXIIIa.

Platelets—also known as thrombocytes—derive from their cellular predecessor, megakaryocytes. Normal resting platelets freely flow throughout the blood circulation when the endothelium is intact. When the single-layered endothelial barrier is damaged, resting platelets adhere to subendothelial structures by means of glycoprotein (GP) receptors. For example, GPIaIIa and GPVI bind collagen; GPIcIIa binds fibronectin; GPIc*IIa binds laminin and GPIb-V-IX binds von Willebrand Factor (vWF) polymers. Adhesion of platelets in this manner causes them to change shape and release their alpha and dense granules. In turn, this results in the exposure of a plethora of other glycoprotein platelet receptors, such as GPIIbIIIa (which binds fibrinogen/fibrin) and TREM-like transcript 1 (TLT-1); as well as the release of coagulation factors I (fibrinogen), V and XI; other procoagulants such as ADP, $Ca^{2+}$, serotonin and Platelet Factors 3/4; anti-coagulants such as tissue factor pathway inhibitor (TFPI); and compounds such as platelet derived growth factor (PDGF), essential to platelet replenishment and healing. Activated platelets bind to one other and cross-link fibrin in a rapid reaction for example via the GPIIbIIIa receptor complex.

Hence, activated platelets and the fibrin polymer product of the coagulation cascade together form the blood clot. Platelet aggregation of coagulation is known as the primary hemostatic response, while the coagulation cascade response is known as the secondary hemostatic response. Although fibrin is produced during the primary hemostatic response, via the so-called coagulation initiation (independent of FIX/FVIIIa), the amount produced at this point is insufficient for a strong coagel. Initial fibrin serves as an aggregater of activated platelets at site of injury, which again provides an optimal cell surface for the function of activated coagulation factors.

In subjects with a coagulopathy, such as in human beings with haemophilia A and B, various steps of the coagulation cascade are rendered dysfunctional due to, for example, the absence or insufficient presence of a coagulation factor. Such dysfunction of one part of coagulation results in insufficient blood coagulation and potentially life-threatening bleeding.

An object of the current invention is to provide a compound that is suitable for use as a procoagulant drug in such subjects. A second object of the current invention is to provide a compound that enables a physical point of initiation of blood coagulation to be mobilised, such that extrinsic coagulation is not solely dependent on subendothelial, cell-bound tissue factor. A third object of the current invention is to provide a compound that up-regulates blood coagulation in a physiologically suitable microenvironment. A further object of the current invention is to direct a soluble tissue factor, or a biologically functional fragment or variant thereof, to the surface of activated platelets. A further object of the invention is to enhance the proteolytic activity of endogenous Factor VIIa towards its physiological substrates, Factors IX and X. Thus, the object is to enable the initiation of blood coagulation on the surface of activated platelets that are located intravascularly or extravascularly. This is in addition to the normal and exclusively subendothelial—typically extravascular—initiation of blood coagulation.

WO06/096828 discloses chimeric proteins that comprise soluble tissue factor (sTF) and a phosphatidyl serine (PS) binding domain, such as Annexin V. PS is exposed on the surface of activated cells, such as monocytes, endothelial cells and cells undergoing apoptosis, as well as on activated and resting platelets. The chimeric proteins are both procoagulant and anti-coagulant; the latter due to the fact that, in higher doses, constructs compete with coagulation factors in binding to PS on activated platelets. Thus, the chimeric proteins of WO06/096828 have a different set of properties than the fusion proteins described herein.

SUMMARY OF THE INVENTION

The current invention provides a fusion protein comprising (i) at least one tissue factor polypeptide, or biologically functional variant(s) or fragment(s) thereof, which is/are covalently attached to (ii) a ligand that is capable of binding (iii) a receptor, and/or a fragment thereof, wherein the receptor is only expressed on the surface of activated platelets. The fusion protein/construct may comprise (i) tissue factor, or a biologically functional variant or fragment thereof, and (ii) a ligand that binds (iii) TLT-1. According to the current invention, (ii) may be a monoclonal antibody, or an antigen-binding portion of a monoclonal antibody. For example, (ii) may be selected from the group consisting of: a Fab fragment, a F(ab')$_2$ fragment, a Fab' fragment, a Fd fragment, a Fv fragment, a dAb fragment or an isolated complementarity determining region (CDR). According to the current invention, (ii) may comprise the variable domain of 0012 (2F105) LC. According to the current invention, (ii) may comprise the variable domain of 0012 (otherwise referred to as 2F105) LC together with the constant region of human LC, kappa and a HPC4 tag (pTT-0012LC.HPC4, also referred to as pTT-2F105LC.HPC4).

The fusion proteins/constructs of the present invention target the initial stages of platelet-clot growth through the specific targeting of activated platelets, while concurrently recruiting resting or basal platelets directly to the site of injury, thereby activating said resting or basal platelets systemically. The compositions of the present invention are based upon the identification of particular receptors and component epitopes, that appear on platelet membranes when platelets are no longer resting but in the process of being activated.

The current invention also provides the following: an isolated nucleotide sequence that encodes any fusion protein/construct according to the current invention; a vector that comprises an isolated nucleotide sequence that, in turn, encodes any fusion protein/construct according to the current invention; an isolated cell that comprises a nucleotide sequence that encodes any fusion protein/construct of the current invention. Said nucleotide sequence may, in turn, be expressed by an intracellular vector. Said isolated cell may be a eukaryotic cell, such as a mammalian cell, such as a BHK or a CHO or a HEK cell.

Furthermore, the current invention provides a method of targeting tissue factor to the surface of activated platelets, said method comprising contacting activated platelets with any construct comprising (i) tissue factor, or a functional variant thereof, and (ii) a ligand that is capable of binding (iii) a receptor present on an activated platelet, such as TLT-1. In this way, the invention also relates to a method of up-regulating FX activation on the surface of activated platelets, wherein said method comprises the contacting of activated platelets with said construct in the simultaneous presence of FX.

Similarly, the invention relates to fusion proteins for use as a medicament and for use in the treatment of a coagulopathy. In one embodiment, a therapeutically effective amount of said construct is parenterally administered, such as intravenously or subcutaneously administered, to an individual in need thereof. Such individual in need may have any congenital, acquired and/or iatrogenic coagulopathy.

DESCRIPTION OF THE DRAWINGS

FIG. 1: Human TLT-1 nucleotide (SEQ ID NO: 1) and amino acid (SEQ ID NO: 2) sequences. In FIG. 1, the nucleotide- and amino acid sequences representing hTLT-1 are shown. Here, nucleotide sequence position 1-45 encode the predicted signal peptide, the nucleotide sequence at position 46-486 encode the extracellular domain of hTLT-1, the nucleotide sequence position 487-555 encode the transmembrane region and the nucleotide sequence at position 556-933 encode the intracellular domain of hTLT-1.

FIG. 2: Nucleotide (SEQ ID NO: 3) and amino acid (SEQ ID NO: 4) sequences representing the extracellular domain of human TLT-1 containing a C-terminal His-6 tag. In FIG. 2, the nucleotide- and amino acid sequences representing the extracellular domain of hTLT-1 with a C-terminal His tag are shown. Here, the underlined sequence (7-15) indicates the positions of a kozak sequence, the nucleotide sequence at position 16-60 encodes the predicted signal peptide, the nucleotide sequence at position 61-501 encode the extracellular domain of hTLT-1 and the nucleotide sequence at position 502-519 encodes the 6×His tag (in bold). The restriction enzyme sites HindIII (nucleotide sequence at position 1-6) and EcoRI (nucleotide sequence at position 523-528) are also shown and the stop codon is marked with an asterisk (520-522).

FIG. 3: The variable domain of 0012LC and 0012HC including Kabat numbering:
  A) The variable domain of 0012LC
  B) The variable domain of 0012LC—Kabat numbering
  C) The variable domain of 0012HC
  D) The variable domain of 0012HC—Kabat numbering.

In FIG. 3A, the nucleotide sequence (SEQ ID NO: 9) at position 1-57 encodes the LC signal peptide (SEQ ID NO: 10) sequence; the nucleotide sequences at position 58-396 encodes the variable domain of 0012LC. In FIG. 3B (SEQ ID NO: 164), the sequences in bold and grey represent positions of the 0012LC CDRs according to Kabat numbering. In FIG. 3C (SEQ ID NO: 11 and SEQ ID NO: 12), the nucleotide sequence at position 1-54 encodes the 0012HC signal peptide, the nucleotide sequence at position 55-396 encodes the variable domain of 0012HC. In FIG. 3D (SEQ ID NO: 165), the sequences in bold and grey represent positions of the 0012HC CDRs according to Kabat numbering.

FIG. 4: The variable domain of 0012LC together with constant region of human LC,kappa and a HPC4 tag (encoded by pTT-0012LC.HPC4) (SEQ ID NO: 166 and SEQ ID NO: 167). In FIG. 4, the nucleotide sequences at position 1-57 encodes the LC signal peptide, the nucleotide sequence 58-396 encodes the variable domain of 0012LC, the nucleotide sequence 397-714 encodes the constant region of human 0012LC, kappa and the nucleotide sequence 715-750 encodes a HPC4 tag.

FIG. 5: The variable domain of 0012HC together with the constant region of human IgG4 (pTT-0012HC) (SEQ ID NO: 17 and SEQ ID NO: 39). In FIG. 5 the nucleotide sequence 1-54 encodes the HC signal peptide, the nucleotide sequence 55-396 encodes the variable domain of 0012HC and the nucleotide sequence 397-1377 encodes the constant region of human IgG4 (in bold).

FIG. 6: The nucleotide- (SEQ ID NO: 169) and amino acid (SEQ ID NO: 168) sequences of 0012V$_H$-CH1-L4a-hTF.1-219, as encoded by pTT-0012V$_H$-CH1-L4a-hTF.1-219. The pTT-0012V$_H$-CH1-L4a-hTF.1-219 construct encoding the Gly-Ser linker L4a and the extracellular domain AA 1-219 of human tissue factor. Here, the nucleotide sequence at position 1-54 encodes the predicted signal peptide, the nucleotide sequence at position 55-396 encode the variable domain of 0012HC, the nucleotide sequence at position 397-699 (in bold) encode the human IgG4 CH$_1$ constant region, the nucleotide sequence at position 700-750 (underlined) encodes the Gly-Ser linker designated L4a and the nucleotide sequence at position 701-1407 encodes the extracellular domain of human tissue factor (amino acid 1-219, dotted sequence). The 0012$V_H$-CH1-L4a-hTF.1-219 amino acid sequence is composed of SEQ ID no. 51 (0012VH-VH1), SEQ ID no. 61 (L4a) and SEQ ID no. 14 (hTF.1-219).

FIG. 8: Binding of protein ID no. 0010 and 0011 to activated platelets by FACS analysis. Detection via an anti-HPC4 tag (FIG. 8A) or an anti-LC antibody (FIG. 8B).

FIG. 9A shows the effect of i) 0.03 nM INNOVIN® (lipidated tissue factor) ii) 10 nM sTF, iii) 10 nM 0011 Fab-hTF.1-219, iv) 10 nM 0010 Fab anti-TLT-1 antibody or v) 10 nM 0012 mAb anti-TLT-1 antibody on FVIIa-mediated FX activation in the absence or presence of platelets. FIG. 9B shows the effect of replacing rFVIIa in the assay with the zymogen, rFVII.

FIG. 10: The data in FIG. 10A shows that binding of 10 nM 0011 Fab-hTF.1-219 to the TLT-1 receptor specifically stimulates FVIIa-mediated FX activation on activated and not on resting platelets. Stimulation increases with the number of activated platelets and is saturated with an $EC_{50} \approx 12.000$ plts/µl. FIG. 10B compares the results in FIG. 10A with the results obtained with 0.1 nM Annexin V-hTF.1-219 fusion protein (AV-hTF.1-219). FIG. 10B shows that binding of AV-hTF.1-219 to platelet phospholipid stimulates FX activation on both activated and resting platelets. A marked stimulation of FX activation is observed with resting platelets which at the maximal platelet number tested exceeds FXa generation on the surface of an equivalent number of activated platelets. FIG. 10B clearly shows that AV-TF cannot be used to selectively enhance FXa generation on activated platelets.

FIG. 11: The data in FIG. 11 shows the FVIIa/FVII concentration dependency of the stimulation of FX activation on activated platelets by 10 nM of Fab-hTF.1-219 fusion proteins. The effect with activated platelets of 0020 Fab-hTF.1-219 is compared to the effect of a 0094 Fab-hTF.1-219 isotype fusion protein which do not bind TLT-1 and to non-fused hTF.1-219. Also shown for comparison is the effect of 0020 Fab-hTF.1-219 with resting platelets. A similar stimulation is obtained at all concentrations with FVIIa and FVII showing that TF-fusion proteins mediate an efficient feed-back activation of FVII on activated platelets and that stimulation is optimal at physiological concentrations of FVII/FVIIa. A marked stimulation is induced upon TLT-1 targeting and not with non-targeting hTF.1-219 derivatives.

FIG. 12: The data in FIG. 12 shows the stimulation of FX activation mediated by 10 nM FVIIa/FVII on activated platelets at various concentrations of Fab-hTF.1-219 fusion proteins. The effect with activated platelets of 0070 Fab-hTF.1-219 is compared to the effect of a 0094 Fab-hTF.1-219 isotype fusion protein which do not bind TLT-1 and to non-fused hTF.1-219. The 0070 Fab-hTF.1-219 markedly stimulates FX activation over a wide concentration range with a mechanism which requires targeting to TLT-1 as indicated by comparison with non-binding controls.

FIG. 13: The data in FIG. 13 shows the stimulation of FX activation mediated by o.1 nM FVIIa/FVII on TLT-1 enriched phospholipids at various concentrations of Fab-hTF.1-219 fusion proteins. The effect of 0070 Fab-hTF.1-219 is compared to the effect of a 0094 Fab-hTF.1-219 isotype fusion protein which do not bind TLT-1 and to non-fused hTF.1-219. The 0070 Fab-hTF.1-219 markedly stimulates FX activation over a wide concentration range with a mechanism which requires targeting to TLT-1 as indicated by comparison with non-binding controls.

FIG. 14: FIG. 14 shows the stimulation of fibrin clot formation in "hemophilia like" human whole blood (HWB) mediated by 0070 Fab-hTF.1-219 fusion protein. FIG. 14A shows TEG traces of clot formation measured at various concentrations (0, 0.1, 0.2, 1.0, and 10 nM) of 0070 Fab-hTF.1-219 fusion protein added to HWB made "hemophilia like" by addition of an antibody against human FVIII. The clotting time is markedly reduced by the FVIII antibody and increasing concentrations of 0070 Fab-hTF.1-219 dramatically revert the effect of the FVIII antibody. FIG. 14B shows the R times for the TEG traces in FIG. 14A and compares the R time for 0070 Fab-hTF.1-219 to the R times obtained for the 0094 Fab-hTF.1-219 isotype fusion protein and hTF.1-219 run in parallel with the same donor. The 0070 Fab-hTF.1-219 markedly stimulates clot formation in "hemophilia like" HWB with a mechanism which requires targeting to TLT-1 as indicated by comparison with non-binding controls.

FIG. 16: Sequence coverage of HX analyzed peptides of TLT-1 in the presence and absence of 0023. The primary sequence (using mature numbering) (SEQ ID NO: 170) is displayed above the HX analyzed peptides (shown as horizontal bars). Peptides showing similar exchange patterns both in the presence and absence of 0023 are displayed in white whereas peptides showing reduced deuterium incorporation upon 0023 binding are coloured black.

FIG. 17: Sequence coverage of HX analyzed peptides of TLT-1 in the presence and absence of 0051. The primary sequence (using mature numbering) (SEQ ID NO: 170) is displayed above the HX analyzed peptides (shown as horizontal bars). Peptides showing similar exchange patterns both in the presence and absence of 0051 are displayed in white whereas peptides showing reduced deuterium incorporation upon 0051 binding are coloured black.

FIG. 18: Sequence coverage of HX analyzed peptides of TLT-1 in the presence and absence of 0062. The primary sequence (using mature numbering) (SEQ ID NO: 170) is displayed above the HX analyzed peptides (shown as horizontal bars). Peptides showing similar exchange patterns both in the presence and absence of 0062 are displayed in white whereas peptides showing reduced deuterium incorporation upon 0062 binding are coloured black.

FIG. 19: Sequence coverage of HX analyzed peptides of TLT-1 in the presence and absence of 0061. The primary sequence (using mature numbering) (SEQ ID NO: 171) is displayed above the HX analyzed peptides (shown as horizontal bars). Peptides showing similar exchange patterns both in the presence and absence of 0061 are displayed in white whereas peptides showing reduced deuterium incorporation upon 0061 binding are coloured black.

FIG. 27: Screening of TF-fusion protein pro-coagulant activity by measuring FVII/FVIIa-mediated activation of FX on i) activated platelets and on ii) TLT-1 enriched phospholipids. Stimulation of FX activation on activated platelets was performed as described in Example 37 on platelets from individual human donors. The stimulation obtained with 0020 Fab-hTF.1-219 was always included and set to 100%. Stimulation of FX activation TLT-1 enriched phospholipids was performed as described in Example 40 with 0.1 nM FVII/FVIIa and 10 nM Fab fusion protein or 1.0 nM mAB fusion protein. The stimulation obtained with 0020 Fab-hTF.1-219 was always included and set to 100%. FIG. 27A lists data on mAb-TF fusion proteins and FIG. 27B lists data on Fab-TF fusion proteins. Also show are data with 0020 Fab-hTF.1-219 on resting platelets and results with non-binding isotype antibodies.

SEQUENCES

Figure 7:
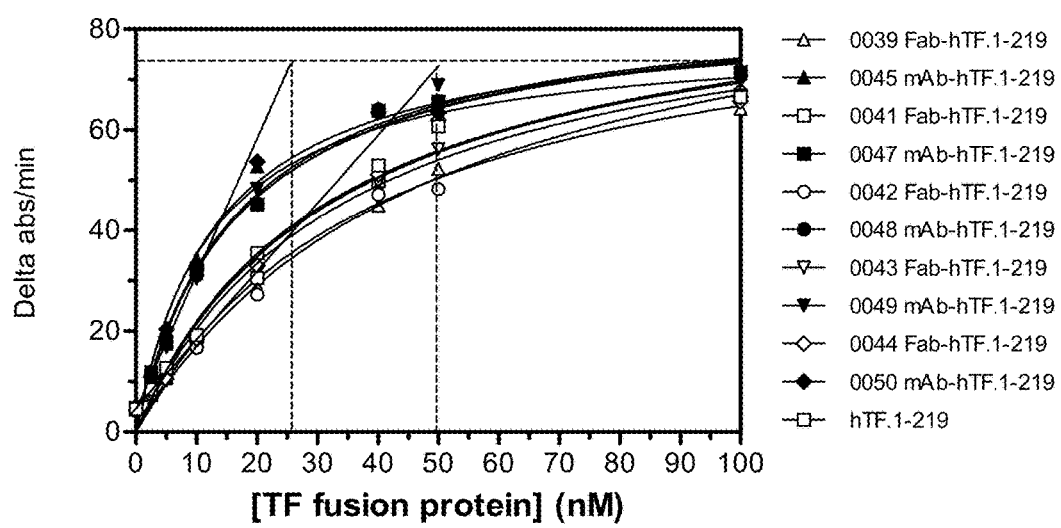
FIG. 7: Stimulation of factor VIIa activity. The data in FIG. 7 demonstrate that a similar concentration-dependent stimulation of FVIIa amidolytic activity was obtained with Fab-hTF.1-219 and mAb-hTF.1-219 fusion proteins as with non-fused hTF.1-219. This indicates that binding of FVIIa to the TF component of TF-fusion proteins was not affected by the linking of TF to Fab or mAb fragments.

The sequences are as follows:

SEQ ID NO: 1 provides the nucleotide sequence of human (h)TLT-1.

SEQ ID NO: 2 provides the amino acid sequence of hTLT-1.

SEQ ID NO: 3 provides the nucleotide sequence of the extracellular domain of hTLT-1-His6.

SEQ ID NO: 4 provides the amino acid sequence of the extracellular domain of hTLT-1-His6.

SEQ ID NOs: 5 to 8 provide the amino acid sequences of hTLT-1 fragments: hTLT-1.20-125, hTLT-1.16-162, hTLT-1.126-162 and hTLT-1.129-142.

SEQ ID NO: 9 provides the nucleotide sequence of the variable domain of mAb 0012 (2F105), LC.

SEQ ID NO: 10 provides the amino acid sequence of the variable domain of mAb 0012 (2F105), LC.

SEQ ID NO: 11 provides the nucleotide sequence of the variable domain of 0012 (2F105) HC.

SEQ ID NO: 12 provides the amino acid sequence of the variable domain of 0012 (2F105) HC.

SEQ ID NO: 13 provides the nucleic acid sequence of hTF.1-219.

SEQ ID NO: 14 provides the amino acid sequence of hTF.1-219.

SEQ ID NO: 15 provides the nucleic acid sequence of human tissue factor.

SEQ ID NO: 16 provides the amino acid sequence of human tissue factor.

SEQ ID NO: 17 provides the nucleotide sequence of the heavy chain of mAb 0012.

SEQ ID NO: 18 provides the nucleotide sequence of the light chain of mAb 0012 and Fab 0012.

SEQ ID NO: 19 provides the nucleotide sequence of the heavy chain of mAb 0023.

SEQ ID NO: 20 provides the nucleotide sequence of the light chain of mAb 0023 and Fab 0023.

SEQ ID NO: 21 provides the nucleotide sequence of the heavy chain of mAb 0051.

SEQ ID NO: 22 provides the nucleotide sequence of the light chain of mAb 0051 and Fab 0051.

SEQ ID NO: 23 provides the nucleotide sequence of the heavy chain of mAb 0052.

SEQ ID NO: 24 provides the nucleotide sequence of the heavy chain of mAb 0062.

SEQ ID NO: 25 provides the nucleotide sequence of the light chain of mAb 0052, Fab 0052 and mAb 0062.

SEQ ID NO: 26 provides the nucleotide sequence of the heavy chain of mAb 0061.

SEQ ID NO: 27 provides the nucleotide sequence of the heavy chain of mAb 0082.

SEQ ID NO: 28 provides the nucleotide sequence of the light chain of mAb 0061, Fab 0061, mAb 0082 and Fab 0082.

SEQ ID NO: 29 provides the nucleotide sequence of Fab 0012 VH-CH1.

SEQ ID NO: 30 provides the nucleotide sequence of Fab 0023 VH-CH1.

SEQ ID NO: 31 provides the nucleotide sequence of Fab 0051 VH-CH1.

SEQ ID NO: 32 provides the nucleotide sequence of Fab 0052 VH-CH1.

SEQ ID NO: 33 provides the nucleotide sequence of Fab 0061 VH-CH1.

SEQ ID NO: 34 provides the nucleotide sequence of Fab 0082 VH-CH1.

SEQ ID NO: 35 provides the nucleotide sequence of Fab AP-3 VH-VH1.

SEQ ID NO: 36 provides the nucleotide sequence of Fab AP-3 LC.

SEQ ID NO: 37 provides the nucleotide sequence of Fab-AP-3 LC.C34S.

SEQ ID NO: 38 provides the nucleotide sequence of hIgG4 hinge-CH2-CH3.

SEQ ID NO: 39 provides the amino acid sequence of mAb 0012, HC (mouse VH-human IgG4 CH1-CH2-CH3).

SEQ ID NO: 40 provides the amino acid sequence of mAb 0012, LC (mouse VL-human Kappa CL) and Fab 0012, LC (mouse VL-human Kappa CL).
SEQ ID NO: 41 provides the amino acid sequence of mAb 0023, HC (mouse VH-human IgG4 CH1-CH2-CH3).
SEQ ID NO: 42 provides the amino acid sequence of mAb 0023, LC (mouse VL-human Kappa CL) and Fab 0023, LC (mouse VL-human Kappa CL).
SEQ ID NO: 43 provides the amino acid sequence of mAb 0051, HC (mouse VH-human IgG4 CH1-CH2-CH3).
SEQ ID NO: 44 provides the amino acid sequence of mAb 0051, LC (mouse VL-human Kappa CL) and Fab 0051, LC (mouse VL-human Kappa CL).
SEQ ID NO: 45 provides the amino acid sequence of mAb 0052, HC (mouse VH-human IgG4 CH1-CH2-CH3).
SEQ ID NO: 46 provides the amino acid sequence of mAb 0052, LC (mouse VL-human Kappa CL); Fab 0052, LC (mouse VL-human Kappa CL); mAb 0062, LC (mouse VL-human Kappa CL).
SEQ ID NO: 47 provides the amino acid sequence of mAb 0061, HC (mouse VH-human IgG4 CH1-CH2-CH3).
SEQ ID NO: 48 provides the amino acid sequence of mAb 0061, LC (mouse VL-human Kappa CL); Fab 0061, LC (mouse VL-human Kappa CL) and mAb 0082, LC (mouse VL-human Kappa CL); Fab 0082, LC (mouse VL-human Kappa CL).
SEQ ID NO: 49 provides the amino acid sequence of mAb 0062, HC (mouse VH-human IgG4 CH1-CH2-CH3).
SEQ ID NO: 50 provides the amino acid sequence of mAb 0082, HC (mouse VH-human IgG4 CH1-CH2-CH3).
SEQ ID NO: 51 provides the amino acid sequence of Fab 0012, mouse VH-human IgG4 CH1.
SEQ ID NO: 52 provides the amino acid sequence of Fab 0023, mouse VH-human IgG4 CH1.
SEQ ID NO: 53 provides the amino acid sequence of Fab 0051, mouse VH-human IgG4 CH1.
SEQ ID NO: 54 provides the amino acid sequence of Fab 0052, mouse VH-human IgG4 CH1.
SEQ ID NO: 55 provides the amino acid sequence of Fab 0082, mouse VH-human IgG4 CH1.
SEQ ID NO: 56 provides the amino acid sequence of Fab AP-3, mouse VH-human IgG4 CH1.
SEQ ID NO: 57 provides the amino acid sequence of Fab AP-3, LC (mouse VL-human Kappa CL).
SEQ ID NO: 58 provides the amino acid sequence of Fab AP-3.LC.C34S, LC (mouse VL-human Kappa CL).
SEQ ID NOs: 59-68 provide the amino acid sequences of optional linkers L2-L10. Optional linkers are numbered and listed in Table 1.
SEQ ID NO: 69 provides the amino acid sequence of purification tag HPC4.
SEQ ID NOs: 70-155 provide the nucleic acid sequences of the primers used during the development of the expression constructs described in examples 4, 5, 6, 7, 8, 9, 10, 11, 12, 13, 14, 15, 17, 18, 19, 20, 24, 25.
SEQ ID NO: 156 provides the amino acid sequence of Fab 0061 VH-CH1.
SEQ ID NO: 157 provides the amino acid sequence of hIgG4-hinge-CH2-CH3.
SEQ ID NO: 158 provides the amino acid sequence of a His6 tag.
SEQ ID NO: 159 provides the amino acid sequence of hTLT-1.18-188.
SEQ ID NO: 160 provides the nucleic acid sequence of primer no. 1004.
SEQ ID NO: 161 provides the nucleic acid sequence of primer no. 1005.
SEQ ID NO: 162 provides the amino acid sequence of Fab 0100 HC.
SEQ ID NO: 163 provides the amino acid sequence of Fab 0100 LC.

DESCRIPTION OF THE INVENTION

The invention relates to fusion proteins: proteins expressed from two or more genes that have been joined artificially, for example via recombinant technology or chemical coupling, and which originally encoded separate proteins. Fusion proteins of the invention are capable of binding to a receptor that is only (in the sense non-ubiquitous) present on a platelet undergoing the conformational and functional changes associated with activation. Examples of such receptors might originate from the alpha- or dense granules of resting platelets. One particular example of such a receptor is TREM-like transcript 1 (TLT-1).

Triggering receptors expressed on myeloid cells (TREMs) have a well-established role in the biology of various myeloid lineages, playing important roles in the regulation of innate and adaptive immunity. TLT-1 belongs to the same family of proteins, though the TLT-1 gene is expressed only in a single lineage, namely megakaryocytes and thrombocytes (platelets) and is exclusively found in the alpha-granules of megakaryocytes and platelets. TLT-1 is a transmembrane protein that is exposed on the surface of activated platelets upon alpha-granule release. To date, TLT-1 has not been found on the surface of resting platelets or on the surface of any other cell types.

The extracellular portion of TLT-1 is known to consist of a single, immunoglobulin-like (Ig-like) domain connected to the platelet cell membrane by a linker region called the stalk (Gattis et al., Jour Biol Chem, 2006, Vol. 281, No. 19, pp. 13396-13403). The Ig-like domain of human TLT-1 (hTLT-1) consists of 105 residues and is attached to the membrane by a 37-amino acid stalk. Thus, the Ig-like domain of TLT-1 is expected to have considerable freedom of movement.

The putative transmembrane segment of hTLT-1 is 20 amino acids long. TLT-1 also has a cytoplasmic Immune-receptor Tyrosine-based Inhibitory-Motif, which may function as an intracellular signal transduction domain.

The role of TLT-1 in platelet biology has not yet been fully elucidated; it is believed that TLT-1 plays a role in regulating coagulation and inflammation at the site of an injury. A soluble form of TLT-1 containing the Ig-like domain has been reported (Gattis et al., Jour Biol Chem, 2006, Vol. 281, No. 19, pp. 13396-13403). The specific functions of soluble versus platelet-bound TLT-1 remain to be established.

A receptor such as TLT-1 comprises epitopes that are useful targets for the fusion proteins/constructs of the current invention. Fusion proteins may bind any part of TLT-1 that would be available for binding in vivo, such as surface accessible residues of the Ig-like domain, or part of the stalk. Hence, fusion proteins may bind one or more residues within TLT-1 (20-125), TLT-1 (16-162), TLT-1 (126-162) and/or TLT-1 (129-142).

In a preferred embodiment, fusion proteins bind the stalk of TLT-1, such as one or more residues of TLT-1 (126-162) or TLT-1 (129-142). Fusion proteins that bind to the stalk of TLT-1 are unlikely to interfere with the function of the Ig-like domain and will probably not separate from the platelet surface if the Ig-like domain is shed. Furthermore, fusion proteins that bind the stalk of TLT-1 place their TF portion in a favorable position and orientation on the cell surface of activated platelets, relative to that of FVII and FVIIa. In another preferred embodiment, fusing TF to the C-terminal of an antibody, or fragment thereof, will position TF even more favourably on the cell surface of activated platelets, relative to that of FVII and FVIIa.

In terms of the current invention, TLT-1 may be from any vertebrate, such as any mammal, such as a rodent (such as a mouse, rat or guinea pig), a lagomorph (such as a rabbit), an artiodactyl (such as a pig, cow, sheep or camel) or a primate (such as a monkey or human being). TLT-1 is, preferably, human TLT-1. TLT-1 may be translated from any naturally occurring genotype or allele that gives rise to a functional TLT-1 protein. A non-limiting example of one human TLT-1 is the polypeptide sequence of SEQ ID NO. 2.

Fusion proteins of the invention comprise a tissue factor-like component. Tissue Factor is a 263 amino acid long, integral membrane glycoprotein receptor. It consists of an extracellular part folded into two compact fibronectin type III-like domains (1-209) that are each stabilized by a single disulfide bond, a short linker (210-219), a transmembrane segment (220-242), and a short cytoplasmic tail (243-263). It forms a tight $Ca^{2+}$-dependent complex with Factor VII/FVIIa.

In terms of the current invention, "tissue factor, or any biologically functional variant or fragment thereof", may be any tissue factor-like polypeptide that is able to bind Factor VII/VIIa, such that blood coagulation is stimulated. "Tissue factor" may be derived from any vertebrate animal, such as any mammal, such as a rodent (such as a mouse, rat or guinea pig), a lagomorph (such as a rabbit), an artiodactyl (such as a pig, cow, sheep or camel) or a primate (such as a monkey or a human being). "Tissue factor, or any biologically functional variant or fragment thereof" may be the extracellular domain of human tissue factor. "Tissue factor, or any biologically functional variant or fragment thereof" may be any polypeptide that is at least 90%, such as at least 91%, such as at least 92%, such as at least 93%, such as at least 94%, such as at least 95%, such as at least 96%, such as at least 97%, such as at least 98%, such as at least 99% identical to the polypeptide sequence of tissue factor. "Tissue factor, or any biologically functional variant or fragment thereof" may be any polypeptide that is at least 90%, such as at least 91%, such as at least 92%, such as at least 93%, such as at least 94%, such as at least 95%, such as at least 96%, such as at least 97%, such as at least 98%, such as at least 99% identical to the polypeptide sequence of the extracellular domain of tissue factor or a variant thereof. "Tissue factor, or any biologically functional variant or fragment thereof" may be any polypeptide that is able to function as co-factor for FVII and FVIIa. Hence, "tissue factor or any biologically functional variant or fragment thereof" may be any polypeptide that is able to stimulate the amidolytic activity of FVIIa. Said "tissue factor, or any biologically functional variant or fragment thereof" may be the extracellular domain of TF (1-219). "Tissue Factor polypeptide" may be a polypeptide comprising the soluble extracellular domain of Tissue Factor, i.e. amino acids 1-219 (in the following referred to as sTF or sTF(1-219)), or a functional variant or truncated form thereof. Preferably, the Tissue Factor polypeptide at least comprises a fragment corresponding to the amino acid sequence 6-209 of Tissue Factor. Examples hereof are sTF(6-209), sTF(1-209), sTF (1-210), sTF (1-211), sTF (1-212), sTF (1-213), sTF (1-214), sTF (1-215), sTF (1-216), sTF (1-217), sTF (1-218), sTF(1-219), sTF(2-219), sTF(3-219), sTF(4-219), sTF(5-219).

In accordance with the current invention, "tissue factor, or any biologically functional variant or fragment thereof" may have any one or more of the features listed above.

Fusion proteins of the invention also comprise a "ligand". The term "ligand" refers to any substance that is able to bind to and form a complex with a biomolecule, in order to serve a biological purpose. In one sense of the term, it is a signal triggering molecule binding to a site on a target protein by means of intermolecular forces such as ionic bonds, hydrogen bonds and Van der Waals forces. The association of a ligand with said biomolecule is usually reversible. Binding of a naturally occurring ligand to its counterpart receptor may or may not alter the conformation of the receptor protein. In terms of the current invention, one object of said ligand is to target the TF-like component to the surface of a platelet that is activated or in the process of being activated.

The ligand may be any naturally occurring or synthetic ligand that binds a receptor that is, preferably, only present on platelets undergoing activation. The ligand of the current invention may be any naturally occurring or synthetic ligand that binds TLT-1, or the ligand may be an antibody, or fragment thereof, that has been raised against TLT1. The ligand of the current invention may or may not result in a change in the conformational structure of TLT-1. Furthermore, the ligand of the current invention may or may not result in intracellular signalling, as a result of binding to TLT-1. In a preferred embodiment, the ligand of the invention is capable of binding to the stalk of TLT-1. Hence, the ligand of the current invention utilises a naturally occurring receptor, or portion thereof, in order to achieve the effect that is unique to and provided by the current invention.

As mentioned above, the ligand component of the invented fusion proteins may be an antibody or a fragment thereof. The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

An antibody of the invention may be a monoclonal antibody or a polyclonal antibody. In one embodiment, an antibody of the invention is a monoclonal antibody. An antibody of the invention may be a chimeric antibody, a CDR-grafted antibody, a human or humanised antibody or an antigen binding portion of any thereof. For the production of both monoclonal and polyclonal antibodies, the experimental animal is a suitable mammal such as a goat, rabbit, rat or mouse.

A monoclonal antibody is, in structural terms, represented by a single molecular species having a single binding specificity and affinity for a particular epitope. Monoclonal antibodies (mAbs) of the present invention can be produced by a variety of well-known techniques, including conventional monoclonal antibody methodology e.g., the standard somatic cell hybridization technique of Kohler and Milstein (1975) *Nature* 256: 495, or viral or oncogenic transformation of B lymphocytes. The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

To generate hybridomas producing monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. The antibody secreting hybridomas can be replated, screened again, and if still positive for suitable IgG, the monoclonal antibodies can be subcloned at least twice by limiting dilution. The stable subclones can then be cultured in vitro to generate small amounts of antibody in tissue culture medium for characterization.

An antibody of the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

Suitable monoclonal antibodies, shown in table 1, are herein identified by means of the prefix "mAb" together with a 4-digit number. Hence, the monoclonal antibody may be mAb 0012 or a variant thereof. (Note that the variable domain of the mAb referred to as "2F105" is identical to that of mAb 0012.) The monoclonal antibody may be mAb 0023 or a variant thereof. The monoclonal antibody may be mAb 0051 or a variant thereof. The monoclonal antibody may be mAb 0061 or a variant thereof. The monoclonal antibody may be mAb 0062 or a variant thereof. The monoclonal antibody may be mAb 0082 or a variant thereof.

TABLE 1

Non-limiting examples of suitable monoclonal antibodies

| mAb ID | HC | LC |
|---|---|---|
| 0012 | SEQ ID NO: 39 | SEQ ID NO: 40 |
| 0023 | SEQ ID NO: 41 | SEQ ID NO: 42 |
| 0051 | SEQ ID NO: 43 | SEQ ID NO: 44 |
| 0052 | SEQ ID NO: 45 | SEQ ID NO: 46 |
| 0061 | SEQ ID NO: 47 | SEQ ID NO: 48 |
| 0062 | SEQ ID NO: 49 | SEQ ID NO: 46 |
| 0082 | SEQ ID NO: 50 | SEQ ID NO: 48 |

The term "antigen-binding portion" of an antibody refers to one or more fragments of an antibody that retain the ability to specifically bind to an antigen, such as TLT-1 or another target receptor as described herein. It has been shown that the antigen-binding function of an antibody can be performed by fragments of a full-length antibody. Examples of binding fragments encompassed within the term "antigen-binding portion" of an antibody include a Fab fragment, a F(ab')$_2$ fragment, a Fab' fragment, a Fd fragment, a Fv fragment, a ScFv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. These antibody fragments may be obtained using conventional techniques known to those of skill in the art, and the fragments may be screened for utility in the same manner as intact antibodies.

Suitable Fab fragments, shown in table 2, are herein identified by means of the prefix "Fab" together with a 4-digit number. Said Fab fragment may be Fab 0012 or a variant thereof. Said Fab fragment may be Fab 0023 or a variant thereof. Said Fab fragment may be Fab 0051 or a variant thereof. Said Fab fragment may be 0052 or a variant thereof. Said Fab fragment may be Fab 0061 or a variant thereof. Said Fab fragment may be Fab 0062 or a variant thereof. Said Fab fragment may be Fab 0082 or a variant thereof.

TABLE 2

Non-limiting examples of suitable Fab fragments

| Fab ID | VH-CH1 | LC |
|---|---|---|
| 0012 | SEQ ID NO: 51 | SEQ ID NO: 40 |
| 0023 | SEQ ID NO: 52 | SEQ ID NO: 42 |
| 0051 | SEQ ID NO: 53 | SEQ ID NO: 44 |
| 0052 | SEQ ID NO: 54 | SEQ ID NO: 46 |
| 0061 | SEQ ID NO: 156 | SEQ ID NO: 48 |
| 0082 | SEQ ID NO: 55 | SEQ ID NO: 48 |
| AP-3 | SEQ ID NO: 56 | SEQ ID NO: 57 |
| AP-3.LC.C34S | SEQ ID NO: 56 | SEQ ID NO: 58 |

An antibody of the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

Antibodies of the invention can be tested for binding to the target protein by, for example, standard ELISA or Western blotting. An ELISA assay can also be used to screen for hybridomas that show positive reactivity with the target protein. The binding specificity of an antibody may also be determined by monitoring binding of the antibody to cells expressing the target protein, for example, by flow cytometry.

The specificity of an antibody of the invention for the target protein may be further studied by determining whether or not the antibody binds to other proteins. For example, where it is desired to produce an antibody that specifically binds TLT-1 or a particular part, e.g. epitope, of TLT-1, the specificity of the antibody may be assessed by determining whether or not the antibody also binds to other molecules or modified forms of TLT-1 that lack the part of interest.

Polypeptide or antibody "fragments" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

An antibody of the invention may be, or may comprise, a fragment of the anti-TLT-1 antibody or a variant thereof. The antibody of the invention may be or may comprise an antigen binding portion of this antibody or a variant thereof, as discussed further above. For example, the antibody of the invention may be a Fab fragment of this antibody, or a variant thereof, or may be a single chain antibody derived from this antibody, or a variant thereof.

Antibodies, as well as fusion proteins that comprise an antibody, or fragment thereof, may be defined in terms of their epitopes and/or paratopes. The term "epitope" includes any protein determinant capable of specific binding to an immunoglobulin (or T-cell receptor). Epitopic determinants usually consist of chemically active surface groupings of molecules such as amino acids or sugar side chains and usually have specific three dimensional structural characteristics, as well as specific charge characteristics. An epitope having antigenic activity is a portion of a polypeptide to which an antibody immunospecifically binds, as determined by any method well known in the art, for example, by immunoassays. Antigenic epitopes need not necessarily be immunogenic.

In terms of the current invention, "epitope" refers to the area or region on an antigen (Ag), which is a receptor on an activated platelet, to which the antibody (Ab) portion of the fusion protein is capable of specifically binding, i.e. the area or region that is in physical contact with the Ab. An antigen's epitope may comprise amino acid residues in the Ag that are directly involved in binding to a Ab (the immunodominant component of the epitope) and other amino acid residues, which are not directly involved in the binding, such as amino acid residues of the Ag which are effectively blocked by the Ab (in other words, the amino acid residue is within the "solvent-excluded surface" and/or the "footprint" of the Ab). The term epitope herein includes both types of binding sites in any particular region of a receptor such as TLT-1 that specifically binds to an anti-TLT-1 antibody, or another TLT-1-specific agent according to the invention, unless otherwise stated (e.g., in some contexts the invention relates to antibodies that bind directly to particular amino acid residues). Receptors such as TLT-1 may comprise a number of different epitopes, which may include, without limitation, (1) linear peptide antigenic determinants, (2) conformational antigenic determinants which consist of one or more non-contiguous amino acids located near each other in the mature receptor conformation; and (3) post-translational antigenic determinants which consist, either in whole or part, of molecular structures covalently attached to TLT-1, such as carbohydrate groups.

The epitope for a given antibody (Ab)/antigen (Ag) pair can be defined and characterized at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods. As each method relies on a unique principle, the description of an epitope is intimately linked to the method by which it has been determined. Thus, the epitope for a given Ab/Ag pair will be defined differently depending on the epitope mapping method employed.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level the epitope can be characterized by the spatial coordinates defining the atomic contacts between the Ag and Ab. At a further less detailed level the epitope can be characterized by the amino acid residues that it comprises as defined by a specific criterium, e.g. distance between atoms in the Ab and the Ag. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag.

In the context of an X-ray derived crystal structure defined by spatial coordinates of a complex between an Ab, e.g. a Fab fragment, and its Ag, the term epitope is herein, unless otherwise specified or contradicted by context, specifically defined as platelet receptor residues characterized by having a heavy atom (i.e. a non-hydrogen atom) within a distance of 4 Å from a heavy atom in the Ab.

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described on the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

Epitopes characterized by competition binding are said to be overlapping if the binding of the corresponding Ab's are mutually exclusive, i.e. if binding of one Ab excludes simultaneous binding of the other Ab. The epitopes are said to be separate (unique) if the Ag is able to accommodate binding of both corresponding Ab's simultaneously. Thus, fusion proteins of the invention may be capable of binding to the same epitope as mAb 0012. Fusion proteins may be capable of binding to the same epitope as mAb 0023. Fusion proteins may be capable of binding to the same epitope as mAb 0051. Fusion proteins may be capable of binding to the same epitope as mAb 0061. Fusion proteins may be capable of binding to the same epitope as mAb 0062.

The epitope may comprise one or more residues selected from the group consisting of K133, I134, G135, S136, L137, A138, N140, A141, F142, S143, D144, P145 and A146 of SEQ ID NO: 4.

The epitope may comprise one or more residues selected from the group consisting of V17, Q18, C19, H20, Y21, R22, L23, Q24, D25, V26, K27, A28, L63, G64, G65, G66, L67, L68, G89, A90, R91, G92, P93, Q94, I95 and L96 of SEQ ID NO: 5.

The epitope may comprise one or more residues selected from the group consisting of L36, P37, E38, G39, C40, Q41, P42, L43, V44, S45, S46, A47, V73, T74, L75, Q76, E77, E78, D79, A80, G81, E82, Y83, G84, C85, M86, R91, G92, P93, Q94, I95, L96, H97, R98, V99, S100 and L101 of SEQ ID NO: 5.

The epitope may comprise one or more residues selected from the group consisting of V17, Q18, C19, H20, Y21, R22, L23, Q24, D25, V26, K27, A28, R91, G92, P93, Q94, I95, L96, H97, R98, V99, S100 and L101 of SEQ ID NO: 5.

The epitope may comprise one or more residues selected from the group consisting of E5, T6, H7, K8, I9, G10, S11, L12, A13, E14, N15, A16, F17, S18, D19, P20 and A21 of SEQ ID NO: 7.

The epitope may comprise one or more residues selected from the group consisting of K133, I134, G135, S136, L137, A138, N140, A141, F142, S143, D144, P145 and A146 of SEQ ID NO: 7.

The definition of the term "paratope" is derived from the above definition of "epitope" by reversing the perspective. Thus, the term "paratope" refers to the area or region on the Ab to which an Ag specifically binds, i.e. to which it makes physical contact to the Ag.

The paratope may comprise one or more residues selected from the group consisting of H50, N52, Y56, H58, Y73, F79, S115, T116, V118 and Y120 of the anti-TLT-1 light (L) chain (SEQ ID NO: 40), and residues V20, F45, R49, Y50, W51, E68, T75, N77, S116, G117, V118 and T120 of the anti-TLT-1 heavy (H) chain (SEQ ID NO: 39)

In the context of an X-ray derived crystal structure defined by spatial coordinates of a complex between an Ab, e.g. a Fab fragment, and its Ag, the term paratope is herein, unless otherwise specified or contradicted by context, specifically defined as Ag residues characterized by having a heavy atom (i.e. a non-hydrogen atom) within a distance of 4 Å from a heavy atom in the platelet receptor.

The epitope and paratope for a given antibody (Ab)/antigen (Ag) pair may be identified by routine methods. For example, the general location of an epitope may be determined by assessing the ability of an antibody to bind to different fragments or variants of TLT-1. The specific amino acids within TLT-1 that make contact with an antibody (epitope) and the specific amino acids in an antibody that make contact with TLT-1 (paratope) may also be determined using routine methods, such as those described in the examples. For example, the antibody and target molecule may be combined and the Ab/Ag complex may be crystallised. The crystal structure of the complex may be determined and used to identify specific sites of interaction between the antibody and its target.

Fusion proteins comprising a ligand that is an antibody or fragment thereof may also be defined in terms of their complementarity-determining regions (CDRs). The term "complementarity-determining region" or "hypervariable region" when used herein refers to the amino acid residues of an antibody that are responsible for antigen binding. The complementarity-determining regions or "CDRs" are generally comprised of amino acid residues 24-34 (L1), 50-56 (L2) and 89-97 (L3) in the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

In one embodiment, the heavy chain comprises:
a CDR1 sequence of amino acids 50 to 54 (DYFMY) of SEQ ID NO: 41, wherein one of these amino acids may be substituted by a different amino acid; and/or
a CDR2 sequence of amino acids 69 to 85 (YISNG-GDSSSYPDTVKG) of SEQ ID NO: 41, wherein one, two, three or four of these amino acids may be substituted by a different amino acid; and/or
a CDR3 sequence of amino acids 118 to 129 (NKNWD-DYYDMDY) of SEQ ID NO: 41, wherein one, two or three of these amino acids may be substituted by a different amino acid.

In another embodiment, the light chain comprises:
a CDR1 sequence of amino acids 44 to 60 (KSSQSLLNSR-TRKNYLA) of SEQ ID NO: 42, wherein one, two, three or four of these amino acids may be substituted with a different amino acid; and/or
a CDR2 sequence of amino acids 76 to 82 (WASTRES) of SEQ ID NO: 42, wherein one or two of these amino acids may be substituted with a different amino acid; and/or
a CDR3 sequence of amino acids 115 to 122 (KQSYNLLT) of SEQ ID NO: 42, wherein one or two of these amino acids may be substituted with a different amino acid.

In another embodiment, the heavy chain comprises:
a CDR1 sequence of amino acids 50 to 54 (DYSMH) of SEQ ID NO: 43, wherein one of these amino acids may be substituted by a different amino acid; and/or
a CDR2 sequence of amino acids 69 to 85 (VISTYYGD-VRYNQKFKG) of SEQ ID NO: 43, wherein one, two, three or four of these amino acids may be substituted by a different amino acid; and/or
a CDR3 sequence of amino acids 118 to 129 (APMITT-GAWFAY) of SEQ ID NO: 43, wherein one, two or three of these amino acids may be substituted by a different amino acid.

In another embodiment, the light chain comprises:
a CDR1 sequence of amino acids 44 to 54 (KASQSVSNDVA) of SEQ ID NO: 44, wherein one, two or three of these amino acids may be substituted with a different amino acid; and/or a CDR2 sequence of amino acids 70 to 76 (YASSRYT) of SEQ ID NO: 44, wherein one or two of these amino acids may be substituted with a different amino acid; and/or a CDR3 sequence of amino acids 109 to 117 (QQDYSSPYT) of SEQ ID NO: 44, wherein one or two of these amino acids may be substituted with a different amino acid.

In another embodiment, the heavy chain comprises:

a CDR1 sequence of amino acids 50 to 54 (SHWIE) of SEQ ID NO: 49, wherein one of these amino acids may be substituted by a different amino acid; and/or a CDR2 sequence of amino acids 69 to 85 (EILPGSGNTNYNEKFKG) of SEQ ID NO: 49, wherein one, two, three or four of these amino acids may be substituted by a different amino acid; and/or a CDR3 sequence of amino acids 118 to 130 (GYYGLNYDWYFDV) of SEQ ID NO: 49, wherein one, two or three of these amino acids may be substituted by a different amino acid.

In another embodiment, the light chain comprises:

a CDR1 sequence of amino acids 44 to 54 (RASQDISNYLN) of SEQ ID NO: 46, wherein one, two or three of these amino acids may be substituted with a different amino acid; and/or a CDR2 sequence of amino acids 70 to 76 (YTSRLHS) of SEQ ID NO: 46, wherein one or two of these amino acids may be substituted with a different amino acid; and/or a CDR3 sequence of amino acids 109 to 117 (QQDTKLPYT) of SEQ ID NO: 46, wherein one or two of these amino acids may be substituted with a different amino acid.

In another embodiment, the heavy chain comprises:

a CDR1 sequence of amino acids 49 to 53 (RYWMT) of SEQ ID NO: 47, wherein one of these amino acids may be substituted by a different amino acid; and/or a CDR2 sequence of amino acids 68 to 84 (EINPDSSTINYNPSLKD) of SEQ ID NO: 47, wherein one, two, three or four of these amino acids may be substituted by a different amino acid; and/or a CDR3 sequence of amino acids 117 to 121 (GVFTS) of SEQ ID NO: 47, wherein one, two or three of these amino acids may be substituted by a different amino acid.

In another embodiment, the light chain comprises:

a CDR1 sequence of amino acids 43 to 58 (RSSQSLVHRNGNTYFH) of SEQ ID NO: 48, wherein one, two, three or four of these amino acids may be substituted with a different amino acid; and/or a CDR2 sequence of amino acids 74 to 80 (KVSNRFS) of SEQ ID NO: 48, wherein one or two of these amino acids may be substituted with a different amino acid; and/or a CDR3 sequence of amino acids 113 to 121 (SQSTHVPYT) of SEQ ID NO: 48, wherein one or two of these amino acids may be substituted with a different amino acid.

In another embodiment, the heavy chain comprises:

a CDR1 sequence of amino acids 49 to 53 (RYWMT) of SEQ ID NO: 39, wherein one of these amino acids may be substituted by a different amino acid; and/or a CDR2 sequence of amino acids 68 to 84 (EINPDSSTINYTPSLKD) of SEQ ID NO: 39, wherein one, two, three or four of these amino acids may be substituted by a different amino acid; and/or a CDR3 sequence of amino acids 117 to 121 (GVFTS) of SEQ ID NO: 39, wherein one, two or three of these amino acids may be substituted by a different amino acid.

In another embodiment, the light chain comprises:

a CDR1 sequence of amino acids 43 to 58 (RSSQSLVHRNGNTYFH) of SEQ ID NO: 40, wherein one, two, three or four of these amino acids may be substituted with a different amino acid; and/or a CDR2 sequence of amino acids 74 to 80 (KVSNRFS) of SEQ ID NO: 40, wherein one or two of these amino acids may be substituted with a different amino acid; and/or a CDR3 sequence of amino acids 113 to 121 (SQSTHVPYT) of SEQ ID NO: 40, wherein one or two of these amino acids may be substituted with a different amino acid.

In yet another embodiment, the heavy chain of (ii) comprises:

a CDR1 sequence of amino acids 50 to 54 (NYWLG) of SEQ ID NO: 56, wherein one of these amino acids may be substituted by a different amino acid; and/or a CDR2 sequence of amino acids 69 to 85 (DIYPGGGYNKYNENFKG) of SEQ ID NO: 56, wherein one, two, three or four of these amino acids may be substituted by a different amino acid; and/or a CDR3 sequence of amino acids 118 to 128 (EYGNYDYAMDS) of SEQ ID NO: 56, wherein one, two or three of these amino acids may be substituted by a different amino acid.

In a further embodiment, the light chain of (ii) comprises:

a CDR1 sequence of amino acids 44 to 59 (RSSRSLLHSNGNTYLC) of SEQ ID NO: 57, wherein one, two, three or four of these amino acids may be substituted with a different amino acid; and/or a CDR2 sequence of amino acids 75 to 81 (RMSNLAS) of SEQ ID NO: 57, wherein one or two of these amino acids may be substituted with a different amino acid; and/or a CDR3 sequence of amino acids 114 to 122 (MQHLEYPFT) of SEQ ID NO: 57, wherein one or two of these amino acids may be substituted with a different amino acid.

Hence, the construct of the current invention is any fusion protein or chimer that comprises (i) at least one TF, or biologically functional variant(s) or fragment(s) thereof, and (ii) a ligand that is capable of binding (iii) a receptor, and/or a fragment thereof, wherein the receptor is present only (in the sense of non-ubiquitous) on the surface of activated platelets. In one preferred embodiment, (iii) is TLT-1. The fusion protein (construct) of the current invention is preferably engineered such that its constituent parts may function independently of one another. For example, said "tissue factor . . . " component of the current invention is able to bind FVII and FVIIa, as opposed to being sterically hindered from doing so due to the presence of said "ligand" component of the invention. Likewise, said "ligand" component of the invention is preferably able to bind a receptor such as TLT-1, unhindered by the presence of said "tissue factor . . . " component. The carboxy terminus of the "TF polypeptide" component may be covalently attached to the amino terminus of the ligand component of the construct, or vice versa. Said ligand component of the construct will preferably not bind any other TREM. The construct of the current invention may or may not comprise a linker between said TF and said ligand constituents. Said optional linker may be any one of the linkers described in Table 3 or may be any other linker that binds both TF and ligand constituent parts of the construct, such that both are functional.

The fusion protein/construct of the present invention may comprise (i) tissue factor and (ii) any ligand that is capable of binding (iii) TLT-1. Said fusion protein/construct may further comprise a linker, which may be any one of linkers L1-L10 provided in Table 3.

The construct of the present invention may comprise (i) tissue factor and (ii) an antibody capable of binding (iii) TLT-1. Said antibody may be a monoclonal antibody. The construct may further comprise a linker. Said linker may be any one of linkers L1-L10 provided in Table 3.

The construct of the present invention may comprise (i) tissue factor and (ii) a Fab fragment capable of binding (iii) TLT-1.

The construct may further comprise a linker, which may be any one of linkers (L1-L10) provided in Table 3.

The construct of the present invention may comprise (i) tissue factor and (ii) a F(ab')$_2$ fragment capable of binding (iii) TLT-1. The construct may further comprise a linker, which may be any one of the linkers (L1-L10) provided in Table 3.

The construct of the present invention may comprise (i) tissue factor and (ii) a Fab' fragment capable of binding (iii) TLT-1. Said construct may further comprise a linker, which may be any one of the linkers (L1-L10) provided in Table 3.

The construct of the present invention may comprise (i) tissue factor and (ii) a Fd fragment capable of binding (iii) TLT-1. Said construct may further comprise a linker, which may be any one of the linkers (L1-L10) provided in Table 3.

The construct of the present invention may comprise (i) tissue factor and (ii) a Fv fragment capable of binding (iii) TLT-1. Said construct may further comprise a linker, which may be any one of the linkers (L1-L10) provided in Table 3.

The construct of the present invention may comprise (i) tissue factor and (ii) a dAb fragment capable of binding (iii) TLT-1. Said construct may further comprise a linker, which may be any one of the linkers (L1-L10) provided in Table 3.

The construct of the present invention may comprise (i) tissue factor and (ii) an isolated complementarity determining region (CDR) capable of binding (iii) TLT-1. Said construct may further comprise a linker, which may be any one of the linkers (L1-L10) provided in Table 3.

The construct of the present invention may comprise (i) any biologically functional variant or fragment of tissue factor and (ii) any ligand capable of binding (iii) TLT-1. Said construct may further comprise a linker, which may be any one of linkers (L1-L10) provided in Table 3.

The construct of the present invention may comprise (i) any biologically functional variant or fragment of tissue factor and (ii) an antibody capable of binding (iii) TLT-1. Said construct may further comprise a linker, which may be any one of linkers (L1-L10) provided in Table 3.

The construct of the present invention may comprise (i) any biologically functional variant or fragment of tissue factor and (ii) a Fab fragment capable of binding (iii) TLT-1. Said construct may further comprise a linker, which may be any one of linkers (L1-L10) provided in Table 3.

The construct of the present invention may comprise (i) any biologically functional variant or fragment of tissue factor and (ii) a F(ab')$_2$ fragment capable of binding (iii) TLT-1. Said construct may further comprise a linker, which may be any one of the linkers (L1-L10) provided in Table 3.

The construct of the present invention may comprise (i) any biologically functional variant or fragment of tissue factor and (ii) a Fab' fragment capable of binding (iii) TLT-1. Said construct may further comprise a linker, which may be any one of the linkers (L1-L10) provided in Table 3.

The construct of the present invention may comprise (i) any biologically functional variant or fragment of tissue factor and (ii) a Fd fragment capable of binding (iii) TLT-1. Said construct may further comprise a linker, which may be any one of the linkers (L1-L10) provided in Table 3.

The construct of the present invention may comprise (i) any biologically functional variant or fragment of tissue factor and (ii) a Fv fragment capable of binding (iii) TLT-1. Said construct may further comprise a linker, which may be any one of the linkers (L1-L10) provided in Table 3.

The construct of the present invention may comprise (i) any biologically functional variant or fragment of tissue factor and (ii) a dAb fragment capable of binding (iii) TLT-1. Said construct may further comprise a linker, which may be any one of the linkers (L1-L10) provided in Table 3.

The construct of the present invention may comprise (i) any biologically functional variant or fragment of tissue factor and (ii) an isolated complementarity determining region (CDR) capable of binding (iii) TLT-1. Said construct may further comprise a linker, which may be any one of the linkers (L1-L10) provided in Table 3.

The construct of the present invention may comprise (i) the extracellular domain of tissue factor and (ii) any ligand capable of binding (iii) TLT-1. Said construct may further comprise a linker. Said linker may be any one of linkers L1-L10 provided in Table 3.

The construct of the present invention may comprise (i) the extracellular domain of tissue factor and (ii) an antibody capable of binding (iii) TLT-1. Said construct may further comprise a linker. Said linker may be any one of linkers L1-L10 provided in Table 3.

The construct of the present invention may comprise (i) the extracellular domain of tissue factor and (ii) a Fab fragment capable of binding (iii) TLT-1. Said construct may further comprise a linker. Said linker may be any one of linkers L1-L10 provided in Table 3.

The construct of the present invention may comprise (i) the extracellular domain of tissue factor and (ii) a F(ab')$_2$ fragment capable of binding (iii) TLT-1. Said construct may further comprise a linker. Said linker may be any one of the linkers (L1-L10) provided in Table 3.

The construct of the present invention may comprise (i) the extracellular domain of tissue factor and (ii) a Fab' fragment capable of binding (iii) TLT-1. Said construct may further comprise a linker. Said linker may be any one of the linkers (L1-L10) provided in Table 3.

The construct of the present invention may comprise (i) the extracellular domain of tissue factor and (ii) a Fd fragment capable of binding (iii) TLT-1. Said construct may further comprise a linker. Said linker may be any one of the linkers (L1-L10) provided in Table 3.

The construct of the present invention may comprise (i) the extracellular domain of tissue factor and (ii) a Fv fragment capable of binding (iii) TLT-1. Said construct may further comprise a linker. Said linker may be any one of the linkers (L1-L10) provided in Table 3.

The construct of the present invention may comprise (i) the extracellular domain of tissue factor and (ii) a dAb fragment capable of binding (iii) TLT-1. Said construct may further comprise a linker. Said linker may be any one of the linkers (L1-L10) provided in Table 3.

The construct of the present invention may comprise (i) the extracellular domain of tissue factor and (ii) an isolated complementarity determining region (CDR) capable of binding (iii) TLT-1. Said construct may further comprise a linker. Said linker may be any one of the linkers (L1-L10) provided in Table 3.

The construct of the current invention may be a fusion protein comprising the variable domain of mAb 0012 (2F105) HC, the human IgG4 CH1 constant region, the glycine-serine linker and the extracellular domain of human Tissue Factor (2F105HC-V-CH1-linker-hTF ECD).

The construct of the current invention may be a fusion protein consisting of the variable domain of mAb 0012 (2F105) HC, the human IgG4 CH1 constant region, the glycine-serine linker and the extracellular domain of human Tissue Factor (2F105HC-V-CH1-linker-hTF ECD).

As mentioned above, the fusion protein of the current invention may comprise a linker. Non-limiting examples of linker amino acid sequences are shown in Table 3. Hence, said linker may be L1. The linker may be L2. The linker may be L3. The linker may be L4. The linker may be L5. The linker may be L6. The linker may be L7. The linker may be L8. The linker may be L9. The linker may be L10.

TABLE 3

Non-limiting examples of optional linkers

| Linker ID | Length (AA) | Linker sequence |
|---|---|---|
| L0 | 0 | no linker |
| L1 | 2 | GS |
| L2 | 7 | GSGGGGS |
| L3 | 12 | GSGGGGSGGGGS |
| L4a | 17 | GSGGGGSGGGGSGGGGS |
| L4b | 17 | GGGGSGGGGSGGGGSGS |
| L5 | 22 | GGGGSGSGGGGSGGGGSGGGGS |
| L6 | 27 | GGGGSGGGGSGSGGGGSGGGGSGGGGS |
| L7 | 32 | GGGGSGGGGSGGGGSGSGGGGSGGGGSGGGGS |
| L8 | 37 | GGGGSGGGGSGGGGSGGGGSGSGGGGSGGGGSGGGGS |
| L9 | 42 | GGGGSGGGGSGGGGSGGGGSGGGGSGSGGGGSGGGSGGGGS |
| L10 | 16 | YGPPSPSSPAPEFLGG |

As mentioned above, the extracellular part of TLT-1 consists of an immunoglobulin-like domain and a stalk. Fusion proteins of the invention may be capable of binding either of these. When part (ii) of the fusion protein is capable of binding the immunoglobulin-like domain, a longer linker may allow part (i) of said fusion protein to adapt a functionally relevant position and orientation on the surface of the activated platelet, thereby facilitating its function. This is because part (i), i.e. the TF polypeptide, must be in the special vicinity of and properly oriented relative to FVII/FVIIa: TF acts as co-factor to FVII/FVIIa, which binds $Ca^{2+}$ and phospholipid on the surface of activated platelets.

A fusion protein that is capable of binding the stalk of TLT-1 is adjacent to the platelet membrane. Hence, a fusion protein that is capable of binding the stalk may comprise a linker; however, the inclusion of a linker does not necessarily affect the function of the TF part of the fusion protein.

Examples of suitable fusion proteins, wherein (ii) is a monoclonal antibody, are provided in table 4. As each mAb has two identical heavy chains (HC) and two identical light chains (LC), fusion proteins wherein part (ii) is a mAb may comprise two TF polypeptides (part (i)). TF may be fused to a HC of the mAb; TF may be fused to a LC of the mAb. TF may be fused to a ligand which, in turn, is fused to a HC of the mAb or a LC of the mAb. Following are examples of how to interpret the names of the fusion proteins provided in table 4:

In fusion protein "mAb 0012-(HC-L0-hTF.1-219)$_2$; LC$_2$":
  "mAb 0012": monoclonal antibody 0012.
  "(HC-L0-hTF.1-219)$_2$": one hTF.1-219 is fused to each HC; the N-terminal of hTF.1-219 is fused to the C-terminal of the heavy chain.
  "L0": no linker is present.
  LC$_2$: there are two light chains, to which nothing is fused.

In fusion protein "mAb 0023-(HC-L4a-hTF.1-219)$_2$(LC-HPC4)$_2$":
  "mAb 0023" is monoclonal antibody 0023.
  "(HC-L4a-hTF.1-219)$_2$" indicates that one hTF.1-219 is fused to each HC via a linker; the N-terminal of hTF.1-219 is fused to the C-terminal of linker L4a, whose N-terminal is fused to the C-terminal of the heavy chain of the mAb.
  "(LC-HPC4)$_2$" indicates that an HPC4 tag is fused to the C-terminal of each LC.

In fusion protein "mAb 0012-(LC-L5-hTF.1-219)$_2$; HC$_2$":
  (LC-L5-hTF.1-219)$_2$ indicates that the N-terminal of hTF.1-219 is fused to the C-terminal of linker L5 whose N-terminal is fused to the C-terminal of the light chain.
  HC$_2$ indicates that there are two heavy chains, to which nothing is fused.

In fusion protein "mAb 0012-(hTF.1-219-L4b-LC)$_2$; HC$_2$":
  (hTF.1-219-L4b-LC)$_2$ indicates that the C-terminal of hTF.1-219 is fused to the linker L4b which is fused to the N-terminal end of the light chain.

TABLE 4

Non-limiting examples of mAb-TF fusion proteins

| mAb-hTF.1-219 fusion protein ID | mAb-hTF.1-219 fusion protein name |
|---|---|
| 0116 | mAb 0012-(HC-L0-hTF.1-219)$_2$; LC$_2$ |
| 0086 | mAb 0012-(HC-L1-hTF.1-219)$_2$; LC$_2$ |
| 0087 | mAb 0012-(HC-L2-hTF.1-219)$_2$; LC$_2$ |
| 0088 | mAb 0012-(HC-L3-hTF.1-219)$_2$; LC$_2$ |
| 0018 | mAb 0012-(HC-L4a-hTF.1-219)$_2$; (LC-HPC4)$_2$ |
| 0013 | mAb 0012-(hTF.1-219-L4b-HC)$_2$; LC$_2$ |
| 0089 | mAb 0012-(HC-L5-hTF.1-219)$_2$; LC$_2$ |
| 0090 | mAb 0012-(HC-L6-hTF.1-219)$_2$; LC$_2$ |
| 0091 | mAb 0012-(HC-L7-hTF.1-219)$_2$; LC$_2$ |
| 0092 | mAb 0012-(HC-L8-hTF.1-219)$_2$; LC$_2$ |
| 0093 | mAb 0012-(HC-L9-hTF.1-219)$_2$; LC$_2$ |
| 0107 | mAb 0012-(LC-L0-hTF.1-219)$_2$; HC$_2$ |
| 0108 | mAb 0012-(LC-L1-hTF.1-219)$_2$; HC$_2$ |
| 0109 | mAb 0012-(LC-L2-hTF.1-219)$_2$; HC$_2$ |
| 0045 | mAb 0012-(LC-L3-hTF.1-219)$_2$; HC$_2$ |
| 0019 | mAb 0012-(LC-L4a-hTF.1-219)$_2$; HC$_2$ |
| 0025 | mAb 0012-(hTF.1-219-L4b-LC)$_2$; HC$_2$ |
| 0046 | mAb 0012-(LC-L5-hTF.1-219)$_2$; HC$_2$ |
| 0047 | mAb 0012-(LC-L6-hTF.1-219)$_2$; HC$_2$ |
| 0048 | mAb 0012-(LC-L7-hTF.1-219)$_2$; HC$_2$ |
| 0049 | mAb 0012-(LC-L8-hTF.1-219)$_2$; HC$_2$ |
| 0050 | mAb 0012-(LC-L9-hTF.1-219)$_2$; HC$_2$ |
| 0034 | mAb 0023-(HC-L4a-hTF.1-219)$_2$; (LC-HPC4)$_2$ |
| 0035 | mAb 0023-(LC-L4a-hTF.1-219)$_2$; HC$_2$ |
| 0056 | mAb 0051-(HC-L4a-hTF.1-219)$_2$; (LC-HPC4)$_2$ |
| 0055 | mAb 0051-(LC-L4a-hTF.1-219)$_2$; HC$_2$ |
| 0060 | mAb 0052-(HC-L4a-hTF.1-219)$_2$; (LC-HPC4)$_2$ |
| 0059 | mAb 0052-(LC-L4a-hTF.1-219)$_2$; HC$_2$ |

Examples of suitable fusion proteins wherein (ii) is a Fab fragment are provided in table 5. TF may be fused to a HC of the mAb; TF may be fused to a LC of the mAb. TF may be fused to a ligand which, in turn, is fused to a HC of the mAb or a LC of the mAb. Following are examples of how to interpret the names of the fusion proteins provided in table 5:

In fusion protein "Fab 0012-$V_H$-CH1-L0-hTF.1-219; LC-HPC4":
"Fab 0012": Fab fragment of mAb 0012.
"$V_H$-CH1-L0-hTF.1-219": the N-terminal of hTF.1-219 is directly fused to the C-terminal of the $V_H$-CH1 domain of the Fab fragment.
"HPC4": a purification tag is at the N-terminal of the light chain. In fusion protein "Fab 0012-hTF.1-219-L4b-$V_H$-CH1; LC-HPC4":
"hTF.1-219-L4b-$V_H$-CH1": indicates that the C-terminal of tissue factor is fused to the N-terminal of linker 4b which is fused to the $V_H$-CH1 domain of the Fab fragment.

TABLE 5

Non-limiting examples of Fab-TF fusion proteins

| Fab-hTF.1-219 fusion protein ID | Fab-hTF.1-219 fusion protein name |
| --- | --- |
| 0073 | Fab 0012-$V_H$-CH1-L0-hTF.1-219; LC-HPC4 |
| 0011 | Fab 0012-$V_H$-CH1-L4a-hTF.1-219; LC-HPC4 |
| 0014 | Fab 0012-hTF.1-219-L4b-$V_H$-CH1; LC-HPC4 |
| 0057 | Fab 0012-$V_H$-CH1-L10-hTF.1-219; LC-HPC4 |
| 0105 | Fab 0061-$V_H$-CH1-L10-hTF.1-219; LC-HPC4 |
| 0106 | Fab 0082-$V_H$-CH1-L10-hTF.1-219; LC-HPC4 |
| 0070 | Fab 0012-LC-L0-hTF.1-219; $V_H$-CH1-HPC4 |
| 0071 | Fab 0012-LC-L1-hTF.1-219; $V_H$-CH1-HPC4 |
| 0072 | Fab 0012-LC-L2-hTF.1-219; $V_H$-CH1-HPC4 |
| 0039 | Fab 0012-LC-L3-hTF.1-219; $V_H$-CH1-HPC4 |
| 0020 | Fab 0012-LC-L4a-hTF.1-219; $V_H$-CH1-HPC4 |
| 0024 | Fab 0012-hTF.1-219-L4b-LC; $V_H$-CH1-HPC4 |
| 0040 | Fab 0012-LC-L5-hTF.1-219; $V_H$-CH1-HPC4 |
| 0041 | Fab 0012-LC-L6-hTF.1-219; $V_H$-CH1-HPC4 |
| 0042 | Fab 0012-LC-L7-hTF.1-219; $V_H$-CH1-HPC4 |
| 0043 | Fab 0012-LC-L8-hTF.1-219; $V_H$-CH1-HPC4 |
| 0044 | Fab 0012-LC-L9-hTF.1-219; $V_H$-CH1-HPC4 |
| 0063 | Fab 0023-LC-L3-hTF.1-219; $V_H$-CH1-HPC4 |
| 0038 | Fab 0023-LC-L4a-hTF.1-219; $V_H$-CH1-HPC4 |
| 0064 | Fab 0023-LC-L5-hTF.1-219; $V_H$-CH1-HPC4 |
| 0065 | Fab 0023-LC-L6-hTF.1-219; $V_H$-CH1-HPC4 |
| 0066 | Fab 0023-LC-L7-hTF.1-219; $V_H$-CH1-HPC4 |
| 0067 | Fab 0023-LC-L8-hTF.1-219; $V_H$-CH1-HPC4 |
| 0068 | Fab 0023-LC-L9-hTF.1-219; $V_H$-CH1-HPC4 |
| 0033 | Fab 0023-$V_H$-CH1-L4a-hTF.1-219; LC-HPC4 |
| 0053 | Fab 0051-LC-L4a-hTF.1-219; $V_H$-CH1-HPC4 |
| 0054 | Fab 0051-$V_H$-CH1-L4a-hTF.1-219; LC-HPC4 |
| 0069 | Fab 0052-LC-L4a-hTF.1-219; $V_H$-CH1-HPC4 |
| 0058 | Fab 0052-$V_H$-CH1-L4a-hTF.1-219; LC-HPC4 |

As described above, fusion proteins of the invention are capable of binding a receptor that is present on platelets undergoing activation, such as TLT-1. The term "binding affinity" is intended to refer to the property of fusion proteins, or the antibody component of fusion proteins to bind or not to bind to their target. Binding affinity may be quantified by determining the binding constant ($K_D$) for an antibody component and its target. Similarly, the specificity of binding of an antibody component to its target may be defined in terms of the comparative binding constants ($K_D$) of the antibody for its target as compared to the binding constant with respect to the antibody and another, non-target molecule.

Typically, the $K_D$ for the antibody with respect to the target will be 2-fold, preferably 5-fold, more preferably 10-fold less than $K_D$ with respect to the other, non-target molecule such as unrelated material or accompanying material in the environment. More preferably, the $K_D$ will be 50-fold less, even more preferably 100-fold less, and yet more preferably 200-fold less.

The value of this binding constant can be determined directly by well-known methods, and can be computed even for complex mixtures by methods such as those, for example, set forth in Caceci et al. (Byte 9:340-362, 1984). For example, the $K_D$ may be established using a double-filter nitrocellulose filter binding assay such as that disclosed by Wong & Lohman (Proc. Natl. Acad. Sci. USA 90, 5428-5432, 1993). Other standard assays to evaluate the binding ability of ligands such as antibodies towards targets are known in the art, including for example, ELISAs, Western blots, RIAs, and flow cytometry analysis. The binding kinetics (e.g., binding affinity) of the antibody can also be assessed by standard assays known in the art, such as by surface plasmon resonce (SPR) analysis.

A competitive binding assay can be conducted in which the binding of the antibody to the target is compared to the binding of the target by another, known ligand of that target, such as another antibody.

$K_D$ values for the ligand, such as an antibody or fragment thereof, of the invention may also be at least $1 \times 10^{-15}$M, such as at least $1 \times 10^{-14}$M, such as at least $1 \times 10^{-13}$M, such as at least $1 \times 10^{-12}$M, such as at least $1 \times 10^{-11}$M, such as at least $1 \times 10^{-10}$M, such as approximately $3 \times 10^{-9}$M, such as at least $1 \times 10^{-9}$M, or at least $1 \times 10^{-8}$M. An antibody of the invention may have a Kd (or Ki) for its target of $1 \times 10^{-7}$M or less, $1 \times 10^{-8}$M or less or $1 \times 10^{-9}$M or less.

Preferred $K_D$ values for the ligand of the invention, such as an antibody or fragment thereof, may be $1 \times 10^{-15}$M to $1 \times 10^{-14}$M, such as $1 \times 10^{-14}$M to $1 \times 10^{-13}$M $1 \times 10^{-13}$M to $1 \times 10^{-12}$M, such as $1 \times 10^{-12}$M to $1 \times 10^{-11}$M, such as $1 \times 10^{-11}$M to $1 \times 10^{-10}$M, such as $1 \times 10^{-10}$M to $1 \times 10^{-9}$M such as approximately $3 \times 10^{-9}$M, such as $1 \times 10^{-9}$M to $2 \times 10^{-8}$M.

An antibody that specifically binds its target may bind its target with a high affinity, such as a $K_D$ as discussed above, and may bind to other, non-target molecules with a lower affinity. For example, the antibody may bind to a non-target molecules with a $K_D$ of $1 \times 10^{-6}$M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. An antibody of the invention is preferably capable of binding to its target with an affinity that is at least two-fold, 10-fold, 50-fold, 100-fold, 200-fold, 500-fold, 1,000-fold or 10,000-fold or greater than its affinity for binding to another non-target molecule, such as other TREMs than TLT-1.

As mentioned above, fusion proteins may comprise a tissue factor-like component that is at least 90% identical to the extracellular domain of tissue factor or a variant thereof. The term "identity", as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci USA 89, 10915-10919 (1992) for the BLOSUM 62 comparison matrix) is also used by the algorithm.

Preferred parameters for a peptide sequence comparison include the following: Algorithm: Needleman et al., 3. Mol. Biol. 48, 443-453 (1970); Comparison matrix: BLOSUM 62 from Henikoff et al., PNAS USA 89, 10915-10919 (1992); Gap Penalty: 12, Gap Length Penalty: 4, Threshold of Similarity: 0.

The GAP program is useful with the above parameters. The aforementioned parameters are the default parameters for peptide comparisons (along with no penalty for end gaps) using the GAP algorithm.

The functional effects of the invented fusion proteins may be assessed by means of various in vitro and in vivo experiments. In vitro experiments may be designed to assess the function of the fusion proteins as a whole, as well as their component (i) TF and (ii) ligand parts. Such experiments are described in detail in the examples. These include methods of testing the ability of:
  fusion proteins to bind FVII/FVIIa;
  fusion proteins' TF component to selectively enhance FVIIa-mediated FX activation on activated platelets;
  fusion proteins' TF component to enhance FVIIa-mediated FX activation on TLT-1-enriched phospholipid vesicles;
  fusion proteins to promote fibrin clot formation in hemophilia-like platelet-rich plasma
  fusion proteins to promote fibrin clot formation in hemophilia-like whole blood; In vivo, fusion proteins may be tested in a tail-bleeding model in haemophilic mice that are transfused with human platelets. Furthermore in vivo, fusion proteins may be tested in a tail-bleeding model in haemophilic mice with the human TLT-1 gene inserted ("humanized" with respect to TLT-1).

The invention also relates to polynucleotides that encode antibodies of the invention. Thus, a polynucleotide of the invention may encode any antibody as described herein. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides of the invention can be synthesised according to methods well known in the art, as described by way of example in Sambrook et al (1989, Molecular Cloning—a laboratory manual; Cold Spring Harbor Press).

The nucleic acid molecules of the present invention may be provided in the form of an expression cassette which includes control sequences operably linked to the inserted sequence, thus allowing for expression of the antibody of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes isolated cells that have been modified to express a construct according to the invention. Such cells include transient, or—preferably—stable higher eukaryotic cell lines, such as mammalian cells or insect cells; lower eukaryotic cells, such as yeast; or prokaryotic cells such as bacterial cells. Particular examples of cells which may be modified by insertion of vectors or expression cassettes encoding for a construct of the invention include mammalian HEK293T, CHO, HeLa and COS cells. Preferably the cell line selected will be one which is not only stable, but also allows for mature glycosylation and cell surface expression of a polypeptide.

Such cell lines of the invention may be cultured using routine methods to produce a fusion protein, antibody or construct according to the invention. Alternatively, polynucleotides, expression cassettes or vectors of the invention may be administered to a cell from a subject ex vivo and the cell then returned to the body of the subject.

In another aspect, the present invention provides compositions and formulations comprising molecules of the invention, such as the fusion proteins, polynucleotides, vectors and cells described herein. For example, the invention provides a pharmaceutical composition that comprises one or more fusion proteins of the invention, formulated together with a pharmaceutically acceptable carrier.

Accordingly, one object of the invention is to provide a pharmaceutical formulation comprising such an antibody which is present in a concentration from 0.25 mg/ml to 250 mg/ml, and wherein said formulation has a pH from 2.0 to 10.0. The formulation may further comprise a buffer system, preservative(s), tonicity agent(s), chelating agent(s), stabilizers and surfactants. The use of preservatives, isotonic agents, chelating agents, stabilizers and surfactants in pharmaceutical compositions is well-known to the skilled person. Reference may be made to Remington: *The Science and Practice of Pharmacy*, 19$^{th}$ edition, 1995.

In one embodiment, the pharmaceutical formulation is an aqueous formulation. Such a formulation is typically a solution or a suspension. The terms "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

The term "treatment", as used herein, refers to the medical therapy of any human or other animal subject in need thereof. Said subject is expected to have undergone physical examination by a [veterinary] medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative.

In terms of the present invention, prophylactic, palliative, symptomatic and/or curative treatments may represent separate aspects of the invention.

A coagulopathy that results in an increased haemorrhagic tendency may be caused by any qualitative or quantitative deficiency of any pro-coagulative component of the normal coagulation cascade or any upregulation of fibrinolysis. Such coagulopathies may be congenital and/or acquired and/or iatrogenic and are identified by a person skilled in the art.

Non-limiting examples of congenital hypocoagulopathies are haemophilia A, haemophilia B, Factor VII deficiency, Factor X deficiency, Factor XI deficiency, von Willebrand's disease and thrombocytopenias such as Glanzmann's thombasthenia and Bernard-Soulier syndrome.

A non-limiting example of an acquired coagulopathy is serine protease deficiency caused by vitamin K deficiency; such vitamin K-deficiency may be caused by administration of a vitamin K antagonist, such as warfarin. Acquired coagulopathy may also occur following extensive trauma. In this case otherwise known as the "bloody vicious cycle", it is characterised by haemodilution (dilutional thrombocytopaenia and dilution of clotting factors), hypothermia, consumption of clotting factors and metabolic derangements (acidosis). Fluid therapy and increased fibrinolysis may exaserbate this situation. Said haemorrhage may be from any part of the body.

Haemophilia A with "inhibitors" (that is, allo-antibodies against factor VIII) and haemophilia B with "inhibitors" (that is, allo-antibodies against factor IX) are non-limiting examples of coagulopathies that are partly congenital and partly acquired.

A non-limiting example of an iatrogenic coagulopathy is an overdosage of anticoagulant medication—such as heparin, aspirin, warfarin and other platelet aggregation inhibitors—that may be prescribed to treat thromboembolic disease. A second, non-limiting example of iatrogenic coagulopathy is that which is induced by excessive and/or inappropriate fluid therapy, such as that which may be induced by a blood transfusion.

In one embodiment of the current invention, haemorrhage is associated with haemophilia A or B. In another embodiment, haemorrhage is associated with haemophilia A or B with acquired inhibitors. In another embodiment, haemorrhage is associated with von Willebrand's disease. In another embodiment, haemorrhage is associated with severe tissue damage. In another embodiment, haemorrhage is associated with severe trauma. In another embodiment, haemorrhage is associated with surgery. In another embodiment, haemorrhage is associated with haemorrhagic gastritis and/or enteritis. In another embodiment, the haemorrhage is profuse uterine bleeding, such as in placental abruption. In another embodiment, haemorrhage occurs in organs with a limited possibility for mechanical haemostasis, such as intracranially, intraaurally or intraocularly. In another embodiment, haemorrhage is associated with anticoagulant therapy.

In a further embodiment, haemorrhage may be associated with thrombocytopaenia. In individuals with thrombocytopaenia, constructs of the current invention may be co-administered with platelets.

EMBODIMENTS

The following is a non-limiting list of embodiments of the present invention:

Embodiment 1

A fusion protein comprising (i) at least one tissue factor polypeptide, or biologically functional variant(s) or fragment(s) thereof, and (ii) a ligand that is capable of binding (iii) a receptor, and/or a fragment or variant thereof, wherein the receptor is present only on the surface of activated platelets.

Embodiment 2

The fusion protein according to embodiment 1, wherein (iii) is TLT-1 or a fragment or variant thereof.

Embodiment 3

The fusion protein according to embodiment 2, wherein (iii) is TLT-1 (16-162).

Embodiment 4

The fusion protein according to embodiment 2, wherein (iii) is TLT-1 (20-125).

Embodiment 5

The fusion protein according to embodiment 2, wherein (iii) is TLT-1 (126-162).

Embodiment 6

The fusion protein according to any one of embodiments 1-5, wherein (i) is a single tissue factor polypeptide, or a biologically functional variant or fragment thereof.

Embodiment 7

The fusion protein according to any one of embodiments 1-5, wherein (i) is two tissue factor polypeptides, or biologically functional variant(s) or fragment(s) thereof.

Embodiment 8

The fusion protein according to any one of embodiments 6-7, wherein (i) is TF (1-219).

Embodiment 9

The fusion protein according to any one of embodiments 6-7, wherein (i) is sTF(6-209).

Embodiment 10

The fusion protein according to any one of embodiments 6-7, wherein (i) is sTF(1-209).

Embodiment 11

The fusion protein according to any one of embodiments 6-7, wherein (i) is sTF (1-210).

Embodiment 12

The fusion protein according to any one of embodiments 6-7, wherein (i) is sTF (1-211).

Embodiment 13

The fusion protein according to any one of embodiments 6-7, wherein (i) is sTF (1-212).

Embodiment 14

The fusion protein according to any one of embodiments 6-7, wherein (i) is sTF (1-213).

Embodiment 15

The fusion protein according to any one of embodiments 6-7, wherein (i) is sTF (1-214).

Embodiment 16

The fusion protein according to any one of embodiments 6-7, wherein (i) is sTF (1-215).

Embodiment 17

The fusion protein according to any one of embodiments 6-7, wherein (i) is sTF (1-216).

Embodiment 18

The fusion protein according to any one of embodiments 6-7, wherein (i) is sTF (1-217).

Embodiment 19

The fusion protein according to any one of embodiments 6-7, wherein (i) is sTF (1-218).

Embodiment 20

The fusion protein according to any one of embodiments 6-7, wherein (i) is sTF (1-219).

Embodiment 21

The fusion protein according to any one of embodiments 1-20, wherein (ii) is a monoclonal antibody or a fragment thereof.

Embodiment 22

The fusion protein according to embodiment 21, wherein (ii) is a Fab fragment, a F(ab')$_2$ fragment, a Fab' fragment, a Fd fragment, a Fv fragment, a ScFv fragment, a dAb fragment or an isolated complementarity determining region (CDR).

Embodiment 23

The fusion protein according to embodiment 22, wherein (ii) is a Fab fragment.

Embodiment 24

The fusion protein according to any one of embodiments 21-23, wherein the epitope of (ii) comprises one or more residues selected from the group consisting of V17, Q18, C19, H20, Y21, R22, L23, Q24, D25, V26, K27, A28, L63, G64, G65, G66, L67, L68, G89, A90, R91, G92, P93, Q94, I95 and L96 of SEQ ID NO: 5.

Embodiment 25

The fusion protein according to any one of embodiments 21-23, wherein (ii) is an antibody, or a fragment thereof, which is capable of binding to the same epitope as mAb 0023.

Embodiment 26

A fusion protein according to any of embodiments 24-25, wherein the heavy chain of (ii) comprises:
   a CDR1 sequence of amino acids 50 to 54 (DYFMY) of SEQ ID NO: 41, wherein one of these amino acids may be substituted by a different amino acid; and/or a CDR2 sequence of amino acids 69 to 85 (YISNG-GDSSSYPDTVKG) of SEQ ID NO: 41, wherein one, two, three or four of these amino acids may be substituted by a different amino acid; and/or a CDR3 sequence of amino acids 118 to 129 (NKNWD-DYYDMDY) of SEQ ID NO: 41, wherein one, two or three of these amino acids may be substituted by a different amino acid.

Embodiment 27

A fusion protein according to any of embodiments 24-26, wherein the light chain of (ii) comprises:
a CDR1 sequence of amino acids 44 to 60 (KSSQSLLNSR-TRKNYLA) of SEQ ID NO: 42, wherein one, two, three or four of these amino acids may be substituted with a different amino acid; and/or
a CDR2 sequence of amino acids 76 to 82 (WASTRES) of SEQ ID NO: 42, wherein one or two of these amino acids may be substituted with a different amino acid; and/or
a CDR3 sequence of amino acids 115 to 122 (KQSYNLLT) of SEQ ID NO: 42, wherein one or two of these amino acids may be substituted with a different amino acid.

Embodiment 28

A fusion protein according to any of embodiments 24-25, wherein the heavy chain of (ii) comprises:
a CDR1 sequence of amino acids 50 to 54 (DYFMY) of SEQ ID NO: 41, wherein one of these amino acids may be substituted by a different amino acid; and/or
a CDR2 sequence of amino acids 69 to 85 (YISNG-GDSSSYPDTVKG) of SEQ ID NO: 41, wherein one, two, three or four of these amino acids may be substituted by a different amino acid; and/or
a CDR3 sequence of amino acids 118 to 129 (NKNWD-DYYDMDY) of SEQ ID NO: 41, wherein one, two or three of these amino acids may be substituted by a different amino acid.
and wherein the light chain of (ii) comprises:
a CDR1 sequence of amino acids 44 to 60 (KSSQSLLNSR-TRKNYLA) of SEQ ID NO: 42, wherein one, two, three or four of these amino acids may be substituted with a different amino acid; and/or
a CDR2 sequence of amino acids 76 to 82 (WASTRES) of SEQ ID NO: 42, wherein one or two of these amino acids may be substituted with a different amino acid; and/or
a CDR3 sequence of amino acids 115 to 122 (KQSYNLLT) of SEQ ID NO: 42, wherein one or two of these amino acids may be substituted with a different amino acid.

Embodiment 29

A fusion protein according to embodiment 28, wherein the heavy chain of (ii) comprises:
a CDR1 sequence of amino acids 50 to 54 (DYFMY) of SEQ ID NO: 41; and
a CDR2 sequence of amino acids 69 to 85 (YISNG-GDSSSYPDTVKG) of SEQ ID NO: 41; and
a CDR3 sequence of amino acids 118 to 129 (NKNWD-DYYDMDY) of SEQ ID NO: 41, and wherein the light chain of (ii) comprises:
a CDR1 sequence of amino acids 44 to 60 (KSSQSLLNSR-TRKNYLA) of SEQ ID NO: 42; and A CDR2 SEQUENCE OF AMINO ACIDS 76 TO 82 (WASTRES) OF SEQ ID NO: 42; AND
a CDR3 sequence of amino acids 115 to 122 (KQSYNLLT) of SEQ ID NO: 42.

Embodiment 30

The fusion protein according to any one of embodiments 21-23, wherein the epitope of (ii) comprises one or more residues selected from the group consisting of L36, P37, E38, G39, C40, Q41, P42, L43, V44, S45, S46, A47, V73, T74, L75, Q76, E77, E78, D79, A80, G81, E82, Y83, G84, C85, M86, R91, G92, P93, Q94, I95, L96, H97, R98, V99, 5100 and L101 of SEQ ID NO: 5.

Embodiment 31

The fusion protein according to any one of embodiments 21-23, wherein (ii) is an antibody, or a fragment thereof, which is capable of binding to the same epitope as mAb 0051.

Embodiment 32

A fusion protein according to any one of embodiments 30-31, wherein the heavy chain of (ii) comprises:
a CDR1 sequence of amino acids 50 to 54 (DYSMH) of SEQ ID NO: 43, wherein one of these amino acids may be substituted by a different amino acid; and/or
a CDR2 sequence of amino acids 69 to 85 (VISTYYGD-VRYNQKFKG) of SEQ ID NO: 43, wherein one, two, three or four of these amino acids may be substituted by a different amino acid; and/or
a CDR3 sequence of amino acids 118 to 129 (APMITT-GAWFAY) of SEQ ID NO: 43, wherein one, two or three of these amino acids may be substituted by a different amino acid.

Embodiment 33

A fusion protein according to any of embodiments 30-32, wherein the light chain of (ii) comprises:
a CDR1 sequence of amino acids 44 to 54 (KASQSVSNDVA) of SEQ ID NO: 44, wherein one, two or three of these amino acids may be substituted with a different amino acid; and/or
a CDR2 sequence of amino acids 70 to 76 (YASSRYT) of SEQ ID NO: 44, wherein one or two of these amino acids may be substituted with a different amino acid; and/or
a CDR3 sequence of amino acids 109 to 117 (QQDYSSPYT) of SEQ ID NO: 44, wherein one or two of these amino acids may be substituted with a different amino acid.

Embodiment 34

A fusion protein according to any one of embodiments 30-31, wherein the heavy chain of (ii) comprises:
a CDR1 sequence of amino acids 50 to 54 (DYSMH) of SEQ ID NO: 43, wherein one of these amino acids may be substituted by a different amino acid; and/or
a CDR2 sequence of amino acids 69 to 85 (VISTYYGD-VRYNQKFKG) of SEQ ID NO: 43, wherein one, two, three or four of these amino acids may be substituted by a different amino acid; and/or a CDR3 sequence of amino acids 118 to 129 (APMITT-GAWFAY) of SEQ ID NO: 43, wherein one, two or three of these amino acids may be substituted by a different amino acid.

and wherein the light chain of (ii) comprises:
a CDR1 sequence of amino acids 44 to 54 (KASQSVSNDVA) of SEQ ID NO: 44, wherein one, two or three of these amino acids may be substituted with a different amino acid; and/or
a CDR2 sequence of amino acids 70 to 76 (YASSRYT) of SEQ ID NO: 44, wherein one or two of these amino acids may be substituted with a different amino acid; and/or
a CDR3 sequence of amino acids 109 to 117 (QQDYSSPYT) of SEQ ID NO: 44, wherein one or two of these amino acids may be substituted with a different amino acid.

Embodiment 35

A fusion protein according to embodiment 34, wherein the heavy chain of (ii) comprises:
a CDR1 sequence of amino acids 50 to 54 (DYSMH) of SEQ ID NO: 43; and
a CDR2 sequence of amino acids 69 to 85 (VISTYYGD-VRYNQKFKG) of SEQ ID NO: 43; and
a CDR3 sequence of amino acids 118 to 129 (APMITT-GAWFAY) of SEQ ID NO: 43; and wherein the light chain of (ii) comprises:
a CDR1 sequence of amino acids 44 to 54 (KASQSVSNDVA) of SEQ ID NO: 44; and
a CDR2 sequence of amino acids 70 to 76 (YASSRYT) of SEQ ID NO: 44; and
a CDR3 sequence of amino acids 109 to 117 (QQDYSSPYT) of SEQ ID NO: 44.

Embodiment 36

The fusion protein according to any one of embodiments 21-23, wherein the epitope of (ii) comprises one or more residues selected from the group consisting of V17, Q18, C19, H20, Y21, R22, L23, Q24, D25, V26, K27, A28, R91, G92, P93, Q94, I95, L96, H97, R98, V99, 5100 and L101 of SEQ ID NO: 5.

Embodiment 37

The fusion protein according to any one of embodiments 21-23, wherein (ii) is an antibody, or a fragment thereof, which is capable of binding to the same epitope as mAb 0062.

Embodiment 38

A fusion protein according to any one of embodiments 36-37, wherein the heavy chain of (ii) comprises:
a CDR1 sequence of amino acids 50 to 54 (SHWIE) of SEQ ID NO: 49, wherein one of these amino acids may be substituted by a different amino acid; and/or
a CDR2 sequence of amino acids 69 to 85 (EILPGSGNT-NYNEKFKG) of SEQ ID NO: 49, wherein one, two, three or four of these amino acids may be substituted by a different amino acid; and/or
a CDR3 sequence of amino acids 118 to 130 (GYYGL-NYDWYFDV) of SEQ ID NO: 49, wherein one, two or three of these amino acids may be substituted by a different amino acid.

Embodiment 39

A fusion protein according to any of embodiments 36-38, wherein the light chain of (ii) comprises:
a CDR1 sequence of amino acids 44 to 54 (RASQDIS-NYLN) of SEQ ID NO: 46, wherein one, two or three of these amino acids may be substituted with a different amino acid; and/or
a CDR2 sequence of amino acids 70 to 76 (YTSRLHS) of SEQ ID NO: 46, wherein one or two of these amino acids may be substituted with a different amino acid; and/or
a CDR3 sequence of amino acids 109 to 117 (QQDT-KLPYT) of SEQ ID NO: 46, wherein one or two of these amino acids may be substituted with a different amino acid.

Embodiment 40

A fusion protein according to any of embodiments 36-39, wherein the heavy chain of (ii) comprises:
a CDR1 sequence of amino acids 50 to 54 (SHWIE) of SEQ ID NO: 49, wherein one of these amino acids may be substituted by a different amino acid; and/or
a CDR2 sequence of amino acids 69 to 85 (EILPGSGNT-NYNEKFKG) of SEQ ID NO: 49, wherein one, two, three or four of these amino acids may be substituted by a different amino acid; and/or
a CDR3 sequence of amino acids 118 to 130 (GYYGL-NYDWYFDV) of SEQ ID NO: 49, wherein one, two or three of these amino acids may be substituted by a different amino acid.
and wherein the light chain of (ii) comprises:
a CDR1 sequence of amino acids 44 to 54 (RASQDIS-NYLN) of SEQ ID NO: 46, wherein one, two or three of these amino acids may be substituted with a different amino acid; and/or
a CDR2 sequence of amino acids 70 to 76 (YTSRLHS) of SEQ ID NO: 46, wherein one or two of these amino acids may be substituted with a different amino acid; and/or
a CDR3 sequence of amino acids 109 to 117 (QQDT-KLPYT) of SEQ ID NO: 46, wherein one or two of these amino acids may be substituted with a different amino acid.

Embodiment 41

A fusion protein according to embodiment 40, wherein the heavy chain of (ii) comprises:
a CDR1 sequence of amino acids 50 to 54 (SHWIE) of SEQ ID NO: 49; and
a CDR2 sequence of amino acids 69 to 85 (EILPGSGNT-NYNEKFKG) of SEQ ID NO: 49; and
a CDR3 sequence of amino acids 118 to 130 (GYYGL-NYDWYFDV) of SEQ ID NO: 49; and wherein the light chain of (ii) comprises:
a CDR1 sequence of amino acids 44 to 54 (RASQDIS-NYLN) of SEQ ID NO: 46; and
a CDR2 sequence of amino acids 70 to 76 (YTSRLHS) of SEQ ID NO: 46; and
a CDR3 sequence of amino acids 109 to 117 (QQDT-KLPYT) of SEQ ID NO: 46.

Embodiment 42

The fusion protein according to any one of embodiments 21-23, wherein the epitope of (ii) comprises one or more residues selected from the group consisting of E5, T6, H7, K8, I9, G10, S11, L12, A13, E14, N15, A16, F17, S18, D19, P20 and A21 of SEQ ID NO: 7.

Embodiment 43

The fusion protein according to embodiment 42 wherein said residues are K8, I9, G10, S11, L12, A13, N15, A16, F17, S18, D19, P20 and A21.

Embodiment 44

The fusion protein according to any one of embodiments 21-23, wherein the epitope of (ii) comprises one or more residues selected from the group consisting of K118, I119, G120, S121, L122, A123, E124, N125, A126, F127 of SEQ ID NO: 6.

Embodiment 45

The fusion protein according to any one of embodiments 21-23, wherein (ii) is an antibody, or a fragment thereof, which is capable of binding to the same epitope as mAb 0061 or mAb 0082.

Embodiment 46

A fusion protein according to any one of embodiments 42-45, wherein the heavy chain of (ii) comprises:
- a CDR1 sequence of amino acids 49 to 53 (RYWMT) of SEQ ID NO: 47, wherein one of these amino acids may be substituted by a different amino acid; and/or
- a CDR2 sequence of amino acids 68 to 84 (EINPDSSTINYNPSLKD) of SEQ ID NO: 47, wherein one, two, three or four of these amino acids may be substituted by a different amino acid; and/or
- a CDR3 sequence of amino acids 117 to 121 (GVFTS) of SEQ ID NO: 47, wherein one, two or three of these amino acids may be substituted by a different amino acid.

Embodiment 47

A fusion protein according to any of embodiments 42-46, wherein the light chain of (ii) comprises:
- a CDR1 sequence of amino acids 43 to 58 (RSSQSLVHRNGNTYFH) of SEQ ID NO: 48, wherein one, two, three or four of these amino acids may be substituted with a different amino acid; and/or
- a CDR2 sequence of amino acids 74 to 80 (KVSNRFS) of SEQ ID NO: 48, wherein one or two of these amino acids may be substituted with a different amino acid; and/or
- a CDR3 sequence of amino acids 113 to 121 (SQSTHVPYT) of SEQ ID NO: 48, wherein one or two of these amino acids may be substituted with a different amino acid.

Embodiment 48

A fusion protein according to any of embodiments 42-47, wherein the heavy chain of (ii) comprises:
- a CDR1 sequence of amino acids 49 to 53 (RYWMT) of SEQ ID NO: 47, wherein one of these amino acids may be substituted by a different amino acid; and/or
- a CDR2 sequence of amino acids 68 to 84 (EINPDSSTINYNPSLKD) of SEQ ID NO: 47, wherein one, two, three or four of these amino acids may be substituted by a different amino acid; and/or
- a CDR3 sequence of amino acids 117 to 121 (GVFTS) of SEQ ID NO: 47, wherein one, two or three of these amino acids may be substituted by a different amino acid.

and wherein the light chain of (ii) comprises:
- a CDR1 sequence of amino acids 43 to 58 (RSSQSLVHRNGNTYFH) of SEQ ID NO: 48, wherein one, two, three or four of these amino acids may be substituted with a different amino acid; and/or
- a CDR2 sequence of amino acids 74 to 80 (KVSNRFS) of SEQ ID NO: 48, wherein one or two of these amino acids may be substituted with a different amino acid; and/or
- a CDR3 sequence of amino acids 113 to 121 (SQSTHVPYT) of SEQ ID NO: 48, wherein one or two of these amino acids may be substituted with a different amino acid.

Embodiment 49

A fusion protein according to embodiment 48, wherein the heavy chain of (ii) comprises:
- a CDR1 sequence of amino acids 49 to 53 (RYWMT) of SEQ ID NO: 47; and
- a CDR2 sequence of amino acids 68 to 84 (EINPDSSTINYNPSLKD) of SEQ ID NO: 47; and
- a CDR3 sequence of amino acids 117 to 121 (GVFTS) of SEQ ID NO: 47;

and wherein the light chain of (ii) comprises:
- a CDR1 sequence of amino acids 43 to 58 (RSSQSLVHRNGNTYFH) of SEQ ID NO: 48; and
- a CDR2 sequence of amino acids 74 to 80 (KVSNRFS) of SEQ ID NO: 48; and
- a CDR3 sequence of amino acids 113 to 121 (SQSTHVPYT) of SEQ ID NO: 48.

Embodiment 50

A fusion protein according to any of embodiments 42-45, wherein the heavy chain of (ii) comprises:
- a CDR1 sequence of amino acids 49 to 53 (RYWMT) of SEQ ID NO: 50, wherein one of these amino acids may be substituted by a different amino acid; and/or
- a CDR2 sequence of amino acids 68 to 84 (EINPDSSTINYAPSLKD) of SEQ ID NO: 50, wherein one, two, three or four of these amino acids may be substituted by a different amino acid; and/or
- a CDR3 sequence of amino acids 117 to 121 (GVFTS) of SEQ ID NO: 50, wherein one of these amino acids may be substituted by a different amino acid;

and wherein the light chain of (ii) comprises:
- a CDR1 sequence of amino acids 43 to 58 (RSSQSLVHRNGNTYFH) of SEQ ID NO: 48, wherein one, two, three or four of these amino acids may be substituted with a different amino acid; and/or
- a CDR2 sequence of amino acids 74 to 80 (KVSNRFS) of SEQ ID NO: 48, wherein one or two of these amino acids may be substituted with a different amino acid; and/or
- a CDR3 sequence of amino acids 113 to 121 (SQSTHVPYT) of SEQ ID NO: 48, wherein one or two of these amino acids may be substituted with a different amino acid.

Embodiment 51

A fusion protein according to embodiment 50, wherein the heavy chain of (ii) comprises:
- a CDR1 sequence of amino acids 49 to 53 (RYWMT) of SEQ ID NO: 50; and
- a CDR2 sequence of amino acids 68 to 84 (EINPDSSTINYAPSLKD) of SEQ ID NO: 50; and
- a CDR3 sequence of amino acids 117 to 121 (GVFTS) of SEQ ID NO: 50;

and wherein the light chain of (ii) comprises:
- a CDR1 sequence of amino acids 43 to 58 (RSSQSLVHRNGNTYFH) of SEQ ID NO: 48; and
- a CDR2 sequence of amino acids 74 to 80 (KVSNRFS) of SEQ ID NO: 48; and
- a CDR3 sequence of amino acids 113 to 121 (SQSTHVPYT) of SEQ ID NO: 48.

Embodiment 52

The fusion protein according to any one of embodiments 21-23, wherein the paratope of (ii) comprises one or more residues selected from the group consisting of H50, N52, Y56, H58, Y73, F79, S115, T116, V118 and Y120 of the anti-TLT1 light (L) chain (SEQ ID NO: 40), and residues V20, F45, R49, Y50, W51, E68, T75, N77, S116, G117, V118 and T120 of the anti-TLT-1 heavy (H) chain (SEQ ID NO: 39)

Embodiment 53

The fusion protein according to any one of embodiments 21-23 and 52, wherein the epitope of (ii) comprises one or more residues selected from the group consisting of K133, I134, G135, S136, L137, A138, N140, A141, F142, S143, D144, P145 and A146 of SEQ ID NO: 4.

Embodiment 54

The fusion protein according to any one of embodiments 21-23, wherein (ii) is an antibody, or a fragment thereof, which is capable of binding to the same epitope as mAb 0012.

Embodiment 55

A fusion protein according to any of embodiments 52-54, wherein the heavy chain of (ii) comprises:
- a CDR1 sequence of amino acids 49 to 53 (RYWMT) of SEQ ID NO: 39, wherein one of these amino acids may be substituted by a different amino acid; and/or
- a CDR2 sequence of amino acids 68 to 84 (EINPDSSTINYTPSLKD) of SEQ ID NO: 39, wherein one, two, three or four of these amino acids may be substituted by a different amino acid; and/or
- a CDR3 sequence of amino acids 117 to 121 (GVFTS) of SEQ ID NO: 39, wherein one, two or three of these amino acids may be substituted by a different amino acid.

Embodiment 56

A fusion protein according to any of embodiments 52-55, wherein the light chain of (ii) comprises:
- a CDR1 sequence of amino acids 43 to 58 (RSSQSLVHRNGNTYFH) of SEQ ID NO: 40, wherein one, two, three or four of these amino acids may be substituted with a different amino acid; and/or
- a CDR2 sequence of amino acids 74 to 80 (KVSNRFS) of SEQ ID NO: 40, wherein one or two of these amino acids may be substituted with a different amino acid; and/or
- a CDR3 sequence of amino acids 113 to 121 (SQSTHVPYT) of SEQ ID NO: 40, wherein one or two of these amino acids may be substituted with a different amino acid.

Embodiment 57

A fusion protein according to any of embodiments 52-56, wherein the heavy chain of (ii) comprises:
- a CDR1 sequence of amino acids 49 to 53 (RYWMT) of SEQ ID NO: 39, wherein one of these amino acids may be substituted by a different amino acid; and/or
- a CDR2 sequence of amino acids 68 to 84 (EINPDSSTINYTPSLKD) of SEQ ID NO: 39, wherein one, two, three or four of these amino acids may be substituted by a different amino acid; and/or
- a CDR3 sequence of amino acids 117 to 121 (GVFTS) of SEQ ID NO: 39, wherein one, two or three of these amino acids may be substituted by a different amino acid.

and wherein the light chain of (ii) comprises:
- a CDR1 sequence of amino acids 43 to 58 (RSSQSLVHRNGNTYFH) of SEQ ID NO: 40, wherein one, two, three or four of these amino acids may be substituted with a different amino acid; and/or
- a CDR2 sequence of amino acids 74 to 80 (KVSNRFS) of SEQ ID NO: 40, wherein one or two of these amino acids may be substituted with a different amino acid; and/or
- a CDR3 sequence of amino acids 113 to 121 (SQSTHVPYT) of SEQ ID NO: 40, wherein one or two of these amino acids may be substituted with a different amino acid.

Embodiment 58

A fusion protein according to embodiment 57, wherein the heavy chain of (ii) comprises:
- a CDR1 sequence of amino acids 49 to 53 (RYWMT) of SEQ ID NO: 39; and
- a CDR2 sequence of amino acids 68 to 84 (EINPDSSTINYTPSLKD) of SEQ ID NO: 39; and
- a CDR3 sequence of amino acids 117 to 121 (GVFTS) of SEQ ID NO: 39;

and wherein the light chain of (ii) comprises:
- a CDR1 sequence of amino acids 43 to 58 (RSSQSLVHRNGNTYFH) of SEQ ID NO: 40; and
- a CDR2 sequence of amino acids 74 to 80 (KVSNRFS) of SEQ ID NO: 40; and
- a CDR3 sequence of amino acids 113 to 121 (SQSTHVPYT) of SEQ ID NO: 40.

Embodiment 59

A fusion protein according to any of embodiments 21-23, wherein the heavy chain of (ii) comprises:
- a CDR1 sequence of amino acids 50 to 54 (NYWLG) of SEQ ID NO: 56, wherein one of these amino acids may be substituted by a different amino acid; and/or
- a CDR2 sequence of amino acids 69 to 85 (DIYPGGGYNKYNENFKG) of SEQ ID NO: 56, wherein one, two, three or four of these amino acids may be substituted by a different amino acid; and/or a CDR3 sequence of amino acids 118 to 128 (EYGNY-DYAMDS) of SEQ ID NO: 56, wherein one, two or three of these amino acids may be substituted by a different amino acid.

Embodiment 60

A fusion protein according to any of embodiments 21-23 and 59, wherein the light chain of (ii) comprises:
- a CDR1 sequence of amino acids 44 to 59 (RSSRSLLH-SNGNTYLC) of SEQ ID NO: 57, wherein one, two, three or four of these amino acids may be substituted with a different amino acid; and/or
- a CDR2 sequence of amino acids 75 to 81 (RMSNLAS) of SEQ ID NO: 57, wherein one or two of these amino acids may be substituted with a different amino acid; and/or
- a CDR3 sequence of amino acids 114 to 122 (MQH-LEYPFT) of SEQ ID NO: 57, wherein one or two of these amino acids may be substituted with a different amino acid.

Embodiment 61

The fusion protein according to any one of embodiments 21-25, 30-31, 36-37, 42-45 and 52-54, wherein (ii) is a human monoclonal antibody or a fragment thereof.

Embodiment 62

The fusion protein according to any one of embodiments 1-60, wherein (ii) is a chimeric antibody or a fragment thereof.

Embodiment 63

The fusion protein according to any one of embodiments 1-60, wherein (ii) is a humanised antibody or a fragment thereof.

Embodiment 64

The fusion protein according to any one of embodiments 1-63, wherein the isotype of (ii) is IgG.

Embodiment 65

The fusion protein according to embodiment 64, wherein the isotype is IgG1, IgG2 or IgG4.

Embodiment 66

The fusion protein according to embodiment 65, wherein the isotype is IgG4.

Embodiment 67

The fusion protein according to any one of embodiments 1-66, further comprising a linker between (i) and (ii).

Embodiment 68

The fusion protein according to any one of embodiments 1-67, in which (ii) has a $K_D$ of less than 100 nM, such as less than 10 nM.

Embodiment 69

The fusion protein according to any one of embodiments 1-68, which stimulates FVIIa-mediated FX activation by at least 10%.

Embodiment 70

A method of targeting tissue factor, or a functional fragment thereof, to the surface of activated platelets, said method comprising the contacting of activated platelets with a fusion protein according to any one of embodiments 1-69.

Embodiment 71

A fusion protein according to any one of embodiments 1-67 for use as a medicament.

Embodiment 72

The fusion protein of embodiment 71 for use as a procoagulant.

Embodiment 73

A pharmaceutical formulation comprising the fusion protein according to any one of embodiments 1-69.

Embodiment 74

The fusion protein according to any one of embodiments 1-69 or the pharmaceutical formulation according to embodiment 73 for use in the treatment of a coagulopathy.

Embodiment 75

The fusion protein according to embodiment 72, wherein said coagulopathy is haemophilia A, with or without inhibitors, and haemophilia B, with or without inhibitors.

Embodiment 76

A method of treating coagulopathy, comprising administering an effective amount of the fusion protein according to any one of embodiments 1-67 to an individual in need thereof.

Embodiment 77

The method according to embodiment 76, wherein said coagulopathy is haemophilia A, with or without inhibitors, and haemophilia B, with or without inhibitors.

Embodiment 78

A polynucleotide that encodes the fusion protein according to any one of embodiments 1-69.

Embodiment 79

An isolated cell that comprises the fusion protein according to any one of embodiments 1-67 and/or the polynucleotide according to embodiment 76.

Embodiment 80

A monoclonal antibody, or fragment thereof, that is capable of binding TLT-1, or a fragment thereof, wherein the paratope of (ii) comprises one or more residues selected from the group consisting of H50, N52, Y56, H58, Y73, F79, S115, T116, V118 and Y120 of the anti-TLT-1 light (L) chain (SEQ ID NO: 40), and residues V20, F45, R49, Y50, W51, E68, T75, N77, S116, G117, V118 and T120 of the anti-TLT-1 heavy (H) chain (SEQ ID NO: 39).

Embodiment 81

A monoclonal antibody, or fragment thereof, that is capable of binding TLT-1, or a fragment thereof, wherein the epitope of (ii) comprises one or more residues selected from the group consisting of K133, I134, G135, S136, L137, A138, N140, A141, F142, S143, D144, P145 and A146 of SEQ ID NO: 4.

Embodiment 82

A monoclonal antibody, or fragment thereof, that is capable of binding TLT-1, or a fragment or variant thereof, wherein the epitope of said monoclonal antibody comprises one or more residues selected from the group consisting of V17, Q18, C19, H20, Y21, R22, L23, Q24, D25, V26, K27, A28, L63, G64, G65, G66, L67, L68, G89, A90, R91, G92, P93, Q94, I95 and L96 of SEQ ID NO: 5.

Embodiment 83

A monoclonal antibody, or fragment thereof, that is capable of binding TLT-1, or a fragment or variant thereof, wherein the epitope of said monoclonal antibody comprises one or more residues selected from the group consisting of L36, P37, E38, G39, C40, Q41, P42, L43, V44, S45, S46, A47, V73, T74, L75, Q76, E77, E78, D79, A80, G81, E82, Y83, G84, C85, M86, R91, G92, P93, Q94, I95, L96, H97, R98, V99, S100 and L101 of SEQ ID NO: 5.

Embodiment 84

A fusion protein comprising a monoclonal antibody, or fragment thereof, that is capable of binding TLT-1, or a fragment or variant thereof, wherein the epitope of said monoclonal antibody comprises one or more residues selected from the group consisting of V17, Q18, C19, H20, Y21, R22, L23, Q24, D25, V26, K27, A28, R91, G92, P93, Q94, I95, L96, H97, R98, V99, S100 and L101 of SEQ ID NO: 5.

Embodiment 85

A monoclonal antibody, or fragment or variant thereof, that is capable of binding TLT-1, or a fragment thereof, wherein the epitope of said antibody comprises one or more residues selected from the group consisting of E5, T6, H7, K8, I9, G10, S11, L12, A13, E14, N15, A16, F17, S18, D19, P20 and A21 of SEQ ID NO: 7.

Embodiment 86

A monoclonal antibody, or fragment or variant thereof, that is capable of binding TLT-1, or a fragment thereof, wherein said residues are K133, I134, G135, S136, L137, A138, N140, A141, F142, S143, D144, P145 and A146 of SEQ ID NO: 7.

Embodiment 87

A monoclonal antibody, or fragment or variant thereof, that is capable of binding TLT-1, or a fragment thereof, wherein the paratope of said antibody comprises one or more residues selected from the group consisting of H50, N52, Y56, H58, Y73, F79, S115, T116, V118 and Y120 of the anti-TLT-1 light (L) chain (SEQ ID NO: 40), and residues V20, F45, R49, Y50, W51, E68, T75, N77, S116, G117, V118 and T120 of the anti-TLT-1 heavy (H) chain (SEQ ID NO: 39)

Embodiment 88

A monoclonal antibody, or fragment or variant thereof, that is capable of binding TLT-1, or a fragment thereof, wherein the epitope comprises one or more residues selected from the group consisting of K133, I134, G135, S136, L137, A138, N140, A141, F142, S143, D144, P145 and A146 of SEQ ID NO: 4.

The present invention is further illustrated by the following examples which should not be construed as further limiting. The contents of all figures and all references cited throughout this application are expressly incorporated herein by reference.

EXAMPLES

Example 1

Cloning and Expression of hTLT-1 ECD-his Antigen.

Nucleotide sequences encoding the extracellular domain of human TLT-1 (hTLT-1) (FIG. 1) together with a C-terminal His-6 tag were PCR amplified with a forward primer containing a HindIII recognition site together with a kozak sequence, and a reverse primer containing a stop codon and an EcoRI recognition site (FIG. 2). The HindIII- and EcoRI digested PCR fragment was inserted into the HindIII- and EcoRI sites of a pTT-based expression vector. The pTT vector is essentially described in Durocher, Y. et al., (2002) Nucleic Acid Res, 30: E9. The resulting expression plasmid was designated pTT-hTLT-1 ECD-His. pTT-hTLT-1 ECD-His was transfected into HEK293-6E suspension cells in order to transiently express hTLT-1 ECD-His. HEK293-6E cells were grown in FREESTYLE HEK293 MEDIUM (animal origin-free, chemically defined, protein-free medium) (GIBCO, cat. no. 12338-018) supplemented with 1% P/S (GIBCO cat. no. 15140-122), 0.1% PLURONIC (clock copolymers based on ethylene oxide and propylene oxide) (GIBCO, cat. no. 24040-032) and 25 ug/mL GENETICIN (aminoglycoside selective agent) (GIBCO, cat. no. 10131-019) and cells were transfected at a cell density of 1 mill/mL using 293FECTIN (cationic lipid-based formulation for transfecting DNA into eukaryotic cells) (Invitrogen, cat. no. 12347-019). For each liter of HEK293-6E cells, the transfection was performed by diluting 1 mg of pTT-hTLT-1 ECD-His DNA into 30 mL OPTIMEM (reduced-serum media) (dilution A) and by diluting 1 mL 293FECTIN (cationic lipid-based formulation for transfecting DNA into eukaryotic cells) into 30 mL OPTIMEM (reduced-serum media) (GIBCO, cat. no. 51985-026, dilution B). Dilution A and B were mixed and incubated at room temperature for 30 minutes. The transfection mix was hereafter added to the HEK293-6E cells and cells were incubated at 37° C. in a humidified incubator with orbital rotation (125 rpm). Seven days post-transfection, cells were removed by centrifugation and the resulting hTLT-1 ECD-His containing supernatants were sterile-filtrated prior to purification.

Example 2

Purification and Characterisation of hTLT1 ECD-his Protein.

Purification of the hTLT1 ECD-His protein was conducted as a 2-step process composed of 1) His-affinity chromatography using the Cobalt-loaded resin TALON (Clontech, cat. no. 635506) and 2) anion-exchange chromatography using the fine-particle resin Source 15Q (GE Healthcare, cat. no. 17-0947). The purifications were conducted using an ÄktaExplorer chromatography system (GE Healthcare, cat. no. 18-1112-41). The buffer systems used for the first purification step was an equilibration buffer composed of 20 mM Hepes, pH 7.0, 150 mM NaCl, a wash buffer composed of 20 mM Hepes, pH 7.0, 0.5 M NaCl and an elution buffer composed of 20 mM Hepes, pH 7.0, 150 mM Imidazole. The cell supernatant was applied directly without any adjustments onto a pre-equilibrated TALON column. The column was washed with 20 column volumes of equilibration buffer, 20 column volumes of wash buffer and last with 20 column volumes of equilibration buffer. The protein was eluted isocratically in approx. 5 column volumes of elution buffer. The molecular mass of the eluted protein was analysed using SDS-PAGE/Coomassie NUPAGE (Bis-Tris gel) 4-12% Bis-Tris gels (Invitrogen, cat. no. NP0321BOX) and Matrix Assisted Laser Desorption Ionisation Time-of-Flight Mass Spectrometry (MALDI-TOF MS) setup on a Micro-flex system (Bruker Daltonics). Here, two distinct protein masses were observed of approx. 16.7 and 33.4 kDa of almost equal amounts. The observed masses corresponded to monomer and dimer forms of hTLT1 ECD-His. Reducing the protein resulted in complete abolishment of the 33.4 kDa protein, while intensifying the 16.7 kDa protein as judged from a SDS-PAGE/Coomassie analysis. Thus, the hTLT-1 ECD-His protein contained an interlinked C—C dimer. To segregate monomer from dimer, a second purification step was employed. The buffer systems used for this purification step was an equilibration buffer composed of 50 mM Hepes, pH 8.0 and an elution buffer composed of 50 mM Hepes, pH 8.0, 1 M NaCl. The sample was adjusted to a pH of 8.0 using 1 M NaOH and then diluted to a conductivity of approx. 10 mS/cm. The protein was applied to a pre-equilibrated Source 15Q column, washed with 5 column volumes of equilibration and eluted using 0-100% elution buffer over 20 column volumes. Based on UV280 monitoring, two peaks were apparent with almost base-line separa-tion. Analyzing fractions over the two peaks using SDS-PAGE/Coomassie, MALDI-TOF MS and Dynamic Light-Scattering (DLS) using a Dynapro instrument (Wyatt Technology) analyses showed the presence of monomer hTLT-1 ECD-His protein in the peak eluting first and Cys-Cys dimer in the peak eluting second. A pool was prepared containing the monomer hTLT-1 ECD-His protein only. The final protein integrity was analyzed based on a Size-Exclusion High-Performance Liquid Chromatographic (SEC-HPLC) method setup on an Agilent LC 1100/1200 system and using a BIOSEP (column for separation biomolecules)-SEC-53000 300×7.8 mm column (Phenomenex, cat. no. OOH-2146-K0) and a running buffer composed of 200 mM NaPhosphate pH 6.9, 300 mM NaCl and 10% isopropanol. The protein eluted as a single symmetric peak at a retention time of approx. 9.9 min at a flow rate of 1 ml/min.

A batch of hTLT-1 ECD-His was prepared for an immunization study for production of monoclonal anti-TLT1 antibodies. Thus, the protein was dialyzed into an isotonic PBS buffer using a SLIDE-A-LYZER Dialysis Cassette 10 kDa MWCO (Pierce, cat. no. 66453). To measure the final protein concentration, a NANODROP spectropho-tometer (Thermo Scientific) was used together with an extinction coefficient of 0.55.

Example 3

Preparation of Monoclonal TLT-1 Antibodies.

RBF mice were immunized by injecting 50 µg of hTLT-1 ECD-His. FCA subcutaneously followed by two injections with 20 µg of hTLT-1 ECD-His in FIA. High responder mice were boosted intravenously with 25 µg of hTLT-1 ECD-His and the spleens were harvested after 3 days. Spleen cells were fused with the myeloma Fox cell line. Supernatants were screened for hTLT-1 specific antibody production in a specific ELISA and in a FACS assay utilizing hTLT-1- or Mock-transfected CHO cells as positive and negative target cells, respectively. A secondary screen was done on resting versus dual agonistic activated platelets of human, cynomolgous monkey, dog, rabbit or mouse origin.

Example 4

Cloning and Sequencing of antiTLT-1 mAb LC and HC cDNAs from Hybridoma.

Total RNA was extracted from four different anti-TLT-1 mAb expressing hybridoma designated: 0012Hyb (a.k.a. 2F105/2F105A3), 0023Hyb, 0051Hyb and 0052Hyb. The RNA was extracted from hybridoma cells using RNEASY (kit for purifying total RNA from cells, tissues, and yeast) mini kit (Qiagen, cat. no. 74106) and an aliquot of the resulting RNA was used as template for first-stranded cDNA synthesis using SMART RACE cDNA Amplification kit (Clontech, cat. no. 634914) following the instruction of the manufacturer for 5' RACE and using 5' RACE CDS primer A together with SMART II A RNA oligonucleotide. The light chain (LC) and heavy chain (HC) coding region cDNAs from each of the four antiTLT-1 hybridomas were hereafter PCR amplified using UPM forward primer mix together with either a mouse LC,kappa specific reverse primer (reverse primer number 339, 348, or 610) or together with a reverse primer recognizing mouse IgG1, IgG2a, IgG2b or IgG3 sequences (reverse primer number 341, 347, 613, 614, 615, or 616, primer sequences are shown in seq no 70-155). The PCR reactions were performed using PHUSION PCR mix (FinnZymes, cat no.: F-531L). The resulting PCR fragments were cloned using ZERO BLUNT Topo PCR cloning kit for sequencing (Invitrogen, cat. no. K287540) and sequenced. The variable domain sequences for 0012LC and HC are shown in FIG. 3.

Example 5

Development of DTT-0012HC, DTT-0023HC, DTT-0051HC and DTT-0052HC Expression Constructs.

The HC variable domain ($V_H$) encoding DNA sequences isolated from each of the four different antiTLT-1 hybridomas were PCR amplified with forward primers containing a HinDIII restriction enzyme site and reverse primers containing a NheI restriction enzyme site for cloning purposes. The $0012V_H$, $0023V_H$, $0051V_H$ and $0052V_H$ DNA sequences were PCR amplified using PHUSION PCR mix (FinnZymes, cat No. F-531L) with the following primer number pairs: 490 (forward)+491 (reverse), 546 (forward)+547 (reverse), 627 (forward)+628 (reverse), and 617 (forward)+618 (reverse, primer sequences are shown in seq no 70-155), respectively, and inserted into the HinDIII and NheI restriction enzyme sites of a pTT based vector (FIG.

Figure 22:
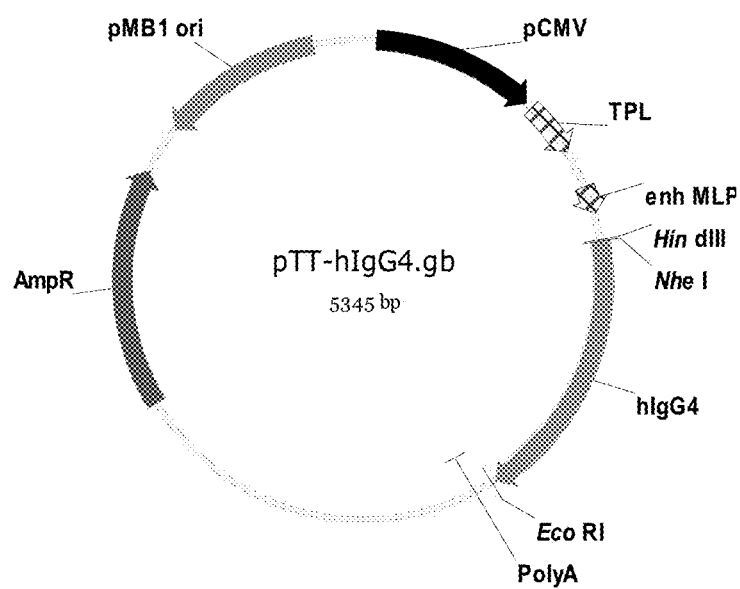
FIG. 22: Plasmid map for the expression vector pTT-hIgG4. The expression vector contains the human IgG4 CH1-hinge-CH2-CH3 DNA sequences. $V_H$ encoding DNA sequences can be inserted into the HinDIII and NheI restriction enzyme sites resulting in a complete HC encoding plasmid.
Figure 23:
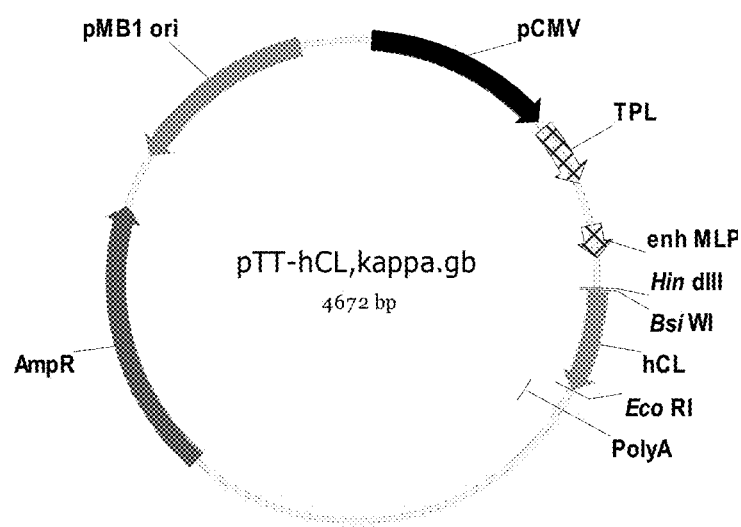
FIG. 23: Plasmid map for the expression vector pTT-hCL, kappa. The expression vector contains the DNA sequences encoding the constant region of human LC,kappa designated hCL,kappa. $V_L$ encoding DNA sequences can be inserted into the HinDIII and BsiWI restriction enzyme sites resulting in a complete LC encoding plasmid.

22+23) designated, pTT-hIgG4, containing the constant region encoding sequences for human IgG4 HC (ie CH1-hinge-CH2-CH3). The pTT vector is essentially described in Durocher, Y. et al., (2002) Nucleic Acid Res, 30: E9 (FIG. 22). The resulting vectors were designated pTT-0012HC (FIG. 5), pTT-0023HC, pTT-0051HC, and pTT-0052HC. The antiTLT-1 HC amino acid sequences encoded by the expression vectors are shown (Seq. ID no.: 0012HC: 39, 0023HC: 41, 0051HC: 43, 0052HC: 45).

Example 6

Development of DTT-0012LC, DTT-0023LC, DTT-0051LC and DTT-0052LC Expression Constructs.

Figure 24:
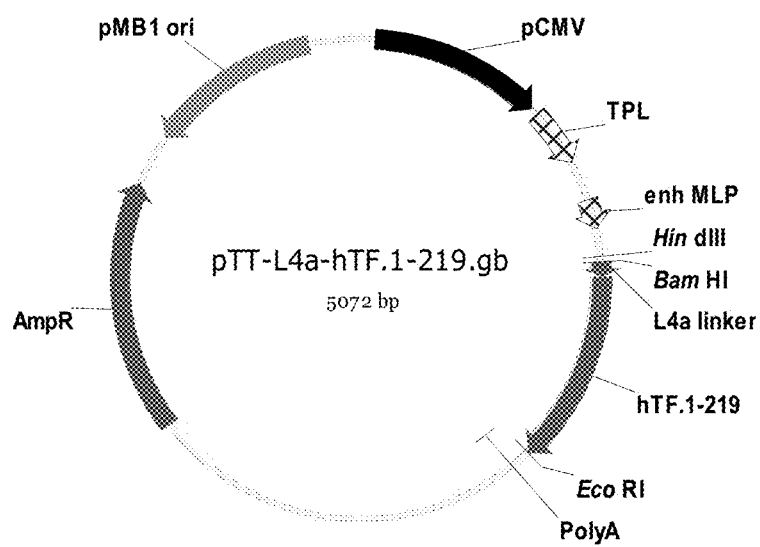
FIG. 24: Plasmid map for the expression vector pTT-L4a-hTF.1-219. The expression vector contains DNA sequences encoding a 17 amino acid long Gly-Ser linker and human TF.1-219. HC, LC or $V_H$-CH1 encoding DNA sequences can be inserted into the HinDIII and BamHI restriction enzyme sites resulting in HC-L4a-hTF.1-219, LC-L4a-hTF.1-219 or $V_H$-CH1-L4a-hTF.1-219 encoding plasmids.

The LC variable domain ($V_L$) encoding DNA sequences isolated from each of the four different antiTLT-1 hybridomas were PCR amplified with forward primers containing a HinDIII restriction enzyme site and reverse primers containing a BsiWI restriction enzyme site for cloning purposes. The $0012V_L$, $0023V_L$, $0051V_L$ and $0052V_L$ DNA sequences were PCR amplified with the following primers number pairs: 493 (forward)+495 (reverse), 548 (forward)+549 (reverse), 492 (forward)+494 (reverse), and 619 (forward)+620 (reverse primer sequences are shown in seq no 70-155), respectively, and inserted into the HinDIII and BsiWI restriction enzyme sites of a pTT-based vector designated, pTT-hLC,Kappa, containing the constant region encoding sequences for human LC, kappa (FIG. 24). The resulting vectors were designated pTT-0012LC, pTT-0023LC, pTT-0051LC, and pTT-0052LC. The antiTLT-1 LC amino acid sequence encoded by the expression vectors are shown in (Seq. ID no.: 0012LC: 40, 0023LC: 42, 0051LC: 44, 0052LC: 46).

Example 7

Development of DTT-0012HC.T60N, DTT-0012HC.T60A, DTT-0012LC.C36A and DTT-0052HC.C91Y.

The $0012V_H$ amino acid sequence contains a potential N-linked glycosylation site (T60, kabat numbering) and the $0012V_L$ and the $0052V_H$ amino acid sequences each contain an unpaired Cys (C36 and C91, respectively, kabat numbering). Expression vectors encoding 0012HC.T60N or 0012HC.T60A or 0012LC.C36A or 0052HC.C91Y were developed using site directed mutagenesis (QUICHANGE II, Stratagene, Catalog number 20523-5) following the instructions of the manufacturer. The site-directed mutagenesis reactions were performed using a) pTT-0012HC DNA as template and primer numbers 682 (forward)+683 (reverse) for pTT-0012HC.T60N, b) pTT-0012HC DNA as template and primer numbers 688 (forward)+689 (reverse) for pTT-0012HC.T60A, c) pTT-0012LC DNA as template and primer numbers 598 (forward)+599 (reverse) for pTT-0012LC.C36A, d) pTT-0052HC DNA as template and the following primer numbers 684 (forward)+685 (reverse, primer sequences are shown in seq no 70-155) for pTT-0052HC.C91Y. The resulting expression vectors were sequenced in order to verify DNA sequences. The antiTLT-1 HC and LC amino acid sequence encoded by the pTT-0012HC.T60N, pTT-0012HC.T60A and pTT-0012LC.C36A expression vectors are shown in (Seq. ID no.: 0012HC.T60N: 47, 0012HC.T60A: 50, 0012LC.C36A: 48).

Example 8

Development of DTT-0012LC-HPC4, DTT-0012LC.C36A-HPC4, DTT-0023LC-HPC4, DTT-0051LC-HPC4 and DTT-0052LC-HPC4 Expression Constructs.

$V_L$ encoding DNA sequences isolated from each of the four different antiTLT-1 hybridomas were PCR amplified with forward primers containing a HinDIII restriction enzyme site and reverse primers containing a BsiWI restriction enzyme site for cloning purposes. $0012V_L$, $0012V_L$.C36A, $0023V_L$, $0051V_L$ and $0052V_L$ DNA sequences were PCR amplified with the following primer numbers: 493 (forward)+495 (reverse), 548 (forward)+549 (reverse), 492 (forward)+494 (reverse), and 619 (forward)+620 (reverse, primer sequences are shown in Seq. ID no. 70-155) respectively, using PHUSION PCR mix (FinnZymes, cat No. F-531L). The human $C_L$,kappa encoding sequence was PCR amplified with forward primer number 486 and reverse primer number 485. Forward primer number 486 contains a BsiWI restriction enzyme site and reverse primer 485 encodes a HPC4 tag (Seq. ID no.: 69) followed by a stop codon and contains a 3' flanking EcoRI site for cloning purposes. The PCR reaction was performed using PHUSION PCR mix (FinnZymes, cat No. F-531L). HindIII+BsiWI digested $0012V_L$ PCR fragment was mixed with BsiWI+EcoRI digested human $C_L$,kappa-HPC4 PCR fragment and inserted into the HinDIII+EcoRI sites of a pTT-based expression vector resulting in pTT-0012LC-HPC4 (FIG. 4). In order to develop corresponding expression vectors encoding the LC-HPC4 version of the remaining three antiTLT-1 LC sequences, the $0012V_L$ sequence in pTT-0012LC-HPC4 was excised with HinDIII+BsiWI and replaced with HinDIII+BsiWI digested $0023V_L$, $0051V_L$, $0052V_L$ and $0012V_L$.C36A PCR fragments. The resulting four expression vectors were designated: pTT-0023LC-HPC4, pTT-0051LC-HPC4, pTT-0052LC-HPC4 and pTT-0012LC.C36A.HPC4.

Example 9

Development of DTT-0012$V_H$-CH1, DTT-0012$V_H$-CH1-HPC4, DTT-0023$V_H$-CH1 DTT-0023$V_H$-CH1-HPC4, DTT-0051$V_H$-CH1, DTT-0051$V_H$-CH1-HPC4, DTT-0052$V_H$-CH1 and DTT-0052$V_H$-CH1-HPC4 Expression Constructs.

The $0012V_H$, $0023V_H$, $0051V_H$, and $0052V_H$ sequences isolated from 0012Hyb, 0023Hyb, 0051Hyb, 0052Hyb were PCR amplified with primer numbers: 490 (forward)+491 (reverse), 546 (forward)+547 (reverse), 627 (forward)+628 (reverse), 617 (forward)+618 (reverse, primer sequences are shown in seq no 70-155), respectively, using PHUSION PCR mix (FinnZymes, cat No. F-531L). All forward primers (490, 546, 627, and 617) contained a HinDIII site and all reverse primers (491, 547, 628, and 618) contained a NheI site for cloning purposes. The human $IgG_4$ CH1 region was PCR amplified either with primer numbers: 489 (forward)+488 (reverse), or primer numbers 489 (forward)+487 (reverse). Forward primer number 489 contained a NheI site, the 488 reverse primer number contained a stop codon and an EcoRI site, and the 487 reverse primer number contained an HPC4 tag encoding sequence, a stop codon followed by an EcoRI site for cloning purposes. HinDIII+NheI digested $0012V_H$ PCR fragment was combined with either NheI+EcoRI digested human $IgG_4$ CH1 PCR fragment or with NheI+EcoRI digested human $IgG_4$ CH1-HPC4 PCR fragment and cloned into the HindIII+EcoRI sites for a pTT based vector. The resulting vectors were designated pTT-0012$V_H$-CH1 and pTT-0012$V_H$-CH1-HPC4, respectively. Subsequently, the $V_H$ domains of pTT-0012$V_H$-CH1 and of pTT-0012$V_H$-CH1-HPC4 were excised by HinDIII+NheI digestion and HinDIII+NheI digested 0197-0000-0023$V_H$, 0197-0000-0051$V_H$ and 0197-0000-0052$V_H$ PCR fragments were inserted. The resulting expression vectors were designated: pTT-0023V$_H$-CH1, pTT-0023V$_H$-CH1-HPC4, pTT-0051V$_H$-CH1, pTT-0051V$_H$-CH1-HPC4, pTT-0052V$_H$-CH1, and pTT-0052V$_H$-CH1-HPC4.

Example 10

Development of DTT-0012V$_H$.T60N-CH1 and DTT-0012V$_H$.T60N-CH1-HPC4 Expression Constructs.

The 0012V$_H$.T60N-CH1 sequence (including the signal peptide encoding sequence) was PCR amplified from pTT-0012HC.T60N using PHUSION PCR mix (FinnZymes, cat No. F-531L) and using forward primer number 572 containing a HinDIII restriction enzyme site and reverse primer number 488 containing a EcoRI site for cloning purposes or reverse primer 487 containing a HPC4 tag encoding sequence together with a EcoRI site for cloning purposes (primer sequences are shown in seq no 70-155). The resulting PCR fragments were digested with HinDIII+EcoRI and inserted into the HinDIII+EcoRI sites of a pTT based vector. The resulting expression vectors were designated pTT-0012V$_H$.T60N-CH1 and pTT-0012V$_H$.T60N-CH1-HPC4.

Example 11

Development of DTT-L4a-hTF.1-219 and DTT-hTF.1-219-L4b Expression Constructs.

Figure 25:
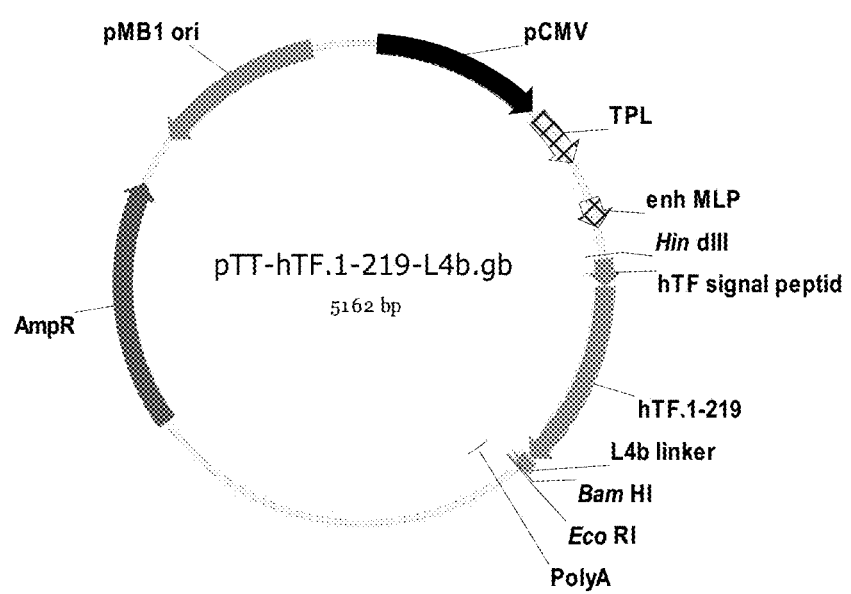
FIG. 25: Plasmid map for the expression vector pTT-hTF.1-219-L4b. The expression vector contains DNA sequences encoding human TF.1-219 and a 17 amino acid long Gly-Ser linker. HC, LC or $V_H$-CH1 encoding DNA sequences can be inserted into the BamHI and EcoRI restriction enzyme sites resulting in hTF.1-219-L4b-HC, hTF.1-219-L4b-LC or hTF.1-219-L4b-$V_H$-CH1 encoding plasmid.

An expression construct was made encoding an N-terminal 17 amino acid Gly-Ser linker (L4a: <u>GS</u>GGGGSGGGGS GGGGS, Seq. ID no. 61) and the extracellular domain of human tissue factor excluding the signal peptide encoding sequence (hTF.1-219, Seq. ID no. 14). At first, the hTF.1-219 cDNA sequence was PCR amplified using PHUSION PCR mix (FinnZymes, cat No. F-531L) and using primer number 466 (forward) containing L4a encoding DNA sequence and reverse primer 449 (primer sequences are shown in seq no 70-155) resulting in the L4a-hTF.1-219 PCR fragment. A second PCR amplification step was performed with primer number 483 (forward) and 449 (reverse) using the first PCR fragment as template. The second PCR step was done in order to incorporate both HinDIII and EcoRI sites into the PCR fragment for cloning purposes. The resulting PCR fragment encoded L4a-hTF.1-219 and contained a BamHI site as part of the Gly-Ser linker (underlined sequence in L4a) for future cloning purposes. The DNA fragment was inserted into the HinDIII and EcoRI sites of a pTT-based vector and the resulting vector was designated pTT-L4a-hTF. 1-219 (FIG. 25).

Figure 26:
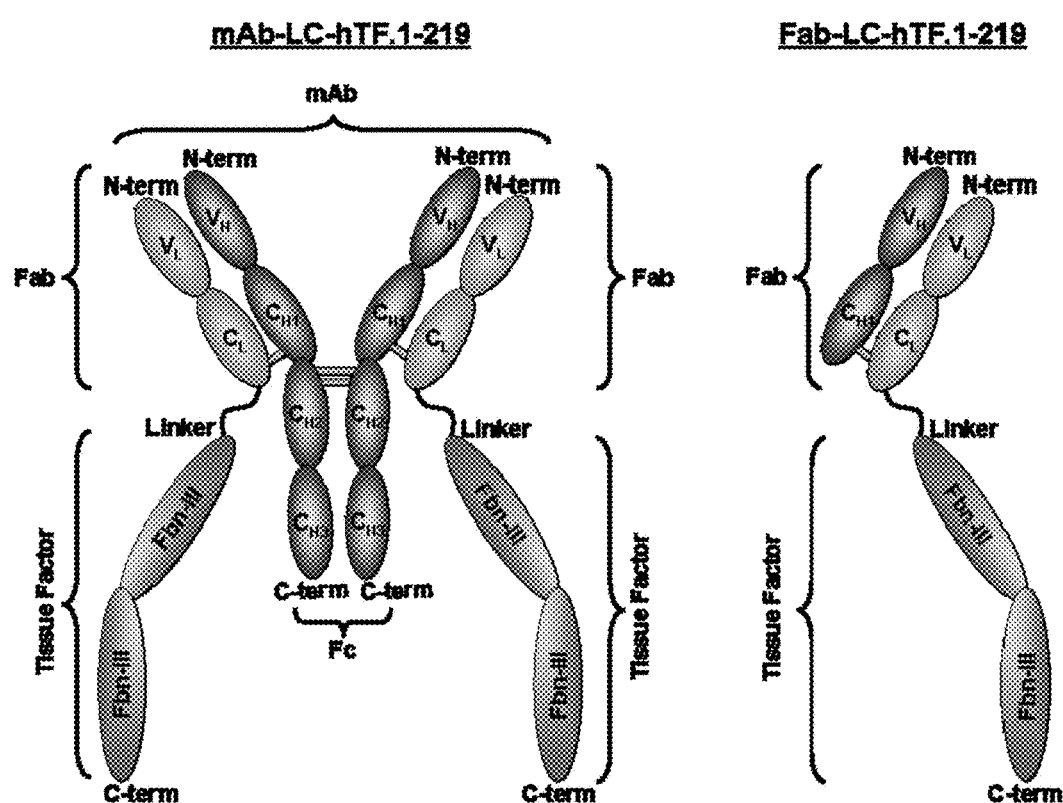
FIG. 26: Scheme of mAb-LC-hTF.1-219 and Fab-LC-hTF.1-219 constructs. Standard denotations for antibody components are shown: VL, CL, VH, CH1, CH2, and CH3. Tissue factor's fibronectin III domains are denoted Fbn-III.

An expression construct was made encoding the extracellular domain of human tissue factor including the signal peptide encoding sequence and a C-terminal 17 amino acid Gly-Ser linker (L4b: GGGGSGGGGSGGGGS <u>GS</u>, Seq. ID no. 62). At first, hTF.1-219 was PCR amplified using PHUSION PCR mix (FinnZymes, cat No. F-531L) and using primer number 448 (forward) and 467 (reverse, primer sequences are shown in seq. ID no 70-155) resulting in a DNA fragment encoding hTF.1-219-L4b (Seq. ID no. 16(AA1-251)+62). A second PCR amplification step was performed with primer number 448 (forward) and 484 (reverse) using the first PCR fragment as template. The second PCR step was done in order to incorporate both HinDIII and EcoRI sites into the PCR fragment for cloning purposes. The resulting hTF.1-219-L4b encoding PCR fragment contained a BamHI site as part of the Gly-Ser linker (underlined sequence in L4b) for future cloning purposes. The DNA fragment was inserted into the HinDIII and EcoRI sites of a pTT-based vector and the resulting vector was designated pTT-hTF.1-219-L4b (FIG. 26).

Example 12

Development of DTT-0012LC-L4a-hTF.1-219, DTT-hTF.1-219-L4b-0012LC Expression and DTT-0012LC.C36A-L4a-hTF.1-219 Constructs.

The 0012LC cDNA (including the signal peptide encoding sequence) was PCR amplified from pTT-0012LC using PHUSION PCR mix (FinnZymes, cat No. F-531L) and using forward primer number 493 and reverse primer number 552. The forward primer 493 inserted a 5' end HinDIII restriction enzyme site and the reverse primer 552 inserted a 3' end BamHI restriction enzyme site for cloning purposes (primer sequences are shown in seq no 70-155). The resulting 0012LC PCR fragment was inserted into the HinDIII+BamHI sites of pTT-L4a-hTF.1-219 resulting in the 0012LC-L4a-hTF.1-219 encoding expression vector designated pTT-0012LC-L4a-hTF.1-219.

The 0012LC cDNA (excluding the signal peptide encoding sequence) was PCR amplified from pTT-0012LC using PHUSION PCR mix (FinnZymes, cat No. F-531L) and using forward primer number 551 and reverse primer number 98. The forward primer 551 inserted a 5' end BamHI restriction enzyme site and the reverse primer 98 inserted a 3' end EcoRI restriction enzyme site for cloning purposes (primer sequences are shown in seq no 70-155). The resulting 0012LC PCR fragment was inserted into the BamHI+EcoRI sites of pTT-hTF.1-219-L4b resulting in the hTF.1-219-L4b-0012LC encoding expression vector designated pTT-hTF.1-219-L4b-0012LC.

The 0012V$_L$.C36A cDNA sequence was excised from pTT-0012LC.C36A using the HinDIII and BsiWI restriction enzymes and the resulting DNA fragment was inserted into the HinDIII+BsiWI restriction enzyme sites of the pTT-0012LC-L4a-hTF.1-219 plasmid i.e. replacing the 0012V$_L$ sequence. The resulting expression plasmid was designated pTT-0012LC.C36A-L4a-hTF.1-219 (also designated 0061LC-L4a-hTF.1-219).

Example 13

Development of DTT-0012HC-L4a-hTF.1-219 and DTT-hTF.1-219-L4b-0012HC Expression Constructs.

The 0012HC sequence (including the signal peptide encoding sequence) was PCR amplified from pTT-0012HC using PHUSION PCR mix (FinnZymes, cat No. F-531L) and using forward primer number 490 and reverse primer number 513. The forward primer 490 inserted a 5' end HinDIII restriction enzyme site and reverse primer 513 inserted a 3' end BamHI restriction enzyme site for cloning purposes. The 0012HC PCR fragment was inserted into the HinDIII+BamHI sites of pTT-L4a-hTF.1-219 resulting in the 0012HC-L4a-hTF.1-219 expression construct designated pTT-0012HC-L4a-hTF.1-219.

The 0012HC sequence (excluding the signal peptide encoding sequence) was PCR amplified from pTT-0012HC using PHUSION PCR mix (FinnZymes, cat No. F-531L) and using forward primer number 512 and reverse primer number 100. The forward primer 512 inserted a 5' end BamHI restriction enzyme site and reverse primer 100 inserted a 3' end EcoRI restriction enzyme site for cloning purposes (primer sequences are shown in seq no 70-155). The 0012HC PCR fragment was inserted into the BamHI+

EcoRI sites of pTT-hTF.1-219-L4b resulting in the hTF.1-219-L4b-0012HC expression construct designated pTT-hTF.1-219-L4b-0012HC.

Example 14

Development of DTT-0012$V_H$-CH1-L4a-hTF.1-219 and DTT-hTF.1-219-L4b-0012$V_H$-CH1 Constructs.

The 0012$V_H$-CH1 encoding DNA sequence (including the signal peptide encoding sequence) was PCR amplified from pTT-0012HC using PHUSION PCR mix (FinnZymes, cat No. F-531L) and using forward primer number 490 and reverse primer number 514 (primer sequences are shown in Seq. ID no 70-155). The forward primer 490 inserted a 5' end HinDIII restriction enzyme site and the reverse primer 514 inserted a 3' end BamHI restriction enzyme site for cloning purposes. The 0012$V_H$-CH1 PCR fragment was inserted into the HinDIII+BamHI sites of pTT-L4a-hTF.1-219 resulting in the 0012$V_H$-CH1-L4a-hTF.1-219 expression construct designated pTT-0012$V_H$-CH1-L4a-hTF.1-219 (FIG. 6).

The 0012$V_H$-CH1 encoding DNA sequence (excluding the signal peptide encoding sequence) was PCR amplified from pTT-0012HC using forward primer number 512 and reverse primer number 488. The forward primer 512 inserted a 5' end BamHI restriction enzyme site and the reverse primer 488 inserted a stop codon and a 3' end EcoRI restriction enzyme site for cloning purposes (primer sequences are shown in seq no 70-155). The 0012$V_H$-CH1 PCR fragment was inserted into the BamHI+EcoRI sites of pTT-hTF.1-219-L4b resulting in the hTF.1-219-L4b-0012$V_H$-CH1 expression construct designated pTT-hTF.1-219-L4b-0012$V_H$-CH1.

Example 15

Development of DTT-0012LC-TF with Different Linker Length: L0 (No Linker), L1 (2GS), L2 (7GS), L3 (12GS), L5 (22GS), L6 (27GS), L7 (32GS), L8 (37GS), L9 (42GS).

The 0012LC cDNA sequence (including the signal peptide encoding sequence) was PCR amplified using PHUSION PCR mix (FinnZymes, cat No. F-531L) and using forward primer number 574 containing a 5' end HinDIII site and reverse primers containing 3' end sequences encoding either GS linker length of 5 GS+a BamHI site (reverse primer number 590), 10GS+a BamHI site (reverse primer number 585), 15GS (reverse primer number 583)+a BamHI site, 20GS+a BamHI site (reverse primer number 584), 25GS+a BamHI site (reverse primer number 591, primer sequences are shown in seq no 70-155). The resulting 0012LC PCR fragments were digested with HinDIII+BamHI and inserted into pTT-L4a-hTF.1-219 resulting in expression vectors designated pTT-0012LC-L5-hTF.1-219 (22GS linker), pTT-0012LC-L6-hTF.1-219 (27GS linker), pTT-0012LC-L7-hTF.1-219 (32GS linker), pTT-0012LC-L8-hTF.1-219 (37GS linker) and pTT-0012LC-L9-hTF.1-219 (42GS linker).

The hTF.1-219 cDNA sequence (excluding the signal peptide encoding sequence) was PCR amplified using PHUSION PCR mix (FinnZymes, cat No. F-531L) and using forward primer number 586, containing a BamHI site (2GS linker) following by a 10 GS linker encoding sequence, or forward primer number 699 containing a BamHI site (2GS linker) followed by a 5GS linker encoding sequence or forward primer number 700 containing a BamHI site (2GS linker) together with reverse primer number 449 containing a EcoRI restriction enzyme site for cloning purposes (primer sequences are shown in seq no 70-155). The resulting PCR fragments were digested with BamHI+EcoRI and inserted into the BamHI+EcoRI sites of pTT-0012LC-L4a-hTF.1-219 i.e. replacing the L4a-hTF.1-219 sequence. The resulting expression vectors were designated: pTT-0012LC-L3-hTF.1-219 (12GS linker), pTT-0012LC-L2-hTF.1-219 (7GS linker) or pTT-0012LC-L1-hTF.1-219 (2GS linker).

The 0012LC cDNA sequence (including the signal peptide encoding sequence) was PCR amplified using PHUSION PCR mix (FinnZymes, cat No. F-531L) and using forward primer number 574 containing a 5' end HinDIII site and the reverse primer number 704 containing sequences from the 5' end of hTF.1-219. The hTF.1-219 cDNA sequence (excluding the signal peptide encoding sequence) was PCR amplified using PHUSION PCR mix (FinnZymes, cat No. F-531L) and using forward primer number 703 containing sequences from the 3' end of 0012LC and reverse primer number 449 containing a 3' end EcoRI site. The 0012LC and hTF.1-219 PCR fragments were combined and a second PCR step (overlap PCR) was performed using forward primer number 574 and reverse primer number 449 (primer sequences are shown in seq no 70-155). The resulting PCR fragment was inserted into the HinDIII+EcoRI sites of a pTT-based expression vector resulting in pTT-0012LC-L0-hTF.1-219 encoding a 0012LC-hTF.1-219 fusion protein without any linker sequences.

Example 16

Development of DTT-0023LC-TF with Different Linker Length: L3 (12GS), L4a (17GS), L5 (22GS), L6 (27GS), L7 (32GS), L8 (37GS), L9 (42GS).

The 0023$V_L$ cDNA sequence (including the signal peptide encoding sequence) was excised from pTT-0023LC using the HinDIII+BsiWI restriction enzymes and inserted into the HinDIII+BsiWI restriction enzyme sites of: pTT-0012LC-L3-hTF.1-219 (12GS linker), pTT-0012LC-L4a-hTF.1-219 (17GS linker), pTT-0012LC-L5-hTF.1-219 (22GS linker), pTT-0012LC-L6-hTF.1-219 (27GS linker), pTT-0012LC-L7-hTF.1-219 (32GS linker), pTT-0012LC-L8-hTF.1-219 (37GS linker) and pTT-0012LC-L9-hTF.1-219 (42GS linker) i.e. replacing the 0012$V_L$ cDNA sequence with 0023$V_L$. The resulting expression vectors were designated: pTT-0023LC-L3-hTF.1-219 (12GS linker), pTT-0023LC-L4a-hTF.1-219 (17GS linker), pTT-0023LC-L5-hTF.1-219 (22GS linker), pTT-0023LC-L6-hTF.1-219 (27GS linker), pTT-0023LC-L7-hTF.1-219 (32GS linker), pTT-0023LC-L8-hTF.1-219 (37GS linker) and pTT-0023LC-L9-hTF.1-219 (42GS linker).

Example 17

Development of DTT-0023HC-TF with Different Linker Length: L1 (2GS), L2 (7GS), L3 (12GS), Loa (17GS), L5 (22GS), L6 (27GS), L7 (32GS), L8 (37GS), L9 (42GS).

The 0023HC cDNA sequence (including the signal peptide encoding sequence) was PCR amplified using PHUSION PCR mix (FinnZymes, cat No. F-531L) and using forward primer number 546 containing a 5'-end HindIII restriction enzyme site and 1) reverse primer number 592 containing a 5GS encoding sequence together with a BamHI site or 2) reverse primer number 589 containing a 10GS encoding sequence together with a BamHI site or 3) reverse primer number 587 containing a 15GS encoding sequence together with a BamHI site or 4) reverse primer number 588 containing a 20GS encoding sequence together with a BamHI site or 5) reverse primer number 593 containing a 25GS encoding sequence together with a BamHI site (primer sequences are shown in seq no 70-155). The resulting PCR fragments were digested with HinDIII+BamHI and inserted into the HinDIII+BamHI restriction enzyme sites of pTT-0012LC-L4a-hTF.1-219 i.e. replacing the 0012LC encoding sequence. The resulting expression vectors were designated: pTT-0023HC-L5-hTF.1-219 (22GS linker), pTT-0023HC-L6-hTF.1-219 (27GS linker), pTT-0023HC-L7-hTF.1-219 (32GS linker), pTT-0023HC-L8-hTF.1-219 (37GS linker), pTT-0023HC-L9-hTF.1-219 (42GS linker).

The hTF.1-219 cDNA sequence (excluding the hTF signal peptide sequence) was PCR amplified using PHUSION PCR mix (FinnZymes, cat No. F-531L) and using a) forward primer number 586 containing a BamHI restriction enzyme site and a 10GS encoding sequence or b) forward primer number 699 containing a BamHI restriction enzyme site and a 5GS encoding sequence or forward primer number 700 containing a BamHI restriction enzyme site together with reverse primer number 449 containing an EcoRI restriction enzyme site for cloning purposes (primer sequences are shown in seq no 70-155). The resulting PCR fragments were digested with BamHI+EcoRI and inserted into the BamHI+EcoRI sites of pTT-0023HC-L4a-hTF.1-219 i.e. replacing the L4a-hTF.1-219 sequence with L3-hTF.1-219 or L2-hTF.1-219 or L1-hTF.1-219 cDNA sequence. The resulting expression vectors were designated pTT-0023HC-L3-hTF.1-219 (12GS linker), pTT-0023HC-L2-hTF.1-219 (7GS linker) and pTT-0023HC-L1-hTF.1-219 (2GS linker), respectively.

The $0023V_H$ DNA sequence was excised from pTT-0023HC using HinDIII+NheI and inserted into the HinDIII+NheI sites of pTT-0012HC-L4a-hTF.1-219 i.e. replacing the $0012V_H$ DNA sequence. The resulting expression vector was designated pTT-0023HC-L4a-hTF.1-219.

Example 18

Development of DTT-0012HC-TF with Different Linker Length: L0 (No Linker), L1 (2GS), L2 (7GS), L3 (12GS), L5 (22GS), L6 (27GS), L7 (32GS), L8 (37GS), L9 (42GS).

The $0012V_H$ encoding cDNA sequence was excised from pTT-0012HC using HinDIII+NheI and the resulting cDNA fragment was inserted into pTT-0023HC-L1-hTF.1-219, pTT-0023HC-L2-hTF.1-219, pTT-0023HC-L3-hTF.1-219, pTT-0023HC-L5-hTF.1-219, pTT-0023HC-L6-hTF.1-219, pTT-0023HC-L7-hTF.1-219, pTT-0023HC-L8-hTF.1-219 or pTT-0023HC-L9-hTF.1-219 i.e. replacing $0023V_H$. The resulting expression vectors were designated: 1) pTT-0012HC-L1-hTF.1-219, pTT-0012HC-L2-hTF.1-219, pTT-0012HC-L3-hTF.1-219, pTT-0012HC-L5-hTF.1-219, pTT-0012HC-L6-hTF.1-219, pTT-0012HC-L7-hTF.1-219, pTT-0012HC-L8-hTF.1-219 or pTT-0012HC-L9-hTF.1-219.

0012HC encoding cDNA (including the signal peptide sequence) was PCR amplified using PHUSION PCR mix (FinnZymes, cat No. F-531L) and using forward primer number 490 containing a 5' end HinDIII restriction enzyme site and reverse primer number 801 containing a part of the 5' end cDNA sequence encoding hTF.1-219. The hTF.1-219 cDNA sequence (excluding the signal peptide encoding sequence) was PCR amplified using forward primer number 800 containing a 5' end sequence encoding the 3' end part of 0012HC cDNA and reverse primer number 449 containing an EcoRI site for cloning purposes (primer sequences are shown in seq no 70-155). The resulting two PCR fragments were combined and used as template in a second PCR step (overlapping PCR) using forward primer number 490 and reverse primer number 449. The PCR fragment obtained was digested with HinDIII+EcoRI and inserted into a pTT based expression vector. The resulting expression vector was designated pTT-0012-L0-hTF.1-219 and encoded a 0012HC-TF fusion protein without linker sequence.

Example 19

Development of DTT-0012$V_H$-CH1-L10-hTF.1-219, DTT-0012$V_H$.T60N-CH1-L10-hTF.1-219 and DTT-0012$V_H$.T60A-CH1-L10-hTF.1-219.

The 0012$V_H$-CH1-hinge cDNA sequence (including the signal peptide encoding sequence) was PCR amplified from the pTT-0012HC plasmid using PHUSION PCR mix (FinnZymes, cat No. F-531L) and using forward primer number 572 containing a 5'-end HindIII restriction enzyme site and reverse primer number 686 containing part of hTF.1-219 5' end sequences. The reverse primer 686 was annealed to the hIgG4 hinge region of the pTT-0012HC plasmid and incorporated two point mutations, C239S and C242S (Kabat numbering) in order to remove two free cysteines. The human TF.1-219 cDNA sequence was PCR amplified using forward primer number 687 containing sequence from the 3' end of the 0012$V_H$-CH1-hinge cDNA and reverse primer number 449 containing an EcoRI restriction enzyme site for cloning purposes (primer sequences are shown in seq no 70-155). The resulting 0012$V_H$-CH1-hinge cDNA and hTF.1-219 PCR fragments were combined and used as template in a second PCR reaction (overlap PCR) using forward primer number 572 and reverse primer number 449. The resulting PCR fragment encoding 0012$V_H$-CH1-hinge-hTF.1-219 was digested with HindIII+EcoRI and inserted into a pTT-based expression vector resulting in the expression vector designated pTT-0012$V_H$-CH1-L10-hTF.1-219.

The 0012$V_H$.T60N and 0012$V_H$.T60A cDNAs (including the signal peptide encoding sequence) were excised from pTT-0012HC.T60N or from pTT-0012HC.T60A, respectively using the HinDIII and NheI restriction enzymes. The resulting variable domains were inserted into the HinDIII+NheI sites of pTT-0012$V_H$-CH1-L10-hTF.1-219 i.e. replacing 0012$V_H$ sequence. The resulting expression vectors were designated: pTT-0012$V_H$.T60N-CH1-L10-hTF.1-219 (also known as pTT-0061$V_H$-CH1-L10-hTF.1-219) and pTT-0012$V_H$.T60A-CH1-L10-hTF.1-219 (also known as pTT-0082$V_H$-CH1-L10-hTF.1-219), respectively.

Example 20

Development of DTT-0012$V_H$-CH1-L0-hTF.1-219.

The 0012$V_H$-CH1 encoding DNA sequence was PCR amplified from the pTT-0012HC plasmid using PHUSION PCR mix (FinnZymes, cat No. F-531L) and using HinDIII containing forward primer number 572 and a reverse primer number 702 containing DNA sequences overlapping with the 5' end of hTF.1-219 cDNA sequence. The hTF.1-219 cDNA sequence was PCR amplified using forward primer number 701 containing cDNA sequences overlapping with the 3' end cDNA sequence for 0012$V_H$-CH1 and reverse primer number 449 containing an EcoRI restriction enzyme site for cloning purposes. The resulting PCR fragments were combined and used in a second PCR reaction (overlapping PCR) using forward primer number 572 and reverse primer number 449. The resulting PCR fragment was digested with HinDIII+EcoRI and inserted into the HinDIII+EcoRI restriction sites of a pTT-based expression vector resulting in an expression vector designated pTT-0012 $V_H$-CH1-no linker-hTF.1-219.

Example 21

Development of DTT-023$V_H$-CH1-L4a-hTF.1-219, DTT-0051HC-L4a-hTF.1-219, DTT-0051$V_H$-CH1-L4a-hTF.1-219, DTT-0052HC-L4a-hTF.1-219 and DTT-0052$V_H$-CH1-L4a-hTF.1-219.

The 0023$V_H$, 0051VH and 0052$V_H$ cDNA sequences were excised from pTT-023HC, pTT-0051HC or from pTT-0052HC using HinDIII+NheI restriction enzymes. The resulting DNA fragments were inserted into the HinDIII+NheI restriction enzyme sites of pTT-0012HC-L4a-hTF.1-219 or of pTT-0012$V_H$-CH1-L4a-hTF.1-219 i.e. replacing the 0012$V_H$ DNA sequence. The resulting expression vectors were designated pTT-0023$V_H$CH1-L4a-hTF.1-219, pTT-0051HC-L4a-hTF.1-219, pTT-0051$V_H$-CH1-L4a-hTF.1-219, pTT-0052HC-L4a-hTF.1-219 and pTT-0052$V_H$-CH1-L4a-hTF.1-219.

Example 22

Development of DTT-0051LC-L4a-hTF.1-219 and DTT-0052LC-L4a-hTF.1-219.

The 0051$V_L$ and 0052$V_L$ cDNA sequences were excised from pTT-0051LC or from pTT-0052LC using HinDIII+BsiWI restriction enzymes. The resulting DNA fragments were inserted into the HinDIII+BsiWI restriction enzyme sites of pTT-0012LC-L4a-hTF.1-219 i.e. replacing the 0012$V_L$ DNA sequence. The resulting expression vectors were designated pTT-0051LC-L4a-hTF.1-219 or pTT-0052LC-L4a-hTF.1-219.

Example 23

Development of DTT-Isotype Control LC-L4a-hTF.1-219, DTT-Isotype Control LC-HPC4, DTT-Isotype Control HC-L4a-hTF.1-219, DTT-Isotype Control HC, DTT-Isotype Control $V_H$-CH1-HPC4, and DTT-Isotype Control $V_H$-CH1-L4a-TF.

In order to express a hTF.1-219 fusion proteins based on an isotype control Fab or mAb sequence, $V_H$ and $V_L$ cDNA sequences were retrieved based on anti-triNitroPhenyl (ATNP) CDR sequences. The ATNP $V_L$ sequence was inserted into the HinDIII+BsiWI restriction enzyme sites of the following plasmids: pTT-0012LC, pTT-0012LC-HPC4 and pTT-0012LC-L4a-hTF.1-219 i.e. replacing the 0012$V_L$ sequence and resulting in the following expression plasmids: pTT-isotype control-LC, pTT-isotype control-LC-HPC4 and pTT-isotype control-LC-L4a-hTF.1-219. The ATNP $V_H$ sequence was inserted into the HinDIII+NheI restriction enzyme sites of the following plasmids: pTT-0012HC, pTT-0012$V_H$-CH1-HPC4, pTT-0012$V_H$-CH1-L4a-hTF.1-219 and pTT-0012HC-L4a-hTF.1-219 i.e. replacing the 0012$V_H$ sequence and resulting in the following expression plasmids: pTT-isotype control-HC, pTT-isotype control-$V_H$-CH1-HPC4, pTT-isotype control-$V_H$-CH1-L4a-hTF.1-219 and pTT-isotype control-HC-L4a-hTF.1-219.

Example 24

Development of DTT-AP-3LC-17GS-TF.1-219, DTT-AP-3LC.C34S-17GS-TF.1-219 and DTT-AP-3$V_H$-CH1-HPC4.

The AP-3 hybridoma expressing an antiGPIIbIIIa mAb was purchased from ATCC (ATCC Number: HB-242) and the variable domain encoding sequences from AP3 LC and HC were determined. Total RNA was isolated from AP-3 hybridoma cells using RNEASY (kit for purifying total RNA from cells, tissues, and yeast) mini kit (Qiagen, cat. no. 74106) and an first stranded cDNA was made using SMART RACE (cDNA amplification kit) (clontech, cat no. PT3269-1), PRIMESCRIPT reverse polymerase (Takara Bio Inc, code no. 2680A) and employing the 5-CDS primer and SMART IIA oligonucleotide (both included in the SMART RACE kit). The LC and HC variable domain sequences were PCR amplified using UPM primer mix (included in the SMART RACE kit) together with primer number 69 for LC and UPM primer mix together with primer number 312 (primer sequences are shown in seq no 70-155) for HC. The PCR fragments were cloned into a sequencing vector using ZEROBLUNT Topo PCR cloning kit for Sequencing (Invitrogen, cat no K287520) following the instructions of the manufacturer. A potential free Cys at position 34 (according to the Kabat numbering system) was identified in the $V_L$ cDNA sequence. The Cys residue was mutated to a Ser by employing site-directed mutagenesis using the QUIKCHANGE Site Directed Mutagenesis Kit (Cat no 200518, Stratagene) and primer number 50 and 51 (primer sequences are shown in seq no 70-155). The resulting $V_L$ cDNA sequence was sequenced in order to verify mutated cDNA sequence.

The AP-3$V_H$, AP-3$V_L$ and AP-3$V_L$.C34S cDNA sequenced was PCR amplified in order to generate expression vectors encoding AP-3$V_H$-CH1-HPC4, AP-3LC-L4a-hTF.1-219 and AP3LC.C34S-L4a-hTF.1-219. AP-3$V_H$ was PCR amplified using PHUSION PCR mix (FinnZymes, cat No. F-531L) and using forward primer number 842 containing a HinDIII restriction enzyme site and reverse primer number 843 containing a NheI restriction enzyme site for cloning purposes. The AP-3$V_L$ and AP-3$V_L$.C34S cDNA sequenced were PCR amplified using PHUSION PCR mix (FinnZymes, cat No. F-531L) and using forward primer number 844 containing a HinDIII restriction enzyme site and reverse primer number 845 (primer sequences are shown in seq no 70-155) containing a BsiWI restriction enzyme site for cloning purposes. The HinDIII+NheI digested AP-3$V_H$ PCR fragment was inserted into the HinDIII and NheI restriction enzyme sites of pTT-0012$V_H$-CH1-HPC4 i.e. replacing the 0012$V_H$ DNA sequence resulting in an expression vector designated pTT-AP3$V_H$-CH1-HPC4. The HinDIII+BsiWI digested AP-3$V_L$ and AP-3$V_L$.C34S PCR fragments were inserted into the HinDIII and BsiWI restriction enzyme sites of pTT-0012LC-L4a-hTF.1-219 i.e. replacing the 0012$V_L$ DNA sequence and resulting in an expression vector designated pTT-AP-3LC-L4a-hTF.1-219 and pTT-AP-3LC.C34S-L4a-hTF.1-219.

Example 25

Development of DTT-0012HC.T60N-His6, DTT-hIgG4-Hinge-CH2-CH3-His6 and DTT-hIgG4-Hinge-CH2-CH3-L4a-hTF.1-219.

In order to develop an expression vector encoding 0012HC.T60N with a C-terminal His-6 tag, site-directed mutagenesis was performed using QUIKCHANGE lightning kit (GenStar Biosolutions, cat No. T113-01). In brief, the site-directed mutagenesis reaction was performed using pTT-0012HC.T60N as template, forward and reverse primer number 1000 and 1001 (primer sequences are shown in seq no 70-155). The primer number 1000+1001 annealed to the 3' end of the 0012HC.T60N cDNA sequence and contained His-6 tag encoding sequences followed by a stop codon. The resulting plasmid was designated pTT-0012HC.T60N-His6.

In order to develop an expression vector encoding hIgG4-hinge-CH2-CH3-L4a-hTF.1-219 site-directed mutagenesis was performed using QUIKCHANGE lightning kit (GenStar Biosolutions, cat No. T113-01) and using pTT-0012HC-L4a-hTF.1-219 as template and forward and reverse primers number 1002 and 1003 (primer sequences are shown in seq no 70-155). The primer numbers 1002+1003 annealed to part of the 0012HC signal peptide and part of the hIgG4 hinge region and deleted the $0012V_H$-CH1 DNA sequences from pTT-0012HC-L4a-hTF.1-219 plasmid. The resulting expression vector was designated pTT-hIgG4-hinge-CH2-CH3-L4a-hTF.1-219. In order to develop an expression vector encoding hIgG4-hinge-CH2-CH3-His6, site-directed mutagenesis was performed using Quichange Lightning kit (Stratagene, cat. no. 200518) and using pTT-hIgG4-hinge-CH2-CH3-L4a-hTF.1-219 as template and forward and reverse primers number 1000 and 1001. Primer number 1000+1001 contained His-6 encoding DNA sequences followed by a stop codon and they annealed to the 3'-end of the hIgG4 CH3 DNA sequence. The resulting expression vector was designated pTT-hIgG4-hinge-CH2-CH3-His6.

Example 26

Transient Transfection of HEK293-6E Cells.

All mAb, Fab, and hTF.1-219 fusion proteins were expressed in HEK293-6E suspension cells by transient transfecting expression plasmids into cells. The individual plasmids combinations underlying the resulting specific protein compounds are shown in Table 6. HEK293-6E cells were grown in FREESTYLE HEK293 MEDIUM (animal origin-free, chemically defined, protein-free medium) (GIBCO, cat. no. 12338-018) supplemented with 1% P/S (GIBCO cat. no. 15140-122), 0.1% PLURONIC (clock copolymers based on ethylene oxide and propylene oxide) (GIBCO, cat. no. 24040-032) and 25 ug/mL GENETICIN (aminoglycoside selective agent) (GIBCO, cat. no. 10131-019) and cells were transfected at a cell density of approximately 1 mill/mL using 293FECTIN (cationic lipid-based formulation for transfecting DNA into eukaryotic cells) (Invitrogen, cat. no. 12347-019) according to the instructions of the manufacturer. In brief, for each liter of HEK293-6E cells, the transfection was performed by diluting a total of 1 mg of DNA into 30 mL OPTIMEM (reduced-serum media) (dilution A) and by diluting 1 mL 293FECTIN (cationic lipid-based formulation for transfecting DNA into eukaryotic cells) into 30 mL OPTIMEM (reduced-serum media) (GIBCO, cat. no. 51985-026, dilution B). Dilution A and B were mixed and incubated at room temperature for 30 minutes. The transfection mix was hereafter added to the HEK293-6E cells and cells were incubated at 37° C. in a humidified incubator with orbital rotation (125 rpm). Five to seven days post-transfection, cells were removed by centrifugation and the resulting cell culture supernatants were sterile-filtrated prior to purification. For all transient transfection experiments using co-transfection of 2 expression plasmids, the plasmids were cotransfected in a 1:1 (ug:ug) plasmid ratio using a total DNA amount of 1 mg for each liter of HEK293-6E cells to be transfected. For the expression of protein 0120 and 0121 (Table 6), 3 expression plasmids were co-transfected into HEK293-6E cells in a 1:1:1 (ug:ug:ug) plasmid ratio.

TABLE 6

| Protein ID | LC plasmid | HC plasmid | mAb/Fab or mAb-/Fab-hTF.1-219 fusion protein name |
|---|---|---|---|
| 0012 | pTT-0012LC | pTT-0012HC | mAb 0012 $HC_2$; $LC_2$ |
| 0061 | pTT-0012LC.C36A | pTT-0012HC.T60N | mAb 0061 $HC_2$; $LC_2$ |
| 0082 | pTT-0012LC.C36A | pTT-0012HC.T60A | mAb 0082 $HC_2$; $LC_2$ |
| 0023 | pTT-0023LC | pTT-0023HC | mAb 0023 $HC_2$; $LC_2$ |
| 0051 | pTT-0051LC | pTT-0051HC | mAb 0051 $HC_2$; $LC_2$ |
| 0052 | pTT-0052LC | pTT-0052HC | mAb 0052 $HC_2$; $LC_2$ |
| 0062 | pTT-0052LC | pTT-0052HC.C91Y | mAb 0062 $HC_2$; $LC_2$ |
| 0116 | pTT-0012LC | pTT-0012HC-L0-hTF.1-219 | mAb 0012-(HC-L0-hTF.1-219)$_2$; $LC_2$ |
| 0086 | pTT-0012LC | pTT-0012HC-L1-hTF.1-219 | mAb 0012-(HC-L1-hTF.1-219)$_2$; $LC_2$ |
| 0087 | pTT-0012LC | pTT-0012HC-L2-hTF.1-219 | mAb 0012-(HC-L2-hTF.1-219)$_2$; $LC_2$ |
| 0088 | pTT-0012LC | pTT-0012HC-L3-hTF.1-219 | mAb 0012-(HC-L3-hTF.1-219)$_2$; $LC_2$ |
| 0018 | pTT-0012LC-HPC4 | pTT-0012HC-L4a-hTF.1-219 | mAb 0012-(HC-L4a-hTF.1-219)$_2$; (LC-HPC4)$_2$ |
| 0013 | pTT-0012LC | pTT-hTF.1-219-L4b-0012HC | mAb 0012-(hTF.1-219-L4b-HC)$_2$; $LC_2$ |
| 0089 | pTT-0012LC | pTT-0012HC-L5-hTF.1-219 | mAb 0012-(HC-L5-hTF.1-219)$_2$; $LC_2$ |
| 0090 | pTT-0012LC | pTT-0012HC-L6-hTF.1-219 | mAb 0012-(HC-L6-hTF.1-219)$_2$; $LC_2$ |
| 0091 | pTT-0012LC | pTT-0012HC-L7-hTF.1-219 | mAb 0012-(HC-L7-hTF.1-219)$_2$; $LC_2$ |
| 0092 | pTT-0012LC | pTT-0012HC-L8-hTF.1-219 | mAb 0012-(HC-L8-hTF.1-219)$_2$; $LC_2$ |
| 0093 | pTT-0012LC | pTT-0012HC-L9-hTF.1-219 | mAb 0012-(HC-L9-hTF.1-219)$_2$; $LC_2$ |
| 0107 | pTT-0012LC-L0-hTF.1-219 | pTT-0012HC | mAb 0012-(LC-L0-hTF.1-219)$_2$; $HC_2$ |
| 0108 | pTT-0012LC-L1-hTF.1-219 | pTT-0012HC | mAb 0012-(LC-L1-hTF.1-219)$_2$; $HC_2$ |
| 0109 | pTT-0012LC-L2-hTF.1-219 | pTT-0012HC | mAb 0012-(LC-L2-hTF.1-219)$_2$; $HC_2$ |
| 0045 | pTT-0012LC-L3-hTF.1-219 | pTT-0012HC | mAb 0012-(LC-L3-hTF.1-219)$_2$; $HC_2$ |
| 0019 | pTT-0012LC-L4a-hTF.1-219 | pTT-0012HC | mAb 0012-(LC-L4a-hTF.1-219)$_2$; $HC_2$ |
| 0025 | pTT-hTF.1-219-L4b-0012LC | pTT-0012HC | mAb 0012-(hTF.1-219-L4b-LC)$_2$; $HC_2$ |
| 0046 | pTT-0012LC-L5-hTF.1-219 | pTT-0012HC | mAb 0012-(LC-L5-hTF.1-219)$_2$; $HC_2$ |
| 0047 | pTT-0012LC-L6-hTF.1-219 | pTT-0012HC | mAb 0012-(LC-L6-hTF.1-219)$_2$; $HC_2$ |
| 0048 | pTT-0012LC-L7-hTF.1-219 | pTT-0012HC | mAb 0012-(LC-L7-hTF.1-219)$_2$; $HC_2$ |
| 0049 | pTT-0012LC-L8-hTF.1-219 | pTT-0012HC | mAb 0012-(LC-L8-hTF.1-219)$_2$; $HC_2$ |
| 0050 | pTT-0012LC-L9-hTF.1-219 | pTT-0012HC | mAb 0012-(LC-L9-hTF.1-219)$_2$; $HC_2$ |
| 0034 | pTT-0023LC-HPC4 | pTT-0023HC-L4a-hTF.1-219 | mAb 0023-(HC-L4a-hTF.1-219)$_2$; (LC-HPC4)$_2$ |
| 0035 | pTT-0023LC-L4a-hTF.1-219 | pTT-0023HC | mAb 0023-(LC-L4a-hTF.1-219)$_2$; $HC_2$ |
| 0056 | pTT-0051LC-HPC4 | pTT-0051HC-L4a-hTF.1-219 | mAb 0051-(HC-L4a-hTF.1-219)$_2$; (LC-HPC4)$_2$ |
| 0055 | pTT-0051LC-L4a-hTF.1-219 | pTT-0051HC | mAb 0051-(LC-L4a-hTF.1-219)$_2$; $HC_2$ |
| 0060 | pTT-0052LC-HPC4 | pTT-0052HC-L4a-hTF.1-219 | mAb 0052-(HC-L4a-hTF.1-219)$_2$; (LC-HPC4)$_2$ |
| 0059 | pTT-0052LC-L4a-hTF.1-219 | pTT-0052HC | mAb 0052-(LC-L4a-hTF.1-219)$_2$; $HC_2$ |
| 0096 | pTT-isotype control LC-HPC4 | pTT-isotype control HC-L4a-hTF.1-219 | mAb isotype control-(HC-L4a-hTF.1-219)$_2$; (LC-HPC4)$_2$ |

TABLE 6-continued

| Protein ID | LC plasmid | HC plasmid | mAb/Fab or mAb-/Fab-hTF.1-219 fusion protein name |
|---|---|---|---|
| 0110 | pTT-isotype control LC-L4a-hTF.1-219 | pTT-isotype control HC | mAb isotype control-(LC-L4a-hTF.1-219)$_2$; HC$_2$ |
| 0010 | pTT-0012LC-HPC4 | pTT-0012V$_H$-CH1 | Fab 0012-LC-HPC4; V$_H$-CH1 |
| 0100 | pTT-0012LC.C36A | pTT-0012V$_H$.T60N-CH1 | Fab 0061 (Fab 0012-LC.C36A; V$_H$.T60N-CH1) |
| 0073 | pTT-0012LC-HPC4 | pTT-0012V$_H$-CH1-L0-hTF.1-219 | Fab 0012-V$_H$-CH1-L0-hTF.1-219; LC-HPC4 |
| 0011 | pTT-0012LC-HPC4 | pTT-0012V$_H$-CH1-L4a-hTF.1-219 | Fab 0012-V$_H$-CH1-L4a-hTF.1-219; LC-HPC4 |
| 0014 | pTT-0012LC-HPC4 | pTT-hTF.1-219-L4b-0012V$_H$-CH1 | Fab 0012-hTF.1-219-L4b-V$_H$-CH1; LC-HPC4 |
| 0057 | pTT-0012LC-HPC4 | pTT-0012V$_H$-CH1-L10-hTF.1-219 | Fab 0012-V$_H$-CH1-L10-hTF.1-219; LC-HPC4 |
| 0105 | pTT-0012LC.C36A-HPC4 | pTT-0012V$_H$.T60N-CH1-L10-hTF.1-219 | Fab 0061-V$_H$-CH1-L10-hTF.1-219; LC-HPC4 |
| 0106 | pTT-0012LC.C36A-HPC4 | pTT-0012V$_H$.T60A-CH1-L10-hTF.1-219 | Fab 0082-V$_H$-CH1-L10-hTF.1-219; LC-HPC4 |
| 0070 | pTT-0012LC-L0-hTF.1-219 | pTT-0012V$_H$-CH1-HPC4 | Fab 0012-LC-L0-hTF.1-219; V$_H$-CH1-HPC4 |
| 0071 | pTT-0012LC-L1-hTF.1-219 | pTT-0012V$_H$-CH1-HPC4 | Fab 0012-LC-L1-hTF.1-219; V$_H$-CH1-HPC4 |
| 0072 | pTT-0012LC-L2-hTF.1-219 | pTT-0012V$_H$-CH1-HPC4 | Fab 0012-LC-L2-hTF.1-219; V$_H$-CH1-HPC4 |
| 0039 | pTT-0012LC-L3-hTF.1-219 | pTT-0012V$_H$-CH1-HPC4 | Fab 0012-LC-L3-hTF.1-219; V$_H$-CH1-HPC4 |
| 0020 | pTT-0012LC-L4a-hTF.1-219 | pTT-0012V$_H$-CH1-HPC4 | Fab 0012-LC-L4a-hTF.1-219; V$_H$-CH1-HPC4 |
| 0024 | pTT-hTF.1-219-L4b-0012LC | pTT-0012V$_H$-CH1-HPC4 | Fab 0012-hTF.1-219-L4b-LC; V$_H$-CH1-HPC4 |
| 0040 | pTT-0012LC-L5-hTF.1-219 | pTT-0012V$_H$-CH1-HPC4 | Fab 0012-LC-L5-hTF.1-219; V$_H$-CH1-HPC4 |
| 0041 | pTT-0012LC-L6-hTF.1-219 | pTT-0012V$_H$-CH1-HPC4 | Fab 0012-LC-L6-hTF.1-219; V$_H$-CH1-HPC4 |
| 0042 | pTT-0012LC-L7-hTF.1-219 | pTT-0012V$_H$-CH1-HPC4 | Fab 0012-LC-L7-hTF.1-219; V$_H$-CH1-HPC4 |
| 0043 | pTT-0012LC-L8-hTF.1-219 | pTT-0012V$_H$-CH1-HPC4 | Fab 0012-LC-L8-hTF.1-219; V$_H$-CH1-HPC4 |
| 0044 | pTT-0012LC-L9-hTF.1-219 | pTT-0012V$_H$-CH1-HPC4 | Fab 0012-LC-L9-hTF.1-219; V$_H$-CH1-HPC4 |
| 0063 | pTT-0023LC-L3-hTF.1-219 | pTT-0023V$_H$-CH1-HPC4 | Fab 0023-LC-L3-hTF.1-219; V$_H$-CH1-HPC4 |
| 0038 | pTT-0023LC-L4a-hTF.1-219 | pTT-0023V$_H$-CH1-HPC4 | Fab 0023-LC-L4a-hTF.1-219; V$_H$-CH1-HPC4 |
| 0064 | pTT-0023LC-L5-hTF.1-219 | pTT-0023V$_H$-CH1-HPC4 | Fab 0023-LC-L5-hTF.1-219; V$_H$-CH1-HPC4 |
| 0065 | pTT-0023LC-L6-hTF.1-219 | pTT-0023V$_H$-CH1-HPC4 | Fab 0023-LC-L6-hTF.1-219; V$_H$-CH1-HPC4 |
| 0066 | pTT-0023LC-L7-hTF.1-219 | pTT-0023V$_H$-CH1-HPC4 | Fab 0023-LC-L7-hTF.1-219; V$_H$-CH1-HPC4 |
| 0067 | pTT-0023LC-L8-hTF.1-219 | pTT-0023V$_H$-CH1-HPC4 | Fab 0023-LC-L8-hTF.1-219; V$_H$-CH1-HPC4 |
| 0068 | pTT-0023LC-L9-hTF.1-219 | pTT-0023V$_H$-CH1-HPC4 | Fab 0023-LC-L9-hTF.1-219; V$_H$-CH1-HPC4 |
| 0033 | pTT-0023LC-HPC4 | pTT-0023V$_H$-CH1-L4a-hTF.1-219 | Fab 0023-V$_H$-CH1-L4a-hTF.1-219; LC-HPC4 |
| 0053 | pTT-0051LC-L4a-hTF.1-219 | pTT-0051V$_H$-CH1-HPC4 | Fab 0051-LC-L4a-hTF.1-219; V$_H$-CH1-HPC4 |
| 0054 | pTT-0051LC-HPC4 | pTT-0051V$_H$-CH1-L4a-hTF.1-219 | Fab 0051-V$_H$-CH1-L4a-hTF.1-219; LC-HPC4 |
| 0069 | pTT-0052LC-L4a-hTF.1-219 | pTT-0052V$_H$-CH1-HPC4 | Fab 0052-LC-L4a-hTF.1-219; V$_H$-CH1-HPC4 |
| 0058 | pTT-0052LC-HPC4 | pTT-0052V$_H$-CH1-L4a-hTF.1-219 | Fab 0052-V$_H$-CH1-L4a-hTF.1-219; LC-HPC4 |
| 0094 | pTT-isotype control LC-L4a-hTF.1-219 | pTT-isotype control V$_H$-CH1-HPC4 | Fab isotype control-LC-L4a-hTF.1-219; V$_H$-CH1-HPC4 |
| 0095 | pTT-isotype control LC-HPC4 | pTT-isotype control V$_H$-CH1-L4a-hTF.1-219 | Fab isotype control-V$_H$-CH1-L4a-hTF.1-219; LC-HPC4 |
| 0128 | pTT-AP-3LC-L4a-hTF.1-219 | pTT-AP-3V$_H$-CH1-HPC4 | Fab AP-3-LC-L4a-hTF.1-219; V$_H$-CH1-HPC4 |
| 0129 | pTT-AP-3LC.C34S-L4a-hTF.1-219 | pTT-AP-3V$_H$-CH1-HPC4 | Fab AP-3-LC.C34S-L4a-hTF.1-219; V$_H$-CH1-HPC4 |
| 0120 | pTT-0012LC.C36A | pTT-0012HC.T60N-His6 pTT-hIgG4-hinge-CH2-CH3-L4a-hTF.1-219 | heterodimer-0061-(0012LC.C36A); (0012HC.T60N-His6); (hinge-CH2-CH3-L4a-hTF.1-219) |
| 0121 | pTT-0012LC.C36A-L4a-hTF.1-219 | pTT-0012HC.T60N pTT-hIgG4-hinge-CH2-CH3-His6 | heterodimer-0061-(0012LC.C36A-L4a-hTF.1-219); (0012HC.T60N); (hinge-CH2-CH3-His6) |

Note#1:
heterodimers designated 0120 and 0121 was produced using the 3 plasmid constructs as indicated.

Note#2:
fusion proteins designated in column four can be compiled from sequences listed in sequence appendix. For example can compound 0011 (Fab 0012-VH-CH1-L4a-hTF.1-219; LC-HPC4) be prepared by fusing the ID sequences 51, 61 and 14 for the chain 0012-VH-CH1-L4a-hTF.1-219 and 40 and 69 for the chain 0012-LC-HPC4. The resulting protein 0011 is a heterodimer of the 0012-VH-CH1-L4a-hTF.1-219 and the LC-HPC4 polypeptide chains.

Example 27

DcDNA3.1(+)-hTLT-1 ECD-HPC4 Ala Mutant Plasmids.

Forty hTLT-1 ECD-HPC4 Ala mutant expression constructs were designed according to table 7. The expression constructs were developed by external contractor GENEART AG (Im Gewerbepark B35, 93059 Regensburg, Germany) and all 40 expression constructs were made based on the expression vector designated pcDNA3.1(+). Aliquots of DNA for each of the 40 hTLT-1 ECD-HPC4 pcDNA3.1 (+) expression construct were transfected into HEK293-6E suspension cells in order to transiently express each hTLT-1 ECD-HPC4 Ala mutant protein (Table 7). Transient transfection and culturing of HEK293-6E cells were performed as described in example Z.

TABLE 7

| wt | Wild-type |
|---|---|
| 1 | L22A |
| 2 | V25A |
| 3 | Q27A |
| 4 | V30A |
| 5 | L35A |
| 6 | H39A |
| 7 | R41A |
| 8 | L42A |
| 9 | Q43A |
| 10 | K46A |
| 11 | Q48A |
| 12 | F54A |
| 13 | L55A |
| 14 | P56A |
| 15 | E57A |

TABLE 7-continued

| wt | Wild-type |
|---|---|
| 16 | Q60A |
| 17 | D68A |
| 18 | R69A |
| 19 | R70A |
| 20 | R75A |
| 21 | L82A |
| 22 | L86A |
| 23 | E90A |
| 24 | M91A |
| 25 | T93A |
| 26 | Q95A |
| 27 | E96A |
| 28 | E97A |
| 29 | D107A |
| 30 | R110A |
| 31 | H116A |
| 32 | R117A |
| 33 | S119A |
| 34 | P125A |
| 35 | E126A |
| 36 | E128A |
| 37 | E130A |
| 38 | S136A |
| 39 | N140A |
| 40 | K159A |

Example 28

Purification and Characterisation of Monoclonal Anti-TLT-1 Antibodies.

Purification of the seven recombinantly expressed monoclonal anti-TLT-1 antibodies described in table 1 was conducted by a 2-step process composed of affinity chromatography using a Protein A MABSELECT SURE resin (GE Healthcare, cat. no. 17-5438-01) and gel filtration chromatography using a 26/60 SUPERDEX 200 (prep grade gel filtration medium) PrepGrade col-umn (GE Healthcare, cat no. 17-1071-01). Purifications were conducted using an AktaExplorer chromatography system (GE Healthcare, cat. no. 18-1112-41). The buffer systems used for the affinity purification step was an equilibration buffer composed of 20 mM NaPhosphate pH 7.2, 150 mM NaCl, an elution buffer composed of 10 mM Formic acid pH 3.5 and an pH-adjustment buffer composed of 0.5 M NaPhosphate pH 9.0. Cell supernatants were applied directly without any adjustments onto a pre-equilibrated MABSELECT SURE column. The column was washed with 15 column volumes of equilibration buffer and the monoclonal antibodies were eluted isocratically in approx. 2-5 column volume of elution buffer. The pooled fractions were adjusted to neutral pH using the described pH-adjustment buffer immediately after elution. The protein was further purified and buffer exchanged using said gel filtration column. The running buffer used for size exclusion chromatography was a 25 mM His pH 6.5, 135 mM NaCl. The flow rate used was 2.5 ml/min and the monoclonal anti-TLT1 antibodies eluted as single peaks at approx. 0.4 column volumes. Based on analyses of fractions over the entire peak using the previously described SEC-HPLC method (as described in example 2), pools were prepared which contained pure antibody protein eluting as symmetric peaks at approx. 8.5 min. and with a minimum content of earlier eluting high-molecular weight protein.

The purified antibodies were characterized using the previously described SDS-PAGE/Coomassie (as described in example 2) and SEC-HPLC methods, showing that all antibody protein preparations produced were highly homogenous. All antibodies displayed expected heavy chain components of approx. 50 kDa and light chain components of approx. 25 kDa when using reducing conditions prior to running the SDS-PAGE/Coomassie analyses. Intact molecular mass determinations were performed using a Liquid Chromatography Electrospray Ionisation Time-of-Flight Mass Spectrometry method setup on an Agilent 6210 instrument and a desalting column MassPREP (Waters, cat. no. USRM10008656). The buffer system used was an equilibration buffer composed of 0.1% Formic acid in LC-MS graded-$H_2O$ and an elution buffer composed of 0.1% Formic acid in LC-MS graded-ACN. All antibodies displayed intact molecular masses of 147.2-148.6 kDa, which is approx. 2.7-3.1 kDa above the theoretical masses of the amino acid sequences for each of the antibodies. Thus, all the recombinantly expressed anti-TLT-1 antibodies displayed post-translational modifications corresponding to expected HC N-glycosylations. Final purities of 95-99% were obtained for the six antibodies. To verify the N-terminal sequence of the cloned and purified anti-TLT-1 antibodies, EDMAN degradations were performed using an automated sequenator system (Applied Biosystems 494 Protein Sequencer). 10-20 degradation cycles were conducted for each antibody. Here, expected light and heavy chain sequences were confirmed for the six cloned anti-TLT-1 antibodies. To measure the final protein concentrations, a NANODROP spectrophotometer (Thermo Scientific) was used together with specific extinction coefficients for each of the six antibodies ranging from 1.34-1.51.

Example 29

Purification and Characterization of Recombinantly Expressed Fab-hTF.1-219 Proteins.

Purification of the Fab-hTF.1-219 fusion proteins outlined in table 6 was conducted using a 2-step process composed of affinity chromatography using an anti-HPC4 resin (Roche, cat. no. 11815024001) and a final buffer shift. The purification was conducted using an ÄktaExplorer chromatography system (GE Healthcare, cat. no. 18-1112-41). The buffer systems used for the purification step was an equilibration buffer composed of 20 mM Hepes, pH 7.5, 1.0 mM $CaCl_2$, 100 mM NaCl and 0.005% (v/v) TWEEN (polysorbate surfactant)-80, a wash buffer composed of 20 mM Hepes, pH 7.5, 1.0 mM $CaCl_2$, 1.0 M NaCl and 0.005% (v/v) TWEEN (polysorbate surfactant)-80, and an elution buffer composed of 20 mM Hepes, pH 7.5, 5.0 mM EDTA and 100 mM NaCl. Cell supernatants were adjusted with 1 mM $CaCl_2$ final concentration and a pH of 7.5 and applied onto a pre-equilibrated anti-HPC4 column. The column was washed with 5 column volumes of equilibration buffer, 5 column volumes of wash buffer and last with 5 column volumes of equilibration buffer. The Fab-hTF1-219 proteins were eluted isocratically in approx. 4 column volumes of elution buffer. The Fab-hTF1-219 proteins were analyzed using SDS-PAGE/Coomassie, SEC-HPLC and MALDI-TOF MS analyses as described previously (as described in examples 1 and 28), showing that pure and homogenous proteins with molecular masses of 78-86 kDa were obtained. Since the theoretical masses of the amino acid sequence for the Fab-hTF1-219 constructs were 73-77 kDa, all the expressed proteins contained post-translational modifications. The proteins were prepared for assay analyses by either dialyzing into PBS buffer or into a buffer composed of 25 mM His, 135 mM NaCl, pH 6.5 using a SLIDE-A-LYZER Dialysis Cassette 10 kDa MWCO (Pierce, cat. no. 66453) or by using the desalting resin Sephadex G-25 (GE, cat. no. 17-0033) packed in an appropriate column. To measure final protein concentrations, a NANODROP spectrophotometer (Thermo Scientific) was used together with extinction coefficients of 1.31-1.47.

Example 30

Purification and Characterization of Recombinantly Expressed mAb-hTF.1-219 Proteins.

Purification of mAb-hTF.1-219 fusion proteins described in table 6 was conducted by a 2-step process composed of affinity chromatography based either on a Protein A MABSELECT SURE-resin (GE Healthcare, cat. no. 17-5438-01) or an anti-HPC4 resin (Roche, cat. no. 11815024001). The anti-HPC4 resin resin was used for purification of mAb-hTF.1-219 constructs, in which hTF.1-219 was fused C-terminally to the heavy chain. These included compounds 0197-0000-0013, 0197-0000-0018, 0197-0000-0086, 0197-0000-0087, 0197-0000-0088, 0197-0000-0089, 0197-0000-0090, 0197-0000-0091, 0197-0000-0092, 0197-0000-0093, 0197-0000-0034, 0197-0000-0056, 0197-0000-0060, 0197-0000-0096, and 0197-0000-0116. The remaining mAb-hTF.1-219 fusion proteins described in table 6 were purified using Protein A MABSELECT SURE resin. A gel filtration chromatography method was used as the final polish purification. Here a 26/60 SUPERDEX 200 (prep grade gel filtration medium) PrepGrade column (GE Healthcare, cat no. 17-1071-01) was used. All purifications were conducted using an AktaExplorer chromatography system (GE Healthcare, cat. no. 18-1112-41) and based essentially using the chromatographic procedures described previously. The mAb-hTF.1-219 proteins eluted as single peaks at approx. 0.4 column volumes. Based on analyses of fractions over the entire peak using the previously described analytical SEC-HPLC method, pools were prepared which pure protein which eluted as symmetric peaks at approx. 9 min. with a minimum content of earlier eluting high-molecular weight protein.

The purified mAb-hTF.1-219 proteins were characterized using the previously described SDS-PAGE/Coomassie and SEC-HPLC methods (as described in example 2), showing that all mAb-hTF.1-219 proteins were highly pure, i.e. above 90% of non-product related impurities. Intact molecular mass determinations were performed using the previously described MALDI-TOF MS method (as described in example 28). All mAb-hTF.1-219 proteins displayed intact molecular weights of 200-206 kDa, which is approx. 8-12 kDa above the theoretical masses of the amino acid sequence for each of the antibodies. Thus, all mAb-hTF.1-219 proteins displayed post-translational modifications. To measure the final protein concentrations, a NANODROP spectrophotometer (Thermo Scientific) was used together with specific extinction coefficients for each of the six antibodies ranging from 1.34-1.51.

Example 31

Purification and Characterisation of Heterodimer Protein Designated 0120.

Purification of the heterodimer protein designated number 0120 in table 6 was conducted as a 4-step process composed of 1) His-affinity chromatography using the Ni-NTA resin (QIAGEN, cat. no. 30430), 2) Buffer change using HIPREP (agarose-based chromatography media) 26/10 Desalting column (GE Healthcare, cat. no. 17-5087-01), 3) anion-exchange chromatography using the Q SEPHAROSE HP (GE Healthcare, cat. no. 17-1014-03), and 4) size-exclusion chromatography using HiLoad 16/60 SUPERDEX 200 (prep grade gel filtration medium) (GE Healthcare, cat. no. 17-1069-01). The purifications were conducted using an ÄktaExplorer chromatography system (GE Healthcare, cat. no. 18-1112-41). The buffer systems used for the first purification step was an equilibration buffer composed of 50 mM Tris, pH7.5, 300 mM NaCl, 10 mM Imidazole, and an elution buffer composed of 50 mM Tris, pH7.5, 300 mM NaCl, 500 mM Imidazole. The cell supernatant was adjusted with 10 mM Imidazole final concentration and a pH of 7.5 and applied onto a pre-equilibrated Ni-NTA column. The column was washed with 4 column volumes of 2% elution buffer. The protein was eluted isocratically in approx. 4 column volumes of 60% elution buffer. The main peak based on UV280 monitoring was collected and pooled. In the second step, the protein was prepared for anion-exchange chromatograph by shifting into 50 mM Tris, pH7.5 buffer using a desalting column. The buffer system used for the third purification step was an equilibration buffer composed of 50 mM Tris, pH7.5, and an elution buffer composed of 50 mM Tris, pH7.5, 1M NaCl. The pool from the second step was directed applied to the pre-equilibrated Q SEPHAROSE HP column, washed with 2 column volumes of equilibration buffer and eluted in a gradient of 0-100% elution buffer over 10 column volumes followed by 3 column volume of 100% elution buffer. The main peak was collected and pooled. The buffer used in the fourth step was PBS. The pool of protein from step 3 was directly applied to HiLoad 16/60 SUPERDEX 200 (prep grade gel filtration medium) column. The main peak was collected and stored at −80° C. SDS-PAGE/Coomassie 8-15% analysis, SEC-HPLC and LC-MS showed that a pure protein was obtained. One dense protein band was observed from the SDS-PAGE/Coomassie analysis which corresponded to said heterodimer protein complex. Reducing the protein resulted in complete abolishment of the protein complex band, while appearance of three bands indicating three subunits of the protein complex. The final protein integrity was analyzed based on a SEC-HPLC method set up on a Waters LC 2795/2996 system and using a BIOSEP (column for separation biomolecules)-SEC-53000 300×7.8 mm column (Phenomenex, cat. no. OOH-2146-K0) and a running buffer composed of PBS. The protein was eluted as a single symmetric peak at a retention time of approx. 8.2 min at a flow rate of 1 ml/min. To measure the final protein concentration, a NANODROP spectrophotometer (Thermo Scientific) was used together with an extinction coefficient of 1.34. The molecular weights of each subunit were determined by LC-MS. Mass deconvolution of the LC subunit indicated a mass equal to the expected value. Mass deconvolution of the HC-His subunit indicated a mass equal to the expected value with G0F, G1F and G2F N-glycans. The mass spectrum signal of Fc-sTF was too low to be deconvoluted due to heavy glycosylation of tissue factor.

Example 32

Purification and Characterisation of Heterodimer Protein Designated 0121.

Purification of the heterodimer protein designated number 121 was essentially the same as described for the heterodimer number 120. Here, the protein was washed in 3 column volumes of equilibration buffer and eluted in 0-40% elution buffer over 8 column volumes followed by 3 column volumes of 100% elution buffer. This gradient elution ensured the complete separation of the heterodimer with Fc-His homodimer. SDS-PAGE/Coomassie 8-15%, SEC-HPLC and LC-MS showed that a pure protein was obtained. One dense protein band was observed on SDS-PAGE/Coomassie which corresponded to said heterodimer protein complex. Reducing the protein resulted in complete abolishment of the protein complex band, while appearance of three bands indicating three subunits of the protein complex. The final protein integrity was analyzed based on a SEC-HPLC method set up on a Waters LC 2795/2996 system and using a BIOSEP (column for separation biomolecules)-SEC-53000 300×7.8 mm column (Phenomenex, cat. no. OOH-2146-K0) and a running buffer composed of PBS. The protein was eluted as a single symmetric peak at a retention time of approx. 8.2 min at a flow rate of 1 ml/min. To measure the final protein concentration, a NANODROP spectrophotometer (Thermo Scientific) was used together with an extinction coefficient of 1.34. The molecular weight of each subunit was determined by LC-MS. Mass deconvolution of the FC-His subunit indicated a mass equal to the expected value with G0F, G1F and G2F N-glycans. Mass deconvolution of the HC subunit indicated that the observed mass correlated with G0F, G1F and G2F N-glycans but with a Lys truncation the C-terminal. The mass spectrum signal of LC-sTF was too low to be deconvoluted due to heavy glycosylation of tissue factor.

Example 33

Binding of TF-Fusion Proteins to FVIIa.

Binding of TF-fusion proteins to FVIIa was tested by its ability to stimulate FVIIa activity using an amidolytic assay. The effect was compared with the stimulation induced by soluble TF (sTF), identical to hTF.1-219. Binding of TF to FVIIa results in a marked increase in FVIIa catalytic activity; and binding of sTF and the TF-construct was conveniently measured using FVIIa's amidolytic activity with the chromogenic substrate 52288 (Ile-Pro-Arg-pNA). Binding of hTF.1-219 to FVIIa increases the FVIIa catalytic activity. The TF-fusion proteins were designed to locate FVII/FVIIa to the surface of activated platelets. Fusion of a protein to TF should therefore not significantly affect its binding to FVIIa, and one will expect the concentration-dependent stimulation of FVIIa activity induced by TF-fusion proteins under optimal conditions to be identical to that obtained with the non-fused TF (hTF.1-219). In FIG. 7 TF-fusion proteins were tested in an assay with 50 nM FVIIa, 50 mM Hepes, 0.1 M NaCl, 5 mM $CaCl_2$, 1 mg/ml BSA pH 7.4 and various concentrations (0-100 nM) of sTF (open square) or Fab-TF-fusion proteins (open symbols) or mAb-TF-fusion proteins (closed symbols). FVIIa amidolytic activity was measured with 1 mM of the chromogenic substrate S2288. The FVIIa activity was measured by the increase in absorbance at 405 nm at room temperature and the reaction was started by addition of 1 mM S2288. Fab-hTF.1-219-fusion proteins stimulate FVIIa amidolytic activity in a concentration dependent manner indistinguishable from that induced by hTF.1-219 showing that these construct bind to FVIIa with a 1:1 stoichiometry and with a similar affinity as hTF.1-219. The mAb-hTF.1-219-fusion proteins similarly stimulate FVIIa activity in a concentration dependent manner identical to that of hTF.1-219. However, in this case the stoichiometry indicates that these construct bind two FVIIa per mAb as expected with free access to both TF moieties on the mAb-TF-fusion proteins.

Example 34 mAb Binding and Competition of Different mABs for Binding to TLT-1.
Materials:

TABLE 8

| Reagents | |
|---|---|
| Reagent | Source |
| TLT1 | NN |
| mAb0061 | NN |
| mAb0023 | NN |
| mAb0051 | NN |
| mAb0062 | NN |
| All other reagents | Biacore Human Antibody Capture Kit (BR-1008-39) |

Method:

The mAbs of interest were either immobilized directly to a CM5 chip or by capture via a human Fc capture mAb immobilized to a CM5 chip. Reagents that were used are shown in table 8.
Direct Capture:

The TLT-1 mAbs were immobilised to a level of approx 500-1000 RU on a CM5 chip (50 µg/ml diluted in Na-acetate, pH 4.0) using the standard procedure recommended by the supplier. Two-fold dilutions of TLT1 from 200 nM to 0.2 nM were tested for binding to the mABs. Running and dilution buffer: 10 mM HEPES, 150 mM, 0.005% p20, pH 7.4. Regeneration was obtained by 10 mM Glycine, pH 1.7.
Capture Via Human Fc mAb:

Human Fc mAb was immobilised to approx 10.000 RU. The mAb of interest was added (approx 100 nM). Two-fold dilutions of TLT1 from 200 nM to 0.2 nM were tested. Running and dilution buffer: 10 mM HEPES, 150 mM, 0.005% p20, pH 7.4. Regeneration was obtained in 3 M $MgCl_2$ Determination of kinetic and binding constants ($k_{on}$, $k_{off}$, $K_D$) was obtained assuming a 1:1 interaction of TLT1 and fibrinogen using the BIACORE T100 (instrument for surface plasmon resonance) evaluation software.
Competition:

Competitional binding interaction analysis was obtained by Surface Plasmon Resonance in a BIACORE T100 (instrument for surface plasmon resonance) analysing binding of various TLT1 mAbs to TLT1 when bound to immobilised mAb0012 (or an alternative mAb). Direct immobilization to a CM5 chip of the mAbs to a level of 5000-10000 RU was achieved in 10 mM sodium acetate pH 4.5-5.0. This was followed by binding of 50 nM TLT1 and after 2 min of dissociation followed by binding of the three other mAbs to be tested for competition. Running and dilution buffer: 10 mM HEPES, 150 mM, 0.005% p20, pH 7.4. Regeneration was obtained by 10 mM Glycine, pH 1.7.
Results:

TABLE 9

| TLT1 binding | ka (1/M) | kd (1/s) | $K_D$ (M) TLT1 | Biacore technique |
|---|---|---|---|---|
| mAb 0061 | 9.32E+05 | 0.003499 | 3.75E−09 | capture |
| mAb 0023 | 2.87E+05 | 0.00125 | 4.36E−09 | direct |
| mAb 0051 | 2.45E+05 | 0.00472 | 1.93E−08 | direct |
| mAb 0062 | 3.26E+05 | 0.00134 | 4.12E−09 | direct |

TABLE 10

SPR analysis. Binding constant for binding to TLT1. Competition with mAB0012

| mAb ID | Competition with mAB 0012 | Competition with 0023 | Competition with 0051 | Competition with 0062 |
|---|---|---|---|---|
| mAb 0061 | yes | No | no | no |
| mAb 0023 | | Yes | no | yes |
| mAb 0051 | | | yes | no |
| mAb 0062 | | | | yes |

Conclusion:

Binding constants for mAb 0061, 0023, 0051 and 0062 were estimated by Biacore analysis (see table 9).

mAb 0061 and mAB 0051 do not compete with any of the other mAbs for binding (see table 10). mAb 0023 and mAb 0062 do compete with each other (see table 10).

Example 35

Binding to Activated Platelets by FACS Analysis.

Binding to activated platelets by FACS analysis was shown to bind to both TLT-1 transfected cells and specifically activated platelets as described below.

Staining with 2F105FabHC-TF fusion protein on platelets using flow cytometry was done by adding platelet preparations (resting versus activated platelets) in 96 well plates together with 50 μl of diluted 2F105FabHC-TF (0011 Fab hTF.1-219) fusion protein or isotype control 2F105Fab (0010 Fab) in titration giving final concentrations from 5 μl/ml to 0.001 μl/ml. Cell preparations were then incubated at 4 degrees Celsius for 1 hour. After incubation and wash (PBS buffer with 5% Fetal calf serum, centrifuge for 5 minutes at 200 g) the secondary RPE-labelled anti-human L+H chain specific antibody (diluted in PBS buffer 1:100) or a HPC4 specific antibody (specific for tag on 2F105Fab HC-TF) was added and incubated for another 1 hour at 4 degrees' Celsius. Finally, cells were washed and fixed by 1% w/v paraformaldehyde) and analysed in the flow cytometer within 36 hours.

Platelets preparations were produced by making a standard Platelet Rich Plasma (PRP). In short, anti-coagulated whole blood was centrifuged (200 g for 15 minutes) without brake. The upper layer containing platelets (Platelet rich plasma) were harvested and prostaglandin (Final conc. 5 μl/ml) was added for inhibition of platelet activation. Platelets were washed and used for staining as described above. For production of activated platelets a dual agonistic activation was performed, for 10 minutes using (62.5 μg/ml Par 1 and Convulxin 100 ng/ml). 50-100.000 cells were used pr well.

FIG. 8 shows with two staining procedures that both the isotype Fab and the 2F105FabHC-TF (0011 Fab hTF.1-219) fusion protein bind specifically and with high affinity to activated platelets and not to resting platelets.

Example 36

Enhancement of FVIIa-Mediated of FX Activation by Localization of the FVIIa/TF Complex to the Surface of Pre-Activated Platelets by Binding of TF-Fusion Proteins to the TLT-1 Receptor.

Figure 9:
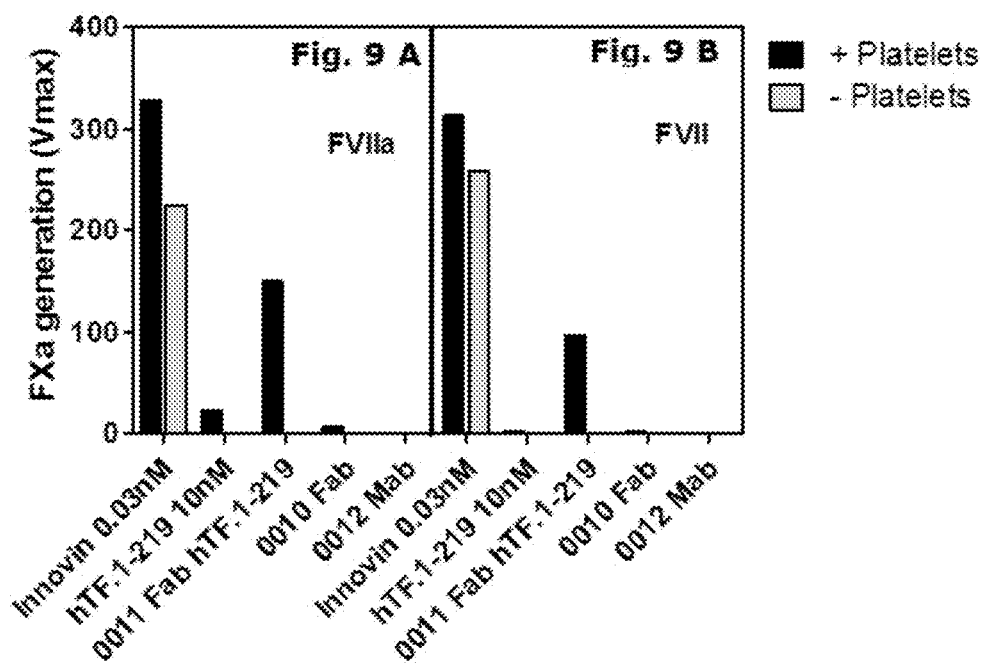
FIG. 9.
Figure 15:
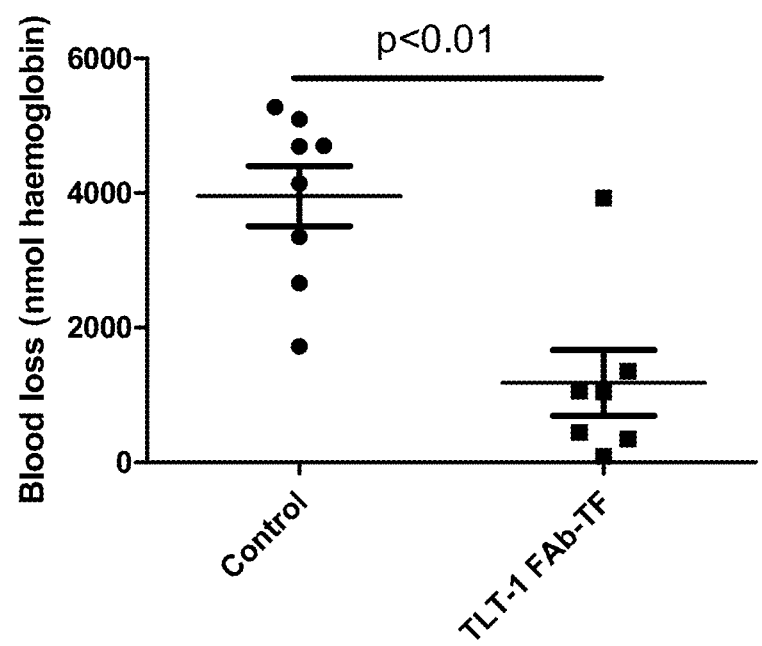
FIG. 15: shows that TLT1-FAb-TF reduces the tail bleeding blood loss in haemophilic mice transfused with human platelets 2 min before induction of bleeding, when compared to an irrelevant FAb-TF-construct.
Figure 20:
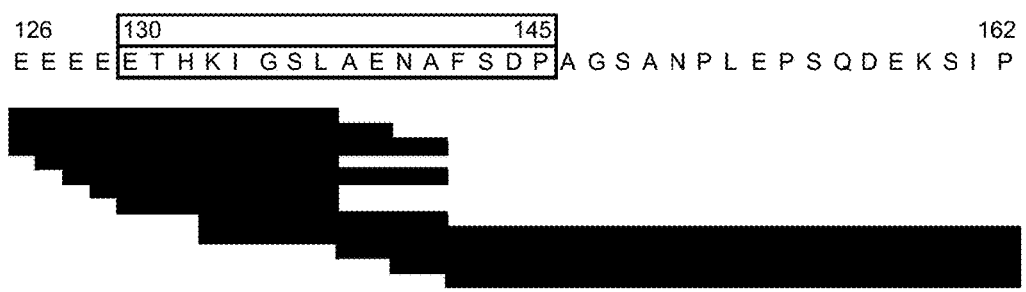
FIG. 20: Sequence coverage of HX analyzed peptides of TLT-1 region 126-162. The primary sequence (using mature numbering) (SEQ ID NO: 172) is displayed above the HX analyzed peptides (shown as horizontal bars). All peptides showed reduced deuterium incorporation upon 0061 binding.
Figure 21:
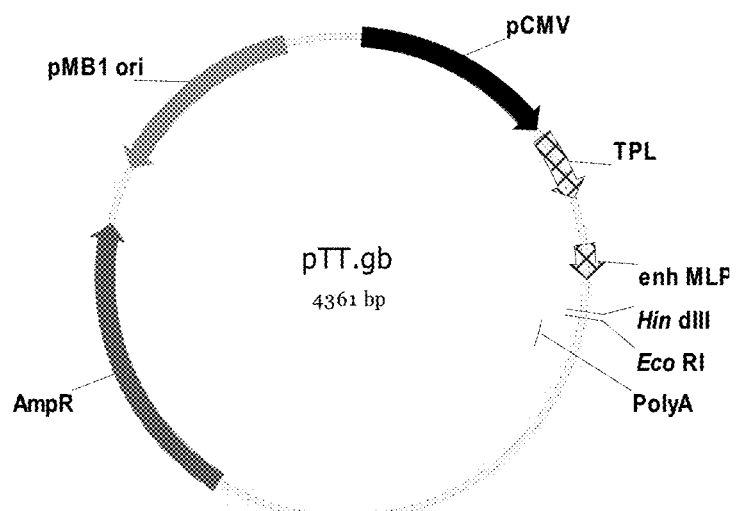
FIG. 21: Plasmid map for the expression vector pTT. DNA fragments can be inserted into the HindIII and EcoRI restriction enzyme sites.

The capability of TF-fusion proteins to specifically stimulate FVIIa-mediated activation on activated platelets was tested in a two-step assay in FIG. 9A. The capability of TF-fusion proteins to also mediate activation of FVII to FVIIa was tested in FIG. 9B. For this purpose we used lyophilized (activated) platelets from Biopal (REF 50710, lot R088001). FX activation was measured in a two step assay in the absence or presence of platelets at a final concentration of 67.000 plt/μl. 100 pM rFVIIa (LASa 15860-008) was mixed with 175 nM FX (Enzyme Research, Human factor X, HFX 3170 PAL) in 50 mM Hepes, 0.1 M NaCl, 5 mM CaCl$_2$, 1 mg/ml BSA pH 7.4 at room temperature. FX activation was arrested after 10 min when an aliquot was removed from each well and added to an equal volume of ice-cold stopping buffer (50 mM Hepes, 0.1 M NaCl, 20 mM EDTA, 1 mg/ml BSA pH 7.5). The amount of FXa generated in the samples was then determined in a chromogenic assay by transferring 50 μl of the mixture to a microtiter plate well and adding 25 μl CHROMOZYME X (final 0.42 mg/ml) to the well. The absorbance at 405 nm was measured continuously in a microplate reader (Molecular Devices). FIG. 9A shows the effect of i) 0.03 nM INNOVIN® (lipidated tissue factor), ii) 10 nM hTF.1-219, iii) 10 nM 0011 Fab-hTF.1-219, iv) 10 nM 0010 Fab antibody or v) 0012 mAB antibody on FVIIa-mediated FX activation in the absence or presence of platelets. FIG. 9B shows the effect of replacing rFVIIa in the assay with the zymogen, rFVII.

Blockage of FX activation (>95%) was obtained in control experiments by pre-incubating with the goat polyclonal anti-human TF antibody (0.5 mg/ml) for 15 min prior to the addition of FVIIa.

The data in FIG. 9A show that fusion of TF with the Fab fragment of an antibody against TLT-1 provides a construct which stimulates FVIIa-catalyzed activation of FX only in the presence of activated platelets. Stimulation of FX activation by the 0011 TF-fusion protein in the presence of platelets was markedly stronger than stimulation by hTF.1-219. The specificity towards activated platelets is a preferred property of the TF-fusion protein, which is not obtained with lipidated TF (INNOVIN®) that stimulates of FVIIa mediated FX activation also in the absence of activated platelets.

FIG. 9B shows the effect of replacing rFVIIa in the assay with the zymogen, rFVII. It is well known that INNOVIN® (lipidated tissue factor) stimulates FVIIa-mediated FX activation (FIG. 9A); and also, as indicated by the data in FIG. 9B, that INNOVIN® (lipidated tissue factor) is capable of stimulating efficient feed-back activation of FVII. This reaction is essentially independent of the presence of platelets. The TF construct, 0011 Fab-hTF.1-219, likewise stimulates FVIIa-mediated activation of FX and is capable of mediating a platelet-dependent feed-back activation of FVII (FIG. 9B), however, in a noticeable platelet-dependent manner, and markedly stronger than hTF.1-219. A significant stimulation of FX activation with the 0010 Fab antibody or 0012 mAb antibody per se was not observed.

Example 37

Enhancement of FVIIa-Mediated of FX Activation by Localization of the FVIIa/TF Complex to the Surface of Activated Platelets by Binding to the TLT-1 Receptor.

In FIG. 10A, 0011 hTF.1-219-fusion protein and hTF.1-219 were tested in a two step assay (see Example 36) in the presence of either resting or activated platelets at various concentrations. Activated (but not resting) platelets exposed the TLT-1 receptor on their surface. Targeting of a TF fusion protein to the TLT-1 receptor is thought to result in assembly of the TF/FVIIa complex in a favourable position for stimulation of FX activation on the phospholipid surface of activated platelets. FIG. 10B shows the results when the 0011 hTF.1-219-fusion protein is replaced by 0.1 nM of an AV-hTF.1-219-fusion protein in which the TLT-1 antibody is replaced by Annexin V (AV).

Freshly purified, washed resting platelets were prepared from citrate stabilized whole blood which was centrifuged 200×g for 10 min. Platelet rich plasma was transferred to 15 ml tubes and supplemented with 1/10 volume 2.5% trisodium citrate, 1.5% citric acid, 2%. D-glucose. Centrifugation at 500×g/15 min, brake 5. The supernatant was discarded and the platelet pellet dissolved in 10 ml Hepes/Tyrodes buffer (100 mM Hepes, 137 mM NaCl, 2.7 mM KCl, 1.7 mM $MgCl_2$, 5.0 mM D-Glucose, 0.4 mM $NaH_2PO_4$ pH=6.5) plus 5 µl 10 mg/ml prostaglandin E1. The platelets were carefully suspended with a plastic pipette and centrifuged at 500×g for 15 min, brake 5. The supernatant was discarded and the pellet re-dissolved in 10 ml Hepes/Tyrodes buffer plus 5 µl 10 mg/ml prostaglandin E1. Platelet number was determined by Medonic. The platelets rested 30 min or more at room temperature before use. Activation of platelets was obtained by treatment with 5 nM thrombin and 100 ng/ml Convulxin.

100 pM rFVIIa was mixed with 10 nM hTF.1-219 or 10 nM 0011 Fab-hTF.1-219 fusion protein or 0.1 nM of a AV-hTF.1-219-fusion protein and with 175 nM FX (Enzyme Research, Human factor X, HFX 3170 PAL) in 50 mM Hepes, 0.1 M NaCl, 5 mM $CaCl_2$, 1 mg/ml BSA pH 7.4 at room temperature, in the presence of either resting or activated platelets at various concentrations (0-100,000 plt/µl). FX activation was arrested after 10 min when an aliquot was removed from each well and added to an equal volume of ice-cold stopping buffer (50 mM Hepes, 0.1 M NaCl, 20 mM EDTA, 1 mg/ml BSA pH 7.5). The amount of FXa generated in the samples was then determined in a chromogenic assay by transferring 50 µl of the mixture to a microtiter plate well and adding 25 µl CHROMOZYME X (final 0.42 mg/ml) to the well. The absorbance at 405 nm was measured continuously in a microplate reader (Molecular Devices).

The data in FIG. 10A illustrates that binding of the 0011 Fab-hTF.1-219 fusion protein to the TLT-1 receptor specifically stimulated FVIIa-mediated FX activation on activated and not on resting platelets. Stimulation increased with the platelet number and is saturable with an $EC_{50}$ of about 12,000 activated plts/µl. Targeting to the platelet surface obtained e.g. by fusion of hTF.1-219 to the TLT-1-binding Fab fragment results in a marked stimulation of FX activation whereas only a minor stimulation is obtained with non-fused hTF.1-219.

FIG. 10B shows the results obtained when 10 nM 0011 Fab-hTF.1-219 fusion protein is replaced by 0.1 nM of AV-hTF.1-219-fusion protein. AV-hTF.1-219-fusion protein is a more efficient stimulator than 0011 Fab-hTF.1-219 of FVIIa-mediated activation of FX on platelets. However, the of AV-hTF.1-219-fusion protein is shown to be less specific towards activated platelets than 0011 Fab-hTF.1-219 and a considerable stimulation is induced by the AV-hTF.1-219-fusion protein with resting platelets. At higher platelet numbers, the stimulation with resting platelets even exceeds that obtained with activated platelets at equivalent numbers.

Example 38

Effect of FVII/FVIIa and TF-Targeting Constructs Concentrations on the Stimulation of FX Activation on Activated Platelets.

A TLT-1-targeting TF-fusion protein with a supposed pro-coagulant effect in haemophilia patients should be able to function under the conditions prevailing at physiological conditions and to rely on the FVII/FVIIa composition in the blood. With the assay described in Example 36 it was possible to examine the stimulatory effect of TF-fusion proteins on the FVIIa-mediated activation of FX on activated platelets at various concentrations of FVII/FVIIa (FIG. 11) and at various concentrations of TF-fusion protein (FIG. 12). Stimulation was obtained in the presence of added rFVIIa or rFVII as indicated in the figures.

The results of FIG. 11 show that of FX activation at a fixed concentration of TF-fusion protein depends on FVII/FVIIa and is stimulated in a concentration dependent manner with maximal stimulation in the physiological relevant range (FVII~10 nM). The results also confirm that the marked stimulation obtained with a TF-fusion protein requires platelet activation and that FVII as well as FVIIa induce stimulation. Furthermore, the results demonstrate the requirement for targeting by showing that marked stimulation was obtained with fusion of hTF.1-219 to an anti TLT-1 Fab fragment but not when TF was fused to an equivalent non-targeting Fab fragment.

At a fixed concentration of FVII/FVIIa (10 nM) FIG. 12 examines the stimulation obtained with the 0070 Fab-hTF.1-219 fusion protein as a function of its concentration. Furthermore FIG. 12 compares this effect with the stimulation induced by various concentrations of hTF.1-219 or a control 0094 isotype Fab-hTF.1-219 fusion protein. The data demonstrate that a marked stimulation was obtained over a wide concentration range of the 0070 Fab hTF.1-219 fusion protein, and again demonstrate the superiority of a targeting TF-fusion protein relative to the non-targeting hTF.1-219 and control 0094 isotype Fab-hTF.1-219 fusion proteins. The 0070 Fab hTF.1-219 fusion protein induced a pro-coagulant stimulation over a large concentration interval and was not anti-coagulant at high concentrations. This was in contrast to AV-TF fusion proteins which were observed to be anti-coagulant at high concentrations (Huang X et al. 2006. Blood 107, 980-986).

Example 39

Preparation of 20:80 PS:PC Vesicles and Cloning, Expression, Refolding and Relipidation of TLT-1.

Relipidated TLT-1 in 20:80 PS:PC vesicles were prepared using TRITON X-100 (nonionic surfactant) as detergent as described in Smith and Morrissey (2005) 3. Thromb. Haemost., 2, 1155-1162 except that TLT-1 was used instead of TF.

Materials

LB medium from Sub. Lab. Ba. Kanamycin (50 mg/ml). Kanamycin Sigma K-0254 1000 mM IPTG (IPTG Sigma I-6758)

Lysis buffer: 1× Bugbuster (Novagen) in 50 mM Tris-HCl, 100 mM NaCl, 2 mM EDTA, pH 8.0. Add 0.5 mg/ml lysozyme+DNAseI. Add 1× COMPLETE INHIBITOR COCKTAIL (inhibits proteases)(Roche)

IB-Wash buffer 1: 1:10 bugbuster in IB-buffer. Add 50 µg/ml lysozyme+0.5× COMPLETE INHIBITOR COCKTAIL (inhibits proteases) (Roche)

IB-Wash buffer 2: 1:10 Bugbuster in IB-buffer

IB-Buffer: 50 mM Tris-HCl, 100 mM NaCl, 2 mM EDTA, pH 8.0

GndHCl buffer: 6M Guanidinium HCl, 50 mM Tris-HCl, 50 mM NaCl, 0.1% TRITON X-100 (nonionic surfactant) red., pH 8.0

Refolding buffer: 50 mM Tris-HCl, 800 mM Arginine, 0.1% TRITON X-100 (nonionic surfactant) red., 5 mM reduced glutathione, 0.5 mM oxidized glutathione pH 8.5
Dialysis buffer: 20 mM Tris-HCl, 0.1% TRITON X-100 (nonionic surfactant) Red., pH 8.0
DTT: Reduced glutathione (Sigma G4251) Oxidized glutathione Sigma G4376
PC: 10 mg/ml L-α-phosphatidylcholine (Egg, chicken) in chloroform (Avanti Polar Lipids Inc.) Catalog No. 840051C. Mw 760.09
PS: 10 mg/ml L-α-phosphatidylserine sodium salt (Brain, porcine) in chloroform. (Avanti Polar Lipids Inc.) Catalog No. 840032C. Mw 812.05
TRITON X-100 (nonionic surfactant): 10% TRITON X-100 (nonionic surfactant), hydrogenated, protein grade detergent, sterile filtered. Calbiochem. Catalog No. 648464 Concentration 159 mM (Mw 628)
HBS buffer: 50 mM HEPES, 100 mM NaCl, pH 7.4
Bio-Beads: Bio-Beads SM2 Adsorbent, 20-50 mesh BioRad Laboratories, Catalog No. 152-3920.
Method
Expression: TLT-1 (TLT-1 18-188; SEQ ID NO 182) including extracellular domain, linker and transmembrane domain was cloned into pET24a using primers 1004 (SEQ ID No 183) and 1005 (SEQ ID No 184) and pTT-hTLT-1 as template. Standard techniques for DNA preparation were employed.

Transformation was performed into BL21 (DE3). Overnight Culture: 1×50 ml LB medium in 250 ml flasks (plastic) and 50 µl of 50 mg/ml Kanamycin_+1 coloni (transformation) from BL21 µlate were mixed. The culture was incubated ON at 37° C., 220 rpm.
Starter-Culture:

2×500 ml LB medium in 2 L flasks (Plastic) with 300 µl of 50 mg/ml Kan was added. 10 ml ON culture TLT-1 lip/pET24a in BL21 (DE3) was added and $OD_{600}$ followed. Incubated at 37° C., 220 rpm
Induction: 2×500 ml with TLT-1 lip/pET24a BL21 (DE3) in LB. 25° C.~0.2 mM IPTG was added (100 µl of 1M) to the cell culture when $OD_{600}$ reached between 0.6-0.8. This was incubated for 3 h at 25° C., 220 rpm. The culture was harvested after 3 h and centrifuged for 30 min at 4600 rpm. The supernatant was discarded. The pellet was stored at −20° C.
Lysis of Inclusion Bodies:

The *E. coli* pellet was resuspended in 5 ml lysis buffer/g pellet. MgSO4 was added to 5 mM to support DNAseI activity. Cell suspension was incubated on shaking platform for 20 min at room temperature. The lysate was cleared by centrifugation 20000 g (8500 rpm) for 20 min at 4° C. The pellet was resuspended in 100 ml IB-Wash buffer. Suspension was mixed by gentle vortexing and incubated at RT for 5 min. Suspension was centrifuged at 20000 g for 20 min at 4° C. to collect inclusion bodies. Inclusion bodies was resuspended in 100 ml IB-Wash buffer 2. Sample was centrifuged at 20000 g for 20 min at 4° C. to collect inclusion bodies. The pellet was resuspended in 100 ml water and centrifuged at 20000 g for 20 min at 4° C. to collect inclusion bodies.
Refolding:

The pellet was resolubilised in×ml GdnHCl buffer (20 ml). The final concentration of TLT-1 (A280 was measured) was 1-2 mg/ml. DTT (400 µl) was added to final concentration of 20 mM. Complete solubilization was ensured by magnetic stirring for ~1-2.5 hrs (1.5 h) at RT. Insolube material was removed by centrifugation at 20000 g for 20 min. A peristaltic pump was used slowly (overnight) to transfer the GdnHCl/protein solution (20 ml) to >20× Refolding buffer (400 ml) at 4° C. The refolding buffer was stirred fast to ensure rapid dilution. Pump run was obtained at Flow rate 1×, speed 2.5, 4° C. and left overnight at 4° C. Precipitated protein was removed by centrifugation at 20000 g (8500 rpm) in 50 ml tubes for 30 min. The TLT1 lip was concentrated from 400 ml to 120 ml in Amico-filter 76 mm dia., 10.000 MWCO at 4.5 bar. The protein was checked on an SDS-Page by EtOH-precipitation because of the GdnHCl in the sample. 2×500 µl and 2×25 µl was concentrated in 0.5 ml tubes with 10.000 MWCO. 50 µl sample+9 vol. ice-cold 99% EtOH (450 µl) was mixed and placed at −20° C. for 10 min. The sample was centrifuged at full speed 13.000 rpm for 5 min. The supernatant was discarded. The pellet was washed with 450 µl ice-cold 96% EtOH+50 µl MQ. Centrifuge again. Let dry (EtOH must be totally eliminated before SDS-PAGE). 100 µl was resuspended 1× sample buffer
PS:PC Preparation and Relipidation:

The exact protocol described in Smith S A & Morrissey J H (2004) "Rapid and efficient incorporation of tissue factor into liposomes". *J. Thromb. Haemost.* 2:1155-1162 was followed for relipidation of TLT-1.

Example 40

Establishment of a FX Activation Screening Assay Based on TLT-1 Enriched Phospholipid Vesicles.

The use of freshly purified platelets as described in Example 37 is well suited to demonstrate proof of principle. However, it is not optimal with activated platelets from individual donors to screen and rank larger series of TLT-1-targeting TF-fusion proteins. Each platelet preparation allows a limited number of tests to be performed and is also subject to donor to donor variations. An alternative FX activation screening assay is established using TLT-1 enriched phospholipid vesicles in stead of activated purified platelets. The surface of the vesicles is composed to mimic the phospholipid composition of activated platelets.

The feasibility of the FX activation assay to measure stimulation by TLT-1 targeting TF-fusion proteins was tested as shown in FIG. 13 and provided the basis for the conditions used for screening of the constructs. 100 pM rFVIIa/rFVII was mixed with various concentrations (0-200 nM) of hTF.1-219 or the 0070 Fab-hTF.1-219 fusion protein or a control 0094 isotype Fab-hTF.1-219 fusion protein and with 175 nM FX (Enzyme Research, Human factor X, HFX 3170 PAL) in 50 mM Hepes, 0.1 M NaCl, 5 mM $CaCl_2$, 1 mg/ml BSA pH 7.4 at room temperature in the presence of the TLT-1 enriched phospholipid vesicle preparation at 1:2,000 dilution. The FX activation was stopped after 10 min when an aliquot was removed from each well and added to an equal volume of ice-cold stopping buffer (50 mM Hepes, 0.1 M NaCl, 20 mM EDTA, 1 mg/ml BSA pH 7.5). The amount of FXa generated in the samples was then determined in a chromogenic assay by transferring 50 µl of the mixture to a microtiter plate well and adding 25 µl CHROMOZYME X (final 0.42 mg/ml) to the well. The absorbance at 405 nm was measured continuously in a microplate reader (Molecular Devices).

The data in FIG. 13 show an essential mimic of the pattern obtained with activated platelets, only we observed a TLT-1 unspecific FX activation with mAb hTF.1-219 fusion proteins at high concentrations of FVII/FVIIa (data not shown). FVII/FVIIa at 0.1 nM with 10 nM Fab TF.1-219-fusion protein and 0.1 nM FVII/FVIIa with 1.0 nM mAb TF.1-219-fusion protein was therefore applied in the screening assay.

Example 41

Screening of TF-Fusion Proteins to Determine Optimal Conditions for Fusion with Anti TLT-1-mAbs or Fractions Thereof is Useful for Selection of Drug Candidates.

The assay with TLT-1 enriched phospholipid vesicles allowed for a comprehensive screening of a large series of TF-fusion proteins. The liability the data obtained by this screening was also tested by comparison to data obtained with the FX activation method applied in example 41. With each preparation of activated platelets the stimulation obtained was compared to the stimulation obtained with the 0020 Fab-hTF.1-219 fusion protein set to 100%. The same relative scale was used for the assay with TLT-1 enriched phospholipid vesicles. The results of such screening are compared in FIGS. 27A (mAB fusion proteins) and 27B (Fab fusion proteins).

The data shows that stimulation of FVII/FVIIa-mediated activation targeted to proteins exposed on activated platelets was obtained with a variety of hTF.1-219 fusion proteins.

The relative efficacy of four different epitopes on TLT-1 to mediate TF targeting was tested with TF-fusion proteins in which different mAb or Fab fragments were fused with identical Linker-hTF.1-219 moieties. Comparison of mAb/Fab 0012, 0023, 0051 and 0052 fusion proteins shows the following ranking of pro-coagulant potency: 0012>0051>0052=0023.

Additionally FIG. 27A/B allows a ranking of the pro-coagulant potency of TF fused to a full mAb or to various parts or compositions this mAb while still retaining its affinity for the TLT-1 epitope intact. Comparison of identical linker-hTF.1-219 constructs fused to either a mAb or a Fab fragment shows that Fab-linker-hTF.1-219-fusion proteins are superior to mAb-linker-hTF.1-219-fusion proteins. Likewise, Fab-hTF.1-219-fusion proteins are also superior to hetero-dimers in which hTF.1-219-fusion proteins are obtained by fusion of hTF.1-219 to the C-terminal of one of the two HC's or one of the two LC's of the mAb.

Fusion of hTF.1-219 to either the N-terminal or the C-terminal of antibody heavy- or light chains is also tested by comparison of otherwise equivalent TF-fusion proteins. The data suggest that C-terminal fusion is superior to N-terminal fusion.

Comparison of equivalent TF-fusion proteins in which only the linker between TF and the mAb/Fab fragment is varied also provides a ranking of linkers useful for drug candidate selection.

Platelet receptors other than TLT-1 can also be targeted with TF-fusion proteins to obtain FVII/FVIIa-mediated activation of FX on activated platelets. This was shown with the TF-fusion proteins 0128 and 0129 produced by fusion of TF with the AP3 Fab fragment. The AP3-Fab was directed towards the GPIIbIIIa receptor which is present on the surface of both activated and resting platelets (Phillips, D. R., and Agin, P. P. (1977) *J. Biol. Chem.* 252, 2121-226). The 0128 Fab-hTF.1-219 and 0129 Fab-hTF.1-219 TF-fusion proteins strongly stimulated the response on activated platelets. However, the response with resting platelets is about 20% of the response with activated platelets under conditions where, in comparison, the response induced by the TLT-1 targeting TF-fusion protein, 0020 Fab-hTF.1-219, with resting platelets is 8% of the response with activated platelets. It is conceivable that the stimulation pattern obtained with TF-fusion proteins is a result of three major factors: i) platelet receptor density and relative surface exposure on resting and activated platelets, ii) surface exposure of acidic phospholipids and iii) a minimum of spontaneous platelet activation during the preparation of washed, resting platelets. The presence of GPIIbIIIa receptor on the surface of resting platelets might account for a relatively high activity of the AP3 TF-fusion proteins on resting platelets. Fusion proteins based on antibodies to platelet receptors of crucial importance to haemostasis like GPIIbIIIa are also likely to possess antagonistic properties and serve as anti-coagulants at high concentrations.

Example 42

TF-Fusion Proteins Promotes Fibrin Clot Formation in Hemophilia-Like Whole Blood.

Hemophilia-like conditions were obtained by incubation of normal citrate-stabilized human whole blood (HWB) with 10 μg/ml anti-FVIII antibody (Sheep anti-Human Factor VIII; Hematologic Technologies Inc) for 30 min at room temp. Spontaneous clotting upon re-calcification of citrated HWB was strongly inhibited by the presence of anti-FVIII antibody. TF-fusion protein was added to HWB to demonstrate the capability of these proteins to revert haemophilia-like conditions induced by addition of anti-FVIII antibody to HWB.

Clot formation was measured by thrombelastography (5000 series TEG analyzer, Haemoscope Corporation, Niles, Ill., USA). Various concentrations (0; 0.02; 0.1; 0.2; 1.0; 10 nM) of 0070 TF-fusion protein, 0094 TF-fusion protein, or hTF.1-219 were added to haemophilia-like citrated HWB. Clotting was initiated when 340 μl of normal or premixed HWB was transferred to a thrombelastograph cup containing 20 μl 0.2 M $CaCl_2$. The TEG trace was followed continuously for up to 120 min. The following TEG variables were recorded: R time (clotting time i.e. the time from initiation of coagulation until an amplitude of 2 mm was obtained), α-angle (clot development measured as the angle between the R value and the inflection point of the TEG trace), K (speed of clot kinetics to reach a certain level of clot strength, amplitude=20 mm), and MA (maximal amplitude of the TEG trace reflecting the maximal mechanical strength of the clot). The TEG traces obtained with normal HWB (NWB), "haemophilia" blood, and "haemophilia" blood supplemented with (0; 0.02; 0.1; 0.2; 1.0; 10 nM) of 0070 Fab-hTF.1-219-fusion protein is shown in FIG. 14A. Shown in FIG. 14B are the R-time values obtained for the depicted TEG traces. FIG. 14B, in addition to R-time values for the 0070 Fab-hTF.1-219-fusion protein, also includes R-time values for equivalent concentrations of hTF.1-219 and the non-targeting 0094 Fab isotype hTF.1-219-fusion control protein. All data were obtained from one representative donor.

The 0070 Fab-hTF.1-219-fusion protein was observed to efficiently normalize clotting of haemophilia-like HWB. The pro-coagulant effect in haemophilia-like HWB of targeting of TF to TLT-1 is demonstrated with the 0070 Fab-hTF.1-219-fusion protein by comparison to the effect obtained with the 0094 Fab isotype hTF.1-219 fusion protein in which TF is fused to a non-binding control Fab.

Example 43

TLT1-Fab0043-TF Reduced Tail-Bleeding in FVIII-KO Mice Transfused with Human Platelets.

The effect of a TLT-1-Fab0043-TF construct was tested in a tail-bleeding model in haemophilic mice (FVIII-KO mice) transfused with human platelets.

Venous human blood was drawn into acid citrate dextrose (ACD; 1.7 ml/10 ml). The blood was incubated with 50 ng/ml $PGE_1$ for 10 min at room temperature (RT), followed by centrifugation (200 g; 10 min). The platelet rich plasma (PRP) was collected, and incubated with 50 ng/ml $PGE_1$ for 10 min at RT, followed by centrifugation at 450 g for 10 min at RT. The plasma was removed and the platelet pellet was resuspended in plasma to a concentration of 1.1-2.8 $10^9$ plts/ml.

The mice were anaesthetized with pentobarbital and catheterisized. The mice were pre-treated with 1 nmol/kg TLT1-Fab0043-TF (5 ml/kg; n=7) or ATNP-FAb-TF (control; irrelevant FAb-TF0095-construct; n=8) through the catheter. After 3 minutes human platelets (as PRP) were transfused to the mice (1.1-2.8×$10^8$ platelets/mouse; 5 ml/kg), and after another 2 minutes tail bleeding was induced followed by a 30 minutes observation period. Blood loss was measured as the amount of lost haemoglobin. One min after platelet transfusion, 6.5 and 7.5% of the total platelet population was human in the control and TLT1-FAb-TF treated group, respectively.

TLT1-FAb-TF reduced blood loss significantly from 3956±447 to 1180±489 nmol haemoglobin (p<0.01).

Example 44

Analysis of Fibrinogen Binding to TLT1 and Binding Competition Between TLT1 mAbs and Fibrinogen.

TLT-1 binds fibrinogen as tested by SPR analysis. Furthermore, simultaneous binding of fibrinogen and each of the four mAbs: mAb 0012, mAb 0023, mAb 0051 and mAb 0062 was tested by SPR analysis in a BIACORE T100 instrument (for surface plasmon resonance).

Materials used are shown in table 11.

TABLE 11

| Reagent | Source |
|---|---|
| TLT1 | NN |
| mAb0012 | NN |
| mAb0023 | |
| mAb0051 | |
| mAb0062 | |
| Fibrinogen | HCl-0150R Haematologic technologies |
| All other reagents | Biacore GE Healthcare |

Method:

Human TLT1 was immobilised to a level of approx 1000 RU on a CM5 chip (50 µg/ml diluted in Na-acetate, pH 4.0) using the standard procedure recommended by the supplier. Four-fold dilutions of human fibrinogen from 200 nM to 0.2 nM were tested for binding to the immobilized TLT1. Running and dilution buffer: 10 mM HEPES, 150 mM, 0.005% p20, pH 7.4. Regeneration was obtained by 10 mM Glycine, pH 1.7. Determination of kinetic and binding constants ($k_{on}$, $k_{off}$, $K_D$) was obtained assuming a 1:1 interaction of TLT1 and fibrinogen using the Biacore T100 evaluation software.

Competition of the different mAbs for binding to TLT1 and fibrinogen simultaneously was tested by immobilisation of each of the mAbs to approximately 10000-15000 RU at a CM5 chip followed by binding of 50 nM TLT1 followed after 2-3 min dissociation by varying concentrations of the mAbs to be tested for competition. Regeneration of the chip was obtained by 10 mM Glycine, pH 1.7.

Results:

TABLE 12

| TLT1 binding to fibrinogen | | | |
|---|---|---|---|
| | ka (1/M) | kd (1/s) | $K_D$ (M) |
| TLT1- fibrinogen binding | 4171 | 3.92 × $10^{-4}$ | 9.40E−08 |

TABLE 13

Competition with fibrinogen. The mAb of interest was immobilised to a chip. Addition of TLT1 was followed by fibrinogen (a sandwich).

| mAb ID | Competition with fibrinogen |
|---|---|
| mAb0012 | no |
| mAb0023 | yes |
| mAb0051 | no |
| mAb0062 | yes |

Conclusion:

Fibrinogen (HCl-0150R) binds fibrinogen. mAb 0023 and mAb 0062 compete with this binding site. mAb 0012 and mAb 0051 do not compete.

Example 45

Epitope Mapping by Hydrogen Exchange Mass Spectrometry (HX-MS).

The HX-MS technique has been employed to identify the TLT-1 binding epitopes covered by the four monoclonal antibodies mAb 0023, mAb 0051, mAb 0062 and mAb 0061.

For the mapping experiments hTLT-1.20-125, hTLT-1.16-162 and hTLT-1.126-162 corresponding to SEQ ID NO 5, 6 and 7, respectively, were used. All proteins were buffer exchanged into PBS pH 7.4 before experiments.

Method: HX-MS experiments.

Instrumentation and Data Recording

The HX experiments were automated by a Leap robot (H/D-x PAL; Leap Technologies Inc.) operated by the Leap-Shell software (Leap Technologies Inc.), which performed initiation of the deuterium exchange reaction, reaction time control, quench reaction, injection onto the UPLC system and digestion time control. The Leap robot was equipped with two temperature controlled stacks maintained at 20° C. for buffer storage and HX reactions and maintained at 2° C. for storage of protein and quench solution, respectively. The Leap robot furthermore contained a cooled Trio VS unit (Leap Technologies Inc.) holding the pepsin-, pre- and analytical columns, and the LC tubing and switching valves at 1° C. The switching valves have been upgraded from HPLC to Microbore UHPLC switch valves (Cheminert, VICI AG). For the inline pepsin digestion, 100 µL quenched sample containing 200 pmol TLT-1 was loaded and passed over a POROSZYME®-Immobilized Pepsin Cartridge (2.1×30 mm (Applied Biosystems)) using a isocratic flow rate of 200 µL/min (0.1% formic acid:$CH_3CN$ 95:5). The resulting peptides were trapped and desalted on a VAN- GUARD (UPLC column) pre-column BEH C18 1.7 μm (2.1×5 mm (Waters Inc.)). Subsequently, the valves were switched to place the pre-column inline with the analytical column, UPLC-BEH C18 1.7 μm (2.1×100 mm (Waters Inc.)), and the peptides separated using a 9 min gradient of 15-40% B delivered at 150 μL/min from an AQUITY UPLC system (Waters Inc.). The mobile phases consisted of A: 0.1% formic acid and B: 0.1% formic acid in $CH_3CN$. The ESI MS data, and the separate data dependent MS/MS acquisitions (CID) and elevated energy ($MS^E$) experiments were acquired in positive ion mode using a Q-Tof Premier MS (Waters Inc.). Leucine-enkephalin was used as the lock mass ($[M+H]^+$ ion at m/z 556.2771) and data was collected in continuum mode.

Data Analysis

Peptic peptides were identified in separate experiments using standard CID MS/MS or $MS^E$ methods (Waters Inc.). $MS^E$ data were processed using BiopharmaLynx 1.2 (version 017). CID data-dependent MS/MS acquisition was analyzed using the Mass-Lynx software and in-house MASCOT database.

HX-MS raw data files were subjected to continuous lockmass-correction. Data analysis, i.e., centroid determination of deuterated peptides and plotting of in-exchange curves, was performed using HX-Express ((Version Beta); Weis et al., J. Am. Soc. Mass Spectrom. 17, 1700 (2006)).

Epitope Mapping of mAb 0023:

Amide hydrogen/deuterium exchange (HX) was initiated by a 30-fold dilution of hTLT-1.20-125 in the presence or absence of mAb 0023 into the corresponding deuterated buffer (i.e. PBS prepared in $D_2O$, 96% $D_2O$ final, pH 7.4 (uncorrected value)). All HX reactions were carried out at 20° C. and contained 4 μM hTLT-1.20-125 in the absence or presence of 2.4 μM mAb 0023 thus giving a 1.2 fold molar excess of mAb binding sites. At appropriate time intervals ranging from 10 sec to 8 hours, aliquots of the HX reaction were quenched by an equal volume of ice-cold quenching buffer (1.35M TCEP) resulting in a final pH of 2.6 (uncorrected value).

Epitope Mapping of mAbs 0051 and 0062:

Epitope mapping of mAb 0051 and mAb 0062 were performed in a separate experiment using hTLT-1.20-125 and carried out similarly to the mapping of mAb 0023 as described above.

Epitope Mapping of mAb 0061:

Epitope mapping of mAb 0061 was performed in two separate experiments using either the hTLT-1.16-162 protein or the hTLT-1.126-162 peptide.

Experiments were performed similarly as described above for mAb 0023. However, the pepsin column was placed at room temperature for experiments using hTLT1.126-162. This results in an increased pepsin digestion efficacy with minimal additional exchange loss.

Results

Epitope Mapping of mAb 0023

The HX time-course of 20 peptides, covering 100% of the primary sequence of TLT-1, were monitored in the presence and absence mAb 0023 for 10 sec to 8 hours.

The observed exchange pattern in the presence or absence of mAb 0023 can be divided into two different groups: One group of TLT-1 peptides display an exchange pattern that is unaffected by the binding of mAb 0023 and another group of TLT-1 peptides that show protection from exchange upon mAb 0023 binding. The regions displaying protection upon mAb 0023 binding encompass peptides covering TLT-1 residues 36-51, 79-91 and 105-120. By comparing the relative amounts of exchange protection within each peptide the epitope for mAb 0023 can be narrowed to residues 36-47, VQCHYRLQDVKA (SEQ ID NO: 174) (50%), 82-87, LGGGLL (SEQ ID NO: 175) (30%), 108-115, GARGPQIL (SEQ ID NO: 176) (20%) with the relative exchange protection for each segment noted in parenthesis. An overview of the peptide map for the 0023 epitope is shown in FIG. 16.

Epitope Mapping of mAb 0051

The HX time-course of 22 peptides, covering 100% of the primary sequence of TLT-1, were monitored in the presence and absence mAb 0051 for 10 sec to 1000 sec.

The observed exchange pattern in the presence or absence of mAb 0051 can be divided into two different groups: One group of TLT-1 peptides display an exchange pattern that is unaffected by the binding of mAb 0051 and a group that is affected. The regions displaying protection upon mAb 0051 binding encompass peptides covering residues 52-66, 92-120. By comparing the relative amounts of exchange protection within each peptide the epitope for mAb 0051 can be narrowed to residues 55-66, LPEGCQPLVSSA (SEQ ID NO: 177) (75%) and 110-120, RGPQILHRVSL (SEQ ID NO: 178) (25%) as well as a weak interaction in the 92-105 stretch. An overview of the peptide map for the 0051 epitope is shown in FIG. 17.

Epitope Mapping of mAb 0062

The HX time-course of 22 peptides, covering 100% of the primary sequence of TLT-1, were monitored in the presence and absence mAb 0062 for 10 sec to 1000 sec.

The observed exchange pattern in the presence or absence of mAb 0062 can be divided into two different groups: One group of TLT-1 peptides display an exchange pattern that is unaffected by the binding of mAb 0062 and another group of TLT-1 peptides that show protection. The regions displaying protection upon mAb 0062 binding encompass peptides covering residues 36-51 and 105-120. By comparing the relative amounts of exchange protection within each peptide the epitope for mAb 0062 can be narrowed to 36-47, VQCHYRLQDVKA (SEQ ID NO: 179) (60%) and 110-120, RGPQILHRVSL (SEQ ID NO: 180) (40%). An overview of the peptide map for the 0062 epitope is shown in FIG. 18.

Epitope Mapping of mAb 0061

The epitope for mAb 0061 was mapped in two separate experiments using either the hTLT-1.16-162 protein or the hTLT-1.126-162.

For hTLT-1.16-162 the HX time-course of 19 peptides, covering 85% of the primary sequence of TLT-1, were monitored in the presence and absence mAb 0061 for 10 sec to 8 hours. Due to an O-glycosylation at residue 5148, no information could be recorded beyond residue 141.

The observed exchange pattern in the presence or absence of mAb 0061 can be divided into two different groups: One group of TLT-1 peptides display an exchange pattern that is unaffected by the binding of mAb 0061 and another group of TLT-1 peptides that show protection from exchange upon mAb 0061 binding. The regions displaying protection upon mAb 0061 binding encompass peptides covering residues 121-141. However, it is important to note that no information is given in this experiment for residue 142 and beyond. By comparing the relative amounts of exchange protection within each peptide the epitope for mAb 0061 can be narrowed to begin at residue 130.

In order to gain full information on the mAb 0061 epitope, the mapping experiment was repeated using the peptide hTLT-1.126-162. This peptide binds mAb 0061 with high affinity and it is not modified by glycosylation. Thus it should be able to give HX-MS information for the entire region.

The HX time-course of 12 peptides, covering the entire 126-162 TLT-1 region were monitored in the presence and absence mAb 0061 for 10 sec to 3000 sec.

All the peptides in this 126-162 region display protection from exchange upon mAb 0061 binding. By comparing the relative amounts of exchange protection within each peptide the epitope for mAb 0061 can be narrowed to be within residues 130-145, ETHKIGSLAENA (SEQ ID NO: 181.) An overview of the peptide map for the 0061 epitope is shown in FIG. 19.

Example 46

Production, Characterization and Binding Analyses of hTLT1 ECD-HPC4 Ala Mutants.

hTLT-1 ECD-HPC4 Alanine mutant constructs were designed according to table 7. The expression constructs were developed by external contractor GENEART AG (Im Gewerbepark B35, 93059 Regensburg, Germany) and all expression constructs were made based on the expression vector designated pcDNA3.1(+). Aliquots of DNA for each of the 40 hTLT-1 ECD-HPC4 pcDNA3.1(+) expression construct were transfected into HEK293-6E suspension cells in order to transiently express each hTLT-1 ECD-HPC4 Ala mutant protein (Table 7). Transient transfection and culturing of HEK293 6e cells were performed as described in example A.

Seven days post-transfection, cells were removed by centrifugation and the resulting hTLT-1 ECD-HPC4 Ala mutant protein containing supernatants were sterile-filtrated prior to analyses. The concentration of expressed hTLT-1 ECD-HPC4 Ala mutant protein in the cleared cell supernatant was determined using a combination of RP-HPLC and SDS-PAGE/Coomassie analyses. These ranged from 4-40 µg/mL containing variable degree of dimer formation. As described previously for production of hTLT protein used for immunization experiments, monomer/dimer forms of the expressed protein were observed for all hTLT ECD-HPC4 Ala mutant constructs. The relative concentration of monomer/dimer hTLT1 ECD-HPC4 protein was estimated by SDS-PAGE/Coomassie and an average Mw for each mutant preparation was calculated.

All binding studies were run at 25° C., and the samples were stored at 15° C. in the sample compartment on a ProteOn Analyzer (BioRad) that measures molecular interactions in real time through surface plasmon resonance. The signal (RU, response units) reported by the ProteOn is directly correlated to the mass on the individual sensor chip surface spots.

Anti-hFc Polyclonal antibody was immobilized onto separate flow cells of a GLM sensor chip using a 1:1 mixture of 0.4 M EDAC [1-ethyl-3-(3-dimethylaminopropyl) carbodiimide hydrochloride] and 0.1 M Sulfo-NHS [N-hydroxysulfosuccinimide]. Each antibody was diluted in 10 mM sodium acetate pH 5.0 to a concentration of 50 µg/ml, and was immobilized to an individual flow cell at 30 µl/min for 240 s. The antibodies were immobilized to flow cells A1-A6 (horizontal direction). After immobilization, the active sites on the flow cell were blocked with 1 M ethanolamine. The final immobilization level of capture antibody typically ranged from approximately 9,000 to 10,000 RU in one experiment. Capture of the anti-TLT1 antibodies 0197-0000-0023, 0197-0000-0051, 0197-0000-0061 and 0197-0000-0062 was conducted by diluting to 0.5 µg/ml into HBS-EP buffer (10 mM HEPES, 150 mM NaCl, 3 mM EDTA, 0.05% surfactant P20, pH 7.4) and injected at 30 µl/min for 60 s in vertical direction, creating interspot reference points with only anti-human Fc antibodies. The final capture level of test antibodies typically ranged from approximately 200 to 300 RU in one experiment. Binding of wt or Ala mutant hTLT1 ECD-HPC4 protein was conducted by injecting over parallel flow cells in horizontal direction to allow for comparative analyses of binding to different captured anti-TLT1 antibodies relative to binding to the interspot references. Each hTLT-1 ECD-HPC4 protein was diluted to 100 nM, based on the calculated average Mw, into HBS-EP buffer and injected at 30 µl/min for 240 s. The GLM chip was regenerated after each injection cycle of analyte via one 18 s injection of 1 M Formic acid followed by a 18 s injection of 50 mM NaOH at 100 µl/min. This regeneration step removed the anti-TLT1 antibody and any bound TLT1 from the immobilized capture antibody surface, and allowed for the subsequent binding of the next test sample pair. The regeneration procedure did not remove the directly immobilized anti-human-Fc capture antibody from the chip surface.

Data analysis was performed using the ProteOn Manager™ Software. No significant non-specific binding to the interspot control surfaces was observed. Binding curves were processed by double referencing (subtraction of interspot control surface signals as well as blank buffer injections over captured anti-TLT1 antibodies). This allowed correction for instrument noise, bulk shift and drift during sample injections. Binding signal at 10 s after stop of analyte injection was normalized to level of captured anti-TLT1 antibody and presented as binding relative to wt hTLT-1 ECD-HPC4 protein.

The following Ala mutations displayed a significant decrease of binding to respective anti-TLT1 compared to wt hTLT-1 ECD-HPC4 protein. 0197-0000-0051: F54A<0.4 wt; M91A<0.2 wt; R117A<0.2 wt; S119A<0.6 wt. 0197-0000-0062: R41A<0.2 wt; L42A<0.6 wt; Q43A<0.4 wt; F54A<0.6 wt; M91A<0.4 wt; R110A<0.2 wt; H116A<0.6 wt. 0197-0000-0023: L42A<0.2 wt; Q43A<0.2 wt; K46A<0.2 wt; M91A<0.4 wt; R110A<0.2 wt. Since decreased binding could be observed for the hTLT1 ECD-HPC4 mutant M91A for all 4 anti-TLT1 antibodies, the residue probably has an important influence on protein stability rather than being part of an actual epitope. 0197-0000-0061 did not show a decreased binding to any of the mutated TLT-1 variants tested, indicating that the epitope is not covered by the mutants introduced in the binding study.

Example 47

Crystal Structures Complexes Between Anti-TLT-1 Fab and TLT-1 Stalk Peptides.

Expression of 100 anti-TLT-1 Fab for crystallization: The anti-TLT-1 Fab fragment, Fab0100, comprising the heavy chain corresponding to SEQ ID NO 162 and the light chain corresponding SEQ ID NO 163 was expressed transiently in HEK293 cells according to the generalized procedure.

Purification of 0100 anti-TLT-1 Fab for crystallization: Purification of said Fab was conducted by a two-step process composed of affinity chromatography using the kappaSelect resin (GE Healthcare, cat. no. 17-5458-01) and size-exclusion chromatography. The purification was conducted using an AktaExplorer chromatography system (GE Healthcare, cat. no. 18-1112-41). The buffer systems used for the purification step was an equilibration buffer composed of 10 mM NaPhosphate, pH 7.5 and 150 mM NaCl and an elution buffer composed of 20 mM Formic acid, pH 3.0. The supernatant was adjusted with 1 M NaOH to a pH of 7.5 and applied onto a pre-equilibrated kappaSelect column. The column was washed with 5 column volumes of equilibration buffer and the Fab protein was isocratically eluted using approximately 5 column volumes of elution buffer. The Fab protein was analyzed using SDS-PAGE/Coomassie and LC-MS analyses, showing that a pure and homogenous protein with an expected molecular weight of 46.9 kDa was obtained. To measure the protein concentration, a NANO-DROP spectrophotometer (Thermo Scientific) was used together with an extinction coefficient of 1.31. The final polish of the Fab protein was conducted using a size-exclusion column (SUPERDEX 200 (prep grade gel filtration medium)).

Preparation of peptides for crystallization: The TLT-1-stalk peptide hTLT-1.126-162 (SEQ ID NO 7) was prepared by solid phase peptide synthesis. Likewise, a shorter version hTLT-1.129-142 of the stalk peptide corresponding to SEQ ID NO 8 was prepared.

Preparation, crystallization and structure determination of the Fab0100:TLT-1 complexes. Preparation of Fab0100: hTLT-1.126-162: The complex between Fab0100 and hTLT-1.126-162 was prepared by adding two times molar excess of hTLT-1.126-162 to a solution of anti-TLT-1 Fab followed by isolation of the complex by separating excess hTLT-1.126-162 using preparative size exclusion chromatography. Thus, the Fab0100: hTLT-1.126-162 complex was prepared by mixing Fab (1100 μl, 98 μM) and hTLT-1.126-162 (155 μl, 1391 μM), both in PBS buffer (pH 7.4). The complex was subjected to gel filtration using a SUPERDEX 200 (prep grade gel filtration medium) HighLoad 26/60 (GE Healthcare) column eluted with PBS-buffer (pH 7.4) at a flow rate of 1 ml/min. Fractions corresponding to a volume of 3 ml were collected. Fractions containing the desired Fab0100: hTLT-1.126-162 complex were pooled and then concentrated using a centrifugal filter device (AMICON, 10 kDa cut-off) to a protein concentration of 8.6 mg/ml. This preparation was used for crystallization of the Fab0100:hTLT-1.126-162 complex.

Preparation of Fab0100:hTLT-1.129-142: The complex between the anti-TLT-1 Fab and the shorter stalk peptide (hTLT-1.129-142) was similarly prepared with the exceptions that the molar ratio between hTLT-1.129-142 and Fab was 1.5:1 and that the gel filtration stop was omitted due to weaker binding of hTLT-1.129-142 compared to that of the longer stalk peptide (hTLT-1.126-162).

Crystallization and data collection of Fab0100:hTLT-1.129-142 and Fab0100:hTLT-1.126-162 complexes: Fab0100:hTLT-1.129-142 and Fab0100:hTLT1.126-162 complexes were at room temperature crystallized by the sitting drop method. Fab0100:hTLT-1.129-142 was crystallized by adding to the protein solution, in a 1:2 volume ratio (precipitant:protein), a precipitation solution containing 0.04 M potassium dihydrogen phosphate, 16% w/v PEG 8,000 and 20% glycerol, while the Fab0100:hTLT1.126-162 complex was crystallized by adding to the protein solution, in a 1:1 volume ratio (precipitant:protein), a precipitation solution containing 20% w/v PEG 10,000 and 0.10 M Hepes pH 7.5. A crystal of the Fab0100:hTLT-1.129-142 complex was flash frozen in liquid $N_2$ and during data collection kept at 100 K by a cryogenic $N_2$ gas stream. Crystallographic data were subsequently collected to 2.14 Å resolution using a Rigaku MicroMax-007 HF rotating anode and a marCCD 165 X-ray detector. Space group determination, integration and scaling of the data were made by the XDS software package (Kabsch, W. (1993) *J. Appl. Crystallogr.* 26, 795-800). Cell parameters of the crystal were determined to be 82.10, 64.99, 107.73 Å, 90°, 95.12° and 90°, for a, b, c, a, 13 and y respectively, and the space group was determined to be C2. $R_{sym}$ for intensities of the data set was calculated to be 6.5%. Coordinates from a Fab model of the PDB-deposited (Berman, H. M. et al. (2000) *Nucleic Acids Res.* 28, 235-242) 1NGZ structure (Yin, J. et al. PNAS us 100, 856-861) was used for structure determination of the anti-TLT-1 Fab molecule. The 1NGZ Fab model was divided into two domains, the variable and the constant domains, which then were used as independent search models in a Molecular replacement run by the PHASER software program (Mccoy, A. J. et al. *Acta Crystallographica Section D Biological Crystallography* 61, 458-464; Mccoy, A. J. et al. *J. Appl. Crystallogr.* 40, 658-674) of the CCP4 suite (Bailey, S. (1994) *Acta Crystallogr. Sect. D-Biol. Crystallogr.* 50, 760-763). The ARP-wARP software package (Evrard, G. X. et al. *Acta Crystallographica Section D* 63, 108-117) was subsequently used for automated model building and phasing. Additional crystallographic refinements, using the REFMAC5 software program (Murshudov, G. N. et al. *Acta Crystallogr. Sect. D-Biol. Crystallogr.* 53, 240-255), followed by computer graphics inspection of the electron density maps, model corrections and building, using the COOT software program (Emsley, P. et al. *Acta Crystallogr. Sect. D-Biol. Crystallogr.* 60, 2126-2132), were applied. The procedure was cycled until no further significant improvements could be made to the model. Final calculated R- and R-free after 3 cycles of manual intervention and following refinements were 0.185 and 0.245, respectively, and the model showed a root-mean-square deviation (RMSD) from ideal bond lengths of 0.022 Å.

A crystal of the Fab0100:hTLT-1.126-162 complex was transferred to a cryo-solution containing 75% of the precipitant solution and 25% of glycerol. The crystal was allowed to soak for about 15 seconds, then flash frozen in liquid $N_2$ and during data collection kept at 100 K by a cryogenic $N_2$ gas stream. Crystallographic data were subsequently collected to 1.85 Å resolution at beam-line BL911-3 (Ursby, T. et al. (2004) AIP Conference Proceedings 705, 1241-1246) at MAX-lab, Lund, Sweden. Space group determination, integration and scaling of the data were made in the XDS software package. Cell parameters for the synchrotron data were determined to be 82.54, 65.32, 108.05 Å, 90°, 95.15° and 90°, for a, b, c, a, 13 and y, respectively, and space group was determined to be C2. $R_{sym}$ for intensities of the data set was calculated to be 6.7%. The crystal was isomorphous with the Fab0100:hTLT-1.129-142 crystals and therefore rigid body refinement of the Fab0100:hTLT-1.129-142 complex was used for the original phasing of the Fab0100:hTLT-1.126-162 followed by automated model building and phasing using the ARP-wARP software package. Additional crystallographic refinements, using the REFMAC5 software program, followed by computer graphics inspection of the electron density maps, model corrections and building, using the COOT software program, were applied. The procedure was cycled until no further significant improvements could be made to the model. Final calculated R- and R-free after 13 cycles of manual intervention and following refinements were 0.171 and 0.223, respectively, and the model showed a RMSD from ideal bond lengths of 0.027 Å (Table 13).

Results

As shown in Tables 14 and 15, AntiTLT-1 effectively binds to the stalk of TLT-1. Using the software program AREAIMOL, of the CCP4 program suite, the average areas excluded in pair-wise interaction between anti-TLT-1 and TLT-1 were calculated to be 764 Å². The average areas excluded in pair-wise interactions gave for the Fab0100: hTLT1.126-162 complex 656 and 871 Å², for anti-TLT-1 and TLT-1 respectively.

Residues in the TLT-1 peptide (hTLT-1.126-162) making direct contacts to the anti-TLT-1 Fab in the Fab0100: hTLT-1.126-162 complex is defined as the epitope and residues in the anti-TLT-1 Fab making direct contacts to hTLT-1.126-162 in the Fab0100: hTLT-1.126-162 complex is defined as the paratope. Epitope and paratope residues were identified by running the CONTACTS software of the CCP4 program suite using a cut-off distance of 4.0 Å between the anti-TLT-1 Fab and the TLT-1 molecule. The results of the contact calculations for the Fab0100:hTLT-1.126-162 complex of the crystal structures are shown in Tables 14 and 15.

The resulting TLT-1 epitope for anti-TLT-1 was found to comprise the following residues of SEQ ID NO 7): Lys 8 (133), Ile 9 (134), Gly 10 (135), Ser 11 (136), Leu 12 (137), Ala 13 (138), Asn 15 (140), Ala 16 (141), Phe 17 (142), Ser 18 (143), Asp 19 (144), Pro 20 (145), Ala 21 (142) where numbers in parenthesis refer to the corresponding residues in SEQ ID NO 2 (Tab. 14 and 15).

The resulting paratope included residues His 31, Asn 33, Tyr 37, His 39, Tyr 54, Phe 60, Ser 96, Thr 97, Val 99 and Tyr 101 of the Fab0100 light chain corresponding to SEQ ID NO 163 (Table 14), and residues Val 2, Phe 27, Arg 31, Tyr 32, Trp 33, Glu 50, Thr 57, Asn 59, Ser 98, Gly 99, Val 100 and Thr 102 of the Fab0100 heavy chain corresponding to SEQ ID NO 162 (Table 15). The TLT-1 epitope residues involved in hydrogen-binding are also indicated in Tables 14 and 15.

TABLE 13

Results from the X-ray model refinement to the observed data of the Fab0100:hTLT-1.126-162 complex by the software program refmac5.

REMARK 3 REFINEMENT.
REMARK 3 PROGRAM: REFMAC 5.5.0109
REMARK 3 AUTHORS: MURSHUDOV, VAGIN, DODSON
REMARK 3
REMARK 3 REFINEMENT TARGET: MAXIMUM LIKELIHOOD
REMARK 3
REMARK 3 DATA USED IN REFINEMENT.
REMARK 3 RESOLUTION RANGE HIGH (ANGSTROMS): 1.85
REMARK 3 RESOLUTION RANGE LOW (ANGSTROMS): 34.18
REMARK 3 DATA CUTOFF (SIGMA(F)): NONE
REMARK 3 COMPLETENESS FOR RANGE (%): 99.89
REMARK 3 NUMBER OF REFLECTIONS: 46512
REMARK 3
REMARK 3 FIT TO DATA USED IN REFINEMENT.
REMARK 3 CROSS-VALIDATION METHOD: THROUGHOUT
REMARK 3 FREE R VALUE TEST SET SELECTION: RANDOM
REMARK 3 R VALUE (WORKING + TEST SET): 0.17330
REMARK 3 R VALUE (WORKING SET): 0.17070
REMARK 3 FREE R VALUE: 0.22260
REMARK 3 FREE R VALUE TEST SET SIZE (%): 5.0
REMARK 3 FREE R VALUE TEST SET COUNT: 2463
REMARK 3
REMARK 3 FIT IN THE HIGHEST RESOLUTION BIN.
REMARK 3 TOTAL NUMBER OF BINS USED: 20
REMARK 3 BIN RESOLUTION RANGE HIGH: 1.850
REMARK 3 BIN RESOLUTION RANGE LOW: 1.898
REMARK 3 REFLECTION IN BIN (WORKING SET): 3409
REMARK 3 BIN COMPLETENESS (WORKING + TEST) (%): 99.81
REMARK 3 BIN R VALUE (WORKING SET): 0.266
REMARK 3 BIN FREE R VALUE SET COUNT: 195
REMARK 3 BIN FREE R VALUE: 0.309
REMARK 3
REMARK 3 NUMBER OF NON-HYDROGEN ATOMS USED IN REFINEMENT.
REMARK 3 ALL ATOMS: 3993
REMARK 3
REMARK 3 B VALUES.
REMARK 3 FROM WILSON PLOT (A**2): NULL
REMARK 3 MEAN B VALUE (OVERALL, A**2): 14.967
REMARK 3 OVERALL ANISOTROPIC B VALUE.
REMARK 3 B11 (A**2): −0.06
REMARK 3 B22 (A**2): 0.23
REMARK 3 B33 (A**2): −0.24
REMARK 3 B12 (A**2): 0.00
REMARK 3 B13 (A**2): −0.36
REMARK 3 B23 (A**2): 0.00
REMARK 3
REMARK 3 ESTIMATED OVERALL COORDINATE ERROR.
REMARK 3 ESU BASED ON R VALUE (A): 0.116
REMARK 3 ESU BASED ON FREE R VALUE (A): 0.123
REMARK 3 ESU BASED ON MAXIMUM LIKELIHOOD (A): 0.084
REMARK 3 ESU FOR B VALUES BASED ON MAXIMUM LIKELIHOOD (A**2): 6.165
REMARK 3
REMARK 3 CORRELATION COEFFICIENTS.
REMARK 3 CORRELATION COEFFICIENT FO-FC: 0.963
REMARK 3 CORRELATION COEFFICIENT FO-FC FREE: 0.939
REMARK 3

TABLE 13-continued

Results from the X-ray model refinement to the observed data of the
Fab0100:hTLT-1.126-162 complex by the software program refmac5.

REMARK 3 RMS DEVIATIONS FROM IDEAL VALUES COUNT RMS WEIGHT
REMARK 3 BOND LENGTHS REFINED ATOMS (A): 3538; 0.027; 0.022
REMARK 3 BOND ANGLES REFINED ATOMS (DEGREES): 4833; 2.132; 1.958
REMARK 3 TORSION ANGLES, PERIOD 1 (DEGREES): 473; 6.972; 5.000
REMARK 3 TORSION ANGLES, PERIOD 2 (DEGREES): 137; 35.607; 24.453
REMARK 3 TORSION ANGLES, PERIOD 3 (DEGREES): 583; 14.216; 15.000
REMARK 3 TORSION ANGLES, PERIOD 4 (DEGREES): 14; 23.096; 15.000
REMARK 3 CHIRAL-CENTER RESTRAINTS (A**3): 552; 0.180; 0.200
REMARK 3 GENERAL PLANES REFINED ATOMS (A): 2664; 0.013; 0.021
REMARK 3
REMARK 3 ISOTROPIC THERMAL FACTOR RESTRAINTS. COUNT RMS WEIGHT
REMARK 3 MAIN-CHAIN BOND REFINED ATOMS (A**2): 2262; 1.399; 1.500
REMARK 3 MAIN-CHAIN ANGLE REFINED ATOMS (A**2): 3679; 2.333; 2.000
REMARK 3 SIDE-CHAIN BOND REFINED ATOMS (A**2): 1276; 3.462; 3.000
REMARK 3 SIDE-CHAIN ANGLE REFINED ATOMS (A**2): 1139; 5.231; 4.500
REMARK 3
REMARK 3 NCS RESTRAINTS STATISTICS
REMARK 3 NUMBER OF NCS GROUPS: NULL
REMARK 3
REMARK 3 TWIN DETAILS
REMARK 3 NUMBER OF TWIN DOMAINS: NULL
REMARK 3
REMARK 3
REMARK 3 TLS DETAILS
REMARK 3 NUMBER OF TLS GROUPS: 2
REMARK 3 ATOM RECORD CONTAINS RESIDUAL B FACTORS ONLY
REMARK 3
REMARK 3 TLS GROUP: 1
REMARK 3 NUMBER OF COMPONENTS GROUP: 3
REMARK 3 COMPONENTS C SSSEQI TO C SSSEQI
REMARK 3 RESIDUE RANGE: L 1 L 109
REMARK 3 RESIDUE RANGE: H 1 H 113
REMARK 3 RESIDUE RANGE: P 7 P 21
REMARK 3 ORIGIN FOR THE GROUP (A): −4.1790 48.4400 34.3450
REMARK 3 T TENSOR
REMARK 3 T11: 0.1731 T22: 0.1937
REMARK 3 T33: 0.1093 T12: −0.0155
REMARK 3 T13: −0.0164 T23: −0.0192
REMARK 3 L TENSOR
REMARK 3 L11: 1.9367 L22: 0.4840
REMARK 3 L33: 3.8383 L12: −0.1522
REMARK 3 L13: −1.2215 L23: −0.1172
REMARK 3 S TENSOR
REMARK 3 S11: 0.0447 S12: −0.2657 S13: 0.0758
REMARK 3 S21: 0.0958 S22: −0.0414 S23: −0.0674
REMARK 3 S31: 0.0036 S32: 0.0098 S33: −0.0032
REMARK 3
REMARK 3 TLS GROUP: 2
REMARK 3 NUMBER OF COMPONENTS GROUP: 2
REMARK 3 COMPONENTS C SSSEQI TO C SSSEQI
REMARK 3 RESIDUE RANGE: L 114 L 219
REMARK 3 RESIDUE RANGE: H 116 H 215
REMARK 3 ORIGIN FOR THE GROUP (A): −24.4360 51.7710 5.9920
REMARK 3 T TENSOR
REMARK 3 T11: 0.0252 T22: 0.0170
REMARK 3 T33: 0.0735 T12: 0.0161
REMARK 3 T13: 0.0018 T23: 0.0048
REMARK 3 L TENSOR
REMARK 3 L11: 2.0324 L22: 1.6905
REMARK 3 L33: 0.8461 L12: 0.7328
REMARK 3 L13: 0.0695 L23: 0.3337
REMARK 3 S TENSOR
REMARK 3 S11: −0.0068 S12: 0.0156 S13: 0.0515
REMARK 3 S21: −0.0127 S22: −0.0101 S23: 0.1316
REMARK 3 S31: −0.0077 S32: −0.0763 S33: 0.0168
REMARK 3
REMARK 3
REMARK 3 BULK SOLVENT MODELLING.
REMARK 3 METHOD USED: MASK
REMARK 3 PARAMETERS FOR MASK CALCULATION
REMARK 3 VDW PROBE RADIUS: 1.40
REMARK 3 ION PROBE RADIUS: 0.80
REMARK 3 SHRINKAGE RADIUS: 0.80
REMARK 3
REMARK 3 OTHER REFINEMENT REMARK 3S:
REMARK 3 HYDROGENS HAVE BEEN ADDED IN THE RIDING POSITIONS
REMARK 3 U VALUES: RESIDUAL ONLY

TABLE 13-continued

Results from the X-ray model refinement to the observed data of the Fab0100:hTLT-1.126-162 complex by the software program refmac5.

REMARK 3
LINKR SG CYS L 13 9SG ACYS L 199 SS
LINKR SG CYS H 22 SG ACYS H 96 SS
LINKR SG ACYS H 141 SG ACYS H 197 SS
CISPEP 1 THR L 7 PRO L 8 0.00
CISPEP 2 VAL L 99 PRO L 100 0.00
CISPEP 3 TYR L 145 PRO L 146 0.00
CISPEP 4 PHE H 147 PRO H 148 0.00
CISPEP 5 GLU H 149 PRO H 150 0.00

TABLE 14 hTLT-1.126-162 "P" (SEQ ID NO 7) interactions with the Fab0100 light chain (SEQ ID NO 163). A cut-off of 4.0 Å was used. The contacts were identified by the CONTACT computer program of the CCP4 suite. In the last column "***" indicates a strong possibility for a hydrogen bond at this contact (distance <3.3 Å) as calculated by CONTACT, " *" indicates a weak possibility (distance >3.3 Å). Blank indicates that the program considered there to be no possibility of a hydrogen bond. Hydrogen-bonds are specific between a donor and an acceptor, are typically strong, and are easily identifiable.

| hTLT-1.126-162 | | | Anti-TLT-1 | | | |
|---|---|---|---|---|---|---|
| Res. Type | Res. # and Chain | Atom name | Res. Type | Res. # and Chain | Atom name | Distance [Å] | Possibly H-bond |
| Ile | 9P | CB | Tyr | 101L | OH | 3.76 | |
| Ile | 9P | CD1 | Ser | 96L | O | 3.58 | |
| | | | Thr | 97L | O | 3.68 | |
| Ile | 9P | CG2 | Val | 99L | CG2 | 3.51 | |
| Ile | 9P | C | Tyr | 101L | OH | 3.95 | |
| Gly | 10P | N | Tyr | 101L | OH | 3.06 | *** |
| Gly | 10P | CA | Tyr | 101L | OH | 3.48 | |
| Gly | 10P | C | Tyr | 101L | OH | 3.67 | |
| Ser | 11P | N | Tyr | 101L | OH | 3.09 | *** |
| Ser | 11P | CB | Ser | 96L | OG | 3.89 | |
| | | | Tyr | 37L | CD1 | 3.94 | |
| | | | Ser | 96L | O | 3.37 | |
| Ser | 11P | OG | Ser | 96L | OG | 2.88 | *** |
| | | | Ser | 96L | CA | 3.76 | |
| | | | Ser | 96L | CB | 3.05 | |
| | | | Ser | 96L | C | 3.33 | |
| | | | Ser | 96L | O | 2.45 | *** |
| | | | Tyr | 101L | CE1 | 3.94 | |
| | | | Tyr | 101L | CZ | 3.59 | |
| | | | Tyr | 101L | OH | 3.37 | * |
| Ser | 11P | O | Tyr | 37L | CE1 | 3.39 | |
| | | | Tyr | 37L | CZ | 3.66 | |
| | | | Tyr | 37L | OH | 3.55 | * |
| Leu | 12P | CG | Asn | 33L | ND2 | 3.41 | |
| | | | Tyr | 37L | OH | 3.86 | |
| Leu | 12P | CD1 | His | 31L | CE1 | 3.73 | |
| | | | His | 31L | NE2 | 3.38 | |
| | | | His | 31L | CD2 | 3.63 | |
| | | | Tyr | 37L | CE2 | 3.65 | |
| | | | Asn | 33L | ND2 | 3.68 | |
| | | | Tyr | 37L | CZ | 3.84 | |
| | | | Tyr | 37L | OH | 3.51 | |
| Leu | 12P | CD2 | His | 31L | CE1 | 3.57 | |
| | | | His | 31L | NE2 | 3.91 | |
| | | | Asn | 33L | ND2 | 3.39 | |
| Phe | 17P | CB | Tyr | 54L | CG | 3.79 | |
| | | | Tyr | 54L | CE1 | 3.70 | |
| | | | Tyr | 54L | CD1 | 3.45 | |
| Phe | 17P | CG | Tyr | 54L | CG | 3.98 | |
| | | | Tyr | 54L | CD1 | 3.63 | |
| Phe | 17P | CD1 | Tyr | 54L | CB | 3.74 | |
| Phe | 17P | CE1 | His | 39L | ND1 | 3.88 | |
| | | | His | 39L | CE1 | 3.32 | |
| | | | His | 39L | NE2 | 3.60 | |
| Phe | 17P | CZ | His | 39L | CE1 | 3.36 | |
| | | | His | 39L | NE2 | 3.66 | |
| | | | Tyr | 37L | CD1 | 3.98 | |
| Phe | 17P | CE2 | Tyr | 37L | CD1 | 3.79 | |
| | | | Tyr | 37L | CE1 | 3.84 | |
| Phe | 17P | O | Phe | 60L | CD1 | 3.84 | |
| | | | Phe | 60L | CE1 | 3.31 | |
| Asp | 19P | N | Phe | 60L | CE1 | 3.88 | |
| Asp | 19P | CA | Phe | 60L | CZ | 3.80 | |
| Asp | 19P | CB | Phe | 60L | CZ | 3.85 | |

TABLE 15 hTLT-1.126-162 "P" (SEQ ID NO 7) interactions with the Fab0100 heavy chain (SEQ ID NO 162). A cut-off of 4.0 Å was used. The contacts were identified by the CONTACT computer program of the CCP4 suite. In the last column "***" indicates a strong possibility for a hydrogen bond at this contact (distance <3.3 Å) as calculated by CONTACT, " *" indicates a weak possibility (distance >3.3 Å). Blank indicates that the program considered there to be no possibility of a hydrogen bond. Hydrogen-bonds are specific between a donor and an acceptor, are typically strong, and are easily identifiable.

| hTLT-1.126-162 | | | Anti-TLT-1 | | | | |
|---|---|---|---|---|---|---|---|
| Res. Type | Res. # and Chain | Atom name | Res. Type | Res. # and Chain | Atom name | Distance [Å] | Possibly H-bond |
| Lys | 8P | C | Asn | 59H | OD1 | 3.95 | |
| Lys | 8P | O | Asn | 59H | CG | 3.69 | |
| | | | Asn | 59H | ND2 | 3.78 | * |
| | | | Trp | 33H | CH2 | 3.86 | |
| | | | Asn | 59H | OD1 | 2.85 | *** |
| | | | Thr | 57H | CG2 | 3.45 | |
| Ile | 9P | CA | Trp | 33H | CH2 | 3.91 | |
| | | | Glu | 50H | OE2 | 3.52 | |
| | | | Asn | 59H | OD1 | 3.79 | |
| Ile | 9P | CB | Glu | 50H | OE2 | 3.81 | |
| Ile | 9P | C | Trp | 33H | CZ3 | 4.00 | |
| | | | Trp | 33H | CH2 | 3.65 | |
| | | | Glu | 50H | OE2 | 3.62 | |
| | | | Trp | 33H | CZ2 | 3.87 | |

TABLE 15-continued hTLT-1.126-162 "P" (SEQ ID NO 7) interactions with the Fab0100 heavy chain (SEQ ID NO 162). A cut-off of 4.0 Å was used. The contacts were identified by the CONTACT computer program of the CCP4 suite. In the last column "***" indicates a strong possibility for a hydrogen bond at this contact (distance <3.3 Å) as calculated by CONTACT, " *" indicates a weak possibility (distance >3.3 Å). Blank indicates that the program considered there to be no possibility of a hydrogen bond. Hydrogen-bonds are specific between a donor and an acceptor, are typically strong, and are easily identifiable.

| hTLT-1.126-162 | | | Anti-TLT-1 | | | | |
|---|---|---|---|---|---|---|---|
| Res. Type | Res. # and Chain | Atom name | Res. Type | Res. # and Chain | Atom name | Distance [Å] | Possibly H-bond |
| Ile | 9P | O | Trp | 33H | CZ2 | 3.92 | |
| Gly | 10P | N | Glu | 50H | CD | 3.40 | |
| | | | Glu | 50H | OE1 | 3.38 | * |
| | | | Trp | 33H | CZ3 | 3.55 | |
| | | | Trp | 33H | CH2 | 3.68 | |
| | | | Glu | 50H | OE2 | 2.77 | *** |
| | | | Trp | 33H | CE3 | 3.85 | |
| | | | Trp | 33H | CZ2 | 3.99 | |
| Gly | 10P | CA | Glu | 50H | CD | 3.79 | |
| | | | Glu | 50H | OE1 | 3.40 | |
| | | | Trp | 33H | CZ3 | 3.80 | |
| | | | Glu | 50H | OE2 | 3.61 | |
| | | | Trp | 33H | CE2 | 3.75 | |
| | | | Trp | 33H | CD2 | 3.55 | |
| | | | Trp | 33H | CE3 | 3.58 | |
| | | | Trp | 33H | CZ2 | 3.99 | |
| Gly | 10P | C | Val | 100H | CG2 | 3.82 | |
| Gly | 10P | O | Val | 100H | CG2 | 3.86 | |
| Ser | 11P | N | Val | 100H | CG2 | 3.78 | |
| Ser | 11P | CA | Val | 100H | CG2 | 3.78 | |
| Ala | 13P | CB | Trp | 33H | CD1 | 3.60 | |
| | | | Trp | 33H | NE1 | 3.52 | |
| Asn | 15P | CG | Tyr | 32H | CD1 | 3.88 | |
| | | | Tyr | 32H | CE1 | 3.83 | |
| Asn | 15P | ND2 | Arg | 31H | C | 3.94 | |
| | | | Arg | 31H | O | 3.09 | *** |
| | | | Tyr | 32H | CG | 3.98 | |
| | | | Tyr | 32H | CD1 | 3.76 | |
| | | | Tyr | 32H | CE1 | 3.70 | |
| | | | Tyr | 32H | CZ | 3.88 | |
| | | | Arg | 31H | NH1 | 3.93 | * |
| Ala | 16P | O | Val | 100H | CB | 3.86 | |
| | | | Val | 100H | CA | 3.80 | |
| | | | Val | 100H | N | 2.91 | *** |
| | | | Thr | 102H | CG2 | 3.46 | |
| | | | Gly | 99H | CA | 3.74 | |
| | | | Gly | 99H | C | 3.78 | |
| Phe | 17P | CA | Thr | 102H | CG2 | 3.64 | |
| Phe | 17P | CD1 | Val | 100H | O | 3.93 | |
| Phe | 17P | CE1 | Val | 100H | CB | 3.46 | |
| | | | Val | 100H | CG1 | 3.52 | |
| | | | Val | 100H | O | 3.86 | |
| Phe | 17P | CZ | Val | 100H | CB | 3.81 | |
| | | | Val | 100H | CG1 | 3.89 | |
| Phe | 17P | C | Thr | 102H | CG2 | 3.59 | |
| Phe | 17P | O | Thr | 102H | CG2 | 3.79 | |
| Ser | 18P | C | Thr | 102H | CG2 | 3.94 | |
| Ser | 18P | O | Thr | 102H | CB | 3.48 | |
| | | | Thr | 102H | OG1 | 3.64 | * |
| | | | Thr | 102H | CG2 | 3.26 | |
| Pro | 20P | CA | Tyr | 32H | OH | 3.47 | |
| | | | Tyr | 32H | CZ | 3.90 | |
| Pro | 20P | CB | Val | 2H | CG2 | 3.92 | |
| | | | Phe | 27H | CB | 3.93 | |
| | | | Phe | 27H | CD1 | 3.86 | |
| | | | Phe | 27H | CG | 3.78 | |
| Pro | 20P | CG | Thr | 102H | OG1 | 3.88 | |
| | | | Ser | 98H | OG | 3.54 | |
| Pro | 20P | CD | Thr | 102H | CB | 3.95 | |
| | | | Thr | 102H | OG1 | 3.83 | |
| Pro | 20P | C | Val | 2H | CG2 | 3.98 | |
| Pro | 20P | O | Phe | 27H | CB | 3.52 | |
| Ala | 21P | N | Val | 2H | CG2 | 3.51 | |
| Ala | 21P | CA | Val | 2H | CG2 | 3.97 | |
| Ala | 21P | CB | Val | 2H | CG2 | 3.77 | |

Example 48

Epitope Mapping by Peptide Walk.

The peptide walking ELISA defined the minimal binding region of the peptide. This was established by coating biotinylated peptides with one residue frameshift in the stalk region of TLT-1 in streptavidin plates followed by binding of the antibody of interest (mAb 0061). A secondary antibody was added for detection and binding was measured at 450 nm. Positive control: binding to biotinylated TLT-1.

Materials

10×PBS: 10×GPBS 14200 Gibco
TWEEN (polysorbate surfactant) 20: Aldrich Cat#27,434-8, Lot#530950-315
Plate: 96-well Streptavidin coated plate Nunc#466014
BSA: A7030-100 g Lot#057K0737
Blocking/Dilute Buffer: 1×PBS pH=7.4
  2% BSA
  0.5% TWEEN (polysorbate surfactant) 20
Wash Buffer: 1×PBS+0.5% TWEEN (polysorbate surfactant) 20
Standard: Biotinylated TLT-1 04/09-08 1 mg/ml
mAb: 0197-0000-0061-4A-0.55 mg/ml
Detecting Ab: Goat anti-Human IgG HRP-labeled 1 mg/ml Prod. no.
  NEF802001EA
TMB Substrate: Ready to use Cat#4390L lot.#70904
Stop Solution: 2M $H_3PO_4$
Dilution of Biotinylated TLT-1:
1 mg/ml->6.3 ng/ml (158500× Dilution)
Concentration in well: 0.63 ng
Dilution of Biotinylated Peptides:
Approx conc 2-5 mg/ml (2.5 mg/ml)
2.5 mg/ml->10000× Dilution (25 ng/well): 100 µl of each peptide in each well.
Dilution of mAb 0061
0.55 mg/ml->100 ng/ml (5500× Dilution)
Concentration in well: 10 ng
Dilution of mAb Goat Anti-Human IaG HRP:
1 mg/ml->0.2 µg/ml (5000× Dilution)

Synthesis of Biotinylated Peptides in 96 Well Format.

The biotinylated peptides were synthesised using standard solid phase peptide synthesis. Solutions of 0.3M Fmoc-protected amino acids in 0.3 M 1-hydroxybenzotriazole (HOBt) in N-methylpyrrolidinone (NMP) were coupled using diisopropylcarbodiimide (DIC) for 1-4 hours. As solid support the Rink amide LL resin (Merck) was used in a 96 microtiter filterplate (Nunc) and ca. 20 mg resin pr well was used. The synthesis was performed using the Multipep RS peptide synthesiser from Intavis, Germany and manufacture protocol was used. The removal of Fmoc was done using 25% piperidin in NMP. All peptides were coupled with biotin at the N-terminal and 8-amino-3,6-dioxaoctanoic acid was used as a spacer between biotin and the peptides. This spacer was also coupled as a Fmoc-protected building block according to the synthesis protocol (IRIS biotech, Germany)

Final Deprotection and Workup

The final deprotection was done using 90% trifluoracetic acid (TFA), 5% triisopropylsilane and 5% H2O for 3 hours. A total of 1 ml TFA was used pr well. The TFA was filtered to 96 deep well (Nunc) and the TFA was reduced in volume by evaporation to ca. 100-200 ul pr well and diethylether was added to all wells in order to precipitate the peptides. The suspension of peptide in diethylether was transferred to solvinert 96 well filter plate (0.47 um, Millipore) and the peptides were washed twice with diethylether and dried. The peptides were redissolved in 80% DMSO and 20% water giving a stock solution of ca. 1-3 mg/ml.

Biotinylated 20mer peptides from stalk region of TLT-1 (SEQ ID NO 6)

2-5 mg/ml in 75% DMSO/H2O (biotinylated in N-terminal):
Number of peptide shown at the left:

| | | | |
|---|---|---|---|
| 2 | A 2 | 2619.8 | bio-Oeg-L-N-I-L-P-P-E-E-E-E-T-H-K-I-G-S-L-A-E |
| 3 | A 3 | 2620.7 | bio-Oeg-N-I-L-P-P-E-E-E-E-T-H-K-I-G-S-L-A-E-N |
| 4 | A 4 | 2577.7 | bio-Oeg-I-L-P-P-E-E-E-E-T-H-K-I-G-S-L-A-E-N-A |
| 5 | A 5 | 2611.7 | bio-Oeg-L-P-P-E-E-E-E-T-H-K-I-G-S-L-A-E-N-A-F |
| 6 | A 6 | 2585.6 | bio-Oeg-P-P-E-E-E-E-T-H-K-I-G-S-L-A-E-N-A-F-S |
| 7 | A 7 | 2603.6 | bio-Oeg-P-E-E-E-E-T-H-K-I-G-S-L-A-E-N-A-F-S-D |
| 8 | A 8 | 2603.6 | bio-Oeg-E-E-E-E-T-H-K-I-G-S-L-A-E-N-A-F-S-D-P |
| 9 | A 9 | 2545.6 | bio-Oeg-E-E-E-T-H-K-I-G-S-L-A-E-N-A-F-S-D-P-A |
| 10 | A10 | 2473.6 | bio-Oeg-E-E-T-H-K-I-G-S-L-A-E-N-A-F-S-D-P-A-G |
| 11 | A11 | 2431.6 | bio-Oeg-E-T-H-K-I-G-S-L-A-E-N-A-F-S-D-P-A-G-S |
| 12 | A12 | 2373.6 | bio-Oeg-T-H-K-I-G-S-L-A-E-N-A-F-S-D-P-A-G-S-A |
| 13 | B 1 | 2358.6 | bio-Oeg-H-K-I-G-S-L-A-E-N-A-F-S-D-P-A-G-S-A-N |
| 14 | B 2 | 2354.6 | bio-Oeg-H-K-I-G-S-L-A-E-N-A-F-S-D-P-A-G-S-A-N-P |
| 15 | B 3 | 2330.7 | bio-Oeg-K-I-G-S-L-A-E-N-A-F-S-D-P-A-G-S-A-N-P-L |
| 16 | B 4 | 2331.6 | bio-Oeg-I-G-S-L-A-E-N-A-F-S-D-P-A-G-S-A-N-P-L-E |
| 17 | B 5 | 2315.5 | bio-Oeg-G-S-L-A-E-N-A-F-S-D-P-A-G-S-A-N-P-L-E-P |
| 18 | B 6 | 2345.5 | bio-Oeg-S-L-A-E-N-A-F-S-D-P-A-G-S-A-N-P-L-E-P-S |
| 19 | B 7 | 2386.5 | bio-Oeg-L-A-E-N-A-F-S-D-P-A-G-S-A-N-P-L-E-P-S-Q |
| 20 | B 8 | 2388.4 | bio-Oeg-A-E-N-A-F-S-D-P-A-G-S-A-N-P-L-E-P-S-Q-D |
| 21 | B 9 | 2446.4 | bio-Oeg-E-N-A-F-S-D-P-A-G-S-A-N-P-L-E-P-S-Q-D-E |
| 22 | B10 | 2445.5 | bio-Oeg-N-A-F-S-D-P-A-G-S-A-N-P-L-E-P-S-Q-D-E-K |
| 23 | B11 | 2418.5 | bio-Oeg-A-F-S-D-P-A-G-S-A-N-P-L-E-P-S-Q-D-E-K-S |
| 24 | B12 | 2460.6 | bio-Oeg-F-S-D-P-A-G-S-A-N-P-L-E-P-S-Q-D-E-K-S-I |
| 25 | C 1 | 2410.5 | bio-Oeg-S-D-P-A-G-S-A-N-P-L-E-P-S-Q-D-E-K-S-I-P |
| 26 | C 2 | 2436.6 | bio-Oeg-D-P-A-G-S-A-N-P-L-E-P-S-Q-D-E-K-S-I-P-L |
| 27 | C 3 | 2434.7 | bio-Oeg-P-A-G-S-A-N-P-L-E-P-S-Q-D-E-K-S-I-P-L-I |

Biotinylated 16mer peptides from the stalk region of hTLT-1 (SEQ ID NO 6)
2-5 mg/ml in 75% DMSO/H2O:

| | | | |
|---|---|---|---|
| 29 | C 5 | 2219.3 | bio-Oeg-L-N-I-L-P-P-E-E-E-E-T-H-K-I-G |
| 30 | C 6 | 2193.2 | bio-Oeg-N-I-L-P-P-E-E-E-E-T-H-K-I-G-S |
| 31 | C 7 | 2192.3 | bio-Oeg-I-L-P-P-E-E-E-E-T-H-K-I-G-S-L |
| 32 | C 8 | 2150.2 | bio-Oeg-L-P-P-E-E-E-E-T-H-K-I-G-S-L-A |

-continued

| | | | |
|---|---|---|---|
| 33 | C 9 | 2166.1 | bio-Oeg-P-P-E-E-E-E-T-H-K-I-G-S-L-A-E |
| 34 | C10 | 2183.1 | bio-Oeg-P-E-E-E-E-T-H-K-I-G-S-L-A-E-N |
| 35 | C11 | 2157.1 | bio-Oeg-E-E-E-E-T-H-K-I-G-S-L-A-E-N-A |
| 36 | C12 | 2175.2 | bio-Oeg-E-E-E-T-H-K-I-G-S-L-A-E-N-A-F |
| 37 | D 1 | 2133.2 | bio-Oeg-E-E-T-H-K-I-G-S-L-A-E-N-A-F-S |
| 38 | D 2 | 2119.2 | bio-Oeg-E-T-H-K-I-G-S-L-A-E-N-A-F-S-D |
| 39 | D 3 | 2087.2 | bio-Oeg-T-H-K-I-G-S-L-A-E-N-A-F-S-D-P |
| 40 | D 4 | 2029.2 | bio-Oeg-H-K-I-G-S-L-A-E-N-A-F-S-D-P-A |
| 41 | D 5 | 1985.2 | bio-Oeg-H-K-I-G-S-L-A-E-N-A-F-S-D-P-A-G |
| 42 | D 6 | 1935.2 | bio-Oeg-K-I-G-S-L-A-E-N-A-F-S-D-P-A-G-S |
| 43 | D 7 | 1878.1 | bio-Oeg-I-G-S-L-A-E-N-A-F-S-D-P-A-G-S-A |
| 44 | D 8 | 1879 | bio-Oeg-G-S-L-A-E-N-A-F-S-D-P-A-G-S-A-N |
| 45 | D 9 | 1919 | bio-Oeg-S-L-A-E-N-A-F-S-D-P-A-G-S-A-N-P |
| 46 | D10 | 1945.1 | bio-Oeg-L-A-E-N-A-F-S-D-P-A-G-S-A-N-P-L |
| 47 | D11 | 1961 | bio-Oeg-A-E-N-A-F-S-D-P-A-G-S-A-N-P-L-E |
| 48 | D12 | 1987 | bio-Oeg-E-N-A-F-S-D-P-A-G-S-A-N-P-L-E-P |
| 49 | E 1 | 1945 | bio-Oeg-N-A-F-S-D-P-A-G-S-A-N-P-L-E-P-S |
| 50 | E 2 | 1959 | bio-Oeg-A-F-S-D-P-A-G-S-A-N-P-L-E-P-S-Q |
| 51 | E 3 | 2003 | bio-Oeg-F-S-D-P-A-G-S-A-N-P-L-E-P-S-Q-D |
| 52 | E 4 | 1984.9 | bio-Oeg-S-D-P-A-G-S-A-N-P-L-E-P-S-Q-D-E |
| 53 | E 5 | 2026 | bio-Oeg-D-P-A-G-S-A-N-P-L-E-P-S-Q-D-E-K |
| 54 | E 6 | 1998 | bio-Oeg-P-A-G-S-A-N-P-L-E-P-S-Q-D-E-K-S |
| 55 | E 7 | 2014.1 | bio-Oeg-A-G-S-A-N-P-L-E-P-S-Q-D-E-K-S-I |
| 56 | E 8 | 2040.1 | bio-Oeg-G-S-A-N-P-L-E-P-S-Q-D-E-K-S-I-P |
| 57 | E 9 | 2096.2 | bio-Oeg-S-A-N-P-L-E-P-S-Q-D-E-K-S-I-P-L |
| 58 | E10 | 2122.3 | bio-Oeg-A-N-P-L-E-P-S-Q-D-E-K-S-I-P-L-I |

Method

The epitope mapping consisted of binding of mAb 0061 to two series of biotinylated peptides from the stalk region of TLT-1. The biotinylated peptides were bound to streptavidin plates.

Stalk Peptide:
LNILPPEEEEETHKIGSLAENAFSDPAGSANPLEPSQDEKSIPL (SEQ ID NO: 173)

1) 20mer peptide mapping with one residue frameshift (20,1) (see materials)
2) 16mer peptide mapping with one residue frameshift (16,1) (see materials)
1. Plate was pre-washed 3× with 250 μl wash buffer
2. 100 μl Biotinylated peptide-solution was added (from Masterplate 10000× diluted, one peptide pr well)
3. Incubated at RT for 1 hour or +5° C. over night
4. Washed 3× with wash buffer
5. 100 μl Primary antibody was added (dilution see above)
6. Incubated at RT for 1 hour
7. Washed 3× with wash buffer
8. 100 μl Secondary antibody was added (dilution see above)
9. Incubated at RT for 1 hour
10. Washed 3× with wash buffer
11. 100 μl Substrate/Develop buffer was added (Reaction time 3 min)
12. 100 μl 2M H3PO4 was added
13. Endpoint was read at 450 nm Binding to biotinylated peptide in a well was recorded as "binding" when the absorption at 450 nm was above 3. "No binding" was recorded when signal was below 1. A signal in between was recorded as "weak binding".

Results

The biotinylated peptides were put into wells in the following way:

Row A: peptide 2-12 (20mers)
Row B: peptide 13-24 (20mers)
Row C: peptide 25-27 (20mers)
Row C: peptide 29-36 (16mers)
Row D: peptide 37-48 (16mers)
Row E: peptide 49-58 (16mers)

Result from triple determination:

|   | 1    | 2    | 3    | 4    | 5    | 6    | 7    | 8    | 9    | 10   | 11   | 12   |
|---|------|------|------|------|------|------|------|------|------|------|------|------|
| A |      | <0.1 | <0.1 | <0.1 | >3   | >3   | >3   | >3   | >3   | >3   | >3   | >3   |
| B | >3   | >3   | >3   | >3   | <0.1 | <0.1 | <0.1 | <0.1 | <0.1 | <0.1 | <0.1 | <0.1 |
| C | <0.1 | <0.1 | <0.1 |      | <0.1 | <0.1 | <0.1 | <0.1 | <0.1 | <0.1 | <0.1 | >3   |
| D | >3   | >3   | >3   | >3   | >3   | >3   | <0.1 | <0.1 | <0.1 | <0.1 | <0.1 | <0.1 |
| E | <0.1 | <0.1 | <0.1 | <0.1 | <0.1 | <0.1 | <0.1 | <0.1 | <0.1 | <0.1 |      |      |
| F |      |      |      |      |      |      |      |      |      |      |      |      |
| G |      |      |      |      |      |      |      |      |      |      |      |      |
| H |      |      |      |      |      |      |      |      |      |      |      |      |

In summary, the 20mer-peptides (5-16) give rise to strong positive signals (<3) corresponding to amino acids: IGSLAENAF (SEQ ID NO: 182). The 16mer peptides 36-42 give rise to a strong positive signals (<3) corresponding to KIGSLAENAF (SEQ ID NO: 182).

CONCLUSION

The peptide walking ELISA has defined the minimal binding area of the epitope for binding to mAb 0061 as the following stretch of amino acid residues: KIGSLAENAF (SEQ ID NO: 182).

This stretch is indeed part of the epitope defined above by the crystal structure: ETHKIGSLAENAFSDP (SEQ ID NO: 183).

---

The invention claimed is:

1. A monoclonal antibody, or fragment thereof, that binds to an epitope on TREM-like transcript 1 (TLT-1) in a region selected from the group consisting of SEQ ID NO:5, SEQ ID NO:6, SEQ ID NO:7, and SEQ ID NO:8.

2. The monoclonal antibody, or fragment thereof, according to claim 1, wherein the fragment is selected from the group consisting of a Fab fragment, a F(ab')₂ fragment, a Fab' fragment, a Fd fragment, a Fv fragment, a ScFv fragment, a dAb fragment, and an isolated complementarity determining region.

3. The monoclonal antibody, or fragment thereof, according to claim 1, wherein the monoclonal antibody is a human monoclonal antibody.

4. The monoclonal antibody, or fragment thereof, according to claim 2, wherein the Fab fragment is humanized.

5. The monoclonal antibody, or fragment thereof, according to claim 1, wherein the TLT-1 region is SEQ ID NO:5.

6. The monoclonal antibody, or fragment thereof, according to claim 1, wherein the TLT-1 region is SEQ ID NO:6.

7. The monoclonal antibody, or fragment thereof, according to claim 1, wherein the TLT-1 region is SEQ ID NO:7.

8. The monoclonal antibody, or fragment thereof, according to claim 1, wherein the TLT-1 region is SEQ ID NO:8.

9. The monoclonal antibody, or fragment thereof, according to claim 1, wherein the epitope comprises residues V17, Q18, C19, H20, Y21, R22, L23, Q24, D25, V26, K27, A28, L63, G64, G65, G66, L67, L68, G89, A90, R91, G92, P93, Q94, I95, and L96 of SEQ ID NO: 5.

10. The monoclonal antibody, or fragment thereof, according to claim 1, wherein the epitope comprises residues L36, P37, E38, G39, C40, Q41, P42, L43, V44, S45, S46, A47, V73, T74, L75, Q76, E77, E78, D79, A80, G81, E82, Y83, G84, C85, M86, R91, G92, P93, Q94, I95, L96, H97, R98, V99, S100, and L111 of SEQ ID NO: 5.

11. The monoclonal antibody, or fragment thereof, according to claim 1, wherein the epitope comprises residues V17, Q18, C19, H20, Y21, R22, L23, Q24, D25, V26, K27, A28, R91, G92, P93, Q94, I95, L96, H97, R98, V99, S100, and L101 of SEQ ID NO: 5.

12. The monoclonal antibody, or fragment thereof, according to claim 1, wherein the epitope comprises residues E5, T6, H7, K8, I9, G10, S11, L12, A13, E14, N15, A16, F17, S18, D19, P20, and A21 of SEQ ID NO: 7.

* * * * *